United States Patent
Kriesel et al.

(10) Patent No.: US 7,449,294 B2
(45) Date of Patent: Nov. 11, 2008

(54) DIAGNOSIS AND TREATMENT OF HERPES SIMPLEX VIRUS DISEASES

(75) Inventors: John D. Kriesel, Holladay, UT (US); Mark F. Leppert, Salt Lake City, UT (US); Sportswood L. Spruance, Salt Lake City, UT (US); Brith E. M. Otterud, Salt Lake City, UT (US); Maurine R. Hobbs, Salt Lake City, UT (US); Brandt B. Jones, Bountiful, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 177 days.

(21) Appl. No.: 11/102,978

(22) Filed: Apr. 11, 2005

(65) Prior Publication Data

US 2005/0250142 A1 Nov. 10, 2005

Related U.S. Application Data

(63) Continuation of application No. PCT/US03/33152, filed on Oct. 18, 2003.

(60) Provisional application No. 60/419,576, filed on Oct. 18, 2002.

(51) Int. Cl.
*C12Q 1/68* (2006.01)
(52) U.S. Cl. ......................................................... 435/6
(58) Field of Classification Search .................... None
See application file for complete search history.

(56) References Cited

OTHER PUBLICATIONS

Ezquerra et al., 1988, Neuroscience Letters 248:1-4.*
Akahane et al., 2002, Schizophrenia Research 58:37-41.*
Itzhaki et al., 1997, The Lancet, 349: 241-244.*
Little et al., 2002, American J of Epidemiology 156: 300-310.*
Arffa R.C., "Viral Diseases of the Cornea" Grayson's Diseases of the Cornea, Mosby: St. Louis. p. 241-265, 1991.
Carpten J.D., et al., "HRPT2, encoding parafibromin, is mutated in the hyperparathyroidism-jaw tumor (HPT-JT) syndrome." Nature Genetics accepted, p. 676-680, 2002.
Carter C.A. "Tsg101: HIV-1's ticket to ride." Trends Microbial. 10(5):203-5, 2002.
Caspary L., Schindling B., et al., "Infections of susceptible and resistant mouse strains with HSV types 1 and 2." Arch. Virol. 65:219-27, 1980.
Chen J., Chiang Y.C. and Denis C.L., "CCR4, a 3'-5' poly(A) RNA and ssDNA exonuclease, is the catalytic component of the cytoplasmic deadenylase." Embo. J. 21(6):1414-26, 2002.
Cherry J.L., Young H., et al., "Enzyme-linked fluorescent detection for automated multiplex DNA sequencing." Genomics 20(1):68-74, 1994.
Coon H., Eckfeldt J.H., et al., "A genome-wide screen reveals evidence for a locus on chromosome 11 influencing variation in LDL cholesterol in the NHLBI Family Heart Study." Hum. Genet. 111(3):263-9., 2002.
Coon H., Leppert M.F., et al., "Genome-wide linkage analysis of lipids in the Hypertension Genetic Epidemiology Network (HyperGEN) Blood Pressure Study." Arterioscler. Thromb. Vasc. Biol. 21(12):1969-76, 2001.
Cottingham R. W., Jr., Idury R.M. and Schaffer A.A., "Faster sequential genetic linkage computations." Am. J. Hum. Genet. 53(1):252-63, 1993.
Dawson C., "Management of herpes simplex eye disease, in Clinical Management of Herpes Viruses", IOS Press: Amsterdam. p. 127-136, 1995.
Elner V.M., Dutt S., et al., "Intercellular adhesion molecule-1 (ICAM-1) and HLA-DR antigens in herpes keratitis." Ophthalmology 99(9):1400-7, 1992.
Embil J.A., Stephens R.G. and Manuel F.R. "Prevalence of recurrent herpes labialis and aphthous ulcers among young adults on six continents". Can. Med. Assoc. J. 113(7):627-30, 1975.
Feitosa M.F., Borecki I.B., et al., "Quantitative-trait loci influencing body-mass index reside on chromosomes 7 and 13: the National Heart, Lung, and Blood Institute Family Heart Study." Am. J. Hum.' Genet. 70(1):72-82, 2002.
Garrus J.E., von Schwedler U.K., et al., "Tsg101 and the vacuolar protein sorting pathway are essential for HIV-1 budding." Cell 107(1):55-65, 2001.
Gerdes J. and Smith D. "Recurrence phenotypes and establishment of latency following rabbit keratitis produced by multiple HSV strains." J. Gen. Virol. 64:2441-54, 1983.
Grout P. and Barber V.E. "Cold sores-an epidemiological survey." J. R. Coll. Gen. Pract. 26(167):428-34, 1976.
Hall M.A., Norman P.J., et al., "Quantitative trait loci on chromosomes 1, 2, 3, 4, 8, 9, 11, 12, and 18 control variation in levels of T and B lymphocyte subpopulations." Am. J. Hum. Genet. 70(5):1172-82, 2002.
Hardy S. W., Weir B.S., et al., "Analysis of single nucleotide polymorphisms in candidate genes using the pedigree disequilibrium test." Genet. Epidemiol. 21(Suppl 1):S441-6, 2001.
Hill J., Garza H., Helmy M., et al., "Nerve growth factor antibody stimulates reactivation of ocular herpes simplex virus type 1 in latently infected rabbits." J. Neurovirology 3:206-11, 1997.
Hobbs M.R., Pole A.R., et al., "Hyperparathyroidism-jaw tumor syndrome: the HRPT2 locus is within a 0.7- cM region on chromosome 1 q." Am. J. Hum. Genet. 64(2):518-25, 1999.
Hobbs M.R., Udhayakumar V., et al., "A New NOS2 Promoter Polymorphism with increased nitric oxide production and protection from severe malaria in Tanzanian and Kenyan children" Lancet, Nov. 9; 360 (9344): 1468-1475, 2002.

(Continued)

Primary Examiner—James Martinell
(74) Attorney, Agent, or Firm—Ballard Spahr Andrews & Ingersoll, LLP

(57) ABSTRACT

The invention maps a herpes simplex labialis (HSL) susceptibility gene associated with HSL to the q11 region of chromosome 21. The invention provides methods of screening for susceptibility or resistance to herpes simplex virus, particularly herpes simplex labialis, and diagnosing herpetic diseases, such as HSL.

44 Claims, 4 Drawing Sheets

OTHER PUBLICATIONS

Hugot J.P., Chamaillard M., et al., "Association of NOD2 leucine-rich repeat variants with susceptibility to Crohn's disease." Nature 411(6837):599-603, 2001.

Jabbar A.A., al-Samarai A.M. and al-Amar N.S. "HLA antigens associated with susceptibility to herpes simplex virus infection." Dis. Markers 9(5):281-7, 1991.

Kamb A., Futreal P.A., et al., "Localization of the VHR phosphatase gene and its analysis as a candidate for BRCA1." Genomics 23(1):163-7, 1994.

Kriesel J.D., Gebhardt B.M., et al., "Anti-Interleukin-6 antibodies inhibit herpes simplex virus reactivation." J. Infect. Dis. 175(4):821-7, 1997.

Lander E.S., Linton L.M., et al., "Initial sequencing and analysis of the human genome." Nature 409(6822):860-921, 2001.

Lathrop G.M. and Lalouel J.M. "Easy calculations of lod scores and genetic risks on small computers." Am. J. Hum. Genet. 36(2):460-5, 1984.

Lathrop G.M., Lalouel J.M. and White R.L. "Construction of human linkage maps: likelihood calculations for multilocus linkage analysis." Genet. Epidemiol. 3(1):39-52, 1986.

Lathrop G.M., Lalouel J.M., et al., "Strategies for multilocus linkage analysis in humans." Proc. Natl. Acad. Sci. U.S.A. 81(11):3443-6, 1984.

Laycock K.A., Lee S.F., et al., "Characterization of a murine model of recurrent HSV keratitis induced by ultraviolet B radiation." Invest. Ophth. Vis. Sci. 32:2741-6, 1991.

Legendre C., Russell A. and Jeannet M. "HLA antigens in patients with recrudescent herpes simplex infections." Tissue Antigens 19:85-9, 1982.

Lekstrom-Himes J.A., et al., "Association of major histocompatibility complex determinants with the development of symptomatic and asymptomatic genital herpes simplex virus type 2 infections." J. Infect. Dis. 179(5):1077-85, 1999.

Levesque M.C., Hobbs M.R., et al., "Nitric oxide synthase type 2 promoter polymorphisms, nitric oxide production, and disease severity in Tanzanian children with malaria." J. Infect. Dis. 180(6):1994-2002, 1999.

Itzhaki et al., "Herpes Simplex Virus type 1 in Brain and Risk of Alzheimer's Disease," 1997, The Lancet, 349: 241-244.

Malo A., Kampgen E. and Wank R. "Recurrent herpes simplex virus-induced erythema multiforme: different HLA-DQB 1 alleles associate with severe mucous membrane versus skin attacks." Scand. J. Immunol. 47(5):408-11, 1998.

Martin E.R., Monks S.A., et al., "A test for linkage and association in general pedigrees: the pedigree disequilibrium test." Am. J. Hum. Genet. 67(1):146-54, 2000.

Marx J., "Ubiquitin lives up to its name." Science 297(5588):1792-4, 2002.

Merette C., Lehner T. and Ott J. "Interpreting nonsignificant outcomes of heterogeneity tests in gene mapping" Am. J. Hum. Genet. 49(6):1381-4, 1991.

Miki Y., Swensen J.J., et al., "A physical map encompassing GP2B, EPB3, D17S183, D17S78, D17S1183, and D17S1184." Genomics 25(1):295-7, 1995.

Neuhausen S.L., Swensen J., et al., "A P1-based physical map of the region from D17S776 to D17578 containing the breast cancer susceptibility gene BRCA1." Hum. Mol. Genet. 3(11): 1919-26, 1994.

Odell W.D., Hobbs M.R. and Benowitz B. "An immunologically anomolous parathyroid hormone variant causing hyperparathyroidism." Clin. Endocrinol. (03c-f)55(3):417-20, 2001.

Olchovsky D., Hobbs M.R., Pras E., Shimon I., Silver J., Irmin L. and Friedman E., "Familial Isolated Primary Hyperparathyroidism in a Large Georgian-Jewish Kindred: Genetic Studies." The Journal of Endocrine Genetics 2: pp. 91-97, 2001.

Padgett D.A., Sheridan J.F., Dome J., Bemtson G.G., Candelora J. and Glaser R. "Social stress and the reactivation of latent herpes simplex virus type 1." Proc. Natl. Acad. Sci. U.S.A 95(12):7231-5, 1998.

Patil N., Berno A.J., et al., "Blocks of limited haplotype diversity revealed by high-resolution scanning of human chromosome 21." Science 294(5547):1719-23, 2001.

Pazin G.J., Ho M. and Jannetta P.J. "Reactivation of HSV after decompression of the trigeminal nerve root." J. Infect. Dis. 138:405-9, 1978.

Pornillos O., Alam S.L., Rich R.L., Myszka D.G., Davis D.R., Sundquist W.I. "Structure and functional interactions of the Tsg101 UEV domain." Embo. J. 21(10):2397-406, 2002.

Russell A. and Schlaut J. "HLA transplantation antigens in subjects susceptible to recrudescent herpes labialis." Tissue Antigens 6:257-61, 1975.

Sawtell N.M. and Thompson R.L. "Rapid in vivo reactivation of HSV in latently infected murine ganlionic neurons after transient hyperthermia." J. Virol. 66:2150-6, 1992.

Schaffer A.A., Gupta S.K., Shriram K. and Cottingham R.W., Jr. "Avoiding recomputation in linkage analysis." Hum. Hered. 44(4):225-37, 1994.

Seppanen M., Lokki M.L., et al., "Complement C4 deficiency and HLA homozygosity in patients with frequent intraoral herpes simplex virus type 1 infections." Clin. Infect. Dis. 33(9):1604-1607, 2001.

Shimizu F., Monma Y., et al., "Establishment of latent ganglionic infection with HSV via maxillary gingiva and viral reactivation in vivo after trauma." J. Dent. Res. 68:472-5, 1989.

Ship I., Miller M. and Ram C. "A retrospective study of recurrent herpes labialis in a professional population, 1958-1971." Oral Surg. 44(5):723-9, 1977.

Ship I., Morris A., Durocher R. and Burket L. "Recurrent aphthous ulcerations and recurrent herpes labialis in a professional school student population." Oral Surg.Oral Med.Oral Pathol. 13:1191-202, 1960.

Spruance S. and Kriesel J., "Treatment of Herpes Simplex Labialis." Herpes vol. 9, No. 3, 2002, pp. 64-69(6).

Spruance S., Crumpacker C. and MacCalman J. Correlation of recurrence rate of herpes labialis with severity of episodes in J. Proc. American Soc. Microbiology, 1979, Los Angeles, California. Abstracts of Annual Meeting, S303, p. 290.

Spruance S.L., Freeman D.J., et al., "The natural history of ultraviolet radiation-induced herpes simplex labialis and response to therapy with peroral and topical formulations of acyclovir." J. Infect. 163(4):728-34, 1991.

Spruance S.L., Kriesel J.D., et al., "Susceptibility to herpes labialis following multiple experimental exposures to ultraviolet radiation." Antiviral-Res. 28(1):57-67, 1995.

Spruance S.L., Rowe N.H., et al., "Peroral famciclovir in the treatment of experimental ultraviolet radiation-induced herpes simplex labialis: A double-blind, dose-ranging, placebo-controlled, multicenter trial." J. Infect. Dis. 179(2):303-10, 1999.

Stroop W.G. and Banks M.C. "Herpes simplex virus type 1 strain KOS-63 does not cause acute or recurrent ocular disease and does not reactivate from ganglionic latency in vivo." Acta. Neuropathol. (Berl.) 87(1):14-22, 1994.

Thoelen I., Magnusson C., Targerud S., Polacek C., Lindberg M. and Van Ranst M. "Identification of alternative splice products encoded by the human coxsackie-adenovirus receptor gene." Biochem. Biophys. Res. Commun. 287(1):216-22, 2001.

Valero R., Bayes M., Francisca Sanchez-Font M., et al., "Characterization of alternatively spliced products and tissue-specific isoforms of USP28 and USP25." Genome Biol. 2(10), 2001.

Valero R., Marfany G., et al., "USP25, a novel gene encoding a deubiquitinating enzyme, is located in the gene-poor region 21q11.2." Genomics 62(3):395-405, 1999.

Varnell E.D., Kaufman H.E., Hill J.M. and Thompson H.W. "Cold stress-induced recurrences of herpetic keratitis in the squirrel monkey." Invest. Ophthal. Vis. Sci. 36:1181-3, 1995.

Weng L., Smits P., et al., "Molecular cloning and characterization of human chondrolectin, a novel type I transmembrane protein homologous to C-type lectins." Genomics 80(1):62-70, 2002.

Xu F., Schillinger J.A., Sternberg M.R., Johnson R.E., Lee F.K., Nahmias A.J. and Markowitz L.E. "Seroprevalence and coinfection with herpes simplex virus type 1 and type 2 in the United States, 1988-1994." J. Infect. Dis. 185(8):1019-24, 2002.

Yoshida Y., Hosoda E., Nakamura T. and Yamamoto T. "Association of ANA, a member of the antiproliferative Tob family proteins, with a Caf1 component of the CCR4 transcriptional regulatory complex." Jpn. J. Cancer Res. 92(6):592-6, 2001.

Yoshida Y., Matsuda S., et al., "ANA, a novel member of Tob/BTG1 family, is expressed in the ventricular zone of the developing central nervous system." Oncogene 16(20):2687-93, 1998.

Young T., Rimm E. and D'Alessio D. "Cross-sectional study of recurrent herpes labialis." Am. J. Epidemiology 127(3):612-25, 1988.

Zaykin D.V., Westfall P.H., et al., "Testing association of statistically inferred haplotypes with discrete and continuous traits in samples of unrelated individuals." Hum. Hered. 53(2):79-91, 2002.

* cited by examiner a) Informative Family.

b) Less informative Family.

○ = Unaffected (seropositive)
▨ = Indeterminate
● = Frequently affected

DIAGNOSIS AND TREATMENT OF HERPES SIMPLEX VIRUS DISEASES

PRIORITY CLAIM

This application is a continuation of International Patent Application Serial No. PCT/US2003/033152, filed Oct. 18, 2003, for DIAGNOSIS AND TREATMENT OF HERPES SIMPLEX VIRUS DISEASES, which application claims the benefit of U.S. Provisional Patent Application Ser. No. 60/419,576, filed Oct. 18, 2002, for DIAGNOSIS AND TREATMENT OF HERPES SIMPLEX VIRUS DISEASES, the entirety of each of which is hereby incorporated by reference.

STATEMENT REGARDING FEDERALLY SPONSORED RESEARCH OR DEVELOPMENT

This invention was supported in part by funding through the University of Utah and a grant through the Keck Foundation. The United States Government may have some rights in the invention.

STATEMENT ACCORDING TO 37 C.F.R. § 1.52(e)(5)-SEQUENCE LISTING SUBMITTED ON COMPACT DISC

Pursuant to 37 C.F.R. § 1.52(e)(1)(iii), a compact disc containing an electronic version of the Sequence Listing has been submitted concomitant with this application, the contents of which are hereby incorporated by reference. A second compact disk is submitted and is an identical copy of the first compact disc. The discs are labeled, "copy 1" and "copy 2," respectively, and each disc contains one file entitled "Sequence Listing ST25.txt" which is 490 KB, and created on Apr. 11, 2005.

TECHNICAL FIELD

The present invention relates to one or more genes conferring resistance or susceptibility to herpes simplex labialis (HSL).

BACKGROUND

Over 50% of the U.S. population is infected with either herpes simplex viruses (HSV) types 1 (HSV-1) and or type 2 (HSV-2). Furthermore, herpes simplex virus has been estimated to affect over one third of the world's population. Reactivations of HSV-1 infection cause herpes simplex labialis (HSL, "cold sores," or "fever blisters"), the most common recurring viral infection in humans. HSV-2 reactivations cause genital herpes, a disease that continues to affect millions of people.

Herpes simplex labialis (HSL) is a common and ubiquitous infection of the skin due to herpes simplex virus (HSV). The vast majority of cases are due to HSV type 1 (HSV-1), although recurrent infections due to HSV type 2 have been reported. Roughly 20-40% of the US population will experience labial or perioral outbreaks of vesicular herpetic lesions.[1-3] The frequency of these outbreaks is extremely variable, ranging, in some individuals, from rare episodes every 5-10 years, to monthly or more frequent outbreaks among a small proportion of subjects.[4] The severity of the illness is most often mild, although uncomfortable and disfiguring for many persons. The psychological impact of a prominent facial infection, particularly in young patients with frequent or severe recurrences, should not be underestimated. Among persons with an underlying immunosuppressing disease, lesions are of longer duration and may spread to cause major morbidity. Lastly, herpetic keratitis and herpes encephalitis are infrequent but grave complications of orofacial HSV-1 infection.

Herpes keratitis, due to HSV-1 infection of the corneal surface, is an important subset of HSV-1-induced diseases. Herpes keratitis is important among ocular infections in developed countries because it is difficult to treat, recurs unexpectedly, and sometimes leads to corneal scarring and blindness. There are approximately 20,000 new cases of herpes keratitis annually in the U.S. and 28,000 recurrent cases, leading to 6000 corneal transplants.[5] It is a recurrent disease where HSV-1 reactivation in the ganglion leads to repeated infections in the cornea with subsequent scarring and opacity.[6]

Recurrences of HSV-2 infection account for the majority of genital herpes cases (a few cases are caused by recurrent HSV-1). A large, recent serosurvey indicates that 21.9% of the U.S. population, some 50 million persons, are infected with HSV-2.[7] Among these HSV-2 infected persons, approximately 10-20% (5-10 million persons) have recognized genital herpes.

Three components are believed to account for reactivation of HSV-induced diseases in animal models and in humans. The first component is viral strain. For instance, the common HSV-1 laboratory strains McKrae and 17 syn⁺ reactivate with reasonable frequency in mouse and rabbit models of disease.[8-11] In contrast, the HSV-1 laboratory strain KOS does not reactivate readily in vivo, requiring explantation of the latently-infected trigeminal ganglion before replicating virus appears.[12] Viral strain differences probably also occur in humans, although this has been less well studied than in animals.

The second component that contributes to expression of HSV-induced diseases are various environmental factors. Social stress, hyperthermia, hypothermia, skin irritation, ultraviolet (UV) light exposure, and immunosuppression are all well-established triggers for HSV reactivation in animal models.[8, 13-16] In humans, fever, wind, sunburn, and surgical manipulation of the ganglion are inducers of HSV reactivation.[17-19] HSV-1 and HSV-2 reactivating stimuli, while not identical, are similar in both animals and humans. For instance, UV exposure causes HSV-1 ocular reactivation in mice and HSV-2 genital reactivation in guinea pigs.

The third component of susceptibility to HSL is host genetics. Differences among inbred strains of mice have a strong influence on the frequency of HSV-1 reactivation in animal models.[20, 21] For instance, Balb/c mice reactivate much more readily than the C57B1/6 strain. Several studies have linked human HLA types to susceptibility to both herpes labialis and genital herpes.[22-26] For instance, the allelic frequency of HLA-B5 and Aw30 are increased in patients with herpes simplex keratitis. Likewise, the frequency of HLA-A1 is increased in patients with frequent genital herpes outbreaks while HLA-B27 appears to have a protective effect. HSV-1 induced erythema multiforme may be strongly linked to certain HLA-DQB 1 alleles,[24] but evidence for HLA linkage of the most common HSV-1 induced disease—herpes labialis—is much weaker. Russell and Schlaut found HLA-A1 was significantly increased in HSL patients,[27] a finding not confirmed by Legendre et. al.[28] These older studies suffer from uncertainties in patient selection due to serologic assays that could not distinguish infection with HSV-1 from infection with HSV-2.

We performed an unbiased study looking at human genes linked to HSL. This was accomplished by HSL phenotyping study subjects genotyped as part of the Utah Genetic Reference Project (UGRP). We have identified human linkage to a human gene(s) that confers resistance or susceptibility to cold sores (referred to as "HSL susceptibility").

SUMMARY OF THE INVENTION

The present invention relates generally to the field of human genetics. More specifically, the present invention relates generally to methods and materials used to isolate and detect genes conferring resistance or susceptibility to herpes simplex labialis (HSL) (HSL susceptibility gene), some alleles of which cause susceptibility to or protection from herpes simplex labialis. The present invention further relates to somatic mutations in the HSL susceptibility gene and the use in diagnosis and prognosis of herpes simplex labialis. Additionally, the invention relates to somatic mutation in the HSL susceptibility gene in other human diseases and the use in the diagnosis and prognosis of human disease.

DETAILED DESCRIPTION OF THE INVENTION

Figure 1:
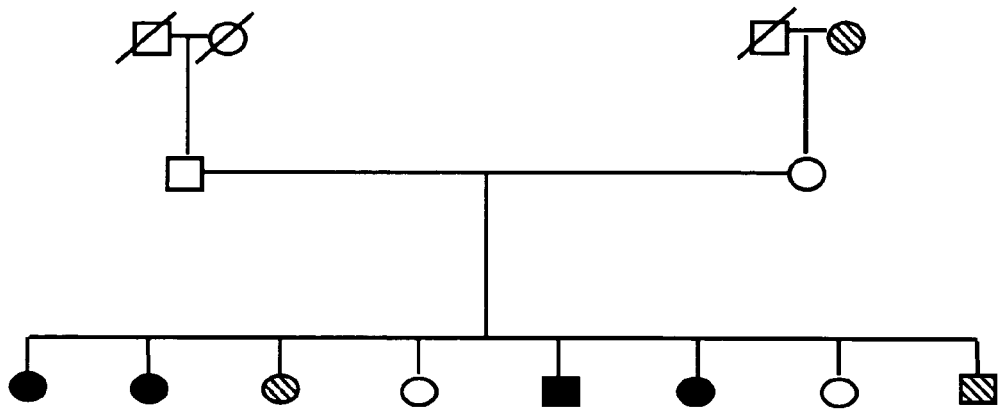
FIG. 1. Informative vs. less informative UGRP families.
Figure 1:
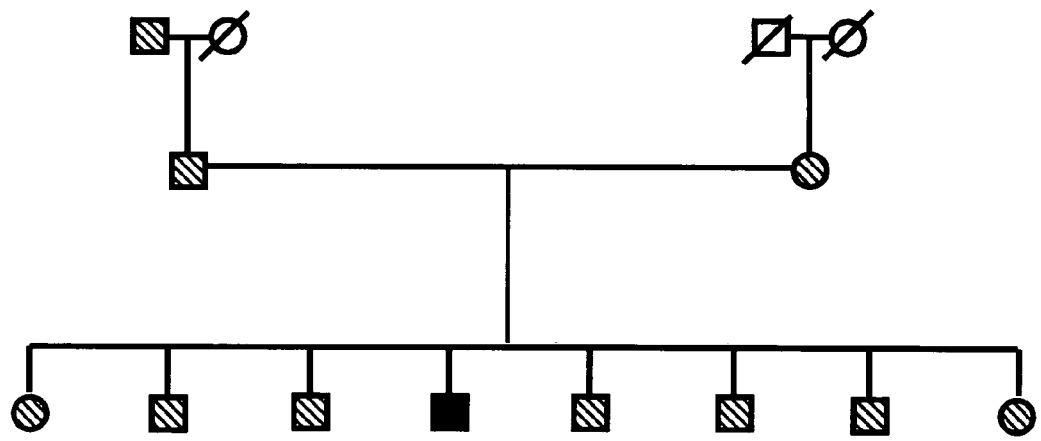

The invention provides methods of identifying patients having a variant allele of a gene associated with susceptability or resistance to HSL. Thus, one embodiment of the invention provides methods useful in identifying persons which may be in need of viral prevention and/or treatment, without the person having to suffer frequent HSL episodes.

Serotyping and phenotyping of 350 subjects in 31 families currently enrolled in the Utah Genetic Reference Project (UGRP) was conducted. Through genetic linkage analysis in 87 individuals in 9 of these families, a 7-cM region of the human genome that is likely to encode one or more genes conferring resistance or susceptibility to HSL (cold sores) (HSL susceptibility gene) was identified. Multipoint linkage analysis shows strong evidence for linkage (logarithm of odds (LOD) score=3.5) near marker abmc65 (D21S409). This apparent linkage was confirmed by a non-parametric genetic linkage analysis of this region (p=0.0005 at marker abmc65 (D21S409)). This human herpes susceptibility or resistance region lies on the long arm of chromosome 21,21q21, and includes 6 genes, which comprise some of the embodiments of the present invention.

Susceptability or resistance may result from a nucleotide change in the gene (addition, deletion or substitution) affecting expression of the gene by altering the timing and/or kinetics of expression or the nature of the resulting expression product. For example, some changes reduce transcription or translation of an expression product. Other changes result in a polypeptide having altered properties (cf the sickle cell mutation). Still other changes introduce a premature stop codon thereby resulting in truncated expression product.

HSV-1 Serologies

HSV-1 type-specific serologies were performed on serum available from 350 individuals included in the UGRP families #1-33. These persons were all 18 years of age or older and volunteers in the Utah Genetic Reference Project (UGRP). Glycoprotein-G-based type-specific ELISA was performed on each individual's serum according to the manufacturer's instructions (Focus Technologies, Cypress, Calif.). Three hundred forty-nine tests were either positive or negative; with 1 equivocal result. Among the 349 serotyped individuals, 251 (72%) were seropositive and 98 (28%) were seronegative.

Serotyping was performed using serum, however, other sample sources known in the art may be used, including, but not limited to, saliva, buccal cells, hair roots, amniotic fluid, and any other suitable cell or tissue having genetic material. In addition, HSV was detected using a type-specific ELISA assay, however, any other appropriate assay may be used to detect the presence or absence of HSV and/or determine the serotype.

Phenotyping of the UGRP Subjects

Each of these 350 UGRP participants was asked to report information about whether they had ever experienced HSL ("cold sores" or "fever blisters") and, if so, the frequency, nature, and triggering stimuli for their outbreaks via a standardized questionnaire. The subjects were asked to distinguish the appearance of "cold sores," which normally occur on the lips, nose, or face, from "canker sores" (apthous ulcers), which normally occur inside the mouth on the tongue, cheeks, or gums. Sufficient information to allow determination of an annual HSL frequency was obtained in 214 of the 251 seropositive individuals (87%). HSL frequency is strongly correlated with severity of the episodes, making information about episode frequency particularly valuable as a measure of phenotype.[29] Information about HSL triggers, lifetime episodes, and prodromal symptoms was also collected.

The annual frequency of HSL was self-reported in 190 of the 251 (76%) seropositive individuals. In another 24 individuals the annual frequency of HSV was estimated based on their ages, the number of reported lifetime HSL episodes, and the age of onset of HSL. Twenty-three of the 24 individuals who had an annual frequency of HSV ended up with the "mild" phenotype and were excluded from the subsequent analysis. One individual reported an estimated 100 lifetime episodes over some 50 years and was therefore included in the "frequently affected" phenotype group. Therefore, sufficient information to allow determination of an annual HSL frequency was obtained in 214 of the 251 seropositive individuals (87%). Among these 214 reporting seropositive individuals, 149 (70%) had experienced one or more HSL episodes in their lifetime. The remaining 65 individuals (30%) were HSV-1 seropositive, but completely unaffected by any recognized HSL episodes. Phenotyping according to self-reported or estimated annual frequency of HSL is shown in Table 1.

TABLE 1

Distribution of HSL Annual Frequency Among HSV-1 Seropositive Reporting Subjects.

| Number of HSL Episodes per Year (Annual Frequency) | HSL Phenotype | N(%) |
|---|---|---|
| None | Unaffected | 65 (30) |
| 0.1–1.9 | Mildly Affected | 86 (40) |
| ≧2.0 | Frequently Affected | 63 (29) |
| All HSV-1 + Reporting Individuals | — | 214 (100) |

Thirty percent of the reporting subjects were completely "unaffected" by HSL episodes. These persons were HSV-1 seropositive but had never had any recognized episodes of HSL, indicating protection from HSV-1 induced disease. At the other end of the spectrum were subjects who were also HSV-1 seropositive and had been definitely and repeatedly afflicted by HSL episodes, indicating susceptibility to HSV-1 induced disease. A cutoff of ≧2 HSL episodes per year was arbitrarily chosen to include the most "frequently affected" 30% of subjects.

The annual frequency of HSL in our population is similar to that reported in other large surveys of HSL. For instance, Ship et. al reported ≧2 HSL episodes per year among one-third of 1399 participants.[30] In another cross-sectional study of blood donors in Wisconsin, among 452 total subjects, 71 (16%) had experienced 2 or more episodes of HSL per year.[31] This figure is comparable with our results, where 63 of 350 (18%) total participants reported ≧2 HSL episodes per year.

Among the 251 HSV-1 seropositive individuals, there were no apparent sex-related differences in reporting (p=0.29, Fishers Exact test) or the annual frequency of HSL (phenotype, p=0.71, $X^2$ test for trend) (Table 2).

The use of stringently defined phenotypes, "unaffected" vs. "frequently affected," gave a high level of confidence in selecting patients for the subsequent genetic analysis. The principle disadvantage of the stringent phenotype rule is that 86 individuals (40%) who experienced some, but less than 2.0 episodes of HSL per year are of uncertain or "mild" phenotype and were excluded to keep the phenotypes as clear-cut as possible. However, the mild phenotype may be used for analysis.

HSL phenotypes were placed on pedigrees of the first 33 UGRP families and examined for informativeness. Families were considered to be potentially informative (UGRP Family #32) if they included both affected and unaffected individuals, preferably in multiple generations (FIG. 1A). Persons who were HSV-1 seronegative (uninfected), did not report, or had some HSL episodes but less than 2 per year ("mildly affected"), were considered to be of indeterminate phenotype and were, excluded from the analysis. Families were considered to be relatively uninformative (for example, UGRP Family #15) for the HSL phenotype if most individuals in the family are of an indeterminate or mild phenotype and were excluded from the analysis (FIG. 1B).

TABLE 2

Sex Distribution and Reporting HSL Phenotypes among HSV-1 Seropositive Individuals.

| HSL Phenotype | Males | Females | Total |
|---|---|---|---|
| Unaffected | 27 | 38 | 65 |
| Mildly affected | 50 | 36 | 86 |
| Frequently affected | 24 | 39 | 63 |
| Total Reporting | 101 | 113 | 214 |
| No Report | 21 | 16 | 37 |
| Total All HSV-1 Seropositives | 122 | 129 | 251 |

Genotyping and Linkage Analysis of the UGRP Participants

Figure 2:
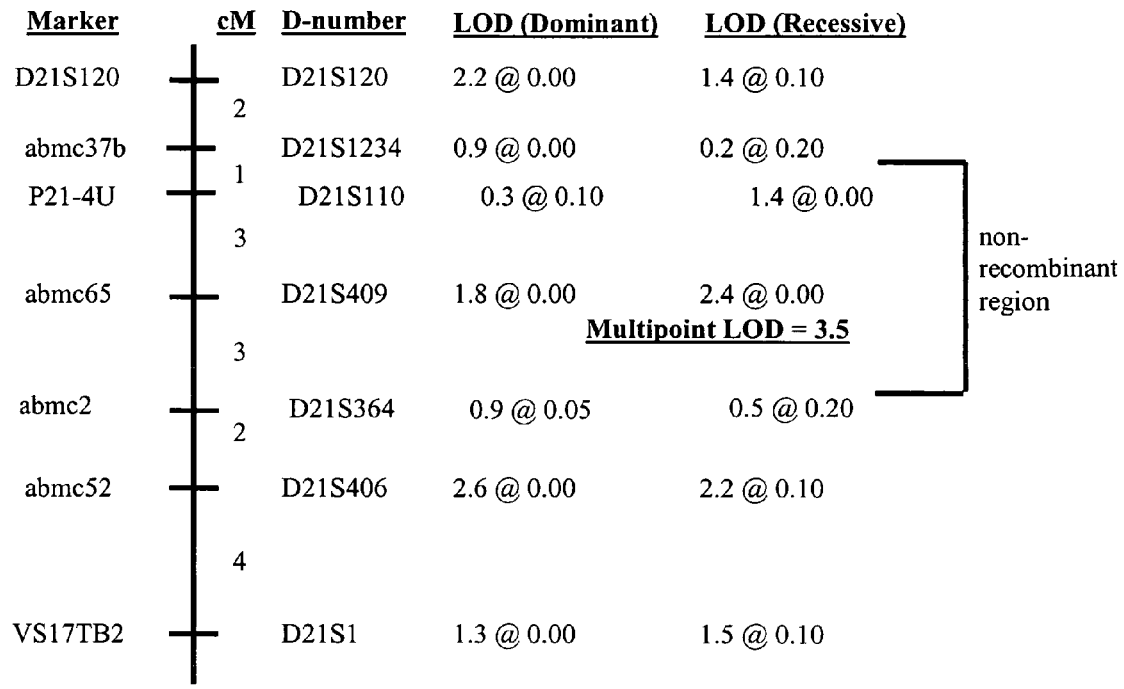
FIG. 2. The HSL phenotype links to a 7-cM non-recombinant region on human chromosome 21. Results of the linkage analysis using the CEPH 9.0 database are displayed. Maximum LOD scores obtained with the dominant and recessive models are displayed.

A genome scan using the CEPH version 9.0 database for all the individuals in the 31 UGRP families phenotyped for HSL was undertaken. Genetic linkage analyses comparing the "frequently affected" and "unaffected" phenotypes, assuming autosomal dominant and recessive modes of inheritance, were performed. Of the 31 UGRP families phenotyped for HSL, chromosome 21 genotyping was completed for 9 families, including 87 HSV-1 seropositive individuals. This data identified a region on human chromosome 21 that generates a cluster of positive LOD scores, demonstrating linkage (Table 3). Positive LOD score clusters were also seen on chromosomes 3, 10, 12, 13, 19, and 20 (data not shown), but the highest LOD scores for both dominant and recessive models were observed at chromosome 21q21.1 (FIG. 2).

TABLE 3

Two-Point LOD Scores for markers on Chromosome 21q.

| | Recombination Fraction | | | | | | |
|---|---|---|---|---|---|---|---|
| Marker | 0.001 | 0.01 | 0.05 | 0.10 | 0.20 | 0.30 | 0.40 |
| Autosomal Dominant Model | | | | | | | |
| D21S120/GT | 2.22 | 2.18 | 2.00 | 1.76 | 1.22 | 0.69 | 0.23 |
| abmc37b/(AC)n | 0.86 | 0.86 | 0.82 | 0.73 | 0.50 | 0.26 | 0.07 |
| p21-4U/MspI | 0.19 | 0.23 | 0.32 | 0.34 | 0.27 | 0.15 | 0.04 |
| abmc65/(AC)n | 1.81 | 1.78 | 1.65 | 1.45 | 1.01 | 0.55 | 0.17 |
| abmc2 | 0.90 | 0.91 | 0.92 | 0.87 | 0.65 | 0.36 | 0.11 |
| abmc52/(AC)n | 2.59 | 2.55 | 2.33 | 2.04 | 1.41 | 0.77 | 0.24 |
| VS17TB2/pcr | 1.30 | 1.29 | 1.22 | 1.10 | 0.80 | 0.47 | 0.18 |
| Autosomal Recessive Model | | | | | | | |
| D21S120/GT | 0.51 | 0.71 | 1.16 | 1.39 | 1.32 | 0.88 | 0.33 |
| abmc37b/(AC)n | −0.97 | −0.78 | −0.33 | −0.01 | 0.23 | 0.19 | 0.07 |
| p21-4U/MspI | 1.39 | 1.36 | 1.22 | 1.05 | 0.71 | 0.39 | 0.12 |
| abmc65/(AC)n | 2.44 | 2.41 | 2.22 | 1.95 | 1.36 | 0.75 | 0.23 |
| abmc2/(AC)n | −0.98 | −0.58 | 0.14 | 0.44 | 0.49 | 0.31 | 0.09 |
| abmc52/(AC)n | 1.10 | 1.56 | 2.16 | 2.19 | 1.69 | 0.97 | 0.31 |
| VS17TB2/pcr | −0.38 | 0.24 | 1.22 | 1.48 | 1.29 | 0.80 | 0.29 |

The highest LOD score at each marker are shown in bold typeface.

The highest LOD score for the dominant model was 2.59 (theta=0.001) at marker abmc52 (D21S406) (Table 3, FIG. 2). The highest LOD score for the recessive model was 2.44 (theta=0.001) at marker abmc65 (D21S409) (Table 3, FIG. 2). Markers abmc 65 and P21-4U are flanked by recombinations at markers abmc37b (D21S1234) and abmc2 (D21S364), in the recessive model. Since recombination events were identified in the recessive model, multipoint analysis could be performed with this model. Multipoint analysis was performed by using LINKMAP, a subroutine of the LINKAGE genetic analysis software. We analyzed adjacent markers carrying out sequential three-point linkage runs across the region from marker abmc37b (D21S1234) to marker abmc52 (D21S406). This multipoint analysis revealed a maximum location score of 3.5 at marker abmc65 (D21S409) in the recessive model. Linkage was confirmed by non-parametric analysis (GENEHUNTER) of this region, resulting in a p value of 0.0005 at marker abmc65 (D21S409).

The non-recombinant region identified in the recessive model defines a 7-cM HSL candidate region which is approximately 2.8 Mb in size. (See UCSC Human Genome Project Working Draft browser [June 2002 release, available online at: genome.cse.ucsc.edu/], which is incorporated by reference herein.) This region of non-recombination (D21S1234-D21S364) includes 4 known human genes and 2 open reading frames (genes).

Thus, the invention provides methods of diagnosing susceptibility to infection and reactivation of HSV by detection of markers linked to the HSL susceptability gene on human chromosome 21. Markers are linked if they occur within 50 cM from each other or the HSL susceptability gene. Preferably, markers occur within 15 cM and more preferably within 5 to 1 cM of the gene. The closer the polymorphic marker is to HSL susceptability locus, the less likely there is to be a meiotic recombination event between the two loci. The polymorphic marker is usually outside the HSL susceptability gene, but may also occur within the gene. The preferred markers include those between D21S1234 and D21S364. In one embodiment, markers within 5 cM of D21S409, abmc 65, are used. In addition, markers within the HSL susceptability gene itself may be used. The methods may analyze for the presence of alleles of two polymorphic markers spaced either side of the HSL susceptability gene, wherein both markers demonstrate linkage disequilibrium with the HSL susceptability gene. Thus, absent a rare double recombination event, the presence of both alleles signals the presence of the variant gene.

The present invention also includes kits for the practice of the methods of the invention. The kits comprise a vial, tube, or any other container which contains one or more oligonucleotides, which are capable of hybridizing to a DNA segment within chromosome 21q21, which DNA segment is linked to the HSL susceptability gene. Preferably, the oligonucleotide are capable of hybridizing to a segment of chromosome 21 between markers D21S1234 and D21S364. The kits may contain two such oligonucleotides, which are capable of priming amplification of a segment of chromosomal DNA. The segment selected for amplification can be a polymorphic marker linked to the HSL susceptability gene or a region from the HSL susceptability gene that includes a site at which a variation is known to occur. The kits may also contain a pair of oligonucleotides for detecting precharacterized variations. For example, a kit may contain oligonucleotides suitable for allele-specific oligonucleotide hybridization, or allele-specific amplification hybridization. The kit may also contain components of the amplification system, including PCR reaction materials such as buffers and a thermostable polymerase. In other embodiments, the kit of the present invention can be used in conjunction with commercially available amplification kits, such as may be obtained from GIBCO BRL (Gaithersburg, Md.) Stratagene (La Jolla, Calif.), Invitrogen (San Diego, Calif.), Boehringer Mannheim (Indianapolis, Ind.) or the like. The kits can also include positive or negative control reactions or markers, molecular weight size markers for gel electrophoresis, and the like. A kit may include instructions indicating the suitability of the kits for diagnosing susceptability to HSV infection or reactivation and indicating how the oligonucleotides are to be used for that purpose. Furthermore, where appropriate, the oligonucleotides may be labeled, for example, with biotin or any other known compound or molecule, or contain materials or instructions regarding labeling of the oligonucleotide.

I. Fine Mapping of Human HSL Susceptibility Genes.

Three hundred and fifty individuals in 31 families have been phenotyped. Among these 31 families, 9 have been genotyped at the chromosome 21 locus using markers available in the CEPH version 9.0 database. Therefore, the HSL linkage is based on results from 87 phenotyped individuals within 9 different families. Using the definitions of "informative" and "uninformative" outlined herein, we have identified 9 more potentially informative families with an additional 73 HSV-1 seropositive individuals (Table 4).

TABLE 4

List of informative families proposed for more intensive genotyping at markers within the herpes susceptibility candidate regions.

|  | Previously Genotyped[†] | Not Yet Genotyped at ch 21 loci, Potentially Informative | Not Yet Genotyped at ch 21 loci, Potentially Uninformative |
|---|---|---|---|
| UGRP Families* | 1, 2, 3, 5, 6, 7, 12, 13, 32 | 11, 20, 21, 23, 24, 26, 28, 30, 33 | 4, 8, 9, 10, 14, 15, 16, 17, 18, 19, 22, 25, 27, 29 |
| Total | N = 9 families N = 87 HSV-1 seropositive individuals | N = 9 additional families N = 73 additional HSV-1 seropositive individuals | N = 14 families N = 92 HSV-1 seropositive individuals |

[†]Genotypic data is presently available for these families which were all included in the analysis disclosed herein.

Further genotyping (including the chromosome 21 HSL candidate gene region) and phenotyping may be performed on all 47 UGRP families including over 500 individuals using the methods described herein.

Six genes have been identified in the 2.8 Mb non-recombinant region. Becuase sequencing 18.8 kb of DNA for 160 people is impractical (Table 5); a two-fold approach is used to refine the present embodiments. Fine mapping of prospective HSL susceptibility loci among the 18 informative families is performed to identify additional boundaries for the non-recombinant region. This fine mapping may be carried out by using five additional polymorphic repeat markers for further linkage analysis (Table 5). Subsequently, single nucleotide polymorphism (SNP) analysis may be used to construct susceptible or resistant haplotypes in the refined regions. The genes embodied herein and associated with susceptible or resistant haplotypes may be prioritized for polymorphism screening.

Fine mapping of human HSL susceptibility genes. Genetic linkage analysis in 9 new informative families with 73 additional individuals using five more polymorphic repeat markers is used to refine the HSL susceptibility region. Single nucleotide polymorphism (SNP) analysis across the refined region is performed to define "resistance" or "susceptibility" haplotypes. The genes in these haplotype regions form one embodiment of the present invention.

Identification of human HSL susceptibility gene(s). The HSL susceptibility gene is sequenced, for example, sequencing in selected members of the informative families. Allelic differences are expected to follow HSL phenotypes through these families.

Sequencing of human HSL susceptibility gene(s) in human populations afflicted with HSV induced diseases. The HSL susceptibility gene(s), identified by Fine mapping of human HSL susceptibility genes and Identification of human HSL susceptibility gene(s), are tested for effects in other unrelated populations of persons afflicted with known HSV-induced diseases. For example, one or more HSL susceptibility genes are tested to determine if allelic differences extend to:
(a) other persons with well-known recurrent, ultraviolet light-inducible HSL (cold sores),
(b) persons with recurrent ocular herpes (herpes simplex keratitis), a particularly problematic subset of HSV-1 infections, and
(c) Persons with recurrent genital herpes caused by HSV-2.

Persons with recurrent HSV-induced diseases ("affecteds") are compared to HSV-1 or HSV-2 seropositive persons without disease ("unaffecteds"). Allelic differences between affecteds and unaffecteds are compared by 1) analysis of SNPs identified as frequently associated with HSL susceptibility, and 2) sequencing genomic DNA of the HSL susceptibility genes.

TABLE 5

Additional repeat markers for fine mapping.

| Marker D - number | Distance from previous marker (kb) | Identified gene - relative location | Major SNP Haplotype blocks |
|---|---|---|---|
| D21S1234(R) | — | | |
| D21S172 | 95 | | |
| | | USP25 | 7 |
| SHGC-52017 | 405 | | |
| D21S173 | 535 | C21orf34 | 5 |
| D21S110 (NR) | 337 | | |
| D21S174 | 303 | | |
| | | CXADR | 4 |
| | | BTG3 | 2 |
| D21S1292 | 557 | | |
| | | C21orf91 | 2 |
| D21S409 (NR) | 463 | CHODL | 3 |
| D21S364 (R) | 44 | | |
| D21S406 | 97 | | |
| Total | 2,836 | 6 | 23 |

Additional markers for fine mapping are indicated in bold type, markers already analyzed are in normal typeface.
(R) refers to a marker where a recombination event was seen,
(NR) refers to markers in which no recombination was seen.
The relative locations of the various candidate genes are indicated in the third column.
The last column indicates the number of major haplotype blocks spanning each candidate gene for SNP haplotype analysis.

Linkage analyses for these studies may be performed using highly polymorphic, PCR-based microsatellite repeat sequences, using methods known in the art.

Genetic linkage analysis. Genetic linkage analysis is conducted by conventional methods.[37] Five markers were selected from the UCSC Human Genome Project Working Draft browser (June 2002 release, available online at: genome.cse.ucsc.edu/, herein incorporated by reference) to lie within the regions defined herein. The refined mapping carried out in all the informative families permits identification of all families that link to the same locus and identify all flanking recombinants. New recombinants are checked by repeat genotyping, including a new blood sample, if necessary. The linkage analysis may be performed using the MLINK subroutine of the computer program FASTLINK v4.0.[38-42] Both an autosomal dominant mode of inheritance and an autosomal recessive mode of inheritance may be used to calculate LOD scores. Actual marker allele frequencies are used in all calculations. If needed, allele frequencies may be determined using DNA from 100 UGRP unrelated grandparents. Linkage data may be examined for evidence of locus heterogeneity using the HOMOG program, version 3R.[43]

SNP haplotype analysis. SNP halplotype analysis may be used to refine the candidate loci.[44] SNP genotype data is used to construct SNP haplotype maps. All 65 unaffected and 63 frequently affected individuals from all phenotyped families are analyzed by SSCP (128 total) since both informative and less informative families (for linkage) are expected to be informative for haplotype analysis.

A unique resource is used to select the SNPs for haplotype mapping. The data in the last column of Table 5 gives information on the number of SNP haplotype blocks to screen to span most exons of each gene in the region. The haplotype blocks were previously identified through the sequencing of chromosome 21 [available online at: perlegen.com/haplotype/] and were defined by Patil et al.[46] Since most blocks can be defined by one SNP each, 23 to 30 SNPs may be screened.

SNPs patterns in all unaffected and frequently affected persons are analyzed for segregation. If the frequency of the SNP in the general population is not known, the frequency is determined by SSCP analysis of DNA from 100 UGRP unrelated grandparents.

Figure 3:
FIG. 3. Examples of a SNP assayed by SSCP gel analysis. Genotypes for the five individuals are given above each lane. In SSCP analysis the sense and anti-sense strand of each sequence assumes a sequence specific conformation resulting in two bands in homozygous and four bands in heterozygous individuals.[45]

Single-Strand Conformational Analysis (SSCP). Single strand conformation polymorphism (SSCP) analysis[45] may be used to genotype known SNPs in the region. PCR primers are designed to amplify a 100-230 bp fragment of DNA containing each SNP of interest for SSCP analysis. PCR reactions amplify both alleles from a given person. When the strands are denatured and resolved on polyacrylamide gels, strands corresponding to the same sequences co-migrate (sense and antisense strands migrate independently), and strands with mutations or polymorphisms appear as unique bands (FIG. 3). The electrophoretic conditions are routinely optimized for each SNP to maximize detection. Alternatively, differences in melting curves, for example, using fluorescent dye incorporation and a Roche Light Cycler, may be utilized to assay the SNP. Two to three products representative of each SSCP band pattern or melting curve may be submitted for sequencing to verify genotypes.

SNP haplotype analysis. The pedigree disequilibrium test (PDT)[47,48] is used to define haplotypes associated with resistance or susceptibility to HSL within families. This method combines information from genotyped parents and each affected child, as well as discordance between affected and unaffected sib pairs, using all information available from large pedigrees. It also identifies regions of linkage disequilibrium that are shared between families, even if the haplotypes themselves are not shared. The truncated product method (TPM) of Zaykin et al.,[49] may be used to combine p-values in overlapping SNP haplotype windows across the genes, to look for associations of specific SNPs with disease category among unrelated individuals.

The non-recombinant region identified by the recessive model linkage analysis described herein is shown to be linked to both the "protective" and "susceptible" embodiments. The multipoint and non-parametric analyses support linkage near marker abmc65.

Fine mapping with additional polymorphic repeat markers may be used to analyze fragments of the disclosed region which confers HSL susceptibility or resistance. For instance, elimination of USP25 from the disclosed region reduces the sequencing burden by 7.7 kb per person (41% of the total sequence) (Table 6).

The frequency and distribution of gene region SNPs are examined in each family. SNPs found to be associated with a particular phenotype are classified as belonging to a resistance or susceptibility haplotype. The PDT method is robust and can identify regions of haplotype disequilibrium that are common to a pedigree and the TPM method further strengthens the analysis, and indicates that significance (p<0.05) can easily be reached with sample sizes of 50 or more, even in instances of excess or deficit heterogeneity in a sample set of unrelated individuals.[49] Using these methods, resistance or susceptibility haplotypes are identified.

The six identified open reading frames or genes in the current 2.8-Mb non-recombinant region are listed in genetic order (centromeric to telomeric, UCSC Human Genome Project Working Draft browser, [available online at: genome.cse.ucsc.edu/]) in Table 6. Following Table 6 is a brief description of each identified gene and its function.

great variety of substrates. Ubiquitinating and deubiquitinating enzymes play an essential role in protein degradation via the 26S proteasome and thus regulate many cellular pathways including protein trafficking, cell cycle regulation, transcription regulation, and chromatin remodeling.[54-57] Genbank Accession AAF24998.

BTG3: Yoshida et al.[58] identified a novel member of Tob/BTG1 family of antiproliferative genes, termed BTG3, which is abundant in neuroepithelium (SEQ ID NO:6 and 7). BTG3 expression was high in the ventricular zone of the developing central nervous system, as well as in the ovary, testis, prostate, thymus, and lung. Overexpression of BTG3 impaired serum-induced cell cycle progression from the G0/G1 to S phase. In more recent work,[59] it has been further shown that BTG3

TABLE 6

List of the six genes in the current 2.8-Mb HSL-candidate region. The six genes found in the HSL-candidate region are listed centromeric to telomeric, top to bottom.

| Gene | Protein | Function/ Associations | # of Exons | mRNA length | potential coding region SNPs |
|---|---|---|---|---|---|
| USP25 | Ubiquitin specific protease 25 | Removes ubiquitin from tagged proteins. Expressed in neuroepithelial cells and postmitotic neurons. | 25 | 5213 bp | 4 |
| C21orf34 | unknown | Protein product with unknown function | 7 | 620 bp | ? |
| CXADR | Coxsackie and adenovirus receptor | Confers susceptibility of cell cultures to Coxsackie and adenovirus infections. | 7 | 2537 bp | 1 |
| BTG3 | B-cell translocation gene | Tob/BTG1 family antiproliferative protein, abundant in neuroepithelium | 6 | 1511 bp | 1 |
| C21orf91 | unknown | Protein product with unknown function | 4 | 1042 bp | 4 |
| CHODL | Chondrolectin | Transmembrane protein found in muscle and spleen | 6 | 2416 bp | 6 |
| Sub-total | | Add 100 bp/exon for sequencing to cover splice sites | 55 | 5,500 | |
| TOTAL | | | 55 | 18,839 bp | 16 |

CXADR: The human cellular receptor for group B coxsackieviruses and adenoviruses (CXADR) is a transmembrane glycoprotein that belongs to the immunoglobulin superfamily (SEQ ID NO:8 and 9). Thoelen et al.[51] describe alternative splicing of the CXADR-gene and the existence of three exon-skipping splice variants in addition to the originally identified seven exon-encompassing MRNA transcript. Expression of the splice variants theoretically results in truncated proteins. These truncated CXADR proteins are believed to lack the transmembrane region of the protein, and to act as soluble receptors or perform other functions important in viral biology within the cell. Genbank Accession NM001338.

USP25: USP25 is a member of the ubiquitin protease family (UBP). The gene spans over 150 kb and is made up of 25 exons encoding a 1087-aa protein, with splice variants (SEQ ID NO:1 and 2).[52] In situ hybridization in mouse embryonic brains showed a clear correlation of expression with proliferative neuroepithelial cells and postmitotic neurons.[53] UBPs belong to a complex family of deubiquitinating enzymes that specifically cleave ubiquitin conjugates on a interacts with the CCR4 transcription factor-associated protein Caf1. The CCR4 complex is involved in several aspects of mRNA metabolism, including transcription initiation, elongation, and niRNA degradation. Chen et al.[60] have shown that the CCR4 complex also has enzymatic properties demonstrating both RNA and single-stranded DNA 3'-5' exonuclease activities. As a member of this complex, polymorphisms in BTG3 may play a role in regulating transcription of HSV genes during viral reactivation, or in the stability of HSV transcripts or genomes. Genbank Accession Q14201.

C21orf34 and C21orf91: C21orf34 (SEQ ID NO:3) and C21orf91 (SEQ ID NO:10 and 11) are open reading frames predicted to encode proteins with no currently know function. Genbank Accession Numbers NM_001005734; NM_001005733; NM_001005732; AP001666; and AF486622 (SEQ ID NO:4 and 5).

Chondrolectin: Chondrolectin has the characteristics of a Type I membrane protein (SEQ ID NO:12 and 13). It shows tissue specific expression in spleen, testis, prostate and fetal liver. Expression is limited to the vascular muscle of testis, smooth muscle of prostate stroma, heart muscle, skeletal muscle, crypts of small intestine, and red pulp of spleen.[61] Genbank Accession Q9H9P2; AAH09418 and NP_079220.

Figure 4:
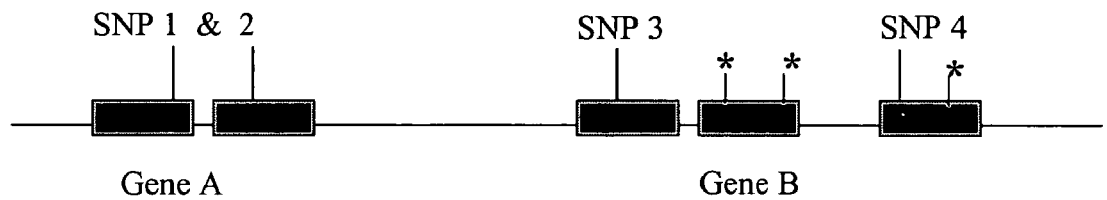
FIG. 4. The case of four polymorphisms found in linkage disequilibrium.

A specific polymorphism in one or more genes which confers resistance or susceptibility to HSL is within the scope of the present invention. For example, one or more polymorphism in each of two genes in a row can be detected. If the polymorphisms associated with resistance or susceptibility are always found in linkage disequilibrium (always travel together) in unaffecteds or frequently affected individuals, respectively (FIG. 4), then it may be necessary to determine which of the two genes (and which polymorphism) is important for the given phenotype. If four polymorphisms (SNPs 1-4) in two genes are in linkage disequilibrium and segregate with affection status, then the phenotype can be identified with an embodiment (see FIG. 4). Unique polymorphisms (*) in families without SNPs 1-4 can be used to resolve the issue (see FIG. 4).

Allele frequencies can be compared between subjects "affected" with HSV-induced diseases vs. "unaffected" controls as described below. Sample size calculations were performed as a difference between 2 proportions with the minimum difference set at 40%, significance of p=0.05, and power-to-detect of 80%. Given these assumptions, 20-30 affected and a similar number of unaffected subjects are screened.

| Affected Allele Frequency | Unaffected Allele Frequency | N (Sample Size) |
|---|---|---|
| 5% | 45% | 22 |
| 25% | 65% | 28 |
| 50% | 90% | 25 |

Recurrent, Ultraviolet Light-Inducible HSL

Approximately 200 known HSV-1 seropositive persons with frequent, UV-inducible herpes labialis were followed.[70, 71] These persons provided informed consent and were studied in one or more clinical trials which have utilized the UV-induction model. These trials involved prevention and treatment of HSL with various antiviral drugs. The subjects were recruited into these previous trials because they identified themselves as suffering from frequent HSL episodes. Thus, the invention provides methods of identifying persons which may be in need of prevention and treatment, without the person having to suffer frequent HSL episodes.

These 200 known frequently affected persons provide a pool of "affecteds." HSV-1 seropositivity is confirmed by type-specific ELISA testing. (HSV-2 seropositivity or seronegativity was considered irrelevant for these subjects with known frequent HSL.) An objective determination of lesion frequency and severity can be drawn from previous study records on these individuals.

The HSV-1 positive but completely "unaffected" controls are recruited from the Herpevac glycoprotein-G vaccine trial. Control subjects are drawn from HSV-1 seropositive, HSV-2 seronegative, (Western blot) screen-failures for the vaccine study. (HSV-2 seropositivite subjects will be excluded here due to supressive effects on expression of HSL.) These control subjects are selected based on having previously identified themselves as never having had herpetic diseases, including HSL, genital herpes, or ocular herpes.

Recurrent Ocular Herpes

These persons are a subset of HSV-1 seropositive persons who are severely affected. Recruitment of these "affected" subjects may be achieved through contact with practicing opthalmologists. "Unaffected" control subjects are drawn from HSV-1 seropositive, HSV-2 seronegative, and Herpevac screening failures without any history of herpetic diseases.

Recurrent Genital Herpes

These persons are selected from HSV-2 seropositive persons who are frequently affected with proven genital herpes. HSV-2 infection is proven, for example, by positive HSV-2 type-specific ELISA (Focus Technologies, Cypress, Calif.) or by Western blotting. Recruitment of these "affected" subjects may be achieved through such sources as an Infectious Disease Clinic, by attracting subjects from previous genital herpes clinical trials, or from a County Health Department Sexually Transmitted Disease Clinic, or the like. The 30 "unaffected" control subjects should be similar to those described in a), but drawn from HSV-2 seropositive, HSV-1 seronegative, Herpevac screening failures without any history of herpetic diseases.

Identification of polymorphisms in these additional patient categories may reveal novel polymorphisms associated with these diseases thus, identifying specific genotypes correlating with specific phenotypes. Detection of differences in the allelic frequencies between "affected" and "unaffected" subjects is related to the size of the subject group.

The region of chromosome 21 (q11) and the embodiments of the present invention may be utilized as functional fragments, identified by the methods described herein. The identification of linkage to the genes and markers of the present invention is important for gaining greater understanding of herpetic diseases and the factors that influence their frequency and severity. The identification of the chromosome 21 HSL gene provides a basis for new experiments centered on understanding herpes infection, latency, reactivation, and disease. Such insights may lead to new therapeutic strategies and interventions for HSV-induced diseases. In addition, methods of diagnosing patients likely to suffer recurrent outbreaks may be identified and provided with more aggressive treatment to reduce or eliminate the outbreaks. The diagnosis may be provided as a kit.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis and PCR-SSCP.

The presence of a susceptibility allele may be determined by methods known in the art, including, but not limited to: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the E. coli mutS protein; 6) allele-specific PCR; 7) chemical mismatch cleavage (CMC); 8) Amplification Refractory Mutation System (ARMS); 9) restriction fragment length polymorphism (RFLP); 10) DNA fingerprinting; and 11) cloning, sequencing and/or amplification.

DNA fingerprinting is a broad term used to designate methods for assessing sequence differences in DNA isolated from various sources, e.g., by comparing the presence of marker DNA in samples of isolated DNA.

While the compositions and/or methods of this invention have been described in terms of embodiments or genes, it will be apparent to those of skill in the art that variations or fragments may be applied to the compositions and/or methods and in the steps or in the sequence of steps of the method described herein without departing from the concept, spirit and scope of the invention. Substitutes and modifications apparent to those skilled in the art are deemed to be within the spirit, scope and concept of the invention as disclosed herein.

All references, including publications, URLs, sequence disclosures (e.g., Genbank Accession Numbers), patents and patent applications, cited herein are hereby incorporated by reference to the same extent as if each referenece were individually and specifically indicated to be incorporated by reference and were set forth in its entirety herein.

The references on the following pages are specifically incorporated herein by reference.

REFERENCES

1. Ship I., Morris A., Durocher R. and Burket L. Recurrent aphthous ulcerations and recurrent herpes labialis in a professional school student population. *Oral Surg. Oral Med. Oral Pathol.* 13:1191-202, 1960.
2. Embil J. A., Stephens R. G. and Manuel F. R. Prevalence of recurrent herpes labialis and aphthous ulcers among young adults on six continents. *Can. Med. Assoc. J.* 113(7):627-30, 1975.
3. Grout P. and Barber V. E. Cold sores-an epidemiological survey. *J. R. Coll. Gen. Pract.* 26(167):428-34, 1976.
4. Spruance S. and Kriesel J. Treatment of Herpes Simplex Labialis. *Herpes* 9(3):6-11, 2002.
5. Dawson C. *Management of herpes simplex eye diseases*, in *Clinical Management of Herpes Viruses*, S. L. Sacks, et al., Editors, 1995, IOS Press: Amsterdam. p. 127-36.
6. Arffa R. C. Viral Diseases of the Cornea, in *Grayson's Diseases of the Cornea*, 1991, Mosby: St. Louis. p. 241-65.
7. Xu F., Schillinger J. A., Sternberg M. R., Johnson R. E., Lee F. K., Nahmias A. J. and Markowitz L. E. Seroprevalence and coinfection with herpes simplex virus type 1 and type 2 in the United States, 1988-1994. *J. Infect. Dis.* 185(8): 1019-24, 2002.
8. Sawtell N. M. and Thompson R. L. Rapid in vivo reactivation of HSV in latently infected murine ganlionic neurons after transient hyperthermia. *J. Virol.* 66:2150-6, 1992.
9. Kriesel J. D., Gebhardt B. M., Hill J. M., Maulden S. A., Hwang I. P., Clinch T. E., Cao X., Spruance S. L. and Araneo B. A. Anti-Interleukin-6 antibodies inhibit herpes simplex virus reactivation. *J. Infect. Dis.* 175(4):821-7, 1997.
10. Hill J., Garza H., Helmy M., Cook S., Osborne P., Johnson E., Thompson H., Green L., O'Callaghan R. and Gebhardt B. Nerve growth factor antibody stimulates reactivation of ocular herpes simplex virus type 1 in latently infected rabbits. *J. Neurovirology* 3:206-11, 1997.
11. Gerdes J. and Smith D. Recurrence phenotypes and establishment of latency following rabbit keratitis produced by multiple HSV strains. *J. Gen. Virol.* 64:2441-54, 1983.
12. Stroop W. G. and Banks M. C. Herpes simplex virus type 1 strain KOS-63 does not cause acute or recurrent ocular disease and does not reactivate from ganglionic latency in vivo. *Acta. Neuropathol. (Berl.)* 87(1):14-22, 1994.
13. Varnell E. D., Kaufman H. E., Hill J. M. and Thompson H. W. Cold stress-induced recurrences of herpetic keratitis in the squirrel monkey. *Invest. Ophthal. Vis. Sci.* 36:1181-3, 1995.
14. Laycock K. A., Lee S. F., Brady R. H. and Pepsose J. S. Characterization of a murine model of recurrent HSV keratitis induced by ultraviolet B radiation. *Invest. Ophth. Vis. Sci.* 32:2741-6, 1991.
15. Hill J. M., Wen R. and Halford W. P. *Pathogenesis and molecular biology of HSV latency and ocular reactivation in the rabbit*, in *Herpes Simplex Virus: Molecular techniques, methods in Molecular Biology*, 1997, Humana Press.
16. Padgett D. A., Sheridan J. F., Dorne J., Berntson G. G., Candelora J. and Glaser R. Social stress and the reactivation of latent herpes simplex virus type 1. *Proc. Natl, Acad. Sci. U.S.A* 95(12):7231-5, 1998.
17. Spruance S. L., Kriesel J. D., Evans T. G. and McKeough M. B. Susceptibility to herpes labialis following multiple experimental exposures to ultraviolet radiation. *Antiviral-Res.* 28(1):57-67, 1995.
18. Shimizu F., Monma Y., Sekizawa T. and Kamiyama K. Establishment of latent ganglionic infection with HSV via maxillary gingiva and viral reactivation in vivo after trauma *J. Dent. Res.* 68:472-5, 1989.
19. Pazin G. J., Ho M. and Jannetta P. J. Reactivation of HSV after decompression of the trigeminal nerve root. *J. Infect. Dis.* 138:405-9, 1978.
20. Kirchner H., Kochen M., Munk K. and Hirt H. M. *Differences in susceptibility to HSV infection of inbred strains of mic.* in *Oncogenesis and Herpesviruses III*, 1977, Cambridge, Mass.: IARC Scientific.
21. Caspary L., Schindling B., Dundarov S. and Falke D. Infections of susceptible and resistant mouse strains with HSV types 1 and 2. *Arch. Virol.* 65:219-27, 1980.
22. Jabbar A. A., al-Samarai A. M. and al-Amar N. S. HLA antigens associated with susceptibility to herpes simplex virus infection. *Dis. Markers* 9(5):281-7, 1991.
23. Seppanen M., Lokki M. L., Timonen T., Lappalainen M., Jarva H., Jarvinen A., Sarna S., Valtonen V. and Meri S. Complement C4 deficiency and HLA homozygosity in patients with frequent intraoral herpes simplex virus type 1 infections. *Clin. Infect. Dis.* 33(9):1604-7, 2001.
24. Malo A., Kampgen E. and Wank R. Recurrent herpes simplex virus-induced erythema multiforme: different HLA-DQB1 alleles associate with severe mucous membrane versus skin attacks. *Scand. J. Immunol.* 47(5):408-11, 1998.
25. Elner V. M., Dutt S., Pavilack M. A., Sugar A., Foster C. S. and Elner S. G. Intercellular adhesion molecule-1 (ICAM-1) and HLA-DR antigens in herpes keratitis. *Ophthalmology* 99(9):1400-7, 1992.
26. Lekstrom-Himes J. A., Hohman P., Warren T., Wald A., Nam J. M., Simonis T., Corey L. and Straus S. E. Association of major histocompatibility complex determinants with the development of symptomatic and asymptomatic genital herpes simplex virus type 2 infections. *J. Infect. Dis.* 179(5):1077-85, 1999.
27. Russell A. and Schlaut J. HLA transplantation antigens in subjects susceptible to recrudescent herpes labialis. *Tissue Antigens* 6:257-61, 1975.
28. Legendre C., Russell A. and Jeannet M. HLA antigens in patients with recrudescent herpes simplex infections. *Tissue Antigens* 19:85-9, 1982.
29. Spruance S., Crumpacker C. and MacCalman J. *Correlation of recurrence rate of herpes labialis with severity of episodes* in *J. Proc. American Soc. Microbiology*, 1979, Los Angeles, Calif.
30. Ship I., Miller M. and Ram C. A retrospective study of recurrent herpes labialis in a professional population, 1958-1971. *Oral Surg.* 44(5):723-9, 1977.
31. Young T., Rimm E. and D'Alessio D. Cross-sectional study of recurrent herpes labialis. *Am. J. Epidemiology* 127(3):612-25, 1988.
32. Cherry J. L., Young H., Di Sera L. J., Ferguson F. M., Kimball A. W., Dunn D. M., Gesteland R. F. and Weiss R.

B. Enzyme-linked fluorescent detection for automated multiplex DNA sequencing. *Genomics* 20(1):68-74, 1994.
33. Coon H., Leppert M. F., Eckfeldt J. H., Oberman A., Myers R. H., Peacock J. M., Province M. A., Hopkins P. N. and Heiss G. Genome-wide linkage analysis of lipids in the Hypertension Genetic Epidemiology Network (Hyper-GEN) Blood Pressure Study. *Arterioscler. Thromb. Vasc. Biol.* 21(12):1969-76, 2001.
34. Coon H., Eckfeldt J. H., Leppert M. F., Myers R. H., Arnett D. K., Heiss G., Province M. A. and Hunt S. C. A genome-wide screen reveals evidence for a locus on chromosome 11 influencing variation in LDL cholesterol in the NHLBI Family Heart Study. *Hum. Genet.* 111(3):263-9, 2002.
35. Feitosa M. F., Borecki I. B., Rich S. S., Arnett D. K., Sholinsky P., Myers R. H., Leppert M. and Province M. A. Quantitative-trait loci influencing body-mass index reside on chromosomes 7 and 13: the National Heart, Lung, and Blood Institute Family Heart Study. *Am. J. Hum. Genet.* 70(1):72-82, 2002.
36. Hall M. A., Norman P. J., Thiel B., Tiwari H., Peiffer A., Vaughan R. W., Prescott S., Leppert M., Schork N. J. and Lanchbury J. S. Quantitative trait loci on chromosomes 1, 2, 3, 4, 8, 9, 11, 12, and 18 control variation in levels of T and B lymphocyte subpopulations. *Am. J. Hum. Genet.* 70(5):1172-82, 2002.
37. Ott J. *Analysis of human genetic linkage*. Revised ed. 1991, Baltimore: Johns Hopkins University Press, 302.
38. Schaffer A. A., Gupta S. K., Shriram K. and Cottingham R. W., Jr. Avoiding recomputation in linkage analysis. *Hum. Hered.* 44(4):225-37, 1994.
39. Lathrop G. M. and Lalouel J. M. Easy calculations of lod scores and genetic risks on small computers. *Am. J. Hum. Genet.* 36(2):460-5, 1984.
40. Lathrop G. M., Lalouel J. M., Julier C. and Ott J. Strategies for multilocus linkage analysis in humans. *Proc. Natl. Acad. Sci. U.S.A.* 81(11):3443-6, 1984.
41. Lathrop G. M., Lalouel J. M. and White R. L. Construction of human linkage maps: likelihood calculations for multilocus linkage analysis. *Genet. Epidemiol.* 3(1):39-52, 1986.
42. Cottingham R. W., Jr., Idury R. M. and Schaffer A. A. Faster sequential genetic linkage computations. *Am. J. Hum. Genet.* 53(1):252-63, 1993.
43. Merette C., Lehner T. and Ott J. Interpreting nonsignificant outcomes of heterogeneity tests in gene mapping [letter]. *Am. J. Hum. Genet.* 49(6):1381-4, 1991.
44. Hugot J. P., Chamaillard M., Zouali H., Lesage S., Cezard J. P., Belaiche J., Almer S., Tysk C., O'Morain C. A., Gassull M., Binder V., Finkel Y., Cortot A., Modigliani R., Laurent-Puig P., Gower-Rousseau C., Macry J., Colombel J. F., Sahbatou M. and Thomas G. Association of NOD2 leucine-rich repeat variants with susceptibility to Crohn's disease. *Nature* 411(6837):599-603, 2001.
45. Hobbs M. R., Udhayakumar V., Levesque M. C., Roberts J. M., Booth J., Tkachuk A. N., Pole A. R., Kariuki S., Nahlen B. L., Mwaikambo E. D., Lal A. L., Granger D. L., Anstey N. M. and Weinberg J. B. A Novel NOS2 Promoter Polymorphism is Significantly Associated with Protection From Cerebral Malaria and Severe Malarial Anemia. *Lancet* Accepted with revisions, 2002.
46. Patil N., Berno A. J., Hinds D. A., Barrett W. A., Doshi J. M., Hacker C. R., Kautzer C. R., Lee D. H., Marjoribanks C., McDonough D. P., Nguyen B. T., Norris M. C., Sheehan J. B., Shen N., Stern D., Stokowski R. P., Thomas D. J., Trulson M. O., Vyas K. R., Frazer K. A., Fodor S. P. and Cox D. R. Blocks of limited haplotype diversity revealed by high-resolution scanning of human chromosome 21. *Science* 294(5547):1719-23, 2001.
47. Martin E. R., Monks S. A., Warren L. L. and Kaplan N. L. A test for linkage and association in general pedigrees: the pedigree disequilibrium test. *Am. J. Hum. Genet.* 67(1): 146-54, 2000.
48. Hardy S. W., Weir B. S., Kaplan N. L. and Martin E. R. Analysis of single nucleotide polymorphisms in candidate genes using the pedigree disequilibrium test *Genet. Epidemiol.* 21(Suppl 1):S441-6, 2001.
49. Zaykin D. V., Westfall P. H., Young S. S., Karnoub M. A., Wagner M. J. and Ehm M. G. Testing association of statistically inferred haplotypes with discrete and continuous traits in samples of unrelated individuals. *Hum. Hered.* 53(2):79-91, 2002.
50. Lander E. S., Linton L. M., Birren B., Nusbaum C. (250 other authors), and Chen Y. J. Initial sequencing and analysis of the human genome. *Nature* 409(6822):860-921, 2001.
51. Thoelen I., Magnusson C., Tagerud S., Polacek C., Lindberg M. and Van Ranst M. Identification of alternative splice products encoded by the human coxsackie-adenovirus receptor gene. *Biochem. Biophys. Res. Commun.* 287 (1):216-22, 2001.
52. Valero R., Bayes M., Francisca Sanchez-Font M., Gonzalez-Angulo O., Gonzalez-Duarte R. and Marfany G. Characterization of alternatively spliced products and tissue-specific isoforms of USP28 and USP25. *Genome Biol.* 2(10), 2001.
53. Valero R., Marfany G., Gonzalez-Angulo O., Gonzalez-Gonzalez G., Puelles L. and Gonzalez-Duarte R. USP25, a novel gene encoding a deubiquitinating enzyme, is located in the gene-poor region 21q11.2. *Genomics* 62(3):395-405, 1999.
54. Marx J. Cell biology. Ubiquitin lives up to its name. *Science* 297(5588):1792-4, 2002.
55. Pornillos O., Alam S. L., Rich R. L., Myszka D. G., Davis D. R., Sundquist W. I. Structure and functional interactions of the Tsg101 UEV domain. *Embo. J.* 21(10):2397-406, 2002.
56. Carter C. A. Tsg101: HIV-1's ticket to ride. *Trends Microbiol.* 10(5):203-5, 2002.
57. Garrus J. E., von Schwedler U. K., Pornillos O. W., Morham S. G., Zavitz K. H., Wang H. E., Wettstein D. A., Stray K. M., Cote M., Rich R. L., Myszka D. G. and Sundquist W. I. Tsg101 and the vacuolar protein sorting pathway are essential for HIV-1 budding. *Cell* 107(1):55-65, 2001.
58. Yoshida Y., Matsuda S., Ikematsu N., Kawamura-Tsuzuku J., Inazawa J., Umemori H. and Yamamoto T. ANA, a novel member of Tob/BTG1 family, is expressed in the ventricular zone of the developing central nervous system. *Oncogene* 16(20):2687-93, 1998.
59. Yoshida Y., Hosoda E., Nakamura T. and Yamamoto T. Association of ANA, a member of the antiproliferative Tob family proteins, with a Caf1 component of the CCR4 transcriptional regulatory complex. *Jpn. J. Cancer Res.* 92(6): 592-6, 2001.
60. Chen J., Chiang Y. C. and Denis C. L. CCR4, a 3'-5' poly(A) RNA and ssDNA exonuclease, is the catalytic component of the cytoplasmic deadenylase. *Embo. J.* 21(6):1414-26, 2002.
61. Weng L., Smits P., Wauters J. and Merregaert J. Molecular cloning and characterization of human chondrolectin, a novel type I transmembrane protein homologous to C-type lectins. *Genomics* 80(1):62-70, 2002.

62. Levesque M. C., Hobbs M. R., Anstey N. M., Vaughn T. N., Chancellor J. A., Pole A., Perkins D. J., Misukonis M. A., Chanock S. J., Granger D. L. and Weinberg J. B. Nitric oxide synthase type 2 promoter polymorphisms, nitric oxide production, and disease severity in Tanzanian children with malaria *J. Infect. Dis.* 180(6):1994-2002, 1999.

63. Kamb A., Futreal P. A., Rosenthal J., Cochran C., Harshman K. D., Liu Q., Phelps R. S., Tavtigian S. V., Tran T., Hussey C. and Hobbs M. R., et al. Localization of the VHR phosphatase gene and its analysis as a candidate for BRCA1. *Genomics* 23(1):163-7, 1994.

64. Miki Y., Swensen J. J., Hobbs M. R., DeHoff B. S., Rosteck P. R., Skolnick M. H. and Neuhausen S. L. A physical map encompassing GP2B, EPB3, D17S183, D17S78, D17S1183, and D17S1184. *Genomics* 25(1):295-7, 1995.

65. Hobbs M. R., Pole A. R., Pidwirny G. N., Rosen I. B., Zarbo R. J., Coon H., Heath H., 3rd, Leppert M. and Jackson C. E. Hyperparathyroidism-jaw tumor syndrome: the HRPT2 locus is within a 0.7-cM region on chromosome 1q. *Am. J. Hum. Genet.* 64(2):518-25, 1999.

66. Olchovsky D., Hobbs M. R., Pras E., Shimon I., Silver J., Irmin L. and Friedman E. Familial Isolated Primary Hyperparathyroidism in a Large Georgian-Jewish Kindred: Genetic Studies. *The Journal of Endocrine Genetics* 2: pp 91-97, 2001.

67. Odell W. D., Hobbs M. R. and Benowitz B. An immunologically anomolous parathyroid hormone variant causing hyperparathyroidism. *Clin. Endocrinol. (Oxf.)* 55(3):417-20, 2001.

68. Neuhausen S. L., Swensen J., Miki Y., Liu Q., Tavtigian S., Shattuck-Eidens D., Kamb A., Hobbs M. R., Gingrich J. and Shizuya H., et al. A P1-based physical map of the region from D17S776 to D17S78 containing the breast cancer susceptibility gene BRCA1. *Hum. Mol. Genet.* 3(11):1919-26, 1994.

69. Carpten J. D., Robbins C. M., Villablanca A., Forsberg L., Presciuttini S., Bailey-Wilson J., Simmonds W. F., Gillanders E. M., Kennedy A. M., Chen J. D., Agarwal S. K., Sood R., Jones M. P., Moses T. Y., Haven C., Petillo D., Leotlela P. D., Harding B., Cameron D., Panett A. A., Höög A., Heath H., James-Newton L. A., Robinson B., Zarbo R., Cavaco B. M., Wassif W., Perrier N. D., Rosen I. R., Kristoffersson U., Turnpenny P. D., Farnebo L.-O., Besser G. M., Jackson C. E., Morreau H., Trent J. M., Thakker R. V., Marx S. J., Teh B. T., Larsson C. and Hobbs M. R. HRPT2, encoding parafibromin, is mutated in the hyperparathyroidism-jaw tumor (HPT-JT) syndrome. *Nature Genetics* accepted, 2002.

70. Spruance S. L., Rowe N. H., Raborn G. W., Thibodeau E. A., D'Ambrosio J. A. and Bernstein D. I. Peroral famciclovir in the treatment of experimental ultraviolet radiation-induced herpes simplex labialis: A double-blind, dose-ranging, placebo-controlled, multicenter trial. *J. Infect. Dis.* 179(2):303-10, 1999.

71. Spruance S. L., Freeman D. J., Stewart J. C., McKeough M. B., Wenerstrom L. G., Krueger G. G., Piepkorn M. W., Stroop W. G. and Rowe N. H. The natural history of ultraviolet radiation-induced herpes simplex labialis and response to therapy with peroral and topical formulations of acyclovir. *J. Infect. Dis.* 163(4):728-34, 1991.

What is claimed is:

1. A method for determining a DNA sequence of C21orf91, the method comprising:
   obtaining a nucleic acid sample from an HSV-1 or HSV-2 seropositive individual;
   analyzing said nucleic acid sample for an allele of C21orf91, wherein the allele is on human chromosome 21q21 and is in linkage disequilibrium with a polymorphic marker between D21S1234 and D21S364; and
   determining the DNA sequence of the allele.

2. The method according to claim 1, wherein analyzing said nucleic acid sample for an allele of C21orf91 comprises amplifying a segment of DNA within chromosome 21q21 that spans the polymorphic marker.

3. The method according to claim 2, further comprising the step of determining the size of the amplified segment.

4. The method according to claim 2, further comprising the step of determining the presence or absence of a restriction enzyme site within the amplified segment.

5. The method according to claim 1, wherein the nucleic acid sample is obtained from saliva, blood or buccal mucosal cells.

6. The method according to claim 1 wherein the polymorphic marker is within about 4 cM of D21S409.

7. The method according to claim 6, wherein the polymorphic marker is D21S110.

8. The method according to claim 1, wherein the polymorphic marker is selected from the group consisting of D21S1234, D21S172, SHGC-52017, D21S173, D21S110, D21S174, D21S1292, D21S409 and D21S364.

9. The method according to claim 8, wherein the polymorphic marker is D21S409.

10. The method according to claim 1, further comprising:
    contacting the nucleic acid sample with an oligonucleotide probe capable of hybridizing to the
    polymorphic marker under stringent conditions; and determining whether hybridization has occurred.

11. The method according to claim 1, wherein establishing that the allele is in linkage disequilibrium comprises determining the presence or absence of the allele in a first and a second relative, the first and second relative each being of known phenotype for susceptibility to herpes simplex virus, at least one of the relatives having a phenotype of susceptibility to herpes simplex virus and being heterozygous for the allele.

12. The method according to claim 1, wherein the allele is on human chromosome 21q21.1.

13. A method of diagnosing potential susceptibility or resistance to herpes simplex virus in a patient, the method comprising:
    determining the presence of an allele of a polymorphic marker in the DNA of a patient, wherein the polymorphic marker is within a segment of chromosome 21q21 bordered by D21S1234 and D21S364 and is linked to C21orf91; and
    establishing that the allele is in linkage disequilibrium with the gene, whereby the presence of the allele in the patient indicates potential susceptibility to herpes simplex virus.

14. The method according to claim 13, wherein the polymorphic marker is D21S409.

15. The method according to claim 13, wherein the polymorphic marker is within about 4 cM of D21S409.

16. The method according to claim 15, wherein the polymorphic marker is D21S110.

17. The method according to claim 13, further comprising diagnosing susceptibility to herpes simplex labialis.

18. The method according to claim 13, wherein the polymorphic marker is selected from the group consisting of D21S1234, D21S172, SHGC-52017, D21S173, D21S110, D21S174, D21S1292, D21S409 and D21S364.

19. The method according to claim 13, wherein establishing that the allele is in linkage disequilibrium comprises determining the presence or absence of the allele in a first and a second relative of the patient, the first and second relative each being of known phenotype for susceptibility to herpes simplex virus, at least one of the relatives having a phenotype of susceptibility to herpes simplex virus and being heterozygous for the allele.

20. The method according to claim 19, further comprising determining the phenotype of the first and the second relative.

21. The method according to claim 20, wherein the phenotype of the first and the second relatives are determined to be unaffected or frequently affected, wherein a frequently affected phenotype comprises two or more episodes per year.

22. The method according to claim 21, wherein one of the first and the second relative is a parent of the patient.

23. The method according to claim 13, further comprising determining the presence or absence of an allele of a second polymorphic marker in the patient.

24. The method according to claim 13, wherein the presence or absence of the allele is determined by amplifying a segment of DNA within chromosome 21q21 that spans the polymorphic marker.

25. The method according to claim 24, further comprising the step of determining the size of the amplified segment.

26. The method according to claim 24, further comprising the step of determining the sequence of the amplified segment.

27. The method according to claim 24, further comprising the step of determining the presence or absence of a restriction enzyme site within the amplified segment.

28. The method according to claim 13, wherein determining the presence or absence of the allele comprises contacting the DNA from the patient with an oligonucleotide probe capable of hybridizing to the allele under stringent conditions; and further comprising:
  determining whether hybridization has occurred, thereby indicating the presence of the allele.

29. The method according to claim 28, further comprising the step of isolating a sample of DNA from the patient.

30. The method according to claim 29, wherein the DNA is genomic and the sample is obtained from saliva, blood or buccal mucosal cells.

31. The method according to claim 13, further comprising the step of informing the patient or a treating physician of the susceptibility of the patient to herpes simplex virus.

32. The method according to claim 31, wherein susceptibility of the patient to herpes simplex virus comprises diagnosis of herpes keratitis.

33. The method according to claim 31, wherein susceptibility of the patient to herpes simplex virus comprises diagnosis of labial or perioral outbreaks of vesicular herpetic lesions.

34. The method according to claim 31, wherein susceptibility of the patient to herpes simplex virus comprises diagnosis of herpes encephalitis.

35. The method according to claim 31, wherein susceptibility of the patient to herpes simplex virus comprises ultraviolet light-inducible HSL.

36. The method according to claim 31, wherein susceptibility of the patient to herpes simplex virus comprises diagnosis of genital herpes.

37. The method according to claim 31, wherein susceptibility of the patient to herpes simplex virus comprises herpes simplex labialis.

38. The method according to claim 13, further comprising determining the presence or absence of herpes simplex virus.

39. The method according to claim 38, further comprising determining the serotype herpes simplex virus.

40. The method according to claim 39, wherein determining the serotype comprises a glycoprotein-G-based type-specific ELISA assay.

41. A method of determining potential resistance or susceptibility to recurrent herpes simplex virus labialis, said method comprising:
  obtaining a nucleic acid sample from a person potentially infected with herpes simplex virus;
  determining the presence or absence of herpes simplex virus;
  analyzing said nucleic acid sample for an allele of C21orf91; and
  determining the potential susceptibility of the person to recurrent herpes simplex labialis, wherein said recurrent herpes simplex labialis comprises at least two episodes of herpes simplex labialis in one year.

42. The method according to claim 41, further comprising serotyping the patient.

43. The method according to claim 42, wherein serotyping the patient determines the presence of herpes simplex virus type 1.

44. A method of performing a linkage analysis, the method comprising:
  a) conducting phenotyping for individuals to identify those positive for HSV;
  b) performing genotyping on those individuals identified from step (a) by calculating a logarithm of odds score between an allele of C21orf91 and a polymorphic marker between D21S1234 and D21S364 on human chromosome 21q21; and
  identifying a positive logarithm of odds score, thereby performing a linkage analysis.

* * * * *

SEQUENCE LISTING

```
<160> NUMBER OF SEQ ID NOS: 13

<210> SEQ ID NO 1
<211> LENGTH: 5213
<212> TYPE: DNA
<213> ORGANISM: Homo sapiens
<220> FEATURE:
<221> NAME/KEY: CDS
<222> LOCATION: (370)..(3633)
<223> OTHER INFORMATION: Homo sapiens ubiquitin specific protease 25
      (USP25), mRNA; NM013396.
<220> FEATURE:
<221> NAME/KEY: misc_feature
<222> LOCATION: (874)..(969)
<223> OTHER INFORMATION: UCH-1 region
<220> FEATURE:
<221> NAME/KEY: misc_feature
<222> LOCATION: (2131)..(2331)
<223> OTHER INFORMATION: UCH-2 region
<220> FEATURE:
<221> NAME/KEY: misc_feature
<222> LOCATION: (2199)..(2199)
<223> OTHER INFORMATION: Alleles may have A or T at this locus.
<220> FEATURE:
<221> NAME/KEY: misc_feature
<222> LOCATION: (4553)..(4553)
<223> OTHER INFORMATION: Alleles may have C or T at this locus.

<400> SEQUENCE: 1
aagcagcccg cggaccggca gcaaaggaac gtgcgaacgc gtgacgccgc ccgactggct      60
cgcgctctcc cgtgccccgg cgtcctccgc ccgctcatgg cccgggccgc cgcggacgat    120
cggcgctgag gcgggccgcg tggagacgtg aggcggccgc cgtggccctc acagtcggcg    180
```

```
tttcgccgcc tgcccgcggt gcccgcgcac gcctgccgcc atcgccttcg cgcctggctg        240 gcggggcgc tgtcctccca ggccgtccgc gccgctccct ggagctcggc ggagcgcggc         300
agccagggcc ggcggaggcg cgaggagccg ggcgccaccg ccgccgccgc cgccgccgcc        360 gcggggcc atg acc gtg gag cag aac gtg ctg cag cag agc gcg gcg cag        411
         Met Thr Val Glu Gln Asn Val Leu Gln Gln Ser Ala Ala Gln
          1               5                  10 aag cac cag cag acg ttt ttg aat caa ctg aga gaa att acg ggg att        459
Lys His Gln Gln Thr Phe Leu Asn Gln Leu Arg Glu Ile Thr Gly Ile
15                  20                  25                  30 aat gac acc cag ata cta cag caa gcc ttg aag gat agt aat gga aac        507
Asn Asp Thr Gln Ile Leu Gln Gln Ala Leu Lys Asp Ser Asn Gly Asn
                35                  40                  45 ttg gaa tta gca gtg gct ttc ctt act gcg aag aat gct aag acc cct        555
Leu Glu Leu Ala Val Ala Phe Leu Thr Ala Lys Asn Ala Lys Thr Pro
    50                  55                  60 cag cag gag gag aca act tac tac caa aca gca ctt cct ggc aat gat        603
Gln Gln Glu Glu Thr Thr Tyr Tyr Gln Thr Ala Leu Pro Gly Asn Asp
65                  70                  75 aga tac atc agt gtg gga agc caa gca gat aca aat gtg att gat ctc        651
Arg Tyr Ile Ser Val Gly Ser Gln Ala Asp Thr Asn Val Ile Asp Leu
        80                  85                  90 act gga gat gat aaa gat gat ctt cag aga gca att gcc ttg agt ttg        699
Thr Gly Asp Asp Lys Asp Asp Leu Gln Arg Ala Ile Ala Leu Ser Leu
95                  100                 105                 110 gcc gaa tca aac agg gca ttc agg gag act gga ata act gat gag gaa        747
Ala Glu Ser Asn Arg Ala Phe Arg Glu Thr Gly Ile Thr Asp Glu Glu
            115                 120                 125 caa gcc att agc aga gtt ctt gaa gcc agc ata gca gag aat aaa gca        795
Gln Ala Ile Ser Arg Val Leu Glu Ala Ser Ile Ala Glu Asn Lys Ala
        130                 135                 140 tgt ttg aag agg aca cct aca gaa gtt tgg agg gat tct cga aac cct        843
Cys Leu Lys Arg Thr Pro Thr Glu Val Trp Arg Asp Ser Arg Asn Pro
145                 150                 155 tat gat aga aaa aga cag gac aaa gct ccc gtt ggg cta aag aat gtt        891
Tyr Asp Arg Lys Arg Gln Asp Lys Ala Pro Val Gly Leu Lys Asn Val
160                 165                 170 ggc aat act tgt tgg ttt agt gct gtt att cag tca tta ttt aat ctt        939
Gly Asn Thr Cys Trp Phe Ser Ala Val Ile Gln Ser Leu Phe Asn Leu
175                 180                 185                 190 ttg gaa ttt aga aga tta gtt ctg aat tac aag cct cca tca aat gct        987
Leu Glu Phe Arg Arg Leu Val Leu Asn Tyr Lys Pro Pro Ser Asn Ala
            195                 200                 205 caa gat tta ccc cga aac caa aag gaa cat cgg aat ttg cct ttt atg        1035
Gln Asp Leu Pro Arg Asn Gln Lys Glu His Arg Asn Leu Pro Phe Met
        210                 215                 220 cgt gag ctg agg tat cta ttt gca ctt ctt gtt ggt acc aaa agg aag        1083
Arg Glu Leu Arg Tyr Leu Phe Ala Leu Leu Val Gly Thr Lys Arg Lys
225                 230                 235 tat gtt gat cca tca aga gca gtt gaa att ctt aag gat gct ttc aaa        1131
Tyr Val Asp Pro Ser Arg Ala Val Glu Ile Leu Lys Asp Ala Phe Lys
240                 245                 250 tca aat gac tca cag cag caa gat gtg agt gag ttt aca cac aaa tta        1179
Ser Asn Asp Ser Gln Gln Gln Asp Val Ser Glu Phe Thr His Lys Leu
255                 260                 265                 270 tta gat tgg tta gaa gat gcc ttc caa atg aaa gct gaa gag gag acg        1227
Leu Asp Trp Leu Glu Asp Ala Phe Gln Met Lys Ala Glu Glu Glu Thr
            275                 280                 285 gat gaa gag aag cca aag aac ccc atg gta gag ttg ttc tat ggc aga        1275
```

```
Asp Glu Glu Lys Pro Lys Asn Pro Met Val Glu Leu Phe Tyr Gly Arg
            290             295             300 ttc ctg gct gtg gga gta ctt gaa ggt aaa aaa ttt gaa aac act gaa    1323
Phe Leu Ala Val Gly Val Leu Glu Gly Lys Lys Phe Glu Asn Thr Glu
            305             310             315 atg ttt ggt cag tac cca ctt cag gtc aat ggg ttc aaa gat ctg cat    1371
Met Phe Gly Gln Tyr Pro Leu Gln Val Asn Gly Phe Lys Asp Leu His
320             325             330 gag tgc cta gaa gct gca atg att gaa gga gaa att gag tct tta cat    1419
Glu Cys Leu Glu Ala Ala Met Ile Glu Gly Glu Ile Glu Ser Leu His
335             340             345             350 tca gag aat tca gga aaa tca ggc caa gag cat tgg ttt act gaa tta    1467
Ser Glu Asn Ser Gly Lys Ser Gly Gln Glu His Trp Phe Thr Glu Leu
            355             360             365 cca cct gtg tta aca ttt gaa ttg tca aga ttt gaa ttt aat cag gca    1515
Pro Pro Val Leu Thr Phe Glu Leu Ser Arg Phe Glu Phe Asn Gln Ala
            370             375             380 ttg gga aga cca gaa aaa att cac aac aaa tta gaa ttt ccc caa gtt    1563
Leu Gly Arg Pro Glu Lys Ile His Asn Lys Leu Glu Phe Pro Gln Val
385             390             395 tta tat ttg gac aga tac atg cac aga aac aga gaa ata aca aga att    1611
Leu Tyr Leu Asp Arg Tyr Met His Arg Asn Arg Glu Ile Thr Arg Ile
        400             405             410 aag agg gaa gag atc aag aga ctg aaa gat tac ctc acg gta tta caa    1659
Lys Arg Glu Glu Ile Lys Arg Leu Lys Asp Tyr Leu Thr Val Leu Gln
415             420             425             430 caa agg cta gaa aga tat tta agc tat ggt tcc ggt ccc aaa cga ttc    1707
Gln Arg Leu Glu Arg Tyr Leu Ser Tyr Gly Ser Gly Pro Lys Arg Phe
            435             440             445 ccc ttg gta gat gtt ctt cag tat gca ttg gaa ttt gcc tca agt aaa    1755
Pro Leu Val Asp Val Leu Gln Tyr Ala Leu Glu Phe Ala Ser Ser Lys
            450             455             460 cct gtt tgc act tct cct gtt gac gat att gac gct agt tcc cca cct    1803
Pro Val Cys Thr Ser Pro Val Asp Asp Ile Asp Ala Ser Ser Pro Pro
            465             470             475 agt ggt tcc ata cca tca cag aca tta cca agc aca aca gaa caa cag    1851
Ser Gly Ser Ile Pro Ser Gln Thr Leu Pro Ser Thr Thr Glu Gln Gln
480             485             490 gga gcc cta tct tca gaa ctg cca agc aca tca cct tca tca gtt gct    1899
Gly Ala Leu Ser Ser Glu Leu Pro Ser Thr Ser Pro Ser Ser Val Ala
495             500             505             510 gcc att tca tcg aga tca gta ata cac aaa cca ttt act cag tcc cgg    1947
Ala Ile Ser Ser Arg Ser Val Ile His Lys Pro Phe Thr Gln Ser Arg
            515             520             525 ata cct cca gat ttg ccc atg cat ccg gca cca agg cac ata acg gag    1995
Ile Pro Pro Asp Leu Pro Met His Pro Ala Pro Arg His Ile Thr Glu
            530             535             540 gaa aaa ctt tct gtg ctg gaa agt tgt tta cat cgc tgg agg aca gaa    2043
Glu Lys Leu Ser Val Leu Glu Ser Cys Leu His Arg Trp Arg Thr Glu
            545             550             555 ata gaa aat gac acc aga gat ttg cag gaa agc ata tcc aga atc cat    2091
Ile Glu Asn Asp Thr Arg Asp Leu Gln Glu Ser Ile Ser Arg Ile His
560             565             570 cga aca att gaa tta atg tac tct gac aaa tct atg ata caa gtt cct    2139
Arg Thr Ile Glu Leu Met Tyr Ser Asp Lys Ser Met Ile Gln Val Pro
575             580             585             590 tat cga tta cat gcc gtt tta gtt cac gaa ggc caa gct aat gct ggg    2187
Tyr Arg Leu His Ala Val Leu Val His Glu Gly Gln Ala Asn Ala Gly
            595             600             605
```

-continued

```
cac tac tgg gca tat att ttt gat cat cgt gaa agc aga tgg atg aag    2235
His Tyr Trp Ala Tyr Ile Phe Asp His Arg Glu Ser Arg Trp Met Lys
            610                 615                 620 tac aat gat att gct gtg aca aaa tca tca tgg gaa gag cta gtg agg    2283
Tyr Asn Asp Ile Ala Val Thr Lys Ser Ser Trp Glu Glu Leu Val Arg
625                 630                 635 gac tct ttt ggt ggt tat aga aat gcc agt gca tac tgt tta atg tac    2331
Asp Ser Phe Gly Gly Tyr Arg Asn Ala Ser Ala Tyr Cys Leu Met Tyr
        640                 645                 650 ata aat gat aag gca cag ttc cta ata caa gag gag ttt aat aaa gaa    2379
Ile Asn Asp Lys Ala Gln Phe Leu Ile Gln Glu Glu Phe Asn Lys Glu
655                 660                 665                 670 act ggg cag ccc ctt gtt ggt ata gaa aca tta ccg ccg gat ttg aga    2427
Thr Gly Gln Pro Leu Val Gly Ile Glu Thr Leu Pro Pro Asp Leu Arg
            675                 680                 685 gat ttt gtt gag gaa gac aac caa cga ttt gaa aaa gaa cta gaa gaa    2475
Asp Phe Val Glu Glu Asp Asn Gln Arg Phe Glu Lys Glu Leu Glu Glu
        690                 695                 700 tgg gat gca caa ctt gcc cag aaa gct ttg cag gaa aag ctt tta gcg    2523
Trp Asp Ala Gln Leu Ala Gln Lys Ala Leu Gln Glu Lys Leu Leu Ala
705                 710                 715 tct cag aaa ttg aga gag tca gag act tct gtg aca aca gca caa gca    2571
Ser Gln Lys Leu Arg Glu Ser Glu Thr Ser Val Thr Thr Ala Gln Ala
    720                 725                 730 gca gga gac cca gaa tat cta gag cag cca tca aga agt gat ttc tca    2619
Ala Gly Asp Pro Glu Tyr Leu Glu Gln Pro Ser Arg Ser Asp Phe Ser
735                 740                 745                 750 aag cac ttg aaa gaa gaa act att caa ata att acc aag gca tca cat    2667
Lys His Leu Lys Glu Glu Thr Ile Gln Ile Ile Thr Lys Ala Ser His
            755                 760                 765 gag cat gaa gat aaa agt cct gaa aca gtt ttg cag tcg atc atg atg    2715
Glu His Glu Asp Lys Ser Pro Glu Thr Val Leu Gln Ser Ile Met Met
        770                 775                 780 aca ccg aac atg caa ggt att atc atg gcg ata ggt aaa tcc agg agt    2763
Thr Pro Asn Met Gln Gly Ile Ile Met Ala Ile Gly Lys Ser Arg Ser
785                 790                 795 gta tat gac agg tgt ggc cct gaa gca ggg ttc ttt aag gca att aag    2811
Val Tyr Asp Arg Cys Gly Pro Glu Ala Gly Phe Phe Lys Ala Ile Lys
    800                 805                 810 ttg gaa tat gca agg ttg gtt aag ttg gcc caa gaa gac acc cca cca    2859
Leu Glu Tyr Ala Arg Leu Val Lys Leu Ala Gln Glu Asp Thr Pro Pro
815                 820                 825                 830 gaa acc gat tat cgt tta cat cat gta gtg gtc tac ttt atc cag aac    2907
Glu Thr Asp Tyr Arg Leu His His Val Val Val Tyr Phe Ile Gln Asn
            835                 840                 845 cag gca cca aag aaa att att gag aaa aca tta cta gaa caa ttt gga    2955
Gln Ala Pro Lys Lys Ile Ile Glu Lys Thr Leu Leu Glu Gln Phe Gly
        850                 855                 860 gat aga aat ttg agt ttt gat gaa agg tgt cac aac ata atg aaa gtt    3003
Asp Arg Asn Leu Ser Phe Asp Glu Arg Cys His Asn Ile Met Lys Val
865                 870                 875 gct caa gcc aaa ctg gaa atg ata aaa cct gaa gaa gta aac ttg gag    3051
Ala Gln Ala Lys Leu Glu Met Ile Lys Pro Glu Glu Val Asn Leu Glu
    880                 885                 890 gaa tat gag gag tgg cat cag gat tat agg aaa ttc agg gaa aca act    3099
Glu Tyr Glu Glu Trp His Gln Asp Tyr Arg Lys Phe Arg Glu Thr Thr
895                 900                 905                 910 atg tat ctc ata att ggg cta gaa aat ttt caa aga gaa agt tat ata    3147
Met Tyr Leu Ile Ile Gly Leu Glu Asn Phe Gln Arg Glu Ser Tyr Ile
            915                 920                 925
```

-continued

```
gat tcc ttg ctg ttc ctc atc tgt gct tat cag aat aac aaa gaa ctc      3195
Asp Ser Leu Leu Phe Leu Ile Cys Ala Tyr Gln Asn Asn Lys Glu Leu
        930                 935                 940 ttg tct aaa ggc tta tac aga gga cat gat gaa gaa ttg ata tca cat      3243
Leu Ser Lys Gly Leu Tyr Arg Gly His Asp Glu Glu Leu Ile Ser His
            945                 950                 955 tat aga aga gaa tgt ttg cta aaa tta aat gag caa gcc gca gaa ctc      3291
Tyr Arg Arg Glu Cys Leu Leu Lys Leu Asn Glu Gln Ala Ala Glu Leu
960                 965                 970 ttc gaa tct gga gag gat cga gaa gta aac aat ggt ttg att atc atg      3339
Phe Glu Ser Gly Glu Asp Arg Glu Val Asn Asn Gly Leu Ile Ile Met
975                 980                 985                 990 aat gag ttt att gtc cca ttt ttg cca tta tta ctg gtg gat gaa atg      3387
Asn Glu Phe Ile Val Pro Phe Leu Pro Leu Leu Leu Val Asp Glu Met
                995                 1000                1005 gaa gaa aag gat ata cta gct gta gaa gat atg aga aat cga tgg          3432
Glu Glu Lys Asp Ile Leu Ala Val Glu Asp Met Arg Asn Arg Trp
                1010                1015                1020 tgt tcc tac ctt ggt caa gaa atg gaa cca cac ctc caa gaa aag          3477
Cys Ser Tyr Leu Gly Gln Glu Met Glu Pro His Leu Gln Glu Lys
                1025                1030                1035 ctg aca gat ttt ttg cca aaa ctg ctt gat tgt tct atg gag att          3522
Leu Thr Asp Phe Leu Pro Lys Leu Leu Asp Cys Ser Met Glu Ile
                1040                1045                1050 aaa agt ttc cat gag cca ccg aag tta cct tca tat tcc acg cat          3567
Lys Ser Phe His Glu Pro Pro Lys Leu Pro Ser Tyr Ser Thr His
                1055                1060                1065 gaa ctc tgt gag cga ttt gcc cga atc atg ttg tcc ctc agt cga          3612
Glu Leu Cys Glu Arg Phe Ala Arg Ile Met Leu Ser Leu Ser Arg
                1070                1075                1080 act cct gct gat gga aga taa actgcacact ttccctgaac acactgtata        3663
Thr Pro Ala Asp Gly Arg
                1085 aactctttt agttcttaac ccttgccttc ctgtcacagg gtttgcttgt tgctgctata     3723 gttttaact tttttttatt ttaataactg caaaagacaa aatgactata cagactttag     3783
tcagactgca gacaataaag ctgaaaatcg catggcgctc agacatttta accggaactg    3843
atgtataatc acaaatctaa ttgatttat tatggccaaa ctatgctttt gccaccttcc     3903
tgttgcagta ttactttgct tttatctttt ctttctcaac agctttccat tcagtctgga    3963
tccttccatg actacagcca tttaagtgtt cagcactgtg tacgatacat aatatttggt    4023
agcttgtaaa tgaaataaag aataaagttt tatttatggc tacctatgtg tttgtaagca    4083
ggtatattgt atattagtgt attagtaata ctagataaat gaattttgtc tggggattaa    4143
gattggatag ttaatagatt aatacaatct tttaattctg ctctaatgct agcaaattgg    4203
aaaatgttta agtctttgac acttaaattt atctatattt ttaacaaagt tcttgaactt    4263
agtatggcac cggaacctgt tttgaattca gtcaggtttt tactcaagta agtggtgttt    4323
tttttaagtc aaactacact gaacttttta tccttttctt agattaatct tactttttaa    4383
atgtatttac aatatacagc aaggtgatta tttcaagaga atcccaaagt acttgaataa    4443
gggctattgt aaaatttaaa agaaatattt atatatacac atatatacac atacacacat    4503
gtatatatat attcttcata atggaggaca atgttttgca atatataaat cattctattt    4563
ttgtaaattg tatatcactt taattgaaaa tgttctctac taattaatac tgtgaaacaa    4623
aattgatgtt gtttaactag aagttatgag tatcttaact gcctttattc cttttcaaaa   4683
```

-continued

```
agaaaaagct gtagaacatt ttgtagatga aactactgtt taagattaat gaattaaatat    4743 tgtgaatgaa aatcaaaatc catactttaa aggtaatcat gttactaacc acctattttt    4803
gaattcataa aaatttcttt ataaatgatg ttttgtgaac atagtaaaat agaccattat    4863
actatgtgta tgtttgatac agcgtcgcca aaactagtgt tctttattag tgcctctcac    4923
aaaagatcct ggatggagga gtaagatgaa atattatgct attatatgat gctgtttgta    4983 aagtattaa tgtactagta aggtgttaat gacaaggaat tagtactatt cctgttgtaa    5043
agttagattt tgcatattgt atctatcaaa atatgtttgg gtttagattt taagttgtct    5103
actgagcaga tttctgcatt ggttttccag tcctgttaaa agtttagaaa cttcatatgt    5163
gtcatcacag cttttgtaaa gaaagtatcc ttaatatttt atgacattct                5213
```

<210> SEQ ID NO 2
<211> LENGTH: 1087
<212> TYPE: PRT
<213> ORGANISM: Homo sapiens

<400> SEQUENCE: 2

```
Met Thr Val Glu Gln Asn Val Leu Gln Gln Ser Ala Ala Gln Lys His
1               5                   10                  15

Gln Gln Thr Phe Leu Asn Gln Leu Arg Glu Ile Thr Gly Ile Asn Asp
            20                  25                  30

Thr Gln Ile Leu Gln Gln Ala Leu Lys Asp Ser Asn Gly Asn Leu Glu
        35                  40                  45

Leu Ala Val Ala Phe Leu Thr Ala Lys Asn Ala Lys Thr Pro Gln Gln
    50                  55                  60

Glu Glu Thr Thr Tyr Tyr Gln Thr Ala Leu Pro Gly Asn Asp Arg Tyr
65                  70                  75                  80

Ile Ser Val Gly Ser Gln Ala Asp Thr Asn Val Ile Asp Leu Thr Gly
                85                  90                  95

Asp Asp Lys Asp Asp Leu Gln Arg Ala Ile Ala Leu Ser Leu Ala Glu
            100                 105                 110

Ser Asn Arg Ala Phe Arg Glu Thr Gly Ile Thr Asp Glu Glu Gln Ala
        115                 120                 125

Ile Ser Arg Val Leu Glu Ala Ser Ile Ala Glu Asn Lys Ala Cys Leu
    130                 135                 140

Lys Arg Thr Pro Thr Glu Val Trp Arg Asp Ser Arg Asn Pro Tyr Asp
145                 150                 155                 160

Arg Lys Arg Gln Asp Lys Ala Pro Val Gly Leu Lys Asn Val Gly Asn
                165                 170                 175

Thr Cys Trp Phe Ser Ala Val Ile Gln Ser Leu Phe Asn Leu Leu Glu
            180                 185                 190

Phe Arg Arg Leu Val Leu Asn Tyr Lys Pro Pro Ser Asn Ala Gln Asp
        195                 200                 205

Leu Pro Arg Asn Gln Lys Glu His Arg Asn Leu Pro Phe Met Arg Glu
    210                 215                 220

Leu Arg Tyr Leu Phe Ala Leu Leu Val Gly Thr Lys Arg Lys Tyr Val
225                 230                 235                 240

Asp Pro Ser Arg Ala Val Glu Ile Leu Lys Asp Ala Phe Lys Ser Asn
                245                 250                 255

Asp Ser Gln Gln Gln Asp Val Ser Glu Phe Thr His Lys Leu Leu Asp
            260                 265                 270

Trp Leu Glu Asp Ala Phe Gln Met Lys Ala Glu Glu Thr Asp Glu
        275                 280                 285
```

-continued

```
Glu Lys Pro Lys Asn Pro Met Val Glu Leu Phe Tyr Gly Arg Phe Leu
290                 295                 300
Ala Val Gly Val Leu Glu Gly Lys Lys Phe Glu Asn Thr Glu Met Phe
305                 310                 315                 320
Gly Gln Tyr Pro Leu Gln Val Asn Gly Phe Lys Asp Leu His Glu Cys
                325                 330                 335
Leu Glu Ala Ala Met Ile Glu Gly Glu Ile Glu Ser Leu His Ser Glu
            340                 345                 350
Asn Ser Gly Lys Ser Gly Gln Glu His Trp Phe Thr Glu Leu Pro Pro
        355                 360                 365
Val Leu Thr Phe Glu Leu Ser Arg Phe Glu Phe Asn Gln Ala Leu Gly
    370                 375                 380
Arg Pro Glu Lys Ile His Asn Lys Leu Glu Phe Pro Gln Val Leu Tyr
385                 390                 395                 400
Leu Asp Arg Tyr Met His Arg Asn Arg Glu Ile Thr Arg Ile Lys Arg
                405                 410                 415
Glu Glu Ile Lys Arg Leu Lys Asp Tyr Leu Thr Val Leu Gln Gln Arg
            420                 425                 430
Leu Glu Arg Tyr Leu Ser Tyr Gly Ser Gly Pro Lys Arg Phe Pro Leu
        435                 440                 445
Val Asp Val Leu Gln Tyr Ala Leu Glu Phe Ala Ser Ser Lys Pro Val
    450                 455                 460
Cys Thr Ser Pro Val Asp Asp Ile Asp Ala Ser Ser Pro Pro Ser Gly
465                 470                 475                 480
Ser Ile Pro Ser Gln Thr Leu Pro Ser Thr Thr Glu Gln Gln Gly Ala
                485                 490                 495
Leu Ser Ser Glu Leu Pro Ser Thr Ser Pro Ser Ser Val Ala Ala Ile
            500                 505                 510
Ser Ser Arg Ser Val Ile His Lys Pro Phe Thr Gln Ser Arg Ile Pro
        515                 520                 525
Pro Asp Leu Pro Met His Pro Ala Pro Arg His Ile Thr Glu Glu Lys
    530                 535                 540
Leu Ser Val Leu Glu Ser Cys Leu His Arg Trp Arg Thr Glu Ile Glu
545                 550                 555                 560
Asn Asp Thr Arg Asp Leu Gln Glu Ser Ile Ser Arg Ile His Arg Thr
                565                 570                 575
Ile Glu Leu Met Tyr Ser Asp Lys Ser Met Ile Gln Val Pro Tyr Arg
            580                 585                 590
Leu His Ala Val Leu Val His Glu Gly Gln Ala Asn Ala Gly His Tyr
        595                 600                 605
Trp Ala Tyr Ile Phe Asp His Arg Glu Ser Arg Trp Met Lys Tyr Asn
    610                 615                 620
Asp Ile Ala Val Thr Lys Ser Ser Trp Glu Glu Leu Val Arg Asp Ser
625                 630                 635                 640
Phe Gly Gly Tyr Arg Asn Ala Ser Ala Tyr Cys Leu Met Tyr Ile Asn
                645                 650                 655
Asp Lys Ala Gln Phe Leu Ile Gln Glu Glu Phe Asn Lys Glu Thr Gly
            660                 665                 670
Gln Pro Leu Val Gly Ile Glu Thr Leu Pro Pro Asp Leu Arg Asp Phe
        675                 680                 685
Val Glu Glu Asp Asn Gln Arg Phe Glu Lys Glu Leu Glu Glu Trp Asp
    690                 695                 700
```

```
Ala Gln Leu Ala Gln Lys Ala Leu Gln Glu Lys Leu Ala Ser Gln
705                 710                 715                 720

Lys Leu Arg Glu Ser Glu Thr Ser Val Thr Thr Ala Gln Ala Ala Gly
                725                 730                 735

Asp Pro Glu Tyr Leu Glu Gln Pro Ser Arg Ser Asp Phe Ser Lys His
                740                 745                 750

Leu Lys Glu Glu Thr Ile Gln Ile Ile Thr Lys Ala Ser His Glu His
                755                 760                 765

Glu Asp Lys Ser Pro Glu Thr Val Leu Gln Ser Ile Met Met Thr Pro
770                 775                 780

Asn Met Gln Gly Ile Ile Met Ala Ile Gly Lys Ser Arg Ser Val Tyr
785                 790                 795                 800

Asp Arg Cys Gly Pro Glu Ala Gly Phe Phe Lys Ala Ile Lys Leu Glu
                805                 810                 815

Tyr Ala Arg Leu Val Lys Leu Ala Gln Glu Asp Thr Pro Pro Glu Thr
                820                 825                 830

Asp Tyr Arg Leu His His Val Val Tyr Phe Ile Gln Asn Gln Ala
                835                 840                 845

Pro Lys Lys Ile Ile Glu Lys Thr Leu Leu Gln Phe Gly Asp Arg
    850                 855                 860

Asn Leu Ser Phe Asp Glu Arg Cys His Asn Ile Met Lys Val Ala Gln
865                 870                 875                 880

Ala Lys Leu Glu Met Ile Lys Pro Glu Glu Val Asn Leu Glu Glu Tyr
                885                 890                 895

Glu Glu Trp His Gln Asp Tyr Arg Lys Phe Arg Glu Thr Thr Met Tyr
                900                 905                 910

Leu Ile Ile Gly Leu Glu Asn Phe Gln Arg Glu Ser Tyr Ile Asp Ser
                915                 920                 925

Leu Leu Phe Leu Ile Cys Ala Tyr Gln Asn Asn Lys Glu Leu Leu Ser
                930                 935                 940

Lys Gly Leu Tyr Arg Gly His Asp Glu Glu Leu Ile Ser His Tyr Arg
945                 950                 955                 960

Arg Glu Cys Leu Leu Lys Leu Asn Glu Gln Ala Ala Glu Leu Phe Glu
                965                 970                 975

Ser Gly Glu Asp Arg Glu Val Asn Asn Gly Leu Ile Ile Met Asn Glu
                980                 985                 990

Phe Ile Val Pro Phe Leu Pro Leu Leu Leu Val Asp Glu Met Glu Glu
                995                 1000                1005

Lys Asp Ile Leu Ala Val Glu Asp Met Arg Asn Arg Trp Cys Ser
    1010                1015                1020

Tyr Leu Gly Gln Glu Met Glu Pro His Leu Gln Glu Lys Leu Thr
    1025                1030                1035

Asp Phe Leu Pro Lys Leu Leu Asp Cys Ser Met Glu Ile Lys Ser
    1040                1045                1050

Phe His Glu Pro Pro Lys Leu Pro Ser Tyr Ser Thr His Glu Leu
    1055                1060                1065

Cys Glu Arg Phe Ala Arg Ile Met Leu Ser Leu Ser Arg Thr Pro
    1070                1075                1080

Ala Asp Gly Arg
    1085

<210> SEQ ID NO 3
<211> LENGTH: 340000
<212> TYPE: DNA
```

```
<213> ORGANISM: Homo sapiens
<220> FEATURE:
<221> NAME/KEY: exon
<222> LOCATION: (56948)..(57115)
<223> OTHER INFORMATION: C21orf34 exon
<220> FEATURE:
<221> NAME/KEY: misc_feature
<222> LOCATION: (80006)..(81089)
<223> OTHER INFORMATION: Gene VDAC2P; voltage-dependent anion channel
      isoform 2 pseudogene
<220> FEATURE:
<221> NAME/KEY: exon
<222> LOCATION: (167308)..(167438)
<223> OTHER INFORMATION: C21orf34 exon
<220> FEATURE:
<221> NAME/KEY: exon
<222> LOCATION: (216732)..(216833)
<223> OTHER INFORMATION: C21orf34 exon

<400> SEQUENCE: 3
```

| | | | | | |
|---|---|---|---|---|---|
| tcttttcac | ggcatcccac | aaattctcag | tgtaattcag | tagtcctctc | ttatccgtgg | 60 |
| ttttgctttc | tgaggtttca | gttttaccca | cagtcaactg | cgatccaaaa | atattaaacg | 120 |
| gaaaattcca | gaaacaaaca | atttagaagt | ttaaattgcg | caccattctg | aataacgtga | 180 |
| tggaatcttg | tgctatcctg | ttctgtccag | cccaggacat | gaaacatcct | tttgtctagc | 240 |
| atatccacat | tgtggaggct | actccgtcct | cagtcactta | gtttctgtct | catcatcaga | 300 |
| tcgaaaaaca | cagtatgtat | caggtttggt | actctctgtg | gttttaggta | tatactgggg | 360 |
| gtcttggaac | acatcctcct | aggattagta | gggactattg | taatattgca | ttgaggacaa | 420 |
| ctctttgtca | agataaatttt | ttttcttttt | tttttaaatt | atactttaag | ttttagggta | 480 |
| catgtgcaca | atgtgcaggt | ttgttgcata | tgtatacatg | tgccatgttg | gtgtgctgca | 540 |
| cccattaact | cgtcatttag | cattaagtat | atctcctaat | gctatccctc | cccctcccc | 600 |
| ccaccccaca | acaggccctg | ctgtgtgatg | ttccccttcc | tgtgtccatg | tgttctcatt | 660 |
| gttcaattcc | cacctatgaa | tgagaacatg | cggtgtttgg | ttttttgtcc | ttgtgatagt | 720 |
| ttactgagaa | tgatggtttc | cagcttcatc | catgtctcta | taaagaacat | gaactcatcc | 780 |
| ttttttatgg | ctgcatagta | ttccatggtg | tatatgtgcc | acatttcttt | aatccactct | 840 |
| atcattgttg | gacatttggg | ttggttgcaa | gtctttgcta | ttgtgaatag | ttccacaata | 900 |
| aacatatgtg | tgcatgtgtc | tttatagcag | catggtttat | aatcctttgg | gtatatacccc | 960 |
| agtaatggga | tggctgggtc | aaatggtatt | tctagttcta | gatccctgag | gaatcgccac | 1020 |
| accgacttcc | acaatggttg | aactagttta | cagtcccacc | aacagtgtta | agtgttcct | 1080 |
| atttctccac | atcctctcca | gtacctgttg | tttcctggct | ttttaatgat | caccattcta | 1140 |
| actggtgtga | gatggtatct | cattgtggtt | ttgatttgca | tttctctgat | ggccagtgat | 1200 |
| ggtgagcatt | ttttcatgtg | tcttttggct | gcataaatgt | cttcttttga | gaagtgtctg | 1260 |
| ttcatatctt | ttgcccactt | tttgatgggg | ttgtttgttt | ttttcttgta | aatttgtttg | 1320 |
| agttccttgt | aggttctgga | tattagccct | ttgtcagatg | agtagattgc | aaaaattttc | 1380 |
| tcccattctg | taggttgcct | gttcactctg | atggtagttt | tttttgctgt | gcagaagctc | 1440 |
| tttagtttaa | ttagatccca | tatgtcaatt | ttggcttttg | ttgccattgc | ttttggtgtt | 1500 |
| ttagacatga | agtcctcgcc | catgcctatg | tcctgaatgg | tattgtctat | gttttcttct | 1560 |
| aggattttta | tggttttagg | tctaacgttt | aagtctttaa | tccatcttga | attaatttt | 1620 |
| gtataagatg | taaggaaggg | atacagtttc | agctttctac | atatggctag | ccagttttcc | 1680 |
| cagcaccgtt | tattaaatag | gggatccttt | ccccattct | tgttttgtc | aggtttgtca | 1740 |

-continued

```
aagatcagat agttgtaggt acgtggcatt atttctgagg cctctgttct gttccattgg    1800
tctatatctc tgttttggta ccagtaccat gctgttttgg ttactttagc cttatagtat    1860
agtttgaagt caggtagcat gatgcctcca gctttgttct tttggtttag gattgacttg    1920
gcaatgcggg ctcttttttg gttccatatg aacttgaaag tagttttttc caattctgtg    1980
aagaaagtca ttggtagctt gatggggatg catggaatc tataaattac cttgggcagt     2040
atggccattt tcacgatatt gattcttcct acccatgagc atggaatgtt cttctgtttg    2100
tttgtatcct cttttatttc attgagcact ggtttgtagt tctccttgaa gaggtccttc    2160
ccatcccttg taagttggat tcctaggtat tttattcttt tgaagcaat tgtgaatggg     2220 agttcactca tgatttggct gtttgtctgt tattggtgta aagaatgct tgtgattttt     2280 gcacattgat tttgtatcct gagactttgc tgaagttgcc tatcagctta aggagataat    2340
ttaaatgact ttctttgcta tagtagtaat taaggcttag tgatccacag agtctttcaa    2400
ccattggaaa taagagcaaa cacattgaaa tttgggacaa atatttcact aacacttttc    2460
atcctaaaac ttgaaatgaa agcaactgat aaagacaata agcctactaa agaaacatgc    2520
catggaacta gctgtaggta gatggacaag ggttgagagg gaaggcaatc agatggctag    2580
agtggtaagt tttcaaaata ttggcattca ccttctttag cttcctcact gctgcttagt    2640
ggagtatttt ttggcagata atttctctgc attttatgt gtttaatgag aaacatcttt     2700
atattttgaa gatgattgag atagtttcac tttgagggct attttatctg tgctccaaaa    2760
cccaaataga agcttttagc tgattaatgt gaatattgaa agcataaata caaattaaac    2820
ttctctccct ctgtgtctct aacccaatc tttctgttta actaacaaaa taagcaaaaa     2880
cagcacacgt ttttatttt agaaacatta tcaaaattaa ggcaagagtt ccaaatgcca     2940
gctgtgccat gaactgtaag taatttctgg aacaattatt agaaaaaata attttgttta    3000
ataaattact tgagaggctc agaatatgtc tcttatgact ttacatattt acataaatga    3060
gaagtactaa aattgaagtc attaaaagat gtttatttac ttcagaactc tacaccaata    3120
atttacttga ttccaccgaa cgcagtctgt tctccctgcc cttaggtaat gacatgtatg    3180
ctaatcgctc atttcgctgg aacatttaaa aaatgtattt tagattgctt tagaaactca    3240
atttataact tcttcagatg ctcaaagcca agtgcaggac tgtaatacat ctttaagaga    3300
cagcggcgtt tttgtgaaaa taactaaaag atcagtaaat agaaaacaga aacattgaa     3360 gacatttcaa ttccttcact taaggaagaa atatttacac tgtcaaatgt ccctgaaagg    3420
cattgaggag atttacatag aacgtcaaat atttctgatt atgaaatggg ttattttaa     3480 agtggtcttt ctcttttgta gcagaattat tagtagaggc agtgctggta tcaatggtag    3540
caatgtctat tgagagctta ctagatacca agcactgtac taaatgctgt gcaagatttc    3600
tcatttaatt gactcttccc ttgctgaaat cctgaagttc attttatttg tattatacag    3660
ataaggaaac tgagtcttag ataagttcat ttgttaaagg tcacaaagct agagggttac    3720
tgagctgaaa ctacagcagc caagcctgta aatgttactt aaattttctg agtcttaaat    3780
ttgttttcct aggtagaata aaaatgataa gaccgatctc tgataatgct tattattact    3840
aaatgaggta acaaatgtga agatacacaa cacatgttta ataaatgtta cttatcctcc    3900
ttaattagct atgcacatgt caccaaaacg ctgccatcta tgcattaca tttaaattat     3960 gtgtatatcc tattactaaa ctatgagctc tgagatgatt tggatggaac catgttttag    4020
tcctccagta tctccttatc tattaccaca tacacacccc agtacgttgt aagcatgcaa    4080
tcgatgttga ctattaaaaa atgaatgggg gagagcgcaa ggaatgcacc catgtgatat    4140
```

```
tggttggaag gcagttggac aatatagttt agattttgaa atgtgcttac tctttggttt    4200
aacaattcca cttctaaaaa ggatggggct tgtgaactaa gatatatttc acctatagtc    4260
atcacaacat tgtcttcaat atgggaaagt caaaaacatc ctaattgtca atttaaaaat    4320
tgtaacaggc caaccatgga atagtatgaa gtcattaaat gatgtgcaaa tgcacttagt    4380
ggtgagagag tctccatttg agggtagagg gtaggggag cgagagaagc agaaaaagta    4440
actattgggt actagattta atacctggat tgttgtcat tatttcacct gtacaacacc    4500
catgacacga gtttacctat ttatgaaacc ttcacatgta ccctctaacc taaaagttta    4560 aaaagatat atttgttaat atgtgaaaag ggatgtgata taaatatatg atcatcttcc    4620
tgatacacac atgcacacta taaaattaat aagtcaaaaa atagttatat ctgggtaaag    4680
gatcacaagc tatctttatt tctcacactt ttctttattc ctttaaaata ttttgtagaa    4740
agtatgtata tcttaatctg cagaaaaaag taagttactt taagagatga atggcatcat    4800
tctcaataat tgggttttg acataaggct tcagcaatgg atggtattag gttttaaaa    4860 tattgagcaa gccataccct aaaagaatca tttggtatta ggaaattatt taaagcaatg    4920
ccttttaggc tattagcaac ttttttttac ttcgttaata attaaatata ggaggcttta    4980
agtcgtttct cagattactt cttttttctac cctttgtgtt tacatgaggt taaacatcta    5040
gaactttgag atagaagatt tgtttgtgtt gtttgatgac ggggaaagat tcgggatgtg    5100
tgtctttgtc cattcaggct actataataa gttaccatag actgggtggc ttaaacacac    5160
agaaatttat ttctcatagt tccagaggct tggaagtcca agtcaacgca ttggcagatt    5220
tggggtctgg tgacggactg ttgcttggtt catacgtgac tccttctcac tgtgtcctta    5280
tatggtgaaa ggggtcaggc agttctctgg ggctccttct ttttttcttt ttctttttc    5340 ttttttggt gacagagtct cactctgtca ccaggctgga gtgtagtggc acaatctcgg    5400
ctcactgcaa cctctgcctc ccgagttcaa atgattctcc tgcctcagcc tcccaagtaa    5460
ctgggaccac aggtgcgtgc cacgacgctc agctaatttt tgtatttta gtagagatgt    5520 ggtttcacca cgttggccaa gatggtctcg atctcctgac ctcgtgatct gctcatcttg    5580
gcctcccagt ggggcctctt cttaaagggc actaatgcca attttaaagc ctcttccctc    5640
ttgatctaat catctcccaa tggccccaac tcctaacatg gtcacattgg tgtttgggtt    5700
tcaacataaa cattttggag ggatacaaac acccagacca cagcaaaatg tttgaaaacc    5760
ttctgttaga taaaactaca ggaaactcca agatggttca ttctatgatt ttttttaaat    5820
gtgagtatac attaatatta aaagggaaga tctgtttcta tgtcagagaa atatcaacaa    5880
gggaacactt ggttctaagc aggttgtctg taagcctact gtaggaagaa gttattttat    5940
gaaaagtaaa acaataaaaa taaaactttc atgttctatc ttgggagaga gaggtatctt    6000
gacaactgct gtttgtcaca gtagacagaa tgagattcag aatggcagac ccaagaagag    6060
gggcaataaa tatagaaaaa actacatatg acatgtgagt atatgaggaa atgtgattct    6120
ggagatcaaa agtgaaatca gaatatgaga tttcaggaaa tctagccatc ttgaggtagc    6180
tatagaataa ttttttaagca tccattttta attttcatga gtcttaaatg attacaaatg    6240
agcctctact agcaaaggtc tgggaaaaat tggacatgat tgccctgcca tgattgccct    6300
gccttgtcca tgattgtcct taaagagaat ttctttcctg gtttattgtt gtctcttatg    6360
atctttgcag ttgagtattc ctaaatgagg tgaagcaact agaacacaga aggactgaat    6420
atggcttgga agaactttgt aacaatggtg gttatctact acgtaattac agttttcttg    6480
```

```
tgattgcagc ttttataaaa tgtatttctc tcacagaaag acatttttata tagagaatac   6540 caaacttagt tttgggcatt agacctaaat tctatactga agaccaccgg gtctctttca   6600
ttatgtgaaa taaatgagat ttagcgccca gtagggtctg tgattattca actctactaa   6660
aagttgctcg agactttgat tttgcagaac acattaatat taattttgtt acttgaacat   6720
ttgcttttca tataacagaa tccacatgct tggttaaggc caacatatgc tgtttattat   6780
gcaggtttat ctgttcctga tgatacagca cataaatcaa atctaaatta aaccaatacc   6840
acttttcccc tatgccatga tatttgggga caatattgtt ggctaaggaa tcatgagaaa   6900
atgaaatact tttgcttgtt gaacaggaca cagtatattt agaattttt tgggagatac    6960 tcctattgac ctcaataata acaccattat tgaacaggaa ttttaggtat tcccattgta   7020
agtcctgctg ttgatgcagt tattttgctt agctttaaaa attttctag tagttacata    7080 tgatcttcca agccaatgaa atttaaaaaa ttaaattggc ttagtgggac tatgactttt   7140
tgcttatttg gttggttttt aaatctggga aagagagtat gacattaatc atatactgca   7200
catgtttgaa aaagtttggg gcactgattt tgttcttttt tgtcttcagt ggaataaaat   7260
gttggtgcaa caacattcag ataaatgttg ggtaatttct tatttgaaaa cggtttatta   7320
aactacagca tggaaggaat atggagagac atctttgtta atggtttta aaattgtctt    7380 tattaccaaa ccccttattt tcatattgag ctgtactgaa gaaagcattt ttgtgataat   7440 ttttgtgtt tccatacct ttattcaatg aggaaatatt tatcaagctc gtaaacacaa     7500
tacactttga attggcgact gtaagcctaa tcccaaggct ctcaaactcc catcataaag   7560
atagacatat tggcacaact aacttgtcaa atagatcagt acatctaaga ctcagctcac   7620
atattacccc ctctggacag ctttcatcta ttcattgagt ttgttttatt catttgcctg   7680
tttgtttcct tccagagcta gaagttatct tccctgcctg tcaactgtca tggcagtttt   7740
tatctctaag ctttggttgc aaggaacaga ttcattcaat tcacctcaaa gtaaaggcaa   7800
gattcttaca agatttctaa gggtttggaa gtggaatctc ctcaggacta aacaggcgc    7860 tctagctcga actgcaactc actctggggc tcagtggtct ctctacttgg cattttcatc   7920
cctctctctc tgcttttgcat gatccttggc gacacttgct ctacttccct acatcacctc   7980
ttactgaccc cactgctggg tttcttggct ctaattccca atgtaagacc ggctactttta  8040 cttttccatgc cagctcccct ccaggggttg tggcaagtct atgaaatgct ttctgacatt  8100
tgtcctgtag tttccactca tagctggcac ttggataagc aagacatgat gaatattgaa   8160
tcattctgtg agtgtctaat aagtggaagg tgagttttta aaacacatac taaaaatgaa   8220
gtgttcagga tttctgtttc tactaaagat tgtcagaaag ctggagaaag gagcatgata   8280
ctcaaaatgg gtttaacaat gcatcaaaaa tattgtctca ttcttttcaa cagaaattaa   8340
agtatttctg cctgaataat tagcaagata atgtatcaaa agaccatatg ttatgaaaat   8400
ataaaaaaag attcagtgaa ttctgtttga tcctcatcat atctggcctg tctgtatttg   8460
acagcattga acactcttgt cttctttacc ctttattctt agcttctaga atacccgtg    8520 ccttgtgtct cttcttaccc atcccccaac taattccctc tcagactcct ctgttggctt   8580
ctcttctctt ttctctgtct ttttaaaaaa cctgcttttc aagtattggt gacattgagg   8640
cgattgttct tggatatatt ctcaactatc caaccaccat gaccaatatc cttctctccc   8700
atgagattat cagtcaactg taatcataaa agctatgttt ccatcctcaa cttctctact   8760
aagttccaac ttcaggaat tttccgtatg gtttactgga cttttccagc tggaaaagtc    8820
atatgtaatc ctgccttgcc aaatccaact atttgtctcc acccctctcc cttgacactt   8880
```

```
tttctgactt ttgtattttt tatgtcaatg aacatttcca actagtcacc caagtcacaa    8940
agggtgaata attatctcct tccttgttct aagtcccgga gtaaatcata ttgtctagtc    9000
tactattttt actcattcag ggcttgtctc cagtctccat tccttctgct cttagtttag    9060
aacttccttg tatctcccat gactcttttc cctatttggg gatcattctt ctctgttcta    9120
tagtcctcat tgcttccaga gtgagttcac tagaatataa atatgtcatg ctactctttt    9180
taaaaaagc cattttaaa ggcttctcaa tgcccacaga atcaagctca tactcaactt      9240
gatgtcatca aagatattca gggatcatgt tcctcctctc tcctttgttc ttatccttcc    9300
ctttcacatg cttcttcctg tacctgtacc tgtacctgac ataaacacat aaagtaagaa    9360
gatctggttt gtatagaaga ttaaataaaa cacaatcttt caacattctt atgaagtctg    9420
tgaattaaaa ttatcacttt aaaattttat attaatcccc tataaactgt gtaaatattt    9480
tttacttctg ataaaacaca taagattatt tttagtaaag attgccataa tacctggctt    9540
agcaatagaa ggggtaacat atattttgg ttttgaatca attaaatgac aaataaaata    9600
tgctactgtg tgacttatga ccaataaaag gtgtaaattg tgtaacttga acctatgata    9660
tcttaattta tgatatagtc atattagcaa tggattggca ttttttttggt tgctcagaaa   9720
aagcaagaac aggccaggcg tggtggctca cacctgtaac cccagcactt tgggaggctg    9780
aggcaggcag atcacctgag gtcaggagtt cgcgaccagc ctggccaacg tggtgaaacc    9840
ctgtctctac taaaaataca aaaattaacc aggagtggtg gtgggcacct ataatcccaa    9900
ctgcttggga agctgaggca ggagaattgc ttgaacccgg gaggtggagg ttgcagttag    9960
ccgagatcat accactgcac tccagtctgg gtgacagagc aagactctgt ctcaaaaaaa   10020
aaaaaaaaaa aaaacaggaa tatatcatac atttaggaaa ataaatggag tccgacgttt   10080
cagtgctcct tctcctgagt gatttcagag actatttggg aacatgattt actgacatat   10140
gacgtggact gtaagaagaa tctgtataga aaagtggggt tggctgagaa aaatggttac   10200
tttcttcagt gtgaagagtt ttgaactaga taatttgtag gaaaggtcag aaattcaatt   10260
ttggctgctt aaaaatgcct ttgttctgtt tcaattgcat catcaaaata tgattttct    10320
cccctatcat ataagttctg tatgactagt tggacagaat gattgttaaa atttaccaaa   10380
ctaattttaa ggtttctagt cgatttgata tcatgttcct tgtataatca ataaacttta   10440
gatgattggt gttcttctaa agtcaacatc gtataagaaa taataaattc cttcctggaa   10500
gaatatactc agaccatata aaacaatcac tgaaattatt ttaatgagaa aaggtaaata   10560
ttttcaacat gtttatttca gtaggcataa aaatgaattg gccaatttaa ataagtataa   10620
tttatcaagt taactgtgta aaacccacaa aaaagttaaa caactaaaga tactactcta   10680
tttaataaaa taggtctatc tatgaaagtc tgtcttttga aagagattac tataagacaa   10740
gatataataa aaatgtaaag aagacataat agaacaatgt cctcctttct cttgtttttt   10800
gtttgttttc atttatata tctcctttgt gtatcatgat gtatatatta agactggttg    10860
ctctttctta tttttattc ctggaaagac tttgttgtt ttgtgtgtct ctgaattctg     10920
aagagtgttg ttatttttt ctgtcactct ttcttaaatc ggttttccca taaaattcat    10980
tcagagaaat aaaatgcaag cagctctttc taatactatg ccttaggagg aaatattact   11040
ctatgtgact tcaaaatttg gtctagtcta ttccaaaggc ttaaacagaa aatgtaagta   11100
gatacatgga agatacatat ggcactgcat tagctcacaa ctataacatg ttttggtcat   11160
gtgtattggt ttcctattgt tgccattaca aatgaccaca aaccccagtg taattatcag   11220
```

```
gttcttaact acttatgtca cactgttaga atgaccatgg attaacatgg attagtttgt    11280
cacaatatgt atggttttct ggaattgtag aatattagga tcagtgccat gtatagaaga    11340
atacttgctt ctttgagaag taggagctgt ctgtccattt ctggtccagg gactaaaagg    11400
gaaactaatg agggaggact gactataaag gtaacataat gtagtgatta attttgtcct    11460
agcctagggc ctaacgtgtg aggaattata tggtctattt gtagaactat acatagaaca    11520
cttgatcgtg cttctcagaa taagacaaag gcctctagga agaggtattt gcttcctcat    11580
tttctagatc ttaatttaag caagccaagg agtcagtgag atgtcccac aggatccgat    11640 ggttagtggg aacaccgttt aacaccaaat catcaaattg tagaagtttg atgctagaaa    11700
ggatcttgaa agaccatgtt ctctaccatt tttaacatga cagagtgtat acattagata    11760
aggaaaataa aaaaaggtg ccgagggtcc atctactcat tataatgggc acagaacagc    11820
aaaactacag gtggactgtt ctccacctcc tacctcctca caagttgcta acttgtaggt    11880
tagaactgta cttggaaaca ggctgtatat aatacttaca tataattgta ttcaactagc    11940
tattaaacat atataaataa ttttttatgtt tttctcacca catagcttta taattctttt    12000 tttttttttcc ttttgagac gcactgtcgc tctgtcgccc aggctggagt gcagtagcgt    12060
gatctcggct cactgcaagc tccacctccc aggttcacgc cattctcctg cctcagcctc    12120
ccgagtagct gggattacag gcgcccgcca ccacgccggg ctaatttttt gtattttta    12180 gtagagatgg ggtttcatcg tgttagccag gatggtctcg atctcctgac ctcgtgatct    12240
gcccgcctcg gcctcccaaa gtgctaggat tacaggcatg agccaccgcg cccggccata    12300
gttttataat tctgaactgg agtagccaaa gtcttccttt tctgtccttc tattccttc    12360 tccaccacta atttgtgtga tttggtctga gctgaacgag tgcttttggc tctaagaccc    12420
tagttactga taacagaatt ttctcagttt ttgctcatgc atttccccaa agtacagctt    12480
ggaaaatcaa gtcctgacca gcgaatagcc ttgaggttgg gctaatatgt tcaatgagta    12540
ttgtggctct tctctactga agttctctgc ctttctgtct atggtgcaca gtgtctacac    12600
ccatgctctc tctggatgct ttagtgtcat gatgggtttg gtgttccagg gtgtctgggt    12660
cacttctcac ttgaaaaata aattgaaaac atcctttcgc cactctgaag tgtgatgcta    12720 cttttccacgt tttatcttta aaatttgttc taaaagaatg gctgggcggg gcgcggtggc    12780
tcacgcctgt catcccagca cttgggagg ccgaggtggg cggaacacga ggtcaggaga    12840
tcgagaccat cctgggtaac atggtgaaac cccatctcta ctaaaaatac aaaaaaatag    12900
ctgggcatgg cggcgggcgc ctgtagtccc agctactcag gaggctgagg caggagaatg    12960
gtgtgaaccc gggaggcgga gcttgcagtg agccgagatt gtgccactgc actccagcct    13020
gggcggcaga gcgagacgcc gtctcaaaaa aaaaaaaaaa gaatggctga ggggtgatga    13080
catttaatca atgtatatcc aatagtgggg gaactacaca tgtgcaacat acagaagaat    13140
gaaattcaga aaaacaagca gattaaaaaa tatacactca ctacccaaac acattttggt    13200
atgcagactt tgccatatt ttttaagaag tttgatttgg ctgtgatctt actactttcg    13260 tgcattttg tttttttccac ttataacaca tatatctatt cctcatattt taaatattgt    13320
ctccttatta ttccacaaag tcaactttc ataacatatg tggtaatctt tctaaagagt    13380
tcgaggagtt gtttctgcta attttactgt aataaacaac tttgtgcatt gtcttcccag    13440
ccttcatatt taagataatt ccttagaact attgtcagaa tctatgtggt agtttgcaaa    13500
attggccaga ttttttccata cttcctgcac ttacgcccct ttgcaatgtc attgagaaat    13560
ttttcccatc aagagtgaag cctgtttctc cactacttga atcagaactt gtgactcgat    13620
```

```
tttaccaata aaatgcagca gaagccatat tcagtggctc acatctgtaa tcccagtact   13680
ttgggaagcc aaggtgggag gattgcttga ggccaggaat ttgagaccag cctgggcaac   13740
acaggaagac actgtctcta caaaaatctt tttaaaaaat atccaggcat ggtggctcat   13800
gcctgtagtc ccagctacta gggaggctga ggcaggagga tcacttgagt ccaagagttt   13860
gaggctgtag tgagctatga ctgtaccaat acactccagc cctggtggaa aagtgagacc   13920
ctgtctttaa aaaattaaat aaaataaaca gagcaggaat gccaactgtg ctagttccaa   13980
acctaggtct taagaggtct tgcagcttct gctctgattc ttgggctcct tccagctaga   14040
ggttcagaac tcatttgccc ctgtcactcc agctgattgt cagccaattg cagaagcagg   14100
gctgccttcg tgattgacac gtgatacaag tgcacaagtg agcccagcat gaccagaacc   14160
actcagttaa aactataata ataaattgtt gtcatttat ttaagttttg aagtggtttt   14220
cacagcaaaa ccaactgata caacctattt ggccaaaaag aataaatata tttaagcctt   14280
ataatttgta ttgatgagtt gtttcccaaa accgtggtaa aaaattgccc tatcaatagt   14340
tttgctgcct tcatcagcca ggcttatatc attgtaaatt tttgctagtt tgataaaaga   14400
taattagtat tttgttttaa ttttaagtgc aacattttaa aacccagttt cttcttaccc   14460
caatgaaata gttactaatt tgatgtcatt tcattaaaac aagtcacatt ttgctgtgaa   14520 tcttttcca aattattttc ctagaattaa tataatattt gtcaggttta tttcctctta   14580
gaagatatag agattgcagc acagatttta atttttaatt tgctaaataa ttctttataa   14640
agtctaagtt gtgacccttt tcccagatat ttttaattca ataactatca aatttatgaa   14700
aatgaagttg gttttattaa agtttctact gacatcatct tactgcattg gatgttgatc   14760
tcagtgattg cgactattct aagttgttaa aagccatgta atcattattg gctcacaagc   14820
aagcaaatga ggtaattgta ttcaaattgg aaaatttgct tctaggtaaa gtgtatgcac   14880
agaaaatata gacaaagtat tggccattat acttgacaga cttttgaagtg ttgccatcac   14940 ccaatgagtt ttcattgcat acagaatgaa agaaaaatta catcatttat gttgtctttg   15000
gccgtaggta acagaaaacc cacttaaaca gcactaaatt atgagactca ttggttggac   15060
tgatggttaa ccaattcata tctggatagg aagagtagtt tttaaaaact tgaaatactt   15120
tttcactgat tgctaaaaaa aaaaaagaat aatagtaact tcaataagta gtaaaattaa   15180
taaaagaaaa ttagtaaata aaattgcacc tgctgcctgt ggccacaaga actcagtgat   15240
atatattaat aaaattttatt tagcttatgg ttttatgaga ttcaggtatt ttcgtgtgag   15300
ctcagctaat ctcagctggg tttgtttctg tggctgctgt tagatacatg ccagctaagg   15360
tgtctttcct gatttggctg gccttgctca catatgttgg ggctggcact ggctttgata   15420
actggagtaa ttcaactctg ctccacctgt ctcaccttgt agaaagttag tccaagtatg   15480
ttctcatagt aaaggcagag gagcaagcac atgcctagtc atacatgtgt ttttcaagcc   15540
tctgcttgga cacgcttact aatattccat ttgtcaggtc actttgtggg tcccagagac   15600
aaagtggatg gcactgcaaa ggtacatgcc ccaaacacac agatgaatgg agtggtgaag   15660
tggtaagatc attgataaca atcaagctac aataaactta ctgattcaag tgaattgtca   15720
taggatgcta ttgataaata gtcctctact tggaatgaga tccaaaacat tagcagttcc   15780
actcacctgg tgtaatcatg tcatggtaag aagcatatgc attctctaaa aagtgttcta   15840
tgttttagga gaatcaacat tttcatcatc ctttagttaa acaagcgcca ttgtttggaa   15900
ctacacatac tcataggaat ttattgggat aattgagagt ttgaatagca atagatgcct   15960
```

```
atgtaataaa catgaatctt tagaatttgt gagagcacag caaaaatata atgaaataaa    16020
ataataaact gcctactggg ccatcttctg atgctaggta aaaatcagaa agtggaatat    16080
gttttgataa tgtcaagaat taatataaaa tataacaaat cattttcatt tattgaataa    16140
aaacaattat ttcaacaaat gtataagtag cttaccattg cttttaagca ttaaaattgc    16200
ttaaactttg tgtcaataat agatgaaagt gcttaacaca tgtatttcat tagtatgttg    16260
atcatgttcc attaaagctc atagttgtaa tgaggaaaat ttgcaaacat caaacaggga    16320
aaattggcaa acatcaaaga ggaaaattgg cctcgcatgg tggtatgcat ctgtagtcct    16380
ggaggctgag gcagtaggac cacttgagcc caagggttca gtgcactgtg atcgcacctg    16440
tgaatagcca ctatactcca gcctgggcaa catagcaagc ccctgtcttt aaattaaaaa    16500
gaataaagaa ggggtggatc atcaatcctt tcaattcaaa tgaaattgaa attatcaatt    16560
ccatttcata tatcacatca atcactttca cataataacg catttgaaat aatatcagct    16620
ttcaaacctt ttttaaagaa tatcaataaa gaatataaaa atttagaaag taccatccaa    16680
acttcatttt acattagaaa tactcaagca tttctagata taaaatatta atagtgcata    16740
acaaaataat attatgtgca tattattata gtccagattt atgtatgact cacttggaaa    16800
catacttttg gaaacagttt atgaaacttt cccacttttg gaaaatgtg tgtataaaga    16860 ctagaatttc aattatcact gatgaagctt caattatttc acgtaaaagt gattaataat    16920
tcacttaaaa tgtgaaattc aagactgaaa atagtttat gtcttcttat tcatcatgga    16980
actagaagaa ataccagaaa taataatata tcaatcttta ttttctttat tcaagacaag    17040
taattggcaa atatttgcat aaaaatctta tgatatattt tcatgtagtt gtgttaacaa    17100
aatctgaagg acaggttgga gtttaggcta aactgtcata aaagttttg gatatttta    17160 tttagtacca cattgttata ttcaattatt tctgggtgag gtgatagaag atgtaaataa    17220
aattaaattc ctttcttgat ggattttata ctattatcat atattagata aacattagaa    17280
ttaaatgata tactaactgg ctgggggaat tgacctaatg aaaattgagt catatacctc    17340
tatttatagc ctgattcact agaatagcaa acacagtttg gaaattttat caaatgttga    17400
atattcaata gaaattgtga agtggaaata attaagaaat tggaaagtgg acttttaaaa    17460
aaagatttgg gttaaatta ttatagtttt atagctttca ctactttaac ttgaaaaatt    17520
tttgttaaag ctggcagatt aatgcatgat aaaagtgatt aagcttataa aactaaataa    17580
tgctgtgaaa gagaagatgt agaaataaag gcatatgatt taacagttga ggcaaaatag    17640
ttataataaa aagactgtta catacactta aattacgtaa aactgatatc acaaatgaaa    17700
tatttaataa atttatgac ctttcaattt attggatcct gacattttc caagtaatat    17760 taggtagatt tatagtttta agattaacat accaataaaa ttaggctaag taattaaata    17820
tgatattcta ataaatatct tatgaattag tagtacatga atttaatatg taaaaatcag    17880
agtattataa aaactagaaa cattttggat ataattttg gtagtttacc agacatgtag    17940
agaagatcca gtataattaa ttacattttg tgtgtgaaga aaaattccct acctgtttag    18000
actatattac ataataacta acatttttat gaggaatttt tggaaggagt tgatatagtt    18060
tcttatgtca aatcatgact caaaaagaga cattatttag ctagaggcag tcacatcaaa    18120
gaaaagatca taacactcta aacatcaaga agcaatttag aagttattag aatgatttga    18180
tgagtgatat gtactgtaag ttatctataa gttacagcat acatcactta ataaagtttc    18240
aggctgggca cggtggctga ggcaagcact ctggagact gaggcaagca gatagcttga    18300
gctcaggagt ttgagaccag actggccaac atgatgaaac cctgtctcca cacaaaatac    18360
```

-continued

```
aaaagttagt cgggcgtggt ggcacggacc tatggtccca gctacttggg aggctgaggt    18420
gggaggattg tttgagcctg ggatgtgcag gttgcagtga gctgagacca cgacactgca    18480
ctccagctca ggtgacaaag taagactttg tctcaaaaag gaaagtttca ttacatatat    18540
gtacacatat atgagtagtt tattatatat tggcttatat gtacatatat aacatactat    18600
acaagttgtt tcatactctt aatatcactc agcttattgg ccctgtacc tggagtccag     18660 agacaggaag ggacttgggg caggctcaag ccggcatttc cacctgtttc tctctaaccc    18720
ctttggttcc gctcttctcc gtacggactt agttctttag cagaagagtt ccatattggt    18780
ggcaaaatgg ttgaagcaat cccaggggtc atccttatgt catgacgagc aaagaaagat    18840
tatctcctag cagcttttctg tccagagcag ttaaacttca tccccataac tttgcaagaa   18900
accgtcgcat cttgcatctt gttccagact gaatcgtgtg catgttctaa atcttgtctc    18960
tgtggtcaag gaatatcaca cacagtctgg tataggctga tttcttgaac aactccttgc    19020
tcagtcgatg gtatgctccc aggcctgaca ggtgcagccc tgaagtctag gtgatgcaat    19080
gaaaggggag ttgagtctgg cctctggtca catccagggc aaacacctg agttaacatg     19140 caataccctac tgtggcccac tatcagcctg aacttctagc tgcaacccctt gctgctatat  19200 tgcctgcacg ttaaaccccg aatcactctg aaccaagtat tgttcactga atcaacacag    19260
tagaataaag cctgtaaacc ccttttttctt catcacctca atctggaatg ttttctactt   19320
ccagtgcatc aaaatcctat tgccccctt tgtcacaaag ttgactttct ttgtgatctg     19380
agactgtatg acataaaaca acagattgac cctttagtta caaaaagtta agtaattcat    19440
tattcattgt cttggaaaga gtgaagatca tttgaatctg caaggatggt atgaaattgc    19500
ttggtttatt aatgtaaatt gaattgagat ttaattttgg ttgtttcctt gagaaagcag    19560
aaaaatggtt ttcctactaa atgagtattt cctactaagt gagggaaatt tagattggat    19620
cacgtgtgcc taacatgggc tgttaaatga ggaacaccta gagctttgag aaatatacgg    19680
tgaaatgtta ggattttttt ttttttttg aaatttcact tgaccgagat atggggcctg     19740
gggagagtat aaggaaaggg ctgtgtcctc tcctagaatg aattaactag gagtgggtca    19800
cggagctgtt tctggacata gtgcagtcca tgttattgtc tgatattcag attattcaca    19860
gtaatttttt ttaattaata accttcttaa ctatatataa tttttttatcc tttccttcct   19920 atacacacaa cacctaatat ggtgttccac ttttcctttt cccccatataa ttggacaaaa   19980 ccacgttgcc tctgattctt caatattggg tgaaattcag tcctccaatt ttactccagg    20040
tttggaagga cgagagacag gaatccagtt tcaagggact aaatgcaggg ccgaccaaag    20100
cctcggaggc cctccctcta ttaagtatct tctctgttac ccagttctcc agcagttaac    20160
tggttaactt gttaagatgt aaatctaaaa gaatccctgg gaaaatggaa cagtgcgaat    20220
ctagggttct aaaatttgta ttagcaaagg gtctaaaact cctttgttta cattgtctta    20280
attattaaag aatccaatag cattaaacag cttgagagaa tgtttgccca ggggaagtct    20340
atattttggg caagcaataa aatgttgaat ataaatgaaa gctatcctga atcctggcat    20400
atgtgtctct actatgttat ttgcttccag attttttcca aatggatact tttaaacata    20460
tttatcagaa tactaaactt atgcatctca ttttttaaat atgtcttaaa attttcccct    20520
tagttgctag ggtcttcata attattatta aatataatca attttccaag aaacactctc    20580
cagttttgta ctgcctaaac aaccttgcat tgtgatcttt tctcctttg aatgtatttt     20640 cttggactac atttccagaa atagaattac tgaataaatg gttggaaat atttacagct     20700
```

```
cataatatga aatgccaaag ttttcaaaa aagagtttaa aacaatttct atctcataat   20760
atagtatgta tatcagtttt ggttatactc cactattatg cattacattt aattatactt   20820
tctttagtct ttgtatttta ctgtcccact tccagactca aagaagatca tagcctcctg   20880
gagaactagg agagtgtatt tattactttt gtatttattt acttctctat aacattagaa   20940
caaggactaa cacatactaa gtaaacatta aatgtttgtt gcattgattt gaattaatca   21000
cgggaattct ttttgcagtt acagtaactg ccaaattact tcatgttttg gtgaattact   21060
ttattatgat tttagctttt tttcattaac tgagactcgt gttcctcttt ttagtgcttt   21120
tttgttttta atgaaatgct tcatgatttt ctgtgtcatc cttaaaagag acatgttta   21180 ttttctctgg attgtgccaa ttttaagata ttttctgcca aagcatgcat catttaattt   21240
aattttactc tttcagtaag caattatatg actgagttta cagttagtat ttgagataca   21300
attgaggtta aacatttta atgtgtgttt attaaaatga tattcttat ttagtgagtt   21360 gtttgctctt gagtttgccc atttgaatct ggagttttat ttgtaaaata attataatta   21420
aattttaaac ttttcctatt acattttgct ctagatgttt tttagctttt ttcaattttt   21480
gtttatggct aaaattcaga aatttcaaaa tttatagtc tcatttgttt tgagggagc   21540 agatacctct ttctcttaga tagttcaaag gttattgact actacttagc actgccacaa   21600
taggctaaat gtccagtttt attctatttg aggcattctg gatattatta atgctttgta   21660
tcatgatata ttgcactttt agagtgtatt tagggatggg atattattag tttgagtagt   21720
ccgcttagat ttttttaaa ctgggaaaac aattatctat tcatatatta attaaaaaca   21780
ttttattttg atgtatgggt cagttttag tttttctac ttttcaatat gatgtaatat   21840
gttgattttt gtaccatact ctttcaccta ttgattgttc agcatatatt ttaatatttg   21900
ctaagcctag tttctcccctt gtttgagact attctgaaat attttttatt aattaattat   21960
ccaaataaaa tttgtcacct gaaggctata gtccaaaaaa gagcttataa ttttatttgg   22020
gattttatta aacgttcata ttactttggg aaggtccaaa attatatatg actgttttc   22080 catccaggag catgattatg tgttctact tattagagaa taaatttctt tccaataaag   22140
ctttataatt tttgtaaagt atgtcctata tctctcatct atgttttcaa gttaagattg   22200
ccactttaat tactattgtg atgagatact tttaaattt tttttatttt ttttgagaca   22260
gcatctcact ctgtcaccca ggctagagtt cagtggcaga tgtctgctca ctgcacccccc   22320 acctccccag ttcaagtgat tctcatgcct cagcctcccg agtagctgga attacagtca   22380
cgtaccaacc caccatgccc acctattatt tatttattta tttattttag tagacagggt   22440
tttatcaggt tggccaggct ggtctcaaac tcctgacctc aagtgatcca cctgtctcag   22500
cctcccaatg tgttgggatt acagatgtga gccacagcac aaggcctaat tttttatttt   22560
ttttaaggca aggtcttacc ctgtcgccca ggttggagtg aagtggtatg atctcagctc   22620
actgcaacct ccgcctcctg ggctcaagcg atcctcccac ctcagtcccc caagtagttt   22680
ggaccacagg ctctcaccac caggcccagc taatttttttt ttgtagaaat ggggttttgc   22740
catgttgccc aggatggtct cgaactcctg agctcaagcg atcctcccac ctcagtttac   22800
caaagtcctg ggattatccg catgagccac tgagcccagc ctgagtgtta ttattatttt   22860
tttagtgtta tattgttatc ctgtctcatt catatatttg attacatgta atagctcgat   22920 ttccttgaaaa tgatatgcat cttctttttcc tgtaggtata aaatttcctt tcagtatatg   22980
ttaacagttg cttcagggta gacactatca tgacaagtta tcatgagaat gtccttccat   23040
tgaacaattg tgggattttt gagctaaatt tgctaggtca taatagatta gcctatcatt   23100
```

```
ctattcaatc tcatatacca ttttttaaag atctgcaatg aagcagaagg caaagtagct    23160
acaatgaagt tagaggtttg ctcaaatatt tcatggcctt aagccaaaat gcttatggga    23220
actctgtctg ctgcggcaat gcctactgac ttccttgcatt tcctgaaggg tggttagaaa   23280
gggatgccca tcatttcttg tgggttggtc agatttccca acacttccta cctgatgtag    23340
gtgtctgggt atggttgggg tttggaggaa tgttctcatg atctaacagt cagactttca    23400
cttatttccc tttgtgccat ccagcttctt gtcttttttt tatcagcggt ttctctatgc    23460
tatggcacag cttatctaga actctcaaag ctgaaaaaat tttgttgcac agactaaaac    23520
aggaagctgg ggttcgaata cttttgtttc agactttta aagcaatctt cctgttttat     23580
gccttcacct ccccacatcc ctactccctg tcctctggag atagtggtta cgttcgattc    23640
ctgagccttt ctggagtttt atggcacaaa tggacttatt tatcctggct tctttccaag    23700
aattcactta cctatctgtt actattattc tatccataag tcagctttca aaattttatt    23760
ggtctcatta gagtgctttt gttttctcat cttatttgtc cttgtgggct aatgatttta    23820
tttttttaaa ctatctgagt gtcatttttag tcaggtttgg ggaggagca gaggtgcaca    23880
tgtctgccat gttttttagg aagtctctgt catgatatat ttttatactg tctgcagtgg    23940
acagagccaa tgaactccct ggcatcagtt tttctgtact cattgttaac aagacatcag    24000
attaccaact atgtgatttt ggaggagtaa gctgttatta acccaaacta atcatcatca    24060
ttgtaggcga agaaggtgaa atgttttcca gctcttggct ttattttttcc ttgtggaggg   24120
acctcaggtg gaataatgct ccccacttct cactcagtcc tccttaagga aaaggaatga    24180
catctgatta tgaggtagaa aaataaagta agtgttctcc agtcagtccc atttcttctt    24240
attaggtttt ctcccctctg caaggcagct tggaataaac tcagtggtac aggctttgtc    24300
tcgatgaggg tctccagaca tctatagttg aaatgtgagc aaattcattt ggccatgagc    24360
taaaccatgt ttcctatcca gccagtcagt aaaaaggctt acatctccat aggtccatcc    24420
cctgtgtttt attttttcact tgtttctaaa cttgggcagg aaagaaaaag ctattatata    24480
tctactttca tctccaccct tgaaacaaat aaacaaaacc cagaccagca agttaatcct    24540
attcctcatg cagcaatatt tggtttaaca gtggacatgg agtctgggtc taagccatta    24600
gtgcttaaca ttcctctgac aatggcgatc ggttcagggt tgggcagcat ctatgttgct    24660
tctgcaaagt aaagaccatg actttccttt gattttttaa acatcaaaac atgtttattc    24720
tttctctgga tggttttgtg agaagccatt atactgggaa aaactgcagc aattttgcac    24780
ccatgacaaa cccagcaagc acatgaagga caaattctcc ttggaggaag agcagaggat    24840
ggagacagaa cccggataga attccatgtg aagtctacac tactcctaga cttttcattt    24900
gtgtggtgta ttagtctgtt ctatgctgtt aataaagaca catccaagac tgggcagttt    24960
ataacggaaa gaggtttaat taactcacag ctctgcaggg ctggggcagc tcaggaaac    25020
ttacaatcat ggtggaaagg gaagcaaaca tgtccttctt cacatggtgg cagcaaggag    25080
aagaatgagg gccagcaaa gggggaagcc ctgtataaaa ccatcatctc tcatgagaac    25140
taattcacta tcacaagaac aagacagggg aaaccacccc catgattcaa tttttctctac   25200
ctggtccctc ccgcaacatg tggggattat gagaactaca attcaagatg agatttgggt    25260
ggggacacag ccaaacaata tcatgtgggt taacacattt cttctatgt ttaaactcac      25320
ttgaagtggg tttcttacca ttaagagcat ctaatcactg cattattgag tttgctttc      25380
taggatttct gtaaaattgt cacattttaa ttacaaatga gtttccaaac agtgtttctc     25440
```

```
agaacataag cgttatgcct agtctgctca agcaaaatct ctgctcttgg gttcagattt    25500
actttcacaa gtcaaaattg gtttcatcct ggattaagtt tacctagcct taagacagga    25560
tacatggtag gccacatggc atgaatggca acaacgaatc agaggaatta ggagacttac    25620
ttcattgcta aaatggacat agtctcagga gatgagacaa gatgagcatg agccacctca    25680
gttcatggaa gctgcatgct ctggtggccc tgtcagcttt tacaccttgt aagattcata    25740
acattctcct catattcaca tgactggccc tcattctcca gtacagtaga atttcactga    25800
tacttgttac tcagtaaaca atttcagcaa tgaggatcaa atgtatggtc tggaatgtag    25860
taacaacaga tgaattctct ataatctagg gtctagtctg ctcctgtgac tcctttaatt    25920
aatatgcaag aaagatttta agaataccaa atcctatcaa tgaagtaagt ctcttaattc    25980
ctctgatttg ttgttgccat tcatgcaatg tggcctatca tgtatcctgt cttaaagcta    26040
agtaaactta gtccaggctg aaacctattt tgacttgtaa aagtcaatct gaactcaaga    26100
gcagagactg tgtttgagca gactaggcat ggcactaatg ttctgggaaa cactgatcgg    26160
aaactcaact tgtaagtaaa aatgtaacaa gtctacaaaa atcctagaaa agctaaccca    26220
aatcctcagc tatctctgag gctaacggtt aaattatgga cctactttta actctattct    26280
aaattagtat cctgtgaata tggacaacaa gaacaataat atatgtcagt tatttaagtg    26340
acaccaatta aagtgctttg catattattg tgtaataaat aatttggctg ccttttttc     26400
ccagttcccg ggagttatct tttaaagcct tagaattccc tgagtgacag gagagttttt    26460
gctattcata gtatgttctg ataggttatg ccaatgaggc gactcatggt gagctcatag    26520
atagtttatg ctaacaagat gactcaggat ggtgttgacc aatccagaga gactagccat    26580
gtttttagag ggttggaact tcgaaccatg tgatattagc ctgacctcca gggaggggag    26640
taggaactgg agatcaagtt caatcacatg gccagtaatt caatatatca tgcccacaaa    26700
atagaactcc aataaaaact tagacactga agctcatatg agtttccttg ggtaacaatg    26760
tgtattgtta cacaacaatg attgaaaggt gatgtgtcct gactctgcag ggagagagga    26820
catcagaagc tacacatttg ggaccttctc aggcttcacc ctatgcacct ctttttgctg    26880
atcctgatttt gtattatttg tgctataata acactgtaat tatatgtata ggactttcct    26940
gaattctctg tcactgtcag tctattaaat gattgagcat gaagagagag taggaacccc    27000
tgagtattta gcttgttggt cagaagtgct ggtggccttg gaactcataa gcttgtggct    27060
agttctgag gtgagtgaga ggtcttgtga aggactgtgc cctcagcctg tgaagtctgc     27120
ctaactctgg ctagtccatc gcaagtcact gcacacgtat taattcaatc agctctatgg    27180
tgtgagtatt ttattactct catcttacat acatagatta ataaagattc ataaataaca    27240
ttgataaatt gctgaatagt acatttcatc tcttcgtttt ataggttata taataaattt    27300
attttcatat tctctcagaa ttttacaac aaaagaatta tctgaatttt ttccttatgt     27360
gtctttaga aatttaagtt gtattgctga gtacatttta cttcctttgg tagaaacatt     27420
tttatcttac tttaagttct gggatatcac ttccttttt aatttgctgt gtaatttttt     27480
ctaagtccaa aattgtttgg aagatttcaa aggaatacag tggaatacat ttaaaggctg    27540
ccagacctca attcaaaagc taatgattat gttaaaccaa tttacaattc tttggagctt    27600
caatttcctc atttctgaaa atagagataa ttatacatat atagaataat gctatgaaga    27660
ggtacgagat aacatatgta ataaatccgg aaaatatatt aggtcaattt cccctttaga    27720
ttcaaacagc ctcagggtaa gggcaagcaa tctacatatt tttattagta taattctttt    27780
agggatgata aagttataga aagacattca ctcttctttc ttctcttcct tgggggttaa    27840
```

-continued

```
tttttcagtg tttgatataa tctcagagca gtgtatgtca gcgtatgggg atggggcagg    27900
ggagagagag agagagaact cttattttaa aataatttcc taacaagaga gcttttgtaa    27960
ataccagcct aaattgttat taatgagact ttcttatttc caaaagcctt ctgaagaatg    28020
ttgtggtggt catggattca caggtctcca tttatagaaa gcagagctaa ctaaggcacg    28080
caaaatgtgt tgccatgttt aggatgaggc cacacttcct atgtgttgct cccagccaat    28140
gactgagcac aacaagtcta ctaagtcagt cagcttccct ggagaaaggg gactctttga    28200
tggccatttt gcttgaattc tccattctta atctgtggtt gctttttttct cttttagctt    28260 actatggaaa tggaaaagaa ctgctgcttt gaaagttgat atttaagtaa ttgggaaaaa    28320
tttgagaaca tttatctttg aaatcctttg aaactatatt atctaaggat ttagtgtttt    28380 tattttttgtc agtaagtaag gtctatgttt atgttttggt ggggaaatgc agtaacaagc    28440
agacagaaaa taaccct taa tattcctcat tctgagttac tggcacaagt aaatatttca    28500
catgccatcc ctttcatata gatatattaa tttgtgagct atattaattc ttgttatggt    28560
taacatgacc ctattttctc accacttctg tcaaattaat aaatatacct gaaatttaaa    28620
tattgttccc tctatgtatt acaggttttt cccatgatag tggggttgga gggtaaaaat    28680
aacctgtcct tatcttttag ctaacccagg cacaacagga atacaacctt ttactacaga    28740
tgtgggattg ttcatgtcat ctactaatgc aaggtacaca gcttttgac ggcgttgttc    28800 taaaagcagc tatttctata gctttaaatt acatgcttaa atttatattt tgcaacctat    28860
taatgtcaga agtaagatag tattaatttc ctctacggaa ttctagataa ttagcacact    28920
tatatttcct cttatcttcc cctccttcct tcaatgtcat aaattttgtt aacatgcttt    28980
aaaatttgtg cctcagttcg tctaattaaa attattattt accaactgac ttttatatag    29040
catatgtcat tcagttatgt gaatattggc attttatatt ataatcattt taaatttta    29100 cctttaaaaa ttaattcaat acctggttgc cactgtaaat atttctttt atcacatggt    29160 gaggcagaca taaaacataa ggcataagaa ataggtcata gctattgaga agtatctgca    29220
ataagtagtt gataagggga acagagctat gggaccaggc atggggtata ttagaattct    29280
ccaaagaaac aaacaaatag gagatacata tattgagaga tttattatgg gaattggttc    29340
ctgtgattgc atagtccaag aaatctccaa aactgttgtt tgcaagctgg agaccaggaa    29400
agcagtggta taattcaatc tcacaccaaa aggccaagaa ccaggggagc agatggtata    29460
aatcccagtt acagtatgaa ggcctgacaa ccaggtggag agaagtggat gctggtgtaa    29520
atcctggagt ctgaattccc aaaaaccagg agattcaatg tcggagttta ggagaagata    29580
tatgtcctag ttcaaggagt gacagggaga gaaagaaaga aaaatagag agagaattca    29640 cccatcttct gccttttgtt ctagttaggt cctcaacaaa ttggatgatg tctggctaca    29700
ttggagagag tggattctct ttactcggtg ctaatgctaa gcccttccac aaacatccta    29760
acagactgac ccaagaataa tgtcttagca gttacttgag catccctcag tgcagtctga    29820
aagatgtgta cccctccac acctgccaaa cccttggaag gttggtggga aggctggatg    29880
actgtctctc ccaggtccta tgtaacattc ttgttttatt cctccgagtt tgtgaggggt    29940
attagcggaa tttgataaaa ttatctccac ttatttacca taaaattaaa gtacgttctt    30000
gcgaaaagga gttgtgttgc agcttatgtt ttgtcagttg gattcaaatt gtgttgtatc    30060
cgataatttt ttttttaagtt tgtgacatgt ggttttaata ttatactttc ctaaatccag    30120
gattgaagga gtttcccttt ctcttctagc ttctatttga tcttttggt tcattttag    30180
```

```
cgtagagttt gtaagtcggg ttcttacatt tctcttattc ccagaatttc atttcatgaa    30240
ttgcgtggac aactttctga aacttttgta gcatgacatg tctggataat gacttaactt    30300
acctcaaata tcttattggt gttcttattt tataatgtcc ttttttgtgac acagtttgtc    30360 ttgccttaat tgcttattac tacttaattg ccattactac taattgtcca aatgaataag    30420
aatgagaaat gaaatgaaa ataaatgag aaaagacat gtgaaatctc ttcattccca    30480
tactcttatc agcaaaacaa tgtttcaggt tatctgttcc ccaacatgga attcttccta    30540 attcccttc tgtcaggctg agattatttc ttgtgcacat aattcctcct gtggtctcat    30600
tattgctgca aaatatttta aaatatatgt ttcatagcct gaagtattag ggaagtgtca    30660
accaaactgc tcctgggaaa taaaatgaag tatatttgat tttaaatact ctttttttaaa   30720 aactcttgct tgttctcaag ctctagttag ttgaaatcag tgtataggca aaactaactt    30780
tttttggtct gttttgaaaa ccactgtctt tttagaatac aacatcatgt aattctgtag    30840
gtttaagaaa gattaagtat aacatagcat ttgtatcttt ataaactaa attctaatta    30900 ttaatactaa agaatggggt tgaggagatt tcattaagat gagtcaaaac ttactcctat    30960
ttttgtgttg ttgttattgc ttttgttttt gttttgtgta actttatcaa ccaacagtat    31020
gcaccaacct ccttttggca aaacagtgaa cattatatct ctcttaaatg atagtgcttt    31080
attatttgaa cttttttcaa aagacaacgt tattttaaca tgacgtaact taatattact    31140
ggagagtttt cattttagc agtttcagag cgctttatgt tagggtttta ttaattccca    31200
taacacattt ataagaaag ccttggaaac agcccttcac caagaaacgg ttaccattca    31260
gggcttgctt ctgtgagaaa acacctcacc gagagtctga aatgaccagc atttagcacc    31320
aatagcctca ctcccctctc ccacagtaat tattttatgga tgagcactta atgtcagtat    31380
ggctcacaaa tttggggtga ggttctagag ttgctgtctc acaaaatctt acattttctc    31440
attctttgca atagttttgc tatattttct gcaattgttc ctataatttc tgcaattttg    31500
ttccttgtat tcttatatgt ttttttaaaat ttagtttgtg taggattttt ttctttccaa    31560
accaagtggt ttctgacaaa gacaacctca aactcgggta agaaatcatg tgttgtattc    31620
ccagccctgt cataaatttg caataatctt gccataaaga actaggtttt tcttgtctct    31680
cctccccaag tattattcat aactctacag cgttatttca tctatatact ctaattttt    31740 gatcatctgt cttccttaga agaagcgatt atttttatttt tatcaccttg atatcttcag    31800
catctactat tgtggttggc tcaataatgt gtgcttgata acttttttgtt gatcaagaaa    31860 caaaccactg actatttgga gtacaagtca ctttataatt cttggatgca gtttgcttag    31920
aaggaatcag aatagagaat ttctaaagtt tcaactacta aaattttacc ggccaggcgc    31980
ggtggctcac gcctgtaatc ccagcacttt gggaggccga ggcgggcgga tcacgaagtc    32040
aggagatcga gaccatcctg actaacacgg tgaaacccca tctctactta aaatataaaa    32100
aattagctgg tgtggtggc aagcgcctgt agtcccagct actcgggagg ctgaggcag    32160 gagaatggcg tgaacccggg aggcggagct tgcagtgagc ggagatcgcg ccactgcact    32220
ccagcctggg cgacagagcg agactccgtc taaaaaaaaa aaaaaattac cattgatctc    32280
tagtttcctg tggttgacat ggacattttt ggttttcctt ttctgtcttg gatgttgttt    32340
tctgcagcta gccctttctt gtcttttgca tgtattagga acaaagtct agcttttggg    32400 atattctttt ctttgtttct gtctctccac atataatttat tttagaggc agtgtctatg    32460 tttgggcttc tataacaaaa tgccataaac tggatggctc ataaacaaca gtttttatta    32520
ctcactgttc tggagactgg acgtttaaga tcgaggcatt gacagggttg gtgtttgaaa    32580
```

```
tgtttcagca tgcagtgcta aggtttaaga attcagtgct tccttttaaa gagtcacatt    32640
ggtttgcaat taagtattag gaaatgaagt tctaatactg ctttgatgta agctagtgtg    32700
cttggcaatt tctaaataca ttaaaattga tttcagcaag atgataaaga tttgtagaaa    32760
aaggcaatta tgtttgcagt gtcacaaata tctttttatt atccttttag tcatttctcc    32820
tgagtgacta aacgcatttc tcctgagtga ctcaacgcat tggttgagtt ggtgtttggt    32880
gagggccctt ttcctggttc gtaggtggga cctctgtgaa agctcttata ggagctttct    32940
ggggcccctt tattagggca ctaatcccag tcatgagggc tccaccctca gaatataatc    33000
acctccctaa agccctacct cctaatgccc tcccactggg gattaggttt caacatatgg    33060
acttgaggag gacatgttct atctacatag caggtgattt ttaaaaaatg ctatagaggt    33120 cctacctta aaagaattta ataagaccgt tattttatag gtgattaata cgtgagatac     33180
aaaaatgtaa aaacactcat gtactcatcc cccagtttcc acaattatca acacgtggct    33240
gattggactt catctctact ttactcaatc ccccagccct gctgggtaat ttaaaagcaa    33300
gtattaaaca tcctatcaat taatctgtaa atattttagt gtgcaactct aaggtttaag    33360
aattcagtgc ttctctttaa agaataaaat tggtttgtaa taatttaagt attaaaaatg    33420
aatttctgat attgctttgt tgtaaactag cgtgcttagc aatttctaaa tagaaaaaaa    33480
ctaaaatata attgagttta gcaaagtgac aaatatttgt agaaaaaggc aattatagct    33540
aaagtgtagc aaatatcttt ttgttatcct tttagtcact tctcagtttc tagtctcttt    33600
tttcagtgct tggctaagat cagtagagaa ctgcaactcc tctcaaatgc tatgcattcc    33660
atcctagtgg tctgagataa ttctccaaaa gttacatcaa accttaaaact ttatagcaaa    33720 tcttactcct acataataac atggattcat gttcactga gcatagtccc taagtattac      33780
cctgggaagt cttcatccag ctgtttcaaa ttattttcat ttcatacgtc atgttaatag    33840
cagggaggag actattgcta atggttttt cttggaaatt aatctgtcaa cctggtgaaa      33900
gtataatgtt tcagcagata agaagggacc cttcagttta acatcctaag catattaata    33960
cacttagcaa aagcatagca agattaagta atcgattaga atttccatta agaatgcgga    34020
aagagcacat agagcggggg attaacagcc cttcaatgtg atgtagtcat aaaatgttta    34080
aaaaatacat ttagatttta ggtagtgatg gttgaattct aatgatgtgc cttgggcctg    34140
ggggtagatg tatataggca gtgtagtggc cagaatttaa tgtaatattt tatgatgtaa    34200
tatgctatac tgagcccgca tttgtggtgt tggaatgggg ggagattttt ccggtgagcc    34260
atgtataaaa taagcttatg atttctctga tggtagtcac tcaaaggatt ttcaaaagtt    34320
gttttatgac tttgtaattg aataagggtg cccaggattc acaatgtttt ttattaatga    34380
gttaggagaa atcttccatt gtgcgaaaac acagattta atcacaggta cagattgtta      34440
tagaatcaaa gacaaagaat gtaatggtgt atcagtcctg gaatgtataa cctcaaacag    34500
attgcaatat ttctctgcct ttggctgtta atgtactgct ttctccagca ttgaatatgc    34560
cagatacttg ttttcactt ctcatccaat aatttatttc atatccttt taattcactc       34620 gtcttttcac tcttaatgca actctcacac tgtagcataa acttaaagct gccataaatt    34680
actttcaatt ttgcatatat attttttcata atttttaatag cttgtgaata gactctaagt    34740
cagatactta taacattaga gttcagcaga ggtgagctaa ttttttctctt gtgatatatg    34800 gatagatctc cagtacagat aatggttata tttctatctt ttatctctat ctgtagcaac    34860
agatactccc tccagatatt tttcactgta tacctcaaaa acttattata ttttttggatt    34920
```

```
attaggcctc ctactgtaaa ggagtataaa atagagaaat cttattgtac tgagaaagag    34980
gcagatctta aatgtcagaa gggaagatgt cattactctt tcccatcctt aggtaccaaa    35040
agcggatgct tattaataga taaaaagtag agtgttccta atacatatta agaattaggc    35100
aaataaaaat gaaaattgtt ttcccactta cacagtaatt ccacttcaga gaatctaagg    35160
aaaacagata agggagaaaa attgaagcac aggataagtt aattacagaa tttttatgat    35220
agcacagaat gaaaatgtcc taaatgtttc attaaaagta ttaataaatg gttcagtaat    35280
gacaagtaaa ttttggaaca catattcaat ttgctataga ggtatatatt aattactcat    35340
ttaaaatgac aagaaaagtt atgtaatttt atggaaattg ctaaagatgg gataattact    35400
attatagaaa acatccacaa gaccttagac aagcaaaaca aaaatatgtt gataaagact    35460
caaatctaaa acctcaatct atgaaactac tacaagaaaa cattggggaa aatctccagg    35520
gcattggtct gggcaaagat ttcttgagca ataccccaca aacacagaca accaaagcaa    35580
aaatggacaa acaggattac atcaagttta aaagcttttg cacagcaaag aaaacaatca    35640
acaaactgaa gagacaacct acagagtggg ataaaatatt tgcaagttgc ccatctagca    35700
aaggactaat gaccagaaca tataaggagc tcaaacaact ctataggaaa aaatctaaaa    35760
attcaatcaa aaagtggaca aaaaatttga acagacattt ctcaaaagaa gacatacaaa    35820
tggcaaacag gcgtatgaaa aggtgctcaa catcattgat aatcagagaa atgcaaatca    35880
gtactacaat gagacattat ctcaccccgt taatatggct aatatccaaa aggcaacaac    35940
aaatgctaat atccaaaagg caataacaaa cgctattatc caaaaggtaa taacaaacgc    36000
ttatatccaa aaggcaataa caaacgctaa tatccaaaag gcaataacaa acgctaatat    36060
ccaaaaggta ataacaaacg cttatatccca aaaggcaata caaacgcta atatccaaaa    36120 ggcaataaca aacgctaata tccaaaaggt aataacaaaa gcttatatcc aaaaggcaat    36180
tacaaacgct aatatccaaa aggcagtaac aaacgcttat atccaaaagg caataacaaa    36240
tgctaatatc caaaaggcaa taacaaacgc ttatatccaa aaggcagtaa caaacgctta    36300
tatccaaaag gcaataacaa atgctaatat ccaaaaggta ataacaaacg cttatatcca    36360
aaaggcaata caaacgcta atatccaaaa ggcaacaaca aacgcttata tccaaaaggc    36420
aataacaaac gctaatatcc aaaaggtaat aacaaacgct tatatccaaa aggcagtaac    36480
aaacgctaat atccaaaagg caataacaaa cgcttatatc caaaaggcaa taacaaacgc    36540
ttatatccaa aaggcagtaa caaatgcctg tatccaaaag gtaataacaa atgcttatat    36600
tcaaaaggca ataacaaacg cttatatcca aaggcaata caaacgctt gtatccaaaa    36660 ggcaataaca aatgcttata tccaaaagac aataacaaac gcttatatcc aaaaggcaat    36720
aacaaatgcc tgtatccaaa aggtaataac aaacgcttat atccaaaagg taataacaaa    36780
tacttgtgag gatgtggagg aaagaaaacc tttgtacact gttggtgaga atgtaaatta    36840
gtacaaccac tattgagaag agtttggagg ttcctcaaca aatctaaaaa ttgagctacc    36900
atataattca gcaatcccac tgctgggtat atatccaaaa gaaaggaaat cagtatatcg    36960
aagagacact gtactcctac atttgttgca gcactgttta caatagctaa gatttggagg    37020
caacctaagt gtccatcaac cgatacatgg ataaaaaaaa tgtggtacat atacacagtg    37080
gagtactatt tagccataaa aaagaatgag atccagtcat ttgcaacaat aacatggatg    37140
gaactggaga tcattatgtt aagtaaaaaa agccaggcat agaaagacaa acattgcatg    37200
ttctcactta tttatgggat ctaaaaaagc aattgaattc atggacatag agagtagaag    37260
gatggttacc aaagggtggc aaagctactg ggggttggta tagttaatag ctacagaaaa    37320
```

```
gaagtactta gaaagaatga ataaggccta ctatttgata gcataatagg ttgacgatag   37380
tcaattacga cttaattttta catttttataa taacttaaag actaaaattg gattgttctt   37440
aactcaaaga ataaatgctt gtgggatgta ttattacccc aatgctatta ttaccatttt   37500
ccatgatgtg cttatttcac attccatacc tgtatcaaac atctcatgta ccctataaac   37560
atatacatct actctgtacc cacaaaaatt taaaaaatat gtattgaaaa aatttttttaa   37620
gcatttatag tggttgcatt tggtgataat acaatggtgg tttatttctc ctatttgctg   37680
tgttttctca gttttttgatt acacagatgc agcaccacta cttaaaccat gtcttgggaa   37740
aggttaaaca acttaatgta agttagtgac atcctgtaag cttaattcaa tttatgtgac   37800
ctaaaacagc attctgctat gagaaagaaa tgtaattaat tattttgaga tatatgttgt   37860
agctattata cagtaataaa atgttagtga gagaagctag gtgtggtggg atacacttat   37920
ttattgtaaa attccttcaa ctttattgaa agcttgaaat attttatgat acaatgttag   37980
ggaggaacaa caaaaatatg ctctgagttt ctgacaacca ccttacagtt aagctttcag   38040
agcatcattt ctacgcaagt cggaggcagt cagtataagg tccattattc attcgtaatt   38100
ctgttttttcc tggtataatc taattagatg tgacatagtc aaatattggg ggttatacaa   38160
attgatctgt taatatgtaa ttttttttctt gtgcttatgg ccattttttac tctaagtttg   38220
attctatggg ttaactataa tattttatta ctcattctcc taaatattat ctcttctatt   38280
atctgcccctt aaaatttctt aatatgttga tgtaatattt gaataattta tttataggga   38340
aacaaaagta catttttcat aaataatatt actatgtata tagtaataga agtctatgta   38400
ttcacatgta tgtaatatat atttttttcct taccacagtg ctgttttata ttttttaaata   38460
acctaaagtt tttttttttctt tttttttttct ttattattat tatactttaa gttttagggt   38520
acatgtgcac aatgtgcagg ttagttacat atgtatacat gtgccatgct ggtgcgctgc   38580
acccactaac tcatcatcta gcatatgtaa tatattatgt gttatatagt tatacaatta   38640
aacattatta agaagatggt aaccagctgt tctccttctt cagtgatgca acagagctag   38700
aatgaatggg gctgggaaaa atataaagca gaaagaattt cattatgcac atgtatttaa   38760
tttgggaaca atacatgttt cagtgaaatg attgtgtgta tgtatatgta taatataggga   38820
atatagaaat aattgccttg agaaggtcta tttgaaaatg catatgtact aagttaacct   38880
aaaatataaa aattttcttt ttatgagctc atgaactgta aaaggctaca ggcaatatat   38940
atttattatc ctgctatcag gatattaata agataaaata tagatcactt caggtgtgtg   39000
tttcctttgt aaatttttaa attttagcat ttttttaaagc acatggatta aaaaggtgaa   39060
ttaagctaat tcatcaaggg agacagaaga tctatgcaaa gcctcctaga gtagtctttc   39120
tgaactgaca tttttctttg gtcaatattt gctgctaact tttagatcaa tcctttgaaa   39180
ttatacatttt gttgggattt tctttggtc aacatagtga caggaaatga accaatgata   39240
taaatttatg tttaactttc ctaaattcaa ctttatctag agacttcctt ttggttcctt   39300
gcttataaac atatcccctt gaagttattt acagtttaac tatcattatg ataaaaatcc   39360
ttctacttat caaaaaatat tttatatata cagagctaat gaaatatatc gcctctgtgt   39420
gtacaaaata tgaagttaa tatgtaatgc aaaatatatt tctgttaaca ttaaatcaga   39480
ttacaagtaa tagaaaaatc caaatagtgg tgatttaaac aagacagaat tgtatttctt   39540
cctcaaattt atgaagcaga gagataattt caggctcgtt ttggtgttca aaagacactg   39600
aaattccttt catcttgttc tgttatatat ggtttccact gtaaaggtta actcttaatc   39660
```

```
caagataact gctgaagttc cagccattgc atctgcattt cagccatcag gatggaagaa    39720
ggcagaaggg catgcccctt ttattttaag gcacacttcc tgaaatttt  acagaacacc    39780
tcagtttata ttttattagc cagaagttag tcacatagtc acacgtagct atacaataga    39840
ctgtcaaatg tagtctttat ttcatctggc tatgcaccaa cctgaaaatc atggttacct    39900
cactgtggta gacaaaacag tagcctccca aagatgtcca tgtcttaata attttacaga    39960
gcaagagaga ctttgctaat gtgattatat taagaatctt gagacaagaa gattatcctg    40020
gattgcacag aaggcccagt ataatcacca gggtctttaa aagagtgaag ttcagaggag    40080
atgggatgat ggaagcagag attggagtga agtgtgtgaa gatggagaag gacgtaaaaa    40140
cctaaagaat gcaggtgacc tctagaagct ggaaaagaaa aggaaacaga ttcttcctga    40200
aagtctttgg aaggaaccag tcctacaaac actttaattt tagttcttta agatgcattt    40260
agattttcaa ctaccagaac tgcaagagaa taaatgtgta ttacttttag ccaccaaatt    40320
tgtactaaat ttctatagga acagaagaaa ataaatatac ttatgaagga aaaggggttt    40380
atggttatta ggcccttaa  tagtctacca tacattttct tttcttttct tttcttttct    40440
tttttttttc ttattttttt ttttgagacg gagtctcact ctgtcaccct ggctggagtg    40500
cagtggtgtg atctcagctc actgcaacct ctgcctccca ggttcaagcg attctcctgc    40560
ctcagcctcc tgagtagctg ggattacaag tgcccaccac cacgccaggc taattttgt     40620
attttagta  gagacggggt ttcaccacgt tggtcaggct ggtcttgaac tcctgacttt     40680
gtgatccacc cgcctcagcc tccaaaagtg ctgggattac aggcatgagc cactgtgccc    40740
ggcctactct accatacatt ttcagtggca tatccataat tttggtcctt gaatctatct    40800
atagttttt  catatttgga ttcagcagtc aagtgtcatt ggcaagtggg taagaactct    40860
aaacaggctg cctaagtaca tagggctcag tttaagcact tggtaattga gaacatctat    40920
tacacagcca ccagtactgt gggagaaggc ctccctcaag tgctttgtct agtatttgca    40980
tgcatattcc ctcaatccta gcatacaaca atcaaatagt aaggcctgga attgaggcca    41040
gagagaaaga gagaacaaaa aacctgggtg tgttgaggag gaggtcccag agagtggcct    41100
gtctctattt gatgtcctgg tcctttctct tagtgcctgg tagtctgtct cctaggtctc    41160
cccatctgtc tgagttcacc ctccattgcc acttctcagg ttgatgattt ctgtctgatt    41220
atctcaccac tcatgctgat cactgctttc taaagtggat tttggtgttg ttcttgaccc    41280
tagattattc ttcaactcaa gttttataca ttggctgagt attaattttc ttttgttaat    41340
ttgagacttg ccctctgtag tagatagaat aacgttcccc caaagatgtc catgttctaa    41400
tccccagaac ctggaagtat gttgcattat gtggcaaagg agatttagaa ttgcatatac    41460
aattaaggat gctaatcagc atatgctgag attaccttgg attttatctg agtgggccca    41520
ttgtaatcac aaagccttaa aaatagaaga gggaggtgga aggtttcagc atatgaggga    41580
gatataacta gagaagaacg atctgtgaga tgcaacactc ctgggtttga atctggagga    41640
agaggccacc agccagggca tgtgggtgcc ctctagaatg tggaaaagac aaggaaacaa    41700
attcttcctt agagcctcca gaagaaacac agcactgcca acactttgat attagctcac    41760
aaaaacccat tttgaacttc tcacttccaa aactgtgaga tgataaattt ggcttgtttt    41820
aagccaataa atttgcaaac atttgttaca gcagcaatgg gaaactaatg atatatccgc    41880
caacctgttt aaaaaaaaaa gacttgagag attagaggtt aaagcactga ataagaggag    41940
acatttatgg gagagaaaaa aaatccctct aacggaagca gaggcagcac aatttataac    42000
acttgtgcaa caaattttgc ttcacatttt ctggcatcaa aggcaaaaag agaaagatct    42060
```

```
ttggttacat agttttcatt atctgatgac agcatataaa tgcacctgaa aatgtagcat    42120
ttttcttcca aatgtactag aactgagatt cattgaagtg tccttgctta aagacactg     42180 gcaaaactga gggccattct ttgaaccatg gtttaggaaa agatagagtt tccactggct   42240
cctaagggag caaagactgt gttgtgattt tgaggtcatc tgagagaggc tccagttatg   42300
tatgcagaga ttttgctttt tgaaagtctt aatgtagaga tatctcctga aagaagtagc   42360
tgaaagaaaa gttaatttag ctgattaaac accaattttc tgattgcaag gagagtaaag   42420
cagctgtgtt ctccttttgga gaagaggtct tttagacaga gacaggcttt aatgaacttg  42480
aataagtcct gttttaggca aatctcagtg aagaagaaaa gtaagggttc aacaaagagg   42540
taagttcagg gctgccattc ctcatcacag caggcaaggt agcctggatc actgctgcca   42600 ggaggggat gctgcccaca accgcggccc ctttcctatc tgccaagggt aggaacccaa    42660
gtcccagcag gtgaagcaga actgaattga ataattgtca tatataactg ctttatatat   42720
aatgctgcaa gctttatcca ctccaggcca gagttggatg gtatgaaaaa agaaagtgta   42780
attgcatagt ggtggctttc tattgagaca cttggatgga tgctaatatc agcaacctgt   42840
taccaagata aacagttaaa aaaaaaataa gtcctggaag agttaacatt gctctcaaaa   42900
ttcagagttg taagataacc tttagccaaa ctctaccttg ttgattcagt cgagaatcac    42960
acgttttcca taagattggt gggaggctgt caatgcaaga gccagatttg catctgtttc    43020
ccgaactata tctgccttag aagatttcac agcagggacc agtttatctc atatgtattt    43080
ttaatgctaa aagaatttta aagttttctc agtttttttt taaatacttc cccaccacca   43140
gggtatattg atcttcaaaa ttctgcatca tataaacagc aaaaaacgat ttttttttt     43200 gagatggagt ctcgctctgt cacccaggct ggagtgcagc ggcgtgatct cagctccctg   43260
caacctccgc ctcccaggtt caagcgattc tcctgtctca gcctctcgag tagctgggac   43320
tacacaaaaa atgatttat tctaagtgct atttagatta ggatatttc agggagactg      43380 aggaagatga catgcatcga gtacattttt gggggctata caccaaggaa gatgttttaa   43440
catgttactt tatttcatca ttgtgacaac attctaaaat aggtttgatg attgatctct   43500
gttttataaa tgaataaatt tcatctcaaa gcagaaaagc caagattgaa acctgtgctt    43560
cctcccaagc ctgtgctttt cttactacct tactttgcta tttagtttat tgaattttca    43620
cctcagaaat acacagttaa tttttttaaga aagaaatgaa tgtaatgtgg ggaagttctt   43680
taatctctgt aactccatat tgaaggaaga caccacaaat gtaaacactc attaaatatt   43740
aactgaggaa gtatctacat ggtcttcacc atctggaaga atgtgggaaa aacaagtgaa   43800
taagccaaat gttcctgaat atctgtacat ttggcatcat gttgctaaat gatgcatatg    43860
cttggtgtca tttctttta acattttatt tagttatatt tgttattaaa aatacagtta    43920
aaagaaaagg tccccatttc ctttcccaac ccatttaata aggagtagca atcttaaca    43980 cattggttgg tatcttccca gatattttaa attctgatta taaatgtagt attcatgcat   44040
gtgcatgtgc acacttgtac acagaattat gcttattgtt ctgtgctctg ctttttaagg   44100
gaattttgtc aacattttc tgtatagata actatcttat ttcctttgtg acattgttgg    44160
attgctaagt gtcatttaca cagagctcaa gatggtataa tcttgtaaat attgtgaaga   44220
aaacaatgta ctcaaaatct cgttctattt cacagaaaac attaagataa gtaaaaacag    44280
aaaagcatta tacatgattt attaagtttt atgtcaaaat gcacttatga attgtagtgt    44340
tgctaaagat ggtacttcat ttagtgtgta gttttggcaa gttttttgac taatattaag   44400
```

```
attacataag ttaggattgt gttttattac atgtaatata tggcgacttt aaaatattgg   44460
agattatttt gctcattttg ggaaaaacta ctcacggccc agctactgaa catctgttca   44520
ggaatatgaa ctaggggagt gggtaccata atttattcgt agctcagaaa ggcctattcc   44580
agttctcagg agaacgtcaa ggcaggacac ttgtgtggag tgaactgagg atggtgatca   44640
ggcaatagtt cacaaaaagg aaagcaggct cttcatcaac ccataaaaag acaaggttca   44700
agctgacatt aattcctcag tacaagaaaa caggacaatg caagaggga tctctgccat    44760 gatctttatc tgttgagtca cactattgcc atctggacat gttgcctctc catgtctaga   44820
gtacaaatgt tgttctggaa tctccccttta ccttggaagg aaatcaagat ttctgtcacc  44880
tctcttctat tttgggttcc atgacactgg catctcatat ctccctcttt tgcattttt    44940 tctttcattt tggtgaagct tagcttccac tacatttttt taaagtttat attagattgt   45000
aacatatata cagtagacaa atcttaaat gtgcatcttg ataaaaactc acacatgtac    45060
acacttgtgt aactgccacc cagattcaga tataaaatct gggtttcctg aacccaaaag   45120
attctcttgt gctccttttt agttaacatt cttttttccca accaaggaaa cactattctg  45180
acctctatca ctatacagga gttatacttg ttcttaactg tcatataaat ggaatcatat   45240
ggtatatata gttttgtgat tgactccttc ggctcaacat ttgtgttgtt taacatggaa   45300
atagttcacc cattttattt atgtgtgcaa ttattttgcc cattctatca ttgatgcact   45360
tttgggctat ttcccaaata ttcttatgca tgtcttttgg tagaaatacc gttctgtttt   45420
gcttgactgt ataccttgag gtggaattat tggatcactg ggcgtatata tattcagatt   45480
tatttgatct tggcaaagag tgggtgtacc aatttatagc caaattagca aagtacaaga   45540
ggcttgattg attcactta ttgaaaacac ttgatattgt cacgggcttc ctggttgtt     45600 gctttgccag ccagacacct ctgcggctgg tggcacctt gcccaaattt tgcttgagcc    45660
cactggactc attctgccca cttagcctgg taggctgtgc ttggcttcg ctattggccg    45720 agattccatg tctgccaagg gcgagccagg cacagagaag tgagtgagtg agtacatgag   45780
tacatgagtg agtacatgag tgagtgagtg aatgcagggt ccagccacta cattcagcta   45840
ggcatgtgag ctgctgtggg gtgggcagca ccaggcgctg gcatgggctc tggttccctg   45900
ctgcagctgg accaggtgta ctgcaagagg cttccactgc aggcaccagg gaacatggta   45960
gcacctggaa gcttggagac agcaggaacc acagagcccc aaatagggtg atatagccct   46020
ggctcaggga cctcctaagt ctgggatccc tgaaaggcct caactcttcc ctttcctctc   46080
cttctcatca cctgtaacat ggcaagtgag gggcatgttt cagccctgct tgtgttacag   46140
ccttttcagt cctgccattt ggtggatcct gagttcttgt cctacatcct ggaagaatga   46200
ggtacacaga caactggagg gtgaacaagg caaagatgtg ctttattcga gcaacagtac   46260
agctctcagg agatccaaag tgggtatctc cttttccacag gcaggttggc ctgatgagtg   46320
cagccctcaa tggagaggag acccagaatg ggtagctcct atctgcgctc aggttatcct   46380
gacatctctc cagccctcag tggagaggag acctggagtg ggtggctcct atccctaggc   46440
aggttgttcc aacgtctctg cagccctcaa cagagaggaa acctggactg ggtagctcct   46500
atctgcaggc aggccatccc attgtttgcc tgagtctggc tgagtccaga gtttttatgg   46560
gcttcagagg ggaggaagtg catgttgatt ggttcatggg tggccatggg cacacctgga   46620
gaaagcaccg taagtttcca ctctggtctg tggaaccggc agcttagccc ccaggcttca   46680
ggccatctct ggcgtgaagg tggggtttta atggggatct tcctgtttct gcccaggaac   46740
ctgtctgcct cctgctacca ttcatgatgc ccaggctgtt tgtgccctcg ccaagttgcc   46800
```

```
ctaagcccca cctcggcctc cttcccatgc tcctcagtgc ccaaagttca gaggaggcct   46860 aggggggctgg gtgctggcat gtcagtaccg ccctaagcgt gtacacgcct ggctgggtca   46920
tgacagtgcc caggtttggc cacaactttg ctctgaaatc agagtgggtg ccaggagtgg   46980
ggagatgcca ggcagtggga gcaggcactt ccaagcctgc aggggcaggg gggcttcctg   47040
ggccccagaa gcacaggatg cctaggtctg aagccgtggt tatgtggctg cagccgtgcc   47100
caggtgggcg ggctctcacc acaccaactt gggggagaaa ctcccacctg ttcccagctc   47160
ccaccagctc tgctcgagca cgcggcccca gccgtgcctt tccccgctgc agccagcatc   47220
tttgcagcag cagcttcata tgggccactg ctgctatcag taatgttaat cttctgaatt   47280
tttgcaattt tgttagctat gtagtcgtat ctaattgtag cttaaatttt tatatccttg   47340
gtgaattgct tatttctatt tcccattttt aactgggttg cctacatttt ttctttactt   47400
atttgtagga attcttttt ttttttttttt ttttgagac ggagtcttgc tctgttgccc   47460
aggctggagt gcagtggtgc catttcgcct cactgcaagc tccgcctccc aggttcacgc   47520
cattttcctg cctcagcctc ccgagcagct gggactacag gtgcttgcca ccacgcccgg   47580
ctaatttttt gcatttttta gtagagacgg ggtttcacca tgttagccag attggtctcg   47640
atttcctgac cttgtgatct gctcaccttg gcctcccaaa gtgctggcat tacaggtgtg   47700
agctactgcg cccggtcagg aattctttat atattttgaa tgtgacccct ttatatatat   47760
tgcatggact gaaccttctt gcaatatatt tcttgctata taagttatct ctttccataa   47820
tattgtcaaa aaacagacaa taaaaaaatc cgggagtcac agagcaatag cacttattta   47880
acttgagatt ctctaagttt cggatggttt catgctctct catgcatttg tggtcatctg   47940
tgggaaaaca agctgctcta ccgttattag ctggactcat tgcacgtct gggttggctg   48000 cctattgact gatctagcat ggctgtatct ggtgaaactg aagcagtttg actctgctcc   48060
acatgcttca tcttccagaa agcaagtttc agtattttct tataatcatg gcagacaaac   48120
aagagctgaa acagaaatgg tcagctcttt cagcttcctt tagctgtctg tcatatctgt   48180
taacatccca ttggccaaag caaatcagaa agctgatacg aaattaaggg ttggagtaaa   48240
atctctacct ctgtagtaag aggaattgaa agtttcatga aaaagcatga aaaactgggg   48300
acattaatgc aatcaatctt ttgtacttgc cttttactc tattaaatgg tgacttttga   48360
tgaatataac tttcttattt tatacaatat aatttattat tcttttatta acaatatggc   48420
tagtcacttt ttgctgtttc ttaaatatat gtctacccca agcttataaa aaaaactgtc   48480
ctaggttttt taaatagaaa cttttctttt ttttcttttt tcccattttg ggtctataag   48540
tcactataaa ttaattgtta tacagggtgt taaaaaccat atatatctaa ttgtttaaca   48600
caatcactgg aaaacttctc ttctgaataa aaagaaaaaa taatatttat agtatattat   48660
cagataattg tttatgagta gatctgcttt agaatgctat tctgttttat gctgtttttt   48720
ttgtctgccc ttgcacaaat acaatacagt cttaattagt ttaattgcat agtaattctt   48780
gatatctgat atagaagtct tgatattatc ttggctattc taagccttt acttttatat   48840 ataaattttg gaatcaacat aattttcacc aaaacgtggt gattttgatt ttgatttgat   48900
agaatttatt gatcaattgg acagaactga tgtgattcta atattaaaaa tcagaatcca   48960
taaacatgac atatatcttg atttatttag gttctttaaa atttctttca gtaatatttt   49020
aaagttgtct gtctagtact ttttgttgat ttattgctaa agatttattt ttatggtatt   49080
gttaaaaggg aattttaaaa ttttaaaatt ttaattggtt tcggtatata aactacaatt   49140
```

```
gattttttgta gtttgacttt atattctgat acatttactt attaattcta atagttgatt   49200
tgtatgtttt ggatttccat tatgcatcat cgagtcatct ccaaatattg acaattttac   49260
atgaaacttt gatgtattta taccatttt cttgacttt cctacatgtt aagaactgca    49320
caatgctgag cataagtgac aatagtggag attattatct tgtttctgaa gtaaggggaa   49380
aagcattcaa tatttactt ttaagaatct atccatctat tacctatcta tctatctatc   49440
tatctatcta tatctatc tattataagc taagaaaata tcttcatttt actagtttgg     49500
taagagtttt tatcttgaat aaatgttaaa gttgatcaaa taaattttct gcatctatta   49560
ggatggttgc atggttttgc ttcttcatta tttaatgcga tgaattatat tgatgctttt   49620
aaaaaagtga aaacatttca gtcctagaat aaactctact tggtcaggat gttttatcct   49680
tttatatata catgacttca aggcatgaat tttttgatta gaaattctgc ttagatattt   49740
atgaaaatat tgttctgtag ttttcatttt ttgtgtgtaa aattttgtc aggctttgtt    49800 atcaatgtta tgccagactc acaagacgtt tgcaattgtt ccatcattct ctggtttctg   49860
aatgatttgg tatgggatta gtattgtgac tatcttaaat ttttgaaaaa ttttaccagt   49920
aaagccattt ggtcttggag ttttcttct agggaggtgc ttaattcagg ttcaatatgt    49980
gattattcat gtttttgtt ttcttgtatg ccaattttgg taagttgtgt tttttaagga    50040
attaatccat ttcatgtaag ttttctagtt actggtgcaa tgctatttct aatatcctct   50100
gtgcaccttt ttaatgcctt tagtgtctgt agccatgttc tctttttca ttaatgatgt    50160 tggcattatc ttgctccttt ttcataatat atgtttgtta ggaatttatt attttaaatt   50220
attttcaaag gaccactatt tttctgtact gagtttctct attttatgac tgcttttgt    50280 ttcattgatt tctgcagtta atatatattt tttcttttac tttcattggg attaacttgt   50340
ttttattttt ctagcttttt taaataaaag cttaaatttt agtgttttaa aaaatatata   50400
tatttacctc tatagtattt tttaaatcac tgttacagtt acatgcattt cacaaatttg   50460
gcaggttgta ttttattact atgcagttaa aaacattttc taattttcat tttgttttct   50520
tctttgacac atgggttaat tataatatgt tacataactt tcaattatgt agacattttt   50580
gagttatttt tatgtgttgt tttcaaatta tctttatagt tctactttg aattatcttt    50640 ataactgttt atctgtttaa ttctactttg gtccgataaa atatatggta taattacaat   50700
tctttgaaat ttgctggtac ttacgctatg gtccaacatc tttttcaatt aagtatttgt   50760
aaagataata ttctgcatgt aattataaaa ggatgaaata tatatgctga agttttttat   50820
tgacatgttc tctatatatt gataaaagtc attttggtta attttgtact taaaataatc   50880
cttctaggag atgaccagtt ttttcctaaa atattataaa attatgatag tagattaata   50940
taaatgtaag ctgttatatc ttcctattta attaacgtat ttgttattac aaaatgccct   51000
atttgttttc tataattttt ttccttcaat tctttgtctc gtatcattgt aatctgtttc   51060
ttttttttta atgtagtgtt tggggatttc tttcttcatc tttttactt tcaattggtc    51120 tctatactta tatttaaagt ttgtctctta taaacagcac acagttaata tgttttata    51180 cttagtctaa aaatccttga gttcaatatt tatgaacata tttaatgtag ttactgaaaa   51240
actggcttta aatcaatact cttttgattg tcttttagtt gttccactta ttatttcttc   51300
ttttgccttt ctttggatta atcagttttt aaatttatt catcttgtta acagctttgc    51360
agtaataaat tcctatgtta ttatttaga gattatccta catatcatga tatcatctct    51420
gactttctag tcttcctgac tttagtactt tcaccagttc cccaccaaag caataatttt   51480
atcacagttt atccatttag gtaatctagg aaaatctccc tattttaatg tcaactgatt   51540
```

```
agcaaccttc attccatcag gatccttaat tatcctttgc tacataatgt aatatatgca   51600
gtttctaggg atcaggatgt ggaaaatttt ggaggaccat ctatctgtca cctaagagga   51660
aataactcag aagaggctgt tgaaaccaaa aagcaatgag ataaattaat tggcaaattt   51720
aatttcttct ccttatccgt aattacacag tggggtagag catataatga aaattagatc   51780
acttttagaa aatgaagaag ccatgttttcc tttgcgcatc tgtggtatac agtgaacaat   51840
ttttttact gccctacatg cagattgtga gatacaatct gacaactttc ttgttaatca   51900
ttaatttaat aactactgct taatataatt ctggacttag tctatggctt gagcttgagt   51960
agagcatgtc tttctttttc tttttctttt ctttctttct ttcttttttt ttttttttt   52020
ttgacagagt tttactctgc tgcccaggct ggagtataat ggtgtgatct ggctcactg   52080
caacctctgt ctactcgggt taagagatt ctcgtgcctc agcctcccta gtagctggga   52140
ttacaggcgt gtaccgccat gcctggctaa ttttgtatt tttagtagag acagggtttc   52200
accatgttgg tcaggctggt ctcgaactcc tgacctcatg tgatccacca gccttagcct   52260
cccaaagtgc tgggaataca ggtgtgagcc accgtgcctg gctacagata atatttcttt   52320
ctaattcatc tggatattaa aaataatttt tatttgcatg aaaatcatta ctctgagaca   52380
atgagatagt cctagatact tggtggcaac ttctcagatg aaaggttttc atttttcttt   52440
ctaaatttct ctgctgtttc ttgtatgtag gaaaagaaat catagtaatt atagaccatc   52500
agattcaagt taaaagttgc tgaaacctgt ggctgttttt ttctaataaa atatttctca   52560
ttagctggtt aatctgcttg aagattttct tttcctttgg gtatttagat gtcatgattt   52620
attatgttat ctttatgaag taattgtatc tttagtaaat aatcccatta aaagagtttg   52680
ggaacttgc aagagaagaa gccagtttta aaaattgagg tgccatgttt cccacaggg   52740
atacactgtt caccttttgg aggtcaatat aaacaagatc aaccataact gtgcactgag   52800
aagtgttttt tggtatcaga atgtagacta attgaaccat caatgacacc tttaaaattc   52860
ttatgccttt cacatcctat aaagatgatc attattaaat agttcaaggg ttgtgtattt   52920
gaaatccaaa gcataaacac tgaatttta atctataagt ttgtgggcaa aaagcagtca   52980
gatatttagg gccattctga tgatgagctg catcttgttc tgtcatctga atgcttgtca   53040
ttttgtagat gggggataaa cagtggtctc ttcatgttaa tgaatatttt ccatacttat   53100
taaaactaag tttttttaa taagaataag tcaatgagca gacagacaag ttgctttta   53160
ttattttgt gtctcttttc aagttcactc ttccttataga atgcattgta ttattcataa   53220
agttaatgcg attggctgct atttcacatt cttacagcca atttgtgcag acttcactct   53280
tttggtgaga tcatcatgat tgtatgtctc aggttgagct tttgatctt gtaaagaagt   53340
ttgctttcct tcatcctggg aacatagatg acgtttatat tctccataca gttatgttat   53400
aaatgcatgt ctttgatctt atgggaggag gtcataaatt ccttatctat agtaaaactc   53460
aaccaattaa aaatatcctg acagcagccg atcagaatcg tatttaattt aaggatagca   53520
gcatgatagg gtggaaatac actaactagt tactaatttt ccttggatgt cctatataaa   53580
aggatggttt aaatttctaa ggtctacttt ttgattaact tacctagtaa agtggttcca   53640
aataaaattt tattgcaaaa ttatttcaaa tttgagtagt atattaaaat ttcatcattg   53700
caatttgtgt ttgggatctg agagggctag taaaaactgg atagtagaat accataagaa   53760
atgcaatatt ttttcgagt atgtctagca actcaatggc agagtgtttc taagtaggaa   53820
gcctagcttg tctggtttaa tgaattgtag tatttaagaa aggcctccca tatttttagt   53880
```

```
gtttgtttac aaatactatt ttgtgaaatg agtcagatat gaatcatcca ctaatcttgt    53940
ttatgaaatt aatatattca gtaaaattct ttgaataaca gtagtttcca aacacattct    54000
atgtgttagt gggatctaaa tctatgtgat attatgacag tttgaactct gttttgattt    54060
ttacttagca aaatggtgaa ctcacagtta agtatgacct ctttgatttt cctaagcttt    54120
ttttgttgtt gttcagtgtc agttcaaaga attgggatga gtgggtagaa aagtcacaca    54180
ttcttatgaa ataaaaagga cagccacagt tttatacata tgtgtattta catatatgac    54240
atatatgtat atgtgtatgt acatatgtat atatatgt gtgtgtgaaa gtgaggggga     54300
gagaggaatg aggtctacat aatttaattt tattactagt acattttat ggttaattca    54360
aatatttagg caaatttgcc tttaatagga aaatcatcaa aaaggcaagg caagtagttg    54420
cataagcttt gctttttct gaaattacct gcattcactt agagaaaaaa ggattttaca    54480
ttatctatca agcaactaat ttacatatat gatttcaggt atttcaattt caatgtgtgt    54540
agcagttcag gaataaaaat gcagtatttt cttatattat ttgtgttttt tatgattgag    54600
ccgtacgatc ttttggttta gttaggaatt tggcttcccc atccctccta ttaaaacttg    54660
attttggaa agtatagata gaagagctgt gcttttcttt taaaatgctt ataaaattca    54720
aaagcaactg gaatacattt tatgatacca attttacata tatttaaaaa ccaggactac    54780
aaaatataaa tttataaaaa attataaaaa atgattggga ttctttctct ttggaatgat    54840
tatatgttat aaacatacag caccgtgagt ataaataggt tactgtttct cctaatgtgc    54900
ctactttaat gatgaattgc attcctgatt acagaatcat gagctatcaa aatacaccaa    54960
taaatacagg caaacattgg taaaattccg acttagaaaa taatcaaagc ttaaagctta    55020
gcattctgat ttggagcaag aaatatgtaa attgtgaaat aatgagcagc ttctgagcac    55080
atcccctta ttttacctgc aaggacctga gtcagaagtc tgcatttcaa aatgcttctt    55140
tttttttaca gtgtggatga atggccacga ataatacaaa ttggctttac tttccaagtt    55200
tattatactt aaacatttgt tggcaggtta gcgacatcat ttattatata atgaggtaaa    55260
ccccaaatgg aaccccaaa catcttctct tcctggtcat cataggctgc cattcttccc    55320
ctagaaatta atacatctgt atgcgggatc gtgccttctc atcccctgct gcagaatcct    55380
cggtcataac agcttttgtg ttcatgaata tgtaaatgta acatgcataa aataaaataa    55440
aaaagcagac agtttctacc acagactgcc taactctgtt gaactaatac acaaaaagcg    55500
aagatttaat ttttcaagca ttttgagtca gtgtttcaag gcatgacata attatgtaat    55560
ataaaaatac ataaattagg catatgcaga tgtgcatgac agttagactc aaaataaatc    55620
ggcatgtagt catggctata gtgattcatg cagattcact tactccttca ctctgatgcc    55680
tagtaatacg gggtaaatgc cttaggtatt taatgacctt gtatttactg actagattct    55740
actcctatac ttcaccccaa taaatgacta ggaaaatgtt taattaatat gtattatttg    55800
tatatgtatg tatatatatg tattatacac acacatatgc ttttttcttt tgaagggaa     55860
aagcgatggc tatcttccac tgaagtattc tggaggaagc tgtgggaaga aaattggtgg    55920
attttattat tgaaataagc aggcatgttc atgcatattt ttacggcatg catggctatg    55980
cgccactctg tgcaaacagt gctattgcag cttgtgcgcg taattaggt tgatgtaatt     56040
atggtgaaat aaaggcagtc gcactgataa tttcacagtg aatattaaag acatatgtgc    56100
cttccagtgt acaatgaatg aacctgaact gctgtcaggg tctaggagga cagtgtggcc    56160
aatgcaccta ttgtgtccct gctgcagaaa ggagcctgcc gattggccac tgtctgcagc    56220
acatagcact ggctggttat aaaggacttg tctagggag agcctgtagg tactccattg     56280
```

-continued

```
tctggtaaag ttcatatgac tgcattcttt ttgcaagggg ggtggaggga gagcgggaa   56340 ggaggggtg tcagctcaac tgtaaaagct gcacagattt ttttcttc tctctctctg    56400 cctctccata gattgtttct gtttcatgcc ctgtctcatt tcgcatagct aaaaaagaat  56460
gctaattaag atcccttgtc ttaacctgaa aaataatgac tcggctgtaa ttagaaatct  56520
ggtgagagtt taaaaattct ggtagggac caaaaacatc agttacggtg cttaggaaga  56580
aaatgaagaa ttatttttct gaaatcaagg taaacatggg agagggggt tccccccatc   56640 tttttaacca attttaacca atggtgttct actgcagatg agaagatact gtatttcaaa  56700
aactatttta accatcaaat tgaaggaaca caaatcagta gcaatagaag ccttcttaat  56760
cctccttagg atgcaattca gatgaaagaa ctgcttttc tattttctt tttgtgtgtg   56820 tgtgttatag atggatctga aacgctgtc tgggcttggt accaagagct ggtatttcac   56880
agcagcgacc gcctcacaga cgagctgtgg aagcaggag ggagactctc tcttagggtg   56940 ccactac tat gga gac aca gct ggg ctg aac aag att tgc ttc aaa cga   56989
        Tyr Gly Asp Thr Ala Gly Leu Asn Lys Ile Cys Phe Lys Arg
          1               5                   10 caa caa gag aga cag aaa gta tct ggt tca acc gct gcc cga gca ggc   57037
Gln Gln Glu Arg Gln Lys Val Ser Gly Ser Thr Ala Ala Arg Ala Gly
 15                  20                  25                  30 agg cac cag aag agc tag cag cca atc cgg cca tgc tcg aag cca gct   57085
Arg His Gln Lys Ser     Gln Pro Ile Arg Pro Cys Ser Lys Pro Ala
             35                  40                  45 ctg cag ctc agc caa tca gtg aca tca ttg gtgagaaact catttacatc     57135
Leu Gln Leu Ser Gln Ser Val Thr Ser Leu
             50                  55 atgcagtaat gaactttgtt aacatagac ttccccctt cctgtcaccc ccccccttt    57195 ccatattagg tccttccatt aattattctg ctggcataat ttaaaccgct atgcaaaaat  57255
gtggctacat tctctctgat ggcttttacc tccccccccc ccccccccat tggtgtctgc  57315
cgtcactgaa agtgattctg ggtacaattc tattttgttt tgaacttgca aaaattatct  57375
tctcttcctt aaaaaaaatt cttaacaaca ttaaacctct gtttatattg tctgatcct   57435 cttcttatga atgaatacat gcttctccaa gttggggttc agaattgtac aaggcaacag  57495
agaataaggt gtgcattgcc atggaagttg caggttttc aaacaatctg tatcttagaa   57555
cttcctttaa cgtttccaga ttttatgctg cagtggccat tttacataca gtgctttatc  57615
caaaaagcac ttgtatgcat ctgtcacatg gaggaaagtt cactcttgtt atatttcatt  57675
ctccactgct ctcagccaac attgtcattt tattaatgaa tagaactgag gtcatttctg  57735
gacaaatctc cccttccca tcccagcaca atgcacctga tttgcatcca tttactagaa  57795
aaaatgaata caagaaccag cttgaaaaga agttaaggga ccagcttacg tattatttca  57855
gaatatattg cagtaataca gtttgttttt taaaatgtg taatatttaa catttgcctt   57915
agtgtttcta taaaaatgcc tgctatccat ttgcaatgta ataccttag caaatttata   57975 ggattgttac ataaccaaag tagatcaaat taaataacgt tcacaaatga gttcatttat  58035
ctgcagaaaa cctgtggaaa tacaattttg ccttgcacat ttgtatttag ttgtcaggga  58095
taaagtcatt ttttctatag ataacttaaa gaggctggaa catgtggcat gtgaagattt  58155
caggttgctt tataaaatcc cagagagcaa aactgggtca cacttcaatg caatttctat  58215
taagtcatat ctttattgca tatttgcgtt aaaggcgcac agttttctag cagagaaggt  58275
gaagtttcat tgtctttctt ttaaaaggat gttttgaata taattattca aaaacatgga  58335
```

```
attttaaaaa tattgacaag ggtttcataa tagtgcatga ttcatttaag aagcttagag      58395
aatgcaatga taggcatagt cacttttta agcatatgaa ggatttagat gggaaaccat       58455
ggccctttta attcatgagg tattccatca tcccatcatc agtattcagg gggcgactgt      58515
cctgaatcag tcacgagctc ccctgctgca gatcctgtaa tttgaatcat gtgtaataat      58575
atattatcct actgggggcc ttctttcagt aggagaatgg tttatacatt ctgctgtaag      58635
agaacttttg gcttctagcc gactcacagc tattactcac ataggcaatc acgatcgtct     58695
tccttaagga ataacatctg cacaacctcc agagccaaaa atctgcaacc tcccgcacag     58755
tatgaattat gatttcttgg aattgggaac acttgacaaa ctgaagtaga aaatggaag      58815 gtttaaagga atggatcaac attttattga gtgtgccatg tggcgacagc gcaaactccc     58875
attcctttga aatgatggag aatggtgagg aaaggggggcc aaaaatatac ctacatgtgt    58935
tcatttgatt tttagacaca gccgaaatgt aatgtgtttt atgaagacgt ggctgcctct    58995 gtgttttct gtggacatcc tagcaaggtc ctgtaaaggg cgtagcaacg tggagaaata     59055 aatgggggc gaaggtggtc gtgaaagcag agaaattgtc tccctcgag aaggaagcaa      59115 tgtaatgtag caggaaccat tttgacccccg gagttaaaaa ttatagtgta cctccgactc   59175
tttctcttgt tatcaccttg atcagatcac ttaatttctt tccattttct cctgcattca    59235
aaaattcaag acaatgccag catagagatt ttctctttgt gtgaaatgcc ttcccatttt    59295
ttaagagtct agatccttt ttgcttcaag gaccaagtta aatgtctcct cttctgtgaa     59355
atctctccaa atcatcacga ccagaatctc tcacttctcc accccttttc atctccttta    59415
ttgcctgtgt gccagtcagt attgctgtag ggccacatgt gtgtacgtct ttgccactag    59475
actgaaagcc ccttggggac agagaccaca ttgaattctt ccacccccag ctctaagaat    59535
aatgaatgat gctcctaagg ttcaaatcca tgttttaatt aatgaattat aagtacatta    59595
taaattgcag agggagggtc atacaaattc tggggattac aattattgtt gtcaactatt    59655
accactatgt accagttgat gtcagcttta cctcatcaat gttaagcctt ttatttcact    59715
ggcccttcat aataaatctc agattaaatg gtccttgtat tatttttctt aaatagccag    59775
tcataaggaa atgcaaatca ttttgtttat taaatataaa attgagccaa cttagttggt   59835
gtttaaaaac ttaaaatag gtgaaattta tgtagattca agcaaccatg ataagcaaat     59895
tacagtatcc agctctactg ttcatgatat gaaaaattac ttggaaaagg taagcagtta   59955
acatggaatg ttgaaatgct ttacaaagca taataaatca ggaaatatag aatcccatgt    60015
cagcgttata attaatgtat gtatttttaa tctgtaaact agtacaataa tcttgagtga    60075
tttctagatg ttttttgatat aatctgataa cataatgcca aagcatgatt gattttatgt   60135
tagttatcta tttaagttta acttttggt tattatacta ctgctaagag gaaattaatg     60195
ttttggcaaa aatgatattt ttgttaatgt ttgaaaatcg tctttagatt taaaaatata    60255
ttttaaactg tttttcacta ccttttatga gaagagaatg aaataattag aaaatatata   60315
tatctttact tttatatctg gaaaatagaa aatttcagag cttgaaatca gcttaagtct   60375
ttattttgta aaagtattag agaggaaaag tatctcgccc aaaatacgta ctttcaagtt   60435
cccgggacag ctaagactgg tgtcaagaat tcggaaagac tgggtcaata ttttttttacc  60495 ctaccaaata atcttcatgt taaaaaccag caagatagga ttatacaatt ttatagtact    60555
aacataaatt acatttactt atgtaatcca atactgtatg tagaattcac atatcatagg    60615 gaaaatggg agactggacc ttattgagct gtattttttcc actatcctac aataatgcaa    60675
ttgggtccta ataaataatc atttatatta gtattcttta aaaataatta tggttatgat    60735
```

```
gaagtaaaaa tggaaatgat atctgggttc actttgctag ctctgaattc agttaacaca    60795
gatattatat cttaatgaca agattggtta aatagatttg ggtgggtcag tttgaacttt    60855
ttttaaccaa tgaattatac tgttattctt aatctttttt attctgctta agtctccagt    60915
tatcccaaag atgagatatt tgcatctagc caattattta aaaatataat tctggacctt    60975
gtaaatactg agagatgaat tgtgcccact tagaaacgaa tgtttctcaa agacaataaa    61035
aatagtagga ctgtccagca tcttctgttt agaaaattac agttaagagt tcagagagtg    61095
actgagaaaa tgtaaagcat cttaaagaaa atgttacttt acttcctaat ttaagacgtg    61155
gtaactgaca gccgtgtgca tttgaatact attttgtttt tctaaattta ttaaagtaat    61215
gataaacaag atagaaataa tgtaacaccc cccatactg gtacttattg ataccataat    61275
tgtacggtcc ttattccaaa attaattatt gaattaggaa agtggagtaa atattagggc    61335
ataggcttac acagcaaaac tagtaagttt gtgattgaga attgcttatt tgtaagatgg    61395
caaagaaata gataaaactg acctaaaaca tttgcatatt ctggcttttt ttcctgctta    61455
acccttacga catgatttaa aagcagtatc aatatatttc ggtgtttacc gagtatttcc    61515
acgaactgaa gataacacat cttgttattg atcagtgagg ttgctctgta actggttgct    61575
gaaccaagag gaggaacaaa aggctttgag ttaatggcta atatttgctg gggcctaata    61635
tttccactat atgccatatg ctacactatg tgctatgcac acattctttc atttaattct    61695
caaatcaatc ctttggtata attactatcc ttattttaca aaactgagaa aattgagttt    61755
caaaaaggct aagccactcc tcaaagtcac atgactaaca agcagcaaaa gagggatttg    61815
aacgaaggat tctgacttga gagaatgcat tcctaatcat tccaaactga ataatcagta    61875
catgtgattt tgctgtttgc tgtagaaaca gattttttat atatattaca ttcattaatg    61935
gtgtatctgg ttcagttttt taaatgttca catatatttt taccttagca ttttataggt    61995
cagtttgaaa gctattgagt tcgcaataat atctacatta atattttctt catattttgg    62055
tatttctgca cccaatcaga tcatttaggt aatacatacc aaaacaattt ctaaacagtg    62115
acataccaga caaatgtaag gtcatgttag tagtaaaatg tctttgtaag tctgaattac    62175
taaaaataag tattagacta aatgtttcca tttcctcttt ttcctagata ttttacttat    62235
taaatataac acctatttta tgacaaaatt aattctcatt aatttggcag ttgcagaatg    62295
tcactttggc ttatttagac cctgactatc cagacatgta aggtagttca ggttctcact    62355
cctgtttaca catcttgtgt ctacaaccca ctgcaatcca caggatgtta aaagaatctt    62415
acaattactg aatatgtagt aatatatttt atgcctaatg ctagattttt tagtttttat    62475
ctacagtggt caagactaga gggcatagct gacaagttgt tgactttcag ggaatcagct    62535
taatttgggg aagggaaagg agaaaacaga attgtgtagt ttcttagctt cctgatgaaa    62595
tgttgtccag tttctttctc aattttctat ttctttctag aacaatgttg tacacttacc    62655
atatgtcaga aactgtgcag gcaataaaat gatcctctca tgaactccaa cttcaacatt    62715
gttattgatt tcataatga aaacactata tcaatatatg ttcatgtata attgaggtgt    62775
ttagtttggt tacataattt atggtaccct cttttaaaaa aatctagaaa agcagaagtt    62835
ttgaccccta tgattctcat ttgaatgaaa ctccactcca ctgtgctctc cactgtgcct    62895
ttgcctcttc tatgatcctg ataccctagaa ctcaatacac tgctccttgg aaggtttgag    62955
gaatgcaggg tgaaggagga ctatcatctc tgtgtttggg ggccactagg cccatggatg    63015
tggtgcaaag acctcaatag caggtttaag gatcatattc tgattttgcc catgccttac    63075
```

```
gctattctcg gtacagttag aatttgatat tattttttct cgcaagattc cttgatgttc    63135
gcattactaa taattacctt tgtgggaaag aatcaaggtc aacatagcag ttcctttcat    63195
tgcttctgaa cttactgaga aagcacttaa agtataggac ttaagcacta gtaaagtact    63255
taaaacattt attttcagaa tgttaatttt tacacagtga aaactagaga taatagtgtc    63315
aatgactact tagtgatcac ttaactccat gaggtactgt gagaagtggt taggagcata    63375
aaatctctgt acagatgcct ggttctgatt ctgaacttca tgacttagta gatacataac    63435
cttggacaag ttacataact tccccgggcc ccagttttct catctgtgca atagtacata    63495
ccttaaaaga ctgtgaggat tctagtgcat ttttgcaaag gatggcatta taagatgtg    63555 caaattcatg ttctttactc ttcgaagtat ggaatgtaga gagtatgtgt ttgtatatat    63615
ttaaataaat attaatgcag tgtagttaag tgctatacca gagatgtatt tatgcttcat    63675
aaatactttt aaagtttaat tttacttcac ctctttaacc aagttttgtt tttatttgaa    63735
caagttgtca accattgtta taatcatcag ttttatccca tcaaatattg gtttcattta    63795
aaaagttgtt taaaaagact ctatgttatt ttaataatat ctatataagt ttacaatttc    63855
aggcaactaa taatattcaa tccattgatt ctacttttc ctccattgct cagtgtatat    63915
atcagaaaat acaaatgtcc gaagtcacat gtaaaaatac atgaaaccat ttattctgat    63975
ttttgcaaag ctcgatggta gagctaatat tttagaccat gatacctag aatgaccaga    64035 ggttaggttc ctagttagtg gcattctgta aagacaatta atccatagtc caagtgtcta    64095
atgttcaaga atcagatact tgatcacgta gactgtcctt taacaatctc cattgtactc    64155
aggaagaaaa taatagattc taatccgaag acctgaccta aaacccttg taagtgctcc    64215 aagcctcact tttcttatta tgaaatgggg atagtaatgc ctaactggaa agataattgt    64275
gtgggctaaa taagaggacc tgtggagtac tgttaggttt tctcttctgt aagttttgca    64335
aagtctgttc aagtgtgtgt ttcaatgtca atgagagcaa caggacttca aataaaatgc    64395
aagcttctga ggaggcaaac tctagtatga tgtattctat agaatagaga atgacaagat    64455 tcttttaaaaa tatttctcat taaaaccccc attagttcaa atgatttcag gggattgtga    64515
atgcaagtta attaaatcag aattctttct catcttatcc tgggaatgac tgaaactaaa    64575
aatggtttca tttaaaaaag aggttcatga gctcgctccc tctctccacc tccatctcta    64635
tctctgtctt tccctgcctc tgagagaaac tgacgtattt gggtagagaa gagcatcagt    64695 aagtgttttcc agtgattgag gcagagggat gttcaaaggc atgagtattt ttagattaat    64755
agtaacgatg caactaattt tcaggtgtct cattaaggtg aaaaataata tactataaat    64815
agcatcatat ttggacacct atgtgccaat tttatgatgc ttttacaatt tcatctaatc    64875
tattacaatt tgttattact cccttcaagt tttatccatg ctttcatggt actaataatg    64935
aagatgacga tcaactgaac tttgccatga tattttgtag gtgtacctgt tgtttgaact    64995
atgtatataa atcataaagc aaagaaatta cacattctgt ttgggatatc ttatagtaat    65055
attgcctttt aataatcccc gtttctcctt ttatttaaca gcaattaccc aacatcctat    65115
taaacatcaa cagagatcgt cttgcatgtc attatagtgc aataagatct gtttagcttt    65175
tcagctctta caagatattc attttgcagt ggagttaagc ttttctatta ccttcctagg    65235
atgatggttt aggagtcttt aaaaattttt attaaactca ttttagttat tttttcccctt    65295 tgttagttaa ttgattttc taggactgag aaagtgggtt tttaacatat ctcttctcta    65355
gggataggct tcagtatggg ggctgttgga gagaccatat accccatttc tccggggata    65415
tgtctagttt atgcctattg taccagggta attattgatg gtgccctctt tcattttcag    65475
```

```
tagtgaccca ttttcatta gaaattatgt ggccattcta taatataaag ttaatttctg    65535
aatgttttgg taaagattat atttttggat atgcaaatct gttgtcatca tgaaagtatt    65595
tgtactttgc agattgtgta acatgagttt aggttttgca aatgtggtca ctacagtaat    65655
agataatttt gttgatatgt gttagacatg caatgagtaa ttgttgatct aaactcactc    65715
atttgagcat cagatttcat tagtactcta gtctagacta acagcaggaa gaagtccagc    65775
atgtcaattc atttaacaaa tattggttga gcactatgtg ccaatcattg ctataagcac    65835
tgagggacac agcagtaaag caaatagaca aagtccgctg tgctcataaa gcttgtgttc    65895
tgaggtcctt tatagggtaa taatatatat ttattaagtt ataccaatga cattttgctc    65955
tcttatacaa attgctttga caaaggaag gtttcattta aaatccagcc tgttttatt      66015 cagactgctc catgatgtag gctaacttta taccatgaat tcctactggg tacgttttc     66075 tttctctcac tcagtagctt acctgacatc ttaggccctc ctggagttga tggtgccagc    66135
tgcccatgat ttttatgttt tatttagtca agaagcagct cagaaatcct aataacttga    66195
gatcttctta tgttctagct aacacacaaa ggtacatgga aaatgtacta ccttatttgt    66255
ttttggaaac ttttctttc tccctgagaa caggttattg tcatttttgc ctatatatat     66315
aaaattcatg tttttaaatg tatcctcgag cttttcaagt gatttctctc ctgtggaagc    66375
accttctctt gttatttggc tttttataaa gcccacgaat atttttaaaat tttaaatgac   66435 ttatgtgcat aaaaaaataa gcaatttata tattaagaat acatatttaa gcaatttatc    66495
tgttaagagt acatatttaa aatgagaaca attatatcat aaaaccagaa ctgtttggag    66555
tttgacatag acttgagaca attgtttaat tcctttattt tttaaatgtg cccagaaaat    66615
gtgtaaagaa atggtattca acttgctcag atttacagag tagtttgtga tagactcaga    66675
aaaaaaagat tttttaaaat ttgaattttt aaagttttga ttataaaaat attttctctg    66735
ctctaaattt gaaaaatttt agagttatat gaaagaaaat tgaaatattt agttatttta    66795
ctctgtataa attaccatag ttgcacaaat tctaaaaata catatgtctt ttgaataata    66855
ttgaagtttc actatataaa tatttatatc ttgttttaa acatgaagag agaaaatatt     66915
atgtggtatg atataaggga tgcacattta gatgaaaaat aaaggaagaa agaattgata    66975
agacaggcat ttaaaaacct aggtattttt gaattacaac ttcacaaatt atatgaggct    67035
atataggata tatatagaag tgaatatgaa tatgtcaatg tcatttcata aaaatgtttt    67095
gtggtacact gaagagagac atgtcaaagt gacaatgctg tcatagatgt ggatgccctt    67155
tcttgctcct gggaagtagt atctcttccc tccacatata ctctgggtta taccctctct    67215
taaatcctca tggaattttt ccatcgatga tccttctcct gtatcatcac cttcctctca    67275
accagttctt ccctcccaga actcaaaaat gaccaacttt cactcatcct aagtaaacag    67335
atgaggaaaa caataatagc cacccccccat aaacctattt cctcttgtat ctcttactta   67395
tccattctgt tgctggacac gaagtcagga gagctgagaa aagactctaa ctcactcggg    67455
acaagtagtg taacttcttt gcactccagc agaattgata gttttatatt tcataaaata    67515
taaaacggtg ttaaaaagct atagtttttt tttttccaaa agtactttgt ccaccttgaa    67575
caccacataa atgtaaagga gaagagagga aatatcctct acaagctact ttttaattgt    67635
tatttttagg gagctctaaa gtaactctaa aggtgttttt gacataatat aattaccatt    67695
tacagccatg atctcatttc catttattta ttttgagatt ctgttcccac tcagggttct    67755
aatggtgcag gggtggtagt agggtcaagt tatttaaat aacgatcaag gaaacaatct    67815
```

```
attttttaaag gaaataagct ctttgtgcta ttgaacaaag atcgctgcac ttgaagtcta   67875
tttgttactc caaaattatt tcaatgagag taggaatcag atgatctcat atctattgct   67935
agctatgcca ctagtcattt gtgtgacatt ggaaaactgg tgtttattgg tttatcagga   67995
tggacaggag accagatcag gactttcaac aacttttctt aaagtagaat tctttcttaa   68055
ataaaatcga ctcggaatct caaaatattt ttagaaagtg caatgaccct gtttggatta   68115
gggttgggaa cctcagagct gtattctttt actcctcatg cactttaggt ggtgcctaag   68175
atgccctcat tacagcctcg taactccatg agaataaagc cactagagta gataattgtt   68235
gacattgctt agagtttgaa aattagactg tttttttttt gttgttgttt tgttttggtt   68295
ttgcttcttt tggtcagcca ttaattaata taaattaaac ttccactaga tggcagtaga   68355
tcaaatcttt gatcttgaca atcttcagtc taatatttaa aagcacatat ttggacttct   68415
tacacaaatt ttagaagaat tttattgtct tatattttaa actttaaaat tcttttttcaa  68475 cctctgaatt ttcacttggt attctgtttt caagacatta cgaactattg gttagtccag   68535
tctttatgat gtctggtaaa aaatattact tgctctgatt atagaaattt ttaaaaattg   68595
cataatgttc aagtgaacac attttcatga gcatctaaat ttattattca tacagtcttg   68655
attttacagc ttcactggaa ggctaatttt taacccaaaa tttacagtga cctggtcatt   68715
cattttgcta tcccataacg cccactccct tccacagcaa tgcaattcca atgatagtct   68775
gcattgtgta tactcttaac tttgcagaga ggggatgctt tcaaattata ttagatgatg   68835
ggaatttgtg ataaggataa ctagcgaaat gaggtatctc aggaagctgc ttcatatccc   68895
taaggttaaa ggtatagtaa tttcttggag gtacagagca acaccttcct ttgggattca   68955
gcaggtcctc ctggaaccca acagctctgg taccctcatg ccaacaatga gcctcccaga   69015
agttgcctct gctcctcttt ttggatacca cttatttata ctccccagga aagaagaact   69075
ggttgagtca gtttgttgta gttgtacaca gatcatccct taagtgcagt ctcttgctaa   69135
gtaagtcccc tgagttggtt agacccgact gaggacagct tattctttaa ctagtgtatt   69195
agtctgtctc atgctgctaa aaagacatcc ctgagactgg gtaatttatc aaggaaagag   69255
gtttaataga ctcatagttc cacatggctg gggaggcctc acaatcgtgg cagaagatga   69315
aggaagcgca aagggacgtc ctacatggtg gcaggcaagg gagcatgtgc aagggaactc   69375
ctctctataa aaccatcaga tcccgtgaga cttattcgct atcatgagaa tggcacagga   69435
aagactcgcc cccatgatac aattacctcc catcgggtcc ctcccacaac actcgggaat   69495
tatggaagcc acaattcaag gtgagatttg gatgggacg cagacaaacc atatcaaata   69555
gccaacataa aaggtcaaag tttatgcctg ttttccaggt gaaactagtg atagctctag   69615
ctccccattt tactctcaaa gtgatcccaa ttcaaaagct caatgatatg atcacctgaa   69675
cacacagtta tctttacctt gagaactaag tctgatcttc aagccagagt cgtagacaca   69735
agacttgtct aatgaaaata attgtctgtg gcaactttct taggaaggag ctgtgggaca   69795 caggtatta gagttgtatg aactgccaat tatgtagtcc ttagaagaaa agaaaagaga    69855
aattaaagat gaaagctaac tttaaactca aattcctacc tcactggttc aattttatcc   69915
actagatacc atcttttttct aatgcattgt ggaaagagt attattttca ttgttaagga    69975
tagtataaaa ctagaaaaga aattaagtgg cttgcctgta tcacattgta aatatcagag   70035
agaattccaa aattagaact ttagagatgg ttagtcacaa tctattaggc ataagtagta   70095
gactgagtct tttaattatc actctgtata ataattcaca tgccaccaaa tgtattggaa   70155
atagttatct ttccatcaaa actattaccc ccaatttttt aagtaatcat atttttagat   70215
```

```
tttaaataca ttttctccca cattagtcct ctatcacttt aatgagtata gttaatatgg    70275
tgaatcgtag attctaaagc cctttctctt ttttttttgcc ctcagaacag atttataatg   70335
aaaaaaaaac ttaagtgact gaaatgttca acctgaggaa gagaagccag actcactggt   70395
cccattcctc agaatgtagt ttctttcaga gagggctgtg atgaaatttt ggcctatctc   70455
aatgtacaac accagaaaga gagatgatat tataatttga dacattttgt ttagaacgat   70515
ttcatgcatt cttctaatca gaatgggcta ttgaaaacat ttgtgctaag cctgtcctct   70575
ggaaatcatt tatttcattt gtggtatttc aaacatcatc gtgctgagtt ggagggcagt   70635
ggccattata gtcatacaaa taatactgta tcactttgtt taaagtatag aaagacccgc   70695
ttgttggttg aaaacctcct atgtctttct gaaagattag cttctgttca ccaaattcca   70755
tgttattttc cttctcctga atacaaagaa agagtagatt tcttagccgc taaacggtta   70815
ggtggcagca tgtgactaat tctggctcat gaaatttgat cagaaggcat cagagtcact   70875
tcaccgactc tggcctgtgt cctgagatgg ccaagctcca gcatggaaac agcctggatt   70935
tctaagactc tgcttggaaa ggagccgcac caaagtgaag gatgaagtga atacactga    70995 gtactaagtg aagatgaaag atttttatga cataagttac tgaaatttca agattcattt   71055
gttaccattg tatagcctgg attttcctga ctaccatagg aaatatatga agtttagctt   71115
tataatttaa ttttattttt ctgacttagc ttagtctttg ccgtagctga gattctttca   71175
agcaagtagt gagtgagatg gatcattact taagtgttca ttacttaaat gttcattcca   71235
atattacacc gaattggatg atatcttgta tcatatgttt atgtggccag actgatcagt   71295
gacagtttgg aagacatgta tctggtgcag ctaaattttg tgagccagaa ttagtcacat   71355
ttcatgagcc agaattagtc acatggtgcc acctaactgt ttaggggcta agaaatctac   71415
tctttccttg tacgccggag aaagaaaata acgtgagatt tggtgaacag tacaaaagac   71475
atgaattgag attatcatcc aaatcatttt taacctgcct aaaatatgag aaatcattta   71535
gaacatatag aatctgtagg caaatgtaag ctgtaaatcc gtatagtaag agaaggaaaa   71595
aggcagtaat attttgtagt ttgtgatttt aaaaaatcaa cgtataatct tagagttctc   71655 agatttatt tgtaaagtaa tagtgttgtg gaactagcaa ataatcatta agtttctgtg    71715
atacattaac tctttcagca taagaacatg tgaatatttg ccttgtagat acggcgatga   71775
gaggttctgg tttatttggg ggcagtctca gtttatatct tttgtttcat tacaattctt   71835
aatagtgtcg cttttcattc aaatattaca ctgaattaga tgatatcttg tatcatgtgt   71895
ctatgaggct agactgatca gtgacagttt ggaaaacacg tatctggtgc agctaaattt   71955
cttttttttt cctcagttct gtggaacata atacggcatg aaaatatcat tatatgagga   72015
tgttaccaca tccccatgta atgggatcag cccacaaaat attttgaat ccataactta    72075 gtgaaagcat tgtgatgagt acatctaaaa taaacatttc taggtttctg tggatggact   72135
caggaaccta atcatcaggt atataaaaca ttaaatcaaa tgaaaagtgc agtctagttt   72195
tcaataacta acttgccaaa gagctttagg acgtaactgt ttgtcatttc agcataagca   72255
gtggttttta aatgcagctt tcagttgtat taattgtgta ggtatttat ttttattat     72315 ggagaatttt gaaaaatacc aaaattacat aatagtatat caaactacct tgcagctatt   72375
aaccagtcca aatagacatc aaccaattgt gagttctgtc ctatccatac ccccatctaa   72435
atttccccct atattatttt gaagtaaatc cagacatcat atcatcttat ttttacatat   72495
tttagcattt gtccccaaca agatgtacac tttggtaaac atagttttat gtggtttctg   72555
```

```
tataatagca tagattgaac aaatatttgt caaaacaaat ttgggttgaa gtttaacatg   72615
tcagcattta cccacattaa atagtcatta tctcttggac taacagtttc ccaatatcac   72675
cttaatcaga acaaattacc tttaaatatt ccaaaagtaa actctaaatt tccctttaga   72735
caatttagag gggtatgtat acgctccaat ccagagatca aggagctctg aaatggattc   72795
tgcagctgtc tcccttttgaa attctttgct ctgacactcc agataacagt acgacttagc   72855
tttcctggga agcaaatagg ctgctcttca aagggtgaat accttagact gacaggttaa   72915
cttcaagaat gtaattctaa taaatggaat ttatggggca aatgttaaaa acactaaaaa   72975 ataccttta ttggcctgtt tattgagact aggaaggaac atcatgttac aaacaaattc   73035
tgttttcttt gtgctaaaac attcctatgt catcttttaa taaacttaac tggatttata   73095
ggaaaggaaa agtattccct ttgttttata cttcagaaaa taattaaaac acatttctga   73155
tttgtatgaa aagagaaagc cagacaaaat ttttaaaatt tatcaaatgt aaaattgaaa   73215
ggaaaagagg aaatcttggt acaggttata tttgtagcaa aattagagaa atttggaagg   73275
ttgcaacata ttgtttatgt attgtaccag tttcctggaa cttactatct atatacataa   73335
tatgtttttt atttgtatgt aaatgatgta aaatgattaa gatggtagag ctaatacggt   73395
ttcttgaaga aggaggacat tagggttaga gcttatatta attgaatcac aggtcttttt   73455
ttggctcctt atatcagtgg atatagatgg cattaactta atttaggcat ttgatttaga   73515
ttacagtgca ggagtaagaa gcatatttaa gggaatagct ctgttttcac cacttagcag   73575
ccatataacc aaggttaaac cttgcttctc taattatgta atgatagtaa tttaacctat   73635
aaagggactg caaggattaa atagaactgt cttggtaaat attttaaaa tgagctctat   73695 tttcatgttt atgcataata aaaatactca catttttaagt gtacaatttg tgtccttggc   73755
aaatacatat agtcatgtag ccaacatcat aatcatgatg gaaaacattt ccatcacctt   73815
ggaaaattcc cttgagtccc tttgtggtca atcggctcca cctaccctca gcttctgcaa   73875
ctactgattt gcattctgtc attacaattt tgcatttct ggaatttcat gtaaatggaa   73935
taacacagta tacagacttt tgtgtctggc ttttttctact tagcataatg ctttggagat   73995
ttattcagat ccttgagggt atcagtagct catctgattt attgctgagc agtctcctgt   74055
attgactgca tatatgacaa gtggatggac actgagattg tttccagtta gggaatgtta   74115
tgaataatgt tctgtgaaca ttaaagtata aggcttttgt ggataaagct ctgatttatc   74175
atagctaatt gtgtagaaat gggattactg ggttgcgtgt taagttcctg cttaactttt   74235
taagtaactt acaaggtatt tttttttta attggctaaa ccatttgcag ttccctcaac   74295
cacataccac ttgctccaca acctcaccaa ccattggtat tggtcattaa aaaaaattat   74355
cccttctaaa atgtgtatgt aatggtatct cattgtagct ttaacttgaa tttgtttggt   74415
tttcaaatca ggtaatttgg actgataaag taagttgaga agtattttat tttctatttt   74475
tcagaagcat gtgtgcaaaa ttgatattat ttttccttaa atgtttagta gaattcacca   74535
gtgtcatcta ggctaatact ttgtagacta atactttcag cctgtttcct tgtgcttatt   74595
gtccattcga gtatcttctt caggatgctc attttttactg catcttttt ctttctgttg   74655 ggttttaaga attctttaaa tatatgac gtaaatcttt tgtcatatat atgtctgcag   74715
atgttgttcc tagtctgtgg catgacttt tattaccta acagtgtttt ttgataaatg   74775
aaacccttta atattaatga tgtccaattt aacaattgat atttcataat ttgcactttt   74835
tgtgtcctgg ccaaagattg tttgcctaag ccaacatcac caagaccttc tcttatattt   74895
ccttttacat gttgtataat ctattatgtt taattctatg aacgatttca ggttaattta   74955
```

```
tgtatatgat ttgaagtcag ggtcgatgtt cattttattt gtgcataaat actcattaga    75015
gtattctttg ttgaaacgac tatgcgtcct ttgttgcata acctaggcac gttttttcaaa   75075 aaataaattg atgagaggcc aaggcaggaa gatcatttga ggtcaggagc tcaagaccag    75135
cctggccaac atggtgaaac cccgtctcta ctaaaaatac aaaaattagc caggcctggt    75195
ggcacacgcc tgtaatccca gctacttaga aggctgaggc acaagaatca cttgaagcaa    75255
cccaggaggg aaaggctgca gcgagccaag atggcacctc tgcactccag cctgggtgac    75315
agagtgagac tctgtcttaa aaaataaaaa atcaaatcaa aataaataaa taaatggata    75375
atatctgtgg actacctatt ctgttgtatt gatcttatgt caattgttaa accacattgc    75435
ttcgataatt ctagctttat aatacatctt agaatcaagt ggtgtaaatt ttccaacatc    75495
gttcttttaa aaaattaagg ctattttgga tctatgcctt gccatttgat tttataatca    75555
ccttgttaat ttctgcataa atgcttgctg aacttttcat tgggatttca taaagctata    75615
gatatatatg gagaaaatta aaaccttttc tagtgttgta tcttgtaatt cgtgaacatg    75675
atatccctct cacttttttaa aattttttta gctctcctta attccaccaa gccatatttt    75735
ggagatttta atatacaggc ctagcatgaa gtttagtaag tatactatcc ctatatgctt    75795
cacgtttgtt cattctattt taaaagacat tttaatttaa atatttagtt gagccttact    75855
agtatataga aacataactg attttgtgt tttcatcttg gattccatgg ctttactacg     75915
ctcagttcca gtaacacttt ttatgggtgt ctttgcgttt tcaacataaa tgatcatctc    75975
atctgtaaat aatgtcagtt tcattttttc ctttccaaca tgtattacat tttatttatt    76035
tatcatactt ttaatcatat tattttttgcc ctattgcact aattgggact cccaatataa   76095
ttttgaaaaa acactggtaa gaacaaatat cttcacattg cccctgatct tagaggaaat    76155
cattcagtct ttcacaaaaa tgatgttagc caattttgct ggatgttttt atcaggttga    76215
ggaagttgct ttccattcat agtttggagg taaattttat tatgactgaa ttgtgaattt    76275
atcaaatgct ctattcttta tctgttgaga tgagcatatg cttttttcttt tttatgtaat   76335 aatatgctgg attatactga ttactggata ttaaatcaac ctccataggg ctgagataat    76395
gtactattgt tttgtctttt tttgcatttt tggatattgt ttactaaaat tttgtttggg    76455
atttttgcaa ctatgtttag gtgacttata ggtctgtttc atgtaaatat gtatacatgt    76515
atttattcat ttattcaaat attgcctttg tttggttttc aaatcaggta atttggactg    76575
ataaagtaag ttgagaagta ttttattttc ttattttttgg aagcatgcat gcaaaattga   76635 tattatttttt ccttaaatgt ttagtagaat tcaccagtgt catctaggca tggagctttt   76695
tttgtaagaa gaatatcaat tatgaattca atttgtttag tagttttaag gctatctatc    76755
tagttctctg tgacttgttg aggaatcttt tgtcagttta tgtatttcaa ggagttaggc    76815
cactacatcc aagatgttga taagcctata gtttgctcat aatattacct tttaatcatt    76875
ttaatgtctg taaaatctgt atttatgtcc attttcttca ttattgatgt tgggtattta    76935 tgtgtttttat ttcctgatta gtccaattaa tgctttagca ttttttccct ctgttcaagg   76995
aaccagattt tagtttcatt gatgtacttt atttttttct cttttttcttg attttttttca  77055 ctcaacttta ttgtcttcct tctaattacg ttgggtttaa tttgtttttc tattttttgtt   77115 tcttacagag aaatcttagc tcactggttt ttagatcgtt attcatgctg tatagttccc    77175
ttgaaacact tattcagctg catcctacaa atttcatata gtatgttttc atttagctta    77235 catttttatct catttattct tacttatggt ttatttacag atgtgttatt taattttttgg  77295
```

```
acctgatgat ttcccaaata ttattgattt ttaaattaaa tctcatttat ttatttattt    77355 attttttga  gacggagtct ccctctgtcc cctggctgg  tgtgcagtgg tgcgatctcg    77415
gctcactgca agctccgcct cctgggttca cgccattctc ctgcctcagc ctccggagta    77475
gctgggacta caggcgccca ccaccacgcc tggctaattt tttatatttt taatacagac    77535
ggggtttcac cgtgttagcc aggatggcct cgatcttctg acctcgtgat ccgcccgcct    77595
cggcctccca aagtgctggg attacaggcg tgagccatcg taaattgatt ctttagtgac    77655
cacagaactt catatgattt caattttctt aaatttattg agactggtca atcttttgtt    77715
caggcacttt ataccttgc  taattttctg ccttctcttt ctatcaacta ctgaaagtgt    77775
tcatatcttc aattataata ttggatatgt gtagttcttt ttcaatcttt atcagtttta    77835
aacctctggt attagtgtat ccacatttag gtttttatg  tatactgatg aattgatccc    77895
ttcaaaatta cgaatatcat tctctgtaaa aatatttaa  ttgaccaaga ttgtaaataa    77955
agtgtacagc acaattatca tatatgtata cctatataa  tgattaccac aatgaaatta    78015
gttaacacat ctattaccat ccaagccgta tattagattt gctggaattg ttcatcttat    78075
aaagtttgta tttttataac atttcttgtt ataaactcta ctttgtctta tataaatatg    78135
aacactctag cttctttta  aaagtgtttg ctttgtgtgt ttattttaat cctttttgctt   78195 ttaacctata tgtcttcata tttaaaatag gtttcttcta gataatgtct taggtattgg    78255
tttttgattc aatctgacaa gcactgcttt ttcattgttt ttaattgaga tgttcagaca    78315
atttaaatgt atcattattt tcagtatagt tgtgtttaca tttatggtat tgcagttttt    78375
ttctacttgt ctcgtccatt cttgttcctt tttctctttt cccttcttta ttttttgatta   78435 attaagattt taaaatttat tttatttta  ccattagttt tacttttgtg ttttttattg    78495
gatacgctaa ggtttctaat atacatcttt accttgcaat agtacttttc caaataatat    78555
tataccagtt catgtataca gtaagaatct tataacaata tacttctatt ttcaaacttt    78615
ccatcgtttc tactatttt  ggtgaaaatt ttatttctct gtatactaca aacaccacaa    78675
tatattttta aagcacacaa ttaatttat  agattaaaaa gtgttacat  ttactcactt    78735 tatttccatt tccagtgctc ttcattcact tgtacagata cagattttttg tctgatttta   78795 ttttccttct gtctaaagaa tgtccttga  cattttttgt agtgcagttc tattgagggt    78855
taattccctc agtggttatt tttatggaaa aaaaaaagta ttaatttcac ctcagttttg    78915
aaaaaatttt cactgggtaa gacttgtagg ttggcagttt cttttttctta tgcagtattt   78975 taaaggttgt gttagtttta agtacttct  aaggagtttg ccgtaattct tatctttgtt    79035
cctcagtatg taatgtgtct tttttcttc  tgactgcttt taagaggtta actttagtag    79095
taattttcag caatttaatt ttgtaatgtc tcaatgtgct tttctttagt ttcattctgc    79155
ttgggacttg tcgggctgct tggatctgta gtttgataat ttctcagcct ttatttcttc    79215
aaaaatctgt ttttttattcc ttctaactct tctccttttg gtactccaat tatatgtaag   79275
atagactatg caatattgtc ttacaggtca cttatttct  gttcattttg gttcccagac    79335
tttttcctct ctgtgcttgc tttattttga ataatttctg tataatgtct tcaatttcac    79395
tgaccttctt tttctgcaat gtataatcag ctattaatct tatccctaat ctcagctcac    79455
tgcaacctcc gcttccagat tcaagtgact cttttgcctca gcctcttgag tagttttgat   79515
gacaggtgca caccaccatg tccagctaat ttttgcagtt ttagtagaga ctgcttggct    79575
gtaccaaagc caggctattt ccaactcctg gcctcaaatg atccaccac  cttggtctcc    79635 caaagtgatg agattacagg catgtaatct cattccttgg cctaaatatc tttattttta    79695
```

```
tttatttatt tatttatttg agacagagtt tcactctgtc acccaggctg gagtgcagtg   79755
gcgcgatctc agctcactgc aacctccccc tcttcggttc aagggattct cgtgcctcag   79815
cctcccaagt agctgggact gcaggtacgt gccaccatgt ctggctaatt tttgtaattt   79875
ttagtagaga cagggtttcg ctatgttggc caggctggtc tcaaactcct ggccacacat   79935
gatctgcctg ctttggcctc ccacagtgct gagattacag gcatgagtca ccacaccagg   79995
cctacgtatc tttaaataat ggatatgtga ctgcacgact gcagcatttg tatccagata   80055
gataatcaat tcatctataa accagctatc aagtaactgt ctaaatattt aaaatacagt   80115
tcttgtttag ctcattctta gttttgatca cctttttttg ttgggtggtg gggagccctg   80175
ctggtcactt tgaaaatata ctacggtcaa atcttctgat atcctgaagg tttctttcag   80235
ctggactaag ctcccaactc caggcaagcc caagtttgtg gcctcccgca ttagtgctct   80295
ttctatctac cagagtcgac agtatttgtt cggctcagta tctgagtgta gctcactcca   80355
gttaactaga gttgttgact tttgcagaaa tagaagcagt gggatccaac cgatatttag   80415
ctacaatgcg aaaatgagtg cagttggtac ctgatgtcca agtacaatgc actgaagtgt   80475
caagattttc acatacttte tgataaattg attctccata ttctgtccca tcattgacat   80535
taatgtgtag ttgaaagtct ccagtcctgt atagcccagc gagaagttat tccttgtcag   80595 cttttgatttg acactgtcaa aggtcatctg gtacccagca agccagcctc atcaccaaag   80655
acagccaaac catggatttg aagtcctgaa aaataaaagt caacatcaca accaaagtgt   80715
atatattctc cttgtaacag gacttgatct tatcactttt ctctcctgtg tttggtgaga   80775
aggtagtatc taatgtcagt ttcaaacctt gaaaaacctg gtctttaact gtgatttctg   80835
ttcccagagt gttctgttcc cagagtgttc tacttttctg tgaaagtcag atcataatca   80895
caccatttat atttggtctc caacgtccca gtaattttac cagtgtctgt atgagatgaa   80955
ccagatgttg agaattccat gccactgcgt gactttttt ttttcacatc cagtttcacc   81015
aaccctgaac caaatccttt gtggaaagta tctctgacag ctatgccaag gtcagcatac   81075
gatggaggaa tacattggcc acactgaggt ctgtttgtag gtcaccatgg tgaagacttg   81135
ggaagagata atctggtggt ctccagatgg ggggtgctcc cactgctgtg ctcacagctg   81195
aggccactgg gtttgcctgc tgttgggtca cagctgcctc gactggagga caaagtggag   81255
gcacatttcc acttgcagcc tgaatgtttt ccaaatgtaa aaatattttt gagctgtatt   81315
agtcagtgtt ctgcttagaa acagaatcag taagatagat agcagtaaga taggtaggta   81375
gatagataga tagatagata gatagataga tagatagata gatagaagac aaaatgagcc   81435
agccgtggtg gctcacacct gtaatcccag cactttggga ggccaagatg gaagggtcat   81495
gaggtcagga gttagagacc agcctgacca acatggtgaa acttcgtctc tactaaaaat   81555
acaaaaatta ggtgggtgtg gtggcgggca cctgtaatcc cagctactca ggaggctgag   81615
gcaggagaat cgcttgaacc tgggaggtgg aggttgcagt gagccgagat catgccattg   81675
cattccagcc ggggtgacag agcgagactc cgtctcaaaa aaaaaaaaa tgaaatgtat   81735 tatgaaaatt gactcacaca gttatggagg tcaagaagtc ccacgatctt tcatctgcaa   81795 cctgacaac taggaaagtc attgttgtaa ttcagcttga gttggaggga ctgattgtgt   81855
aaatcttagt ccaaggccaa atggctgaga accaggggcc tccttggtat aagttccatg   81915
cccaaaggcc tgagaatcag aagctccgat gccctaggc agcataacct ggatgttcca   81975
ccttaaggaa agagagctaa attcttccct tcctctgctt attttgttct atctgggccc   82035
```

```
acaaagtatt ggatggtgca catccatatt ggtaggggcg gatattctct acttagtcta   82095
ctgattcaaa tgagaagctc ttcaagaaac accctcacag acacaccaga aataatattt   82155
taccagctat ctgggtatcc cttaacccag tcaagttgac ttataaaatt aaccatcacg   82215
ttagccttat ttctagtcgt aaattcttgg taaatatttg ttgaatgaac aaatgtcata   82275
ttcttttcca acaacaatag ctatgttcct aataataatt gttaccgagt gtttagtaag   82335
taccaaactc tagactacgt ttttatgatt gaacctcatt tagttctcac aactaattgt   82395
gatggaaaaa atgataagga aactgaggct tagaaacatg aagtaacttg cctgaagtta   82455
gacaactgat cagaagattg acccagagag cttgtctcca gaatccagtc tgaatcacaa   82515
tctactgtgc ctttatttta gccacttatg aacaaataaa tttagtaacc ctcttgctaa   82575
atatctggca cacatggttt ggttgtatag gattgaaaat tttttttgta cagatatcac   82635
ttttcattag aattgttgta gtgattagca tgcttatatt ttcccaaatg tgccatctct   82695
catctcaaat tctaaagtca atgagttgtc tttaggagaa agaactggtt tatatctttt   82755
aggctcaatt cttggagtga tcaatcctgc taatgctcat cttcttttcca gttagtaagg   82815 tctgggtcct tgcactttt tggattctct ttttaaatgt aatagaaaag aagtagctct   82875
gggcttcgtc cagtatgttc ctgaattgtg atgcagttgt ctgtagtaag gatatcaata   82935
actgtggaag tggcgtttcc ctctaacctc ctgggaacaa cattttttcac tgtgtgggtt   82995 tgtctgtgat ggagagagct gcaacaaaaa ctgtggttgc caccattttt acataggatg   83055
gagggataga tacttttcat tgcgattcaa aataagtaat ttctggcaga aataaaaagg   83115
attctcttgc tgtacttatt ccatagctag tgattaatat taatattaca cctccataac   83175
cagaggcctt tactgtgcat gacattggca atgatacatc ctaaaaaaat ttgggaagta   83235
tgaggatgct tgagatatgc catgttttcc tttttttcctt tctaatttc tgctttcctc   83295 tctccttttc tttgtgggct gtgtgtgtgt gtgtttgtgt gtgtgtgtgt gtgtgtgtac   83355
actttggtgt gtctcttaac aaagtctttt catctcaagc tccctgatat atgtggaatt   83415
tgtccacccc tctctgcctc tgttttctct cgtagcttct atcattccca gcgtgaacta   83475
taacctccta actggtgtct tcacttgtgt tctgtttccc tattgttgat tcaccgcata   83535
tcatttaaaa gatgttttac aaatgaaaat ctgagcattc ctgttgctta aaaatatttg   83595
gtggctacct caaatcctta atatttctaa tcttcatgat tatgttcctg aaaatactct   83655
ctagctgcat tcatttacta gatcattaga ttttgtgtgt ttttggctgt catcatagta   83715
agatatttgt gtcatcagta catatacaca cacatacaca cacgtgccta aaacaaaagt   83775
ttcacaaaaa tacctacctt ttctacacac acatatccac gtacctatgt gacatagatg   83835
tataatatat gtgtgaatat ttagtatata ttactcccca ttcatggga ccaggaaata   83895 tgtttgtcct atttgggtac ttatggccaa catttttgaat tttgcccagt acagaatagg   83955
tactcaggat atatttgttt ttaagaaccc ataagctaaa ataaacttta caaaagaatg   84015
ctatgttaag aagccataag ctaaaataat cttcataaaa gaatgctata taagtgtttc   84075
accctcagga gtttccaata aaataatttt ttgtaggaaa agcaaagcta agaaaatatt   84135
ctctatttct atttattgat gtgattttat gtgttaacta aatgtcacac ttataataat   84195
tttcctttga aatcaataat agtagttatt tcagtgatag agtttcacat attgcagatt   84255
ttaatatata ctatacaaat gtaggaaaac aaaccacatt aaaaaatgta tgtgttgctt   84315
tgtttaaggt agaacattac attcattttg ttctgatatg tttggcttta ggcagagata   84375 tatttttcatt tactagacaa gattcatcat tgtagaatcc attaactagg cactgagtac   84435
```

```
ctaaaagctt taggtgttta gaggatgttt ggaaaactga tgaaatggga atctgagctg   84495
cacaggtagg atccatttaa tttggggcat gcaggagtca gccttaaggg agattcatta   84555
tgatggttaa taaaaccatc tagcatatgt aattggtgtg ggattgtatt gataaacttc   84615 cttctagag tatttgagct ggctattgag cctttcagct ttcaatgttg gataaaattt   84675
atattagcct caagcattaa aaccaagtag cttcatgtgt ttactatttg ttggtcttta   84735
tacagtccaa ctttatacca ggatttgaat aaggcaaaag tgcattattt aatcttcaga   84795
gatatcaaca tatatccagt atggtgattg atagatttcc taaagtcatc tattatttgc   84855
ttttcttaat atcaactgtg gctattgtct cttctaaaat tatttaaaag aagaatagga   84915
ttatttctta gtgcttttt ataattaaaa aacaaaagg aaaatagact caaaaattga   84975
tagtagttgg ggtccaatct ttgcattttt ctattaaact cttgaactca tatggataac   85035
atgttcttct tacaattact tactagttag gaatcgacta agttgcaatg aagagatttt   85095
taaattatgg aaatttgaaa gaattcttga aaacagttat tttaacaatt atcccagtaa   85155
attgaaataa tttatagcat gcttttctat ttcctgccca gcctttaaac tttatttg    85215 cagtaatggt attatttttc tttctcagca agatatggag atgataattg tttattccag   85275
ccatgatctt catatttgtg atccttccct gaccagctgt gctagagtat gttgttagtg   85335
ctattctggg aatcatgtaa aagacttggt cacttaatgt caggaggtga tcttggataa   85395
agtcacttag aaaaggaca aggcaactcc taatcttaag aaaaaacaga tgaataagag   85455
tataatatat actcagtata taacagctgc cttttctctc aatcttgcca gcatttgata   85515 ttttttttt ggtcttttg ctagccattc tatttgtagt tctctgatga ttagaaacat   85575
tgagcatttt tttcatatac ctcttggtca tctttatgtc ctcttttgag aaatgtgcac   85635
tcagatcctt tgcccacttt gtagtaggat tatttgttta ttttttgctg ttgaattatt   85695
tgagttcctt gtatattctt gatattagtc ccttgatgga cacatagttt gcaaatattt   85755
tctcccaccc tacagatagt gcaatgcctc cagctatatt cttcttgctt aggattgctt   85815
tggctgttca gggtattttg tagttatgta cacattttag gattgttttt tccatttctg   85875
tgaagagcat tattggtatt ttaataggaa ttgaattgaa cctgcagatt gctttgggta   85935
gtattgtcat tttcatggta ttaattattg tggtccataa tcatgggcta tctttccatt   85995
tgtttgtgtc ctcttcgatc actttaatca gtgttttcta cttttttga tagcggtctc   86055 tcacctcgtt ggataaatgt attcctaggt attttttg gtagctatta taaatgagat   86115
tgctttccag attcttttc agctggttta ttattggttt taaggaatcc tattgatttt   86175
tatattttga ttttgtatcc tacaattgta ctgattttgt tatcagtttt aaggggtttt   86235
ggtgcagtct tcaggttttt ctagatataa gatcatgttg cctgcaaaga gggacacttt   86295
gacttcctct tttccagttt ggattctttt tattttctc ttgcttgatt gctctgtcta   86355
ggactttcag tactatgcta aataggagtg gttaaagtgt gcattcttat cttgtttcca   86415
gttcttgagg aaaggctttc agcttttcc tattcagtgt aatgttagct atgggtttta   86475
tcatatatgg cctttattgt gttgagatat tttccttctg tgcttaattt gttgaaggtt   86535
tttattagga aggtatgttt gatttttatca aatgcttttt cctgcatcta ttgagatgat   86595
cagatagttc ttgtccttta ttctattgat tgatgtatc agatttgtca acgtgcctat   86655
gttgaaccat ccttgcatct gtgggataaa ttccattaga ttttggcaca ttatcttttt   86715
aacatgttgt aagatttagt ttgctagtat tttgttgagg atttttgcat caatattcat   86775
```

```
cagggatatt ggcctgtgat tttcttttgt tgttgttgtt gtgtcttgt ctggttttgt      86835 tttcaggcta atactggcct tatagagtga gttagaaaga attccctctt tttaatttt      86895 tggaatagtt ttagaagaat tggagttagt ttttcttcaa atgtttggaa gaattcagca     86955
ataaagccat cagtcctggg cttttctttg ttaggagact ctttattact tattcaatct     87015
tgttactaat taatggtttg ttcaggtttt ctatttcttc ctggttcaat attggtaggt     87075
tgtatgtgtt caggaacata tccatttcct ctaggttttc caatctgttg ccatgtagtt     87135
gttcataata atctcgaata atctttctta tttctgtggt atcagttgta atgtatttt      87195 tgtttctgat cttattttat tttctttctc ttttcttaat ctagctagca gtttatcaat     87255
tttatctttt ttaaaaaaac aactcttcac tttatctttg tatttttta gtctatactt      87315 tgtttagttc tgctctgatc tttattattt attttcgtct aattttgaga ttagttttt      87375 cttgctgttc tagcttcttg aggtgcataa ttaggctgtt tatttgaaat ctgtctactt     87435
tattgatgta ggtgtttatt gctacaagct tccctcttag cattgctttt gttgcatctc     87495
ataggttttg ggatgttgtg tttccatttt catatgtttt aagaaatttt aaaattcctt     87555
cttaatttct tcattgatca atggttgttc aggattatgt tgcttaattt acacacattt     87615
gtaaatttca aacgtgtttc aaatttcctc ttgtcattac tttctatttt tttccattgt     87675
catttgataa gatgtttgat atgacttaga ttttttaaaaa ttttttgaga ctttgtcttg    87735
tggcttaata tgagatctat cctggacaaa agctctagtt tcttataggt ggactggaga     87795
cagaaaaatc agtctttggc aaagacaaac agagcagata agtagaaaga agtgagcaat     87855
attacaaatt cagaaagaca gaatgagttg ctggtttcat tgttccccat gactatgtta     87915
attcctcttg aaaggtatgt gtataatcta gaaaacatga gatatttctg aatccagaaa     87975
tagtaggagt agcttcctgt tgctaatggc gctgtgctgt cagcttacta atcttggttg     88035
ctaacaaatt atgtcagtga tgttgtgatc ctggagcaag ctgttatact gaaactttcc     88095
aattttccag acagctttct gtcatagaag aggctgtagt ttcctccatg gtgcacttct     88155
gaattgtgac gttaggagtt cttcctgaag gctctgccta gaatattttt gttcatttct     88215
cccagtgatt ctgtaagtca tttaacaccc tgtgatacac aagttgggtc tgaaaatacc     88275
aagtgtggat tattttctct gaaactgaac tttaacaaat acaataatta tagcatttag     88335
aaaactataa ggtgatacta tgtatttatt cattcatatg tgcttgagag tcattggtaa     88395
acagacaata ccctcatgga atttacatgc tagaggaata agacagacaa taagcaataa     88455
acagaaaaga ataagtacat aatatatcat gtgaaaaggt agtaagagct aagaaagaag     88515
aagtggaaag tgtatctgta gttttaaata aggtaggcag ggtaggtgac atctgagcaa     88575
agactcaatt gaaggagatt ttgtattgtt atttcaatat tgtttcatta tacaagcttc     88635
aagatgaaac ttcagtttct ctttaatatt ttatctataa taacactata taacctttta     88695
aaaatttcat atttgtctca tatttgtcaa gtgtcttcat tcatcttctt cagataacgg     88755
atatgcaggc tttaatacaa gtatttgcgc agattatcag gtggttagat tttccttct      88815 tatatctcat ttacagccag agcaatttaa gagtaggttg aaactgataa ggaattaagt     88875
aaagaccatt aggtaacagt tatagaagta atactttaaa ttttggcgat cataacaata     88935
acaaaagaga attttgcata gggtgaaagt ttcagatgat tatgagtagc aagaaagctc     88995
agaaatcata aatgttgaca attcttagaa cgtatgaatc tcttacataa cagcaaagat     89055
cattccaatt tgtcaaaacc tctccaaatg gaacagatat tttatttgtg atttactaag     89115
gccaatgaac atgaagtttt tactttcttt gttgtggcca ctccacccttt atttgcatgg    89175
```

```
cttaaagttt tcactagata ttttcgccct tttatcacac gtcacattat tgaccaataa    89235
tgaacttcaa atttactaaa aaccctgtca ttggtactta ctcaacggtg cctttctaca    89295
tatttgaaat tttaattttg caaattctaa tagctgaatt ttactttttt cattaaattt    89355
tatcttgtta gattggagtc attttatga ctattgaatc taagtaatcc ctgactcttt     89415
tgtcagataa gcaattttg ggttcccttg ttgtcttctt tacattcttc tctactctca     89475
ttcatgagac taatgagtct tcttaaatgt atcaaaatgg aagactaaat ctggcagcag    89535
acaccagaaa tgtttcactg actgcccatc aaaatcccac actcatagga atgatactct    89595
agacatttat acatcgccca gccatttgta cgtaagaatg accattctgc catttataca    89655
tttactggtg taaagtagtg ttcccactga gtgaatgaac ttctgtgtga ttcacttgtg    89715
tatatttgct acagcatttt ttctcttttt aaagtggagt cataccataa ccttgaaatg    89775
ctattaggat taaataaaat aagttagtaa ataatccct aatatatatt aaatgtctta     89835
tgaatttaag ttctcatttc tcactttccc ttctttttg ttatataaat gtcttctttg     89895
aagaaacgtt tattcaggtc gtttgcccat ttttttattg agttgtgtga gttctttata    89955
aattttggat attaacccct taacagatat tttctcccaa tctgtaggct accttttcat    90015
ttcgttgatt atttacttg ctgtgcagaa gagcttttca gtttgatgcc atcctacctg     90075
ttttctcttg tgcgtgtgtt tttttgttt tgttttgttt tgtttttga cagagtct       90135 cgctctgtcg cccaggctgg agtgcagtgg cacaatctcg gctcactgca agctccgcct    90195
cccgggttca cgccattctc ctgcgtcagc ctcccgagta gctgggacta caggcgcccg    90255
ccaccacgcc cggctaattt ttttgtatt tttagtagag acggggtttc accatgttag     90315
ccaggatggt ctcgatctca tgacctcgtg atccgcccgc ctcggcctcc caaagtgctg    90375
ggattacagg cgtgagccac tgtgcccggc catttgtct tgtttgttt gcttttgttg      90435 cctaagcttt tggtataata tccaaaacgt cattgccaag gccaaccca aggagctttt     90495 tcctaatttt cttcttgtag ttttataatt tcaggtttta catttaggtc tgttatttat    90555
tttgatttga ttttttgtat atggtataat ataagggtcc aatttagtg ttttgcatgt     90615 ggatatccag ttttttcatc actatttatt gaagaaacta tccttttcct atagtgtctt    90675
cttggtgacc tgtcaaaaat tagttaatca tatatgcctg ggtttatttt tgcactctct    90735
atgctgttcc attgatctgt gtgcctgctt ttatgccagc accatactgg ggtttttttt    90795
ggttttgttt ttgttttttt tgttttttt ttgatggagt cttgctctgt cacccaggct     90855
ggagtgcagt ggtgcgatct tggctcactg caacctctgc ctcccgggct caagagattc    90915
tcctgcctca gcctcctgag tagctgggac tacaggcatg tgctactatg ccagctaat     90975 ttttgtattt ttagtagaga cagggtttca ccatgttggc caggcttgtc ttgaactcct    91035
gacctcaggc aatccgccca ccttggcctc ccagagtgtt gggattacag gcgtgagcta    91095
ctgtgcccag tccatactgt tttacatact atagctttgt aatataattt aaaattaggc    91155
agtttaatgc ctccaacttt gtttttattt ctcaagtttg ctttggctat tcagtgtctt    91215
ttgcagttct atataatatt agcatttttt tccatttctg tgaaaaatat ggaaattttg    91275
atagagatcg tattgaacct atagatagct ttaggtagta caaatatttt ggcaatactt    91335
acttttccaa tcttgtccaa agtgaaaagg aagaagcaaa attatccctt ttagcagatg    91395
acatagccct gtatatagaa atctttgatg aatccacaaa aaactgttag aactaataaa    91455
tgaattcagt aaatttcag aattcaaaat caacatagga aaatcaggtg catttcttta    91515
```

```
caccaacatg aaacaaaaat attgaaaatg tattttttct ttcaaaactt ttactcactt    91575
tctcatctta cagcaattga ttattaactg aaaatcccaa ggcacctaac ctcatagcct    91635
tatttatttt ctaattattt tattattgaa aaattaatac atgaacaatc agacatacaa    91695
tgaaaataaa tctcactctt tgctatagaa cctccatccc tctcctccta gcaaaataaa    91755
ataagatttt attatgctag accagaacta tctagtggtc ttggaagtca ctaaactgta    91815
aaaggagggg aaaacgacat aaagataaag aagataatct gctaactttg ttgctttcct    91875
aaactgagac tttaattaaa acaattagac cttgggaatt tagcctatca gtctcttata    91935
tattgaccga acaatgtcag atatagacat tggtttgcag attaagttcc tacaaacata    91995
tgattaagaa cccctttaaa tatgctcttt tgtatgaagc acttttcagc ataggtacac    92055
tatttttttg ttttaaattt ataaaataga acctcatttt gtttgttttc aaatagagct    92115
caagcaaaga ggttgccatg attcttacag gatcagaaat agagaaagca gaatcagatt    92175
gaagagagtg gttggctgag atacatttat caatttgatt gaagagacac tacagttgta    92235
ttgtttaaca tgatggtttt tggaagtaca atatcaggat aaaccataat aggtatctca    92295
ttctagaaac catcttttgca aaatagtttt tccaaagtct agggaattaa ttcattatgg    92355
atttgtgttt tgattagtta aaaatagtat tgtatttatc agttataggt acaaactggg    92415
agattcttcg tttgatttac tggttttaaa acaaagatct ttggaaagat ttatctttct    92475
aaaacaacag aaaagaaagg gaagatgggg gaatacgtgg tgtcttagcc tgttttgtgt    92535
tgctataaca gaatatcaaa gattgggtaa catataaagg aaagacatct atttttttaca   92595 atctggaggg tgggagtcca atagccgggt gctggcattg aggagggcct ttttgctgtg    92655
tcatctcatg gcagaaggca gaacagcaaa agagcacaag tgctcatgag agagaggaag    92715
gaggccaaac tcatcctttt atcaggaact cactcctgtg ataatggacc caatccgatg    92775
ataagggcat taatctattc atgagggcaa aacgctcatg acctaattac caattaaaag    92835
tctcacctcc taacactgtt gcattgggga ttaagtttac agcacatgaa ctttggggga    92895
cacattcaac cctagtgtta tagtattcaa gtaaaatctg aattcattct tatttagtta    92955
gaaagtcaaa ccaaaacatt tccaccaatt cattaaatat ttttttggcc atttttttctg   93015 acttttcaat tttatatctt aaccagaaag ggattgatct aaacaaacct taaaacacaa    93075
agtgaatttt gacaaagttt atgagtgttt gcatattttc tacaaggttg tatttcttct    93135
tccatccact tttaaattaa ttaaatacat ctctttcttt caataattta ttcaacaaat    93195
atttactgag atttcacaat attctaggca ctgtgaatac aaataagaaa aagctgtttg    93255
ccctcatgaa gcaaacagga ggaagaacga tgatcaccat ataccagt aaaacatata     93315 aggagacaga tgctgataag tacaatggag aaaaatggag caagaaagag agaaaaggga    93375
ttggaatgac gggctatttc aaacaggttg gtttggaaag acttgagtgg agacttaaca    93435
gaggtgagag agtgatgcag tgctgaggag gaaggctttg catgaaagag aatagcaagg    93495
gcaggccctg acaccaaaga gggcttggca agtttaagta acagcaagat ggccaacgtg    93555
gttgtaagga agagctgcca aggtggactc aaagaaatag ccagggtcaa actgcggagg    93615
gtcctgtagg ccactgtcag cacattgact tttattctga ggatctgaag aagtgacatt    93675
atctcacata ttttagaaga gtcaacctgg ctgttgcatt gagtgtagag cacagaagca    93735
gacatgaggg taaaactaga gagacacaca cacaattgat catcaatatt tgcaggtttc    93795
atatttgtga atttccctac ttggtaataa cccccaaatc tatacttcat acatgcatta    93855
caacacatgc atgtacaatg tgttgaaaaa tttgagatgc acaatgcaca tgttcgaaca    93915
```

```
aggtgattct ctgccctgct ttctggtttt agctctcatg cagtaaacaa gtgtccttat    93975
tgcagtctat ctggggccac atttatttt gcattttcat gggattttgt tgtttaaaat    94035
tgccctgatg caaagtgctg aagtgctgtc tagtgttgct aagtgcaaga agctgtgatg    94095
tgccttacag agaaagtatg tgtgttaggt caatttcatt cagacataag tgatagaact    94155
gttgattatg aatttaatgt taatgaatca acaatgcagt atgcccccaa aatagaggaa    94215
attcactaat atgcacatca ggccacaaaa atgataaatt aacacttatg tattgaagct    94275
atggaaaaaa actcaatttg tgaattcata agatgatgac caatagaaaa agcatatgga    94335
acaacattgt tgcgtggcta aatgaaggcc atagaaaatt tatcatcaca ttacacaggg    94395
tcaggagaat gttaaattct ctgggctag tgctggctaa ctcacagatt tcagaaaatg    94455
ttaaacttgc atgagattca ggttctgcag ataaggaggc tcaagaattg aaaaatacct    94515
gctgtgtctt acgcagtaaa agggtcatgt gaaagaatag gttcacaatg ctgataagac    94575
tgcttgtttt atgatgacat cagcaaacaa acctatgtaa tgcaaatgcc ctctaaagcc    94635
caggctttaa atcattcaaa ggccatgcaa tgaattattt gtgagaaata tgtattaaat    94695
aaagtgtctt taaacagaag cacacataaa acaaggttat gaattgattg tttgacaaaa    94755
acatgaccag ctactgaaac ctaaccctgt atttttccata gaagcaatgg ttctatattt    94815
gttcattcag catctgcaat aacttttag tacatgacta ctacaactaa tgagaatcaa    94875
ctgtatataa acatatatat ttttgtatat gtgtgttttg gactcaattg ttttgccagc    94935
ccccaaccaa attcctgtgt tgaaaccta atccccagta ggtcagaatg agactgtatt    94995
tagagatatg aatttaaaga cacaattaag ttaaaatgag gcccttagga ttggccctaa    95055
tccagtctga ctggtgtcct tgtaagaaga gattctgaca cacaaagag acatcagagg    95115 ggcacacaca tacagaaatg accatgtgag ggttgaccat ctgcaagcca gagagagagg    95175
cctgagaaga acccaactct gccagcacct tgatcttgaa cttccagctt caatgactgt    95235
gagaaaatag attgatttta ttcacctcgt ctgtggtatt ttattatggc agccctagca    95295
aactaagtca acatcaggca catcatgttg gtgtcattga acagccatat gttttatggt    95355
ggtggtgtga aatttatgag acacgattaa atttgtgtat attttgaaaa aggagctaag    95415
gggattttct gaagaattgg atatagctta ttagataaaa atggaagttt gcattcagga    95475
gaaaatgtat tcctattttg ttctttctta ctattcacat gttgcaccat ttttttccca    95535
aagaaaaaca actaagaaag gaaaaaatct tatgatgtga ggataaaaag actgaccacc    95595
ctagtcctat cactgaaaca tttccagtgg aatcagtaaa ggcatgatgt gttttaggaa    95655
atacgatagg gttgtttgtg acaatgtaaa tgtagttgtt cagggttcaa ttttaaaaaa    95715
tttaatttta aaacacttag ttttgaagag ttagaaatat ttgcaaggaa aaatggtttc    95775
ttatttttga ttaatattat ttttcatggt tctctaataa gaagaaatca aacttaactg    95835
cataaactat aattaaattc aagagtaaat gagtaatgaa taagttttaa gatctaatga    95895
tatatttact ctaccatga cacaattatc tgaaagcaaa ttgattattg gataaagga    95955 ctgttttagg gaacaaaagc gttgaaaata aatatgcaaa cactttcttt gtgttgtgga    96015 ttaaaccta ctgttttaa agtattataa agttcaata ataattacat acttagaaaa    96075
atgtactttg aaaagtaatt tctgtgcatt ttattctac cattagtgtt caatttcatt    96135
atttggatta acatttaat gtaataaga tatattttg cgagatagta tcttgggaca    96195
acttttaaga gaaagacatt ttcatacatt cagtttatac ttttttgtat tgaaatgcaa    96255
```

```
tctacatgtt tcactttaat aaggaaccaa atagagtctt aactttgctt ttgtttcctt   96315
atctccaatt ttcattgtgg ttcttattta tattaagggg attatgtggc tactgtaaaa   96375
tattcttttc ataataattg tccacattct aaggctgtat tcttctcttc atgttcatat   96435
attttgtatt tgtttcatag tattccattt cttttatagt gaggaaaaaa tctgtttgaa   96495
gtatctaagt ctctaaccct atgattacct tggcaaatta acatttttag ctgcagaata   96555
gttgttttct aacaaattct tcttccttaa ttcttttcat aagttaccaa gtatctctta   96615
cagctcccaa caagccctac atcttgaaaa tatttaaata ttttcaagat cttaaaatat   96675
ttaattgata ttcaatgata tcaattagaa tttctgatca atgttatttt gagaaataag   96735
agctgcttga tttcatgtag ctaaatgtta cttttataat ttttattttt tgttttttaat  96795
cttttatctg aattcagaca tctacttttc actcttacag ctagctttat ttactccttg   96855
tttttgctct ttttctgcca cagattaagt tttatttctg ttctagaagg agcttgttct   96915
tgaaaggctt actgtctatt gagttattat tcacttctga tatttacatg tttaattagc   96975
aacactttat aaattacctt cataaatatt attttatttg aacctgattg atttcatcct   97035
gtgaaatgaa tgggagatta ttatcttcaa tatgtagata aggtgactga ggttcaaaga   97095
gattctatga cttactttgg gcacacagct gatggaagtg gcacgggtag acttaggaat   97155
cacccagtgc ttctccctta caagtcttgg gctctttcca ctaccatcct attacctttg   97215
caggcaattg aagcttaggt attctgcaat aagcaatact tgcaagatta tcaatcttta   97275
gtataaccat gaatataatt cttaataaat aatgctatgt aaattaatgt aggcatatgt   97335
gaaagtgttt tgtgaattat gtctatgcat acacagcata ttaatatttc gtctggcaaa   97395
atagcactaa tgtaattaga tataattaag aaatacctga tgccttcaaa attatttcgg   97455
gccagcattt ctttatttc ttataaaata taattttggt ttatatcaat aaatcacaca    97515
taccttaaaa agatgtattt ctacaaagct tatatattaa gtagaatata ggcttacatt   97575
attttaacaa agaataaagg gatgatggat taaacaaatc tcatgtctct ctcatgtaaa   97635
agtgcaagat gagaacctgt tgtggttgca tgggaccggg gagggaaggg atagataggg   97695
aagctctgcc ccttgaggtc atccaagatc ccaaatttct tctacattgt tgcttcacca   97755
agcgtttccc ttgtccgcct agtcaaaact cgtcactaca accacagtcc aacacaaggg   97815
aagggaggaa gaagtcaaag ttacccgcag tggcacaaac ctcttctgct ccacatccag   97875
gaggctgttt cttatttgca tagcttttcc tagctgccat gcattcaatt aaatatttag   97935
ggattctgtt actaaaagag taggatgaga gaatgggtat tggttgatga ataccgttat   97995
ttcctagcct gatcactcag atacaaatga gtcatttatt tatttttga tacatttaaa    98055
acatactttt ggacatacag taatccaaag tatttttata ttacttgaca tagctcaagg   98115
aatgtataat tctctctttt gggccagtta aatctaattg ttatctggca acgtatacac   98175
taaaaggtga gttattaatc actcctcccc tgacttacac acaatcactt gtatagtggg   98235
acaggatacc acaaagatac ttcttttcag aaaagccaag aatattatac aaactaaagt   98295
cattggttca ttagagttat caaatcctgc tgagcagtca gtgctagctc ttcctaaact   98355
aaccatcatt attctgcctt tggggagtaa ctattttgtt ctagttttct ccgtggctcc   98415
tggattttcc atttgggaag tttttgtttg tttgtttgtt ttttctatt attctctatg    98475
gattcctgtt aggtgagtgt tagagttgtc ttttccttct tcggaaaaga caaatttcac   98535
agtccatttc ctgctagtac agatttggag acctagagat tgctttgaaa gtttaaaaga   98595
cacaggcttt ttgaaaattt cccttgtggt ttctttgaaa agacaatttc catcaaaatg   98655
```

```
taatcgtttc agtcagttcc atgtgcaggt aagcacaagc agagatttta tttaaccata   98715
gatattaatt ctgaaatctc gtgtttattt actagtcctg tccagctacc aacccacagc   98775
tgacattaca gctaccagga aaagaatgac aaattacaaa aataacattt gtaaaggtat   98835
aatacaacag taaggactca atatcagaga gggcagaacc attctgaagt gatctgaaga   98895
tcaccagctg cttaaaactt cctagaggca ttggccaatt ctgaatcagg cagagaaca    98955
agctcaatgc aagccgaggc tatgattaag gaaaaaaaaa atcaacaaag ctgttagttg   99015
tcatggaaag ctgactgaca agttataaac ttgagaggat tctaacacat ggctgagttc   99075
tgggactact caagaggtca aggagccaga tcaaaggga  aaacaaaatt ttctacagat   99135
ctgtgaatat taaggaaaaa aaaatatcac caaagagcga gagtggctta ctcaagcaca   99195
cagctaatct ccctctgaat agaagtgcca ggattgaagg tcaagtggct aagagctgac   99255
cttggaacct gtgacagtag agcttgatct taaaatcttt cagggttgaa gagaagagta   99315
cttggtaaaa accatttgtc aaaagcccag acaccatga  ctgaggagta ggaattaatc   99375
agatgtaaac agaggcttag caaaactatt accaaatccc aaaactgttc agtctctaat   99435
tagttgtgat catcagttcc ttcttacatt tgtctaacaa aggaaatggg caaccctctc   99495
taatggaaga taacatcata tggaacctct gtggttcttt catgacaatt tccaacatat   99555
aataaccatt actagatatg tacaaaggta ggaaaatatg actgacaata aagagaaaga   99615
aaaatgatcc aagcacaccc atggatgatc tagatattgg aggtaacaaa caagaacttg   99675
aaattaatta agaatgtata attattttaa ttatacttaa aatgctttcc aggcatggaa   99735
gcttatgcct gtaatctttt ggaggctgta ttagtccatt ttcatgctgc cgataaagac   99795
atatccaaga ctgagcaaat tacaaaagaa ggagatttaa ttggattcac agttccacat   99855
ggctggagag gcctcacaat catggcagaa gatgaaaggc acatctcaca tggcagcagg   99915
caagagaaga gagcttgtgc agggaaactc cccattttt tttttttttt gactggagtc    99975
ttgctctgtc gcccaggctg gagtgcagtg gcatgatctt ggctcactgc aagctccgcc  100035
tcccggtttc atgccattct cctgcctcag cctcccaagt agctgggact acaggtgccc  100095
accgccacgt gtggctaatt ttttatattt ttagaagtgg ggtttcactg tgttagccag  100155
gatggtctcg atctcctgac ctcatgatcc acccacctcg gcctcccaaa gaaactctcc  100215
tttctaaaac catcagatct catgagactt attcactatc atgagaaaag catgggaaaa  100275
acctgccccc atgattcaat tacctcccac caagtccctc acacaatgtg agaattcaag  100335
atgagatttg agtgaggaca cagccaaacc atatcagagg ccaaggcagg aggatggctt  100395
cagcccagga atttgagacc agcctgggca acacatggag acccaatttc tacaaaaatg  100455
tttttaaaaa attagccagg catggtggcg catgcctgta gtcccagcta ctcaggaggc  100515
tgaggaggga gggtcactta agccttggag ttccagacaa gctgggcaa  cagagcaata  100575
ccccatctca aaataaataa atacatacat aaaatgttaa taaaaattga ggaaaagttg  100635
gaaaataaat gaaggatgta gactttttaat atagaaatgc tatatatgat ggtgaaacct  100695
catctctact aaaaacacaa aaattagcc  aggcatggtg gtgcacacct gtaatcccag  100755
gtacgtggga ggctgaggca tgagaattgc ttgaacccgg aaggcagagg ttgcagtgag  100815
ccaagattgt gccactgcac tccagcctgg gtgacagggt gagactccac ctcaaaaaaa  100875
gaaaagaaaa gaaaaaaatt ctatctacga aagattcag  acgaacattc aagagctgaa  100935
aaaatgcaat actaaaatta aaaatcaata aatagtctta atagcaaacg gagaaaatca  100995
```

```
taaaatagaa gatatttcaa tagaaaacat caaaacaaaa gcatctagag agaaaaagct    101055
aaaaatgaaa taaaaatgac aaaagagatg tgtgtaacac actcaaaaga tcaacttaat    101115
gaaagctaca ctctgaaacc atctgaaaca gagaacagtc ttttttaactg atctttcctc   101175
atgagaacaa attgcaatgt gactgagaga ggcttgggag tcccatctca tcttttgctg    101235
tttgagatac aggagctggc tagttttcta aactaagtga ggccccaagt gaagttgtct    101295
tcagccaata taaattgaag gtaatgggat gaaagacata catttttagca aagttgtatt   101355
ctcttttgtc tctcctttca aatgaagtaa gtcttgcgaa atttatttct ttgcgacctc    101415
tttttaaagtg gcaacaagca gccaagaagc accaccattt tgactttttc caatgtcctt   101475
gactagagct gtgctgtcta atacggtaag cagtaactat tgtggttac ttagatgtaa     101535
attatgaaaa ttaaatgaag tttgatattc agtacctcag ttgcagtagt cacagttcaa    101595
ctgctcaata gtatcaaaca gcacagatgt aaaaaaattt ccaccatttc ctatattgat    101655
ataaggttct attagatagc agtaacctaa agttatacac tcaataatca tacaattttc    101715
cttttaactt ttactggatg cttaccatgg catagttacc agttttttcc agcttttcag    101775
ctggaaatac taagttaaga gctttacttt agaataactg gccaggggtg cattggtttt    101835
gctggaattt aactatcaga aactacatat cattccttga aggtccatgt tggaagagat    101895
gattctttca tttttttttcc tggtataata aggatggctg ccacttttct cagagcctag   101955
taacaagtga gtttggtggt gtggaggtcc accaatcagc ataaggtggt atttaatttc    102015
tctatttttca gatgccaccc aagccttccc ttctgtacac tgtttctgag tttagtgtcc   102075
ttttagttca gccctgccat agagcagtcc tccattttttg aaaagaaga gactagtgag    102135
agctgatcac caaaaaatct agttgctttt cgcgcagatt ttcaactagt ttccctattt    102195
tctatttcac ttattctctg ttttcagggt tcaccctgtc tcattttttga gcttttttttt 102255
ggcatgtagt gtatgatgat ttcctttggc tttcttttatg cttttggata tttagatttg   102315
aggtttcttc tatatgttgc cttttcaccac ttggccacct tcttttcagc ttcattattt   102375
tattaaaatt tcctattcgt tgccttcttc tctggtattt tcttgtcctc aaggggaccc    102435
tcagtctttt ttttttttaac cctttcacag acattttaga atttttaaag ggaaaggagg   102495
taaaaaaaaa atgtttacta ctccaggttg aaccaggaat actgcattgt tttataactg    102555
agctgtgaat aataggcatg tgaaaaattt gtgttggtag gaactgatat gtactatata    102615
gtcaatatat tctgggaact cacattcttt gaaatataaa taattctatg ccatacttgg    102675
tatttttcac atgaaaaaaa ctgaaattcc aatagattaa atcatatcct ggaggtgcaa    102735
gagcttaata agtaacaatc tgtttatact tgattttgtc atgcttcctt atatcataat    102795
acagtgttta aaggctcaag aatttgtgcc tgggtttgaa ttccagttgt acaacgcaat    102855
agctgcactt aatttcacat tctacttaat ttgtctgtgt ctaacttttg tttgtctctg    102915
tgtgtagaat attgataata taacagcagt atctacctca taggattatt ggaaggatta    102975
aatacattaa tatatgtaaa agattttgaa tagtgcttga catacagtaa gttctataga    103035
tgtgttagta atttctaatt gtattacttt gtgctccatc tatcccaagg aagaaaagat    103095
attgcttctg cttatagatg gtcttttaaa gctaggaaat acgacattaa aggtgtgacg    103155
tctacttgca ctttaaaaac tctcgccttt ctagaacttt ctgttactaa agcttgaaaa    103215
tgaaagaact gttactgagt gagctaatga aagaaaaaca tgctgatttc ttctacttttt  103275
aaaggggaaa tggatgatgt aagttctgaa gatagatctc tacgattttt tttacatcct   103335
ctagattact tttagtggtt tttccatact attttcattc tactcattct aatttcaaaa    103395
```

```
gtccttctaa tttgtatatt tgaattagta tccctagaaa acatttctc  cataaccaaa  103455 ttgatgtaga accatagttt tcaaaatgtt attgcatggg tcataaaaag tagttgtggg  103515
gactttaaaa ctatcttgaa acaatcttct tgtttcatat aaaagccaat cttcttggct  103575
tttatatttc agattaaatc caaaccactc atagcttgag taccatcagc tgttggcaaa  103635
acttagcttc ttggttctat gtaaaagtga atcattttgt aaacactctg acaaccaaga  103695
tataaatcct ttggtttaca caggtgacct catgaatatt cttttccacc ctttgtgtgt  103755
gttagaggga gaaaataccg caggcattga atattgaaat tttttctaat cattgtaact  103815
ggaaggagac gctgacagat ccattctctg gacatgtgtt ttaaagttaa ggaggaaaag  103875
acatgaaaaa ataccgtata ggctttgctg aaaccaaagc atttggagca cagtttaata  103935
cgtttgccaa attttaaata cagctgggtt ctcccacagt ttctttaatt ggaagcagat  103995
ttctgtgcta attctgtaac gtgaagagag ctctaacagt atttctttcc taaaagtagg  104055
gcatatattt gcagtgacca cttctaacat caacaactcc ttaaaaatat ccgacttagc  104115
aattttcaat gcgacttaga aattttcaag agttttcagt agatttatta cctcatgtgg  104175
ttttatatac ttaatagtta agtgtataaa taattaaaat tatttaataa ctgataatta  104235
agttcactgg gtattttgtt tttagaaaaa agtggatcgt atctaaagaa ttaaaaatat  104295
ggaaatgttc atattgtaaa gtaaaagtcc acattctgct tgaatgtgaa agacaaaatg  104355
tttgtttctt tcataagttt aaaaaattta ccaagttctt aacattttaa tatgataaaa  104415
tttagtggaa aaggctaaat tgaaacaaaa atgtatttat attatatact acatatattc  104475
cattcaaaac tacaatacta gtttctgagt caccaaatgt ggaaattaat gtcaatatga  104535
tgaaaataca attttggaaa atttatctgt ttttaatacc tatatattca ctttaacact  104595
caatatatta cattttttaat aagcactaat gatattaata gtaatttgaa agaaacatat  104655
tacaaagttt tataaagaaa gcattaaaat aggttttttgg aagattaacc ttgaggcatt  104715
atttcagtct gctttccaat tacatattgg aaagaggggt acagcatcta cttttttaatg  104775 ctgctcttac tttggtaaga atctaggtag tgggtaaaaa ataaaatcat ttgaaatagt  104835
tttttattta ttgaacattt tttaggctgt acctataaaa tatctttata gcaataaata  104895
cttttatagc aataatctac accagatgtg ttcatcatga cttttttaaac tttctacccct 104955 ttcaaaatta catatctggt ttttgttgac agtactatta aacttagag  aatttacctg  105015 attttaatag cacagcaaaa gagctgtttt aggagaatga gcataattga aatataggca  105075
tttgctaagg agagtctata aagaccattt tcattaagac acaaaaagat tccccaaata  105135
ttagtgtaag ctctaaaaat tgtgccagca gtgtacccctg agaaggcagt tatttcctta 105195 ttattatgca ggcacctaaa taaaaggtcg atgtatgtat cagttttttc cacaagatct  105255
ttattgcttt ctcttggtct ttgtactgtt cccttttgcta atactgcggt atcttaatat  105315 taatctatt  tattgtaagc tttgatatca gttgagctag ccctcccatt tttatttgca  105375
tgcaagcgta cttagctatt catggctctt tcaatttcat ttccatttta gaatcagctg  105435
tatagtcaaa aattctgttg tgatgttggt tggtattgca ctgagtctgt agatcaattt  105495
gtgaaggact gacatatcta tattgccatt catgaacatg atatatatct ccacttgcat  105555
cattaatttc tctccataaa cttttagaat tggtgcatat cttttctttg atttttttcct 105615 tgttgcctaa ttttttgtaca ctatgataag ttgtacctta tattttgtta ctgatgttta  105675
aaaataaaat tgattatggt atactggttt tataaaaaat ggccttgcta aactcttatt  105735
```

-continued

```
aattccatca atttgtagat tatttctatt ttctatttca aaaagctaca tcatctgcaa    105795
atattgacag ctatcaatac tgacatgttg aataaaaatg gtggcatgaa tatctttgtc    105855
ttgtgcttaa tgtcttacca ttgcagattt agcattaagt aattgcagaa aattcctttt    105915
gtagctaccc tttgttatat ggaagaatgt gcccatttgt ttctagtttg ttgagttttt    105975
aaaaaatcat aaatggatgt cgaatttcag taatagctct tcccttaaa  atgtttacgt    106035
ggcaaatttt attgattgat ttttcaacat aagccaaatg tattggtgaa tgtagtaact    106095
cattgctttt tttaactaga attttcccca ttatgagtga ggttgagtat ctttcttta    106155
gtgtgcttat tggctatttg gatatccagt ttgtaaaatg cctgttcaag tcccctctcc    106215
cttttttacaa aatcaggttg cctgaccttc tcgtattgat ttatagatgc tcattatata    106275
ttcctgatat aagcccttgt tagttattcg agttacaaat atcttctccc tcacagcagg    106335
cttgactttt cactttgtta aggatgcctt ctggaaaatg ttacttaatt ttaatgtgat    106395
gaagttgctc aatttttaaa ttaatggttt ttctggtaat gtttaagaag ttttttcttt    106455
ctttctttct tttttttttt tagacgagtc tcactctgtc gcccccaggc tggagtgcag    106515
tggcctgatc ctggctcact gcaaccctct gcctcccagg ttcaggtgat tctcctgcct    106575
cagcctccaa agtagctggg attacaggcg cccgctacca ctcctggcta attttttgtat   106635
tttttgtaga gacgagtttt caccatctgg ccaggctgat cttgaactcc tgacctcaag    106695
tgatccacct gcctcggcct cccaaaatgc tgggattaca ggcgtgagcc acctcgcccg    106755
gctgaggtct tttcttactc tgaggtccta ttgattctct tctatatctt ttagaacatt    106815
tactgttctt ccttttaaat ttacatatat aatcagtctg gaattcatct atatggtatg    106875
aaaatggaaat atttaatttc atacatatgt atattata tgtatataaa ttataaatat      106935
acatatatat gtaaattata tataaagcat aatttccatt ttatttttt  ccagaggatt    106995
gttttctttt aatccttaag gattcagctc cttacaaggg ttttgttgga ggtcatgggg    107055
cagcaccagg aggtctaaat catggtgggt gcattcagta cttcatgaga tccattctca    107115
actaacatgc tgtgaatggc acaactcagg cattaacgta gcttcacata taccttggga    107175
agcacgcagg agtcgaagac actccctttg gaaatgtctg atagctgcag cctcttctgt    107235
tttgaatgac gaacttctta gtagccttgt ccttgggcat acattgggca cagtgtctgc    107295
agcaaatagg ctgcatgtgg ctgtgcctct ttttggcatg acatggttcc ttcttttctt    107355
tgtcatcttg aaagcaagaa cctgagacta atttcatatt tttttttgta aattacataa    107415
aacacctta  ttattgtttt acaaggtcag tgtttaatta catttatcca catttccatc    107475
cccctttctt ttcttttctt tttttccttt tgaacttta  ttttagattc agggagtgcc    107535
tgtgcagatt agtcacatgg gtagattctg tgtctctggg gtttggtgga cagattactt    107595
cctcacccag gtaaggaaca tagtcctgat gggcagtttt tttttttta  attctcacct    107655
tcatccctt  tcttgtgctc ccttttcctt tgcctctctt gagcttccgt ttgggcttca    107715
ggattacatt catccttgct actggtgggg cactggttcc aggaacacca ctccctctc     107775
tcccacgtgg atacccaaat cccagcataa tcaaatcgtg tagttgagga accctggaat    107835
atcgataaga ggaacaactg tgtttattgc aaaaaaatct gcctataagt ggaccgcaca    107895
gttcaaactt ctgctgttga agagtcggct gtattttct  tatgcttgaa gtctatcatt    107955
cagaatttcc tttaatagag gcttgatggt tgtaaagtct cttgcttttt gtttctttga    108015
aaatgtctct tgcaccttca ttcttgaaag ccttttcat  tagatataaa attgtcaatt    108075
gaaatttatt ttatttagt  acattgaaaa aacatatcat ataaatagat atatctttaa    108135
```

```
gatttcctct tgtagttttt ctgaatttca ctatgatttg tcagcttttt atctgcttgg  108195
gtttcattag gttttgaat tgtggattg atatatgttt taattctgga gaattctcag    108255
ccattatcta cttaaatatt gcttatacat tgttctttt ctctctttct gaaaactcca   108315
ataaaatata tgttagattt tattattgta tccttaatgt atcatcaaat cctttcccca  108375
acagttttat attttgtct ttctgagctt tattcttgat gttcttgata ttttttttct   108435
taactatttt gcatttcaca aagtttcttc aattggatcc aatttgttct caaatccatc  108495
cagtttctta ttttggttac catgctttc agttctatac attctatttg gttccttttc   108555
aaatacgctg tgtcatttga aaatactctg ttacattttt ccagcttggc ttttatttc   108615
ttttaaattc taagtacgat tattttataa ttattatatg ataattccaa tatgtgaagt  108675
gtcttgagta tgtttctgtt gggttttata aacggtgcct ttctcttgag tacctagtta  108735
tctttgactg tgggctagac attgtattag agaaaacatt ttagaaaagt attgaggccc  108795
agtataacat tatgtttcta cacagaggat tttggtttgc tttgctaca tgtctagagg   108855
tgctagaaaa cctagatgcc tgtgattcca tttcaaggct tcacattttc taggccttta  108915
taatgcaaac ttgagctgta aagtacgcac attgggtagt ttatttctgg ttcatttgtc  108975
ctcttaggaa gcaatccttt ggagttgtaa ccctggtatg ctttagaagg agtgcttcta  109035
agcccaatat agccaatctt tgaggatcat ggacaccaca gtttgtattt tgacccctgc  109095
aaggcatttt cactactcgt ttctcagctt tttctttata ttggtaagta gcctcaatgc  109155
aaaagtagcc ttaagtactg ggtgtggttt tatgagttct catcctttcc tgaatctcat  109215
cccatatttc atcttgaatt tataagttat ttgataaatt aaaaagaat tcttttaat    109275
agtttatcaa gctatttta gttgttctta gcaggaggac tgatctgaat agcctaccat   109335
cagcagaagc tcctgatact ctcttttcag tgtaatttca cttcaacaga gttgttgga   109395
gtaacgagga tatggcacat catcattttc cttagtcccc atacacaccg ggagataggc  109455
ctaatctcac caatgacagt gaattcagaa acacattaa ctttgaaatc tattcattta   109515
agatcaaatg aaggctgtta ataagtaagt attctgctta cacccaaaaa agcacatttt  109575
atgagtttta tgcgtagtct ttctagtgaa ctatttggag attttttct tctgttttt    109635
cttgttcaat gcataccaca aggccagata acttattatg gacaaatgca gttgagtttg  109695
agcacataat tagagtgact gtttagcaat tttaaattga tataagacat tagcaattgg  109755
aaagtaacta gtgaaaatct gtctgaccat aaggtgcata caatggcatt tagcctaaag  109815
gccatattct aagttaccca aaattaatta cgaacttaat agtataacta ttagtgcatt  109875
atactagtat aaagaaagtg ataaaatgtg ttattaaatt atttagattg tcatcagttt  109935
aaaattataa ataaaagtaa cagtggcata gtatgtcctc agttaaccag aaagcttggg  109995
taagcatatc aaattactgg taataaactt tactatatgt ctcaatcata tttctttgtt  110055
ccttccttgt caaaaatgta gattatctgt ctaactgctt gaaaggaaaa ttttcttaat  110115
attttccctt aggacattcc tgttttattt tgtgtctatt tttttttta acactccata   110175
attttttaaag taacctggca ggagcccaag tgcatggaat gaaaagtcat tcttggacct 110235
attccatatt gcaacaccag tctcttaaat cactttttata tgtaacattt gtattctatt 110295
cagcaaatgg tcatattact tactattctg ttgaaacatt gcataggtat ttgcttaaga  110355
catgcattac tcagaggata ataaatttct tcttgcttaa catgtagcac aatgcatcta  110415
aatacttgta tttttatttc tcaaagctaa agtcactgtt tctctatcag ttctttgcct  110475
```

```
tcaaatacaa aagaggaaaa tgtaattaat gaaccagtaa tttcggagtg atcatctttt    110535
ctcttcctta gctcacagat atttgctgct atctgtttta cgctttcaca ataacttcca    110595
tttgcatcac tctttacatg actacatctg agagaagtgt acggtaagag ttagaaatat    110655
tactcttgtt tagtagtagc aaaactcaag tgcaagaagc tgagagtcac atggccctgt    110715
tcagcttctg gtccggtact ccctccaata accctagttt gtcttttct cttcatttt       110775 actgatttct atcccacccg tgcatttgtt ttgagatttc agctcttgtg acatcatctc    110835
tgcaaattat gcattgagat ttttgagaga tttcttgaaa tttctgttta atgagtggtg    110895
ttaatgtaac atatagattt taatatctgg aaaacttcat tttttatcat ccactacttt    110955
ctcttaatta atttaacatc atttgccttt cttactggtc atagtataat tctgaggtaa    111015
taaggtggca ttttaatt  aactattcat agaacttctg ggagaaattt tatgtctagt     111075
tcagaaggca tggcagcatt ttaaattgga ttgtggagta ttctaaccaa atcttcaaga    111135
gccgtaactc gaggtgaaac ctgccaacag taagttcttc tcgtagccca aggcttgttt    111195
ggttttgatt agttttacta gacttcattt ggtttcaatt aaaccttgag acaggctagt    111255
gactttcatg aaacgtgggt ttctcaagtt agaaaataat tcttttgtgt ggacgagtgt    111315
aacgttttct tcactgaaag aaaatatcta ctcaaagata attttggaag attttataat    111375
cacattgcaa agagatttt  atacattgaa ctgtctcata ttatgtttct taaaaattat    111435
tatattgtat tcttaaatgg caaaatgaaa atcactccat atgcttccaa agcaataata    111495
agaaatattt aactatataa gtataacaac atttttatatt taactgcata ttgttaattt   111555
gattttaaaa taagcagcta ttctggggag ttccagaaat ttttaaattc atttattttt    111615
ctaaaaggct ttcttttagt attacattat cttaggtcgt gttcaaatga atgatttc      111675 ctgagtcgca agtcctttat tacttaaaaa ctgtaacaac ataacatcac tggatatgag    111735
ttgaaaatcg tgcatagtat ttttatgcaa aggtagaagg agaagcataa agttataaac    111795
atattgtata ccctaaacaa agaaaactgt ggtctgtagt cctcagagaa aaatctcagg    111855
tgtaagttcc ttttgtattc caaattttt  ttgatcctaa acaaaatcct ttattaatcc    111915
ttattaaaaa aattccatgt tgggtaataa agataaatag aaaacaaact caaaagtagt    111975
gtttgaagtg atagaagatg tacatttctc tttctgtgaa ttcataaacc ctggcttcag    112035
atactattga tttttaccca gaggcatcat taaataccc   accatctgtt taagattatg     112095
ccaaaaatat tgcagttata aatatagggc acgtgtataa aaattagatg tatcaagtta    112155
aggatattat cataatgctc ttctatattc tcagcatgaa acaaaaatat taataaatat    112215
gtgaatattc tgcttgtaaa tatgtctgta gaatttaaaa ctgataaata aatttgttca    112275
gaaatgtaga atttaacatt taccactcgg aaaacaagag cagatcacct cttgaataag    112335
tgtcttccaa ttttgtttct aacacagcaa atattttata tttacaattt aaaaaattga    112395
attctccaag tattatgttc caagatttaa ataagattaa cgaccccttc aaatattttt    112455
gttgagagct gtttattaat accttatgtg gtcacatcaa ttaaaattaa tgacatctgg    112515
tatacaagtg aataatttct ttacatattt tatcatattt gaataaatag aatgaagaac    112575
aaagcactga ctttttattc atactaccag gtttggattt ggattctgct atgaattcat    112635 catgtgccttt ggatctttt tcctttctgg gcttaccttt catcaaatgg aaagaactag    112695
aagctctcaa tggttctttc taccttaaac attttattgg ttatttacaa attataaaca    112755
tttagtttgg ttagcatagg ctgtatgttt atatataggc tatataatta tgtgcttat     112815 atctctagta attaaaaatt atttttttta ccttgtaaat ttaaatttat catgaaggaa    112875
```

```
gcagaactag ttacattggt aaatatgttc attcactatt acactattac ttctgaatga  112935
acacacatta ttttctctat agaccaagaa ctgtctatta atctattaaa atatattttc  112995
tcaaaactga tcccagggtg ctagggacac aaaattcaaa gataaataag aaattaaatt  113055
tggctgtgtg atgttgaaat gtaagtaagc aaataaaata aaatgtgatc aaactttatc  113115
agttcgagtt tttattacca gcaaattcca attttattga cacagaatta tctcagatta  113175
gcaaaaataa gtggtggtac tttttttctt tttattttt ttattatact ttaagttctg  113235
gggtacaggt gcagaatctg caggtttgtt gcatagatat acatggacca tggtggtttg  113295
ctgcactcat caacccgtca tctacattag gtatttctcc taatgttatc cctcccttg   113355 caccccatgc cccgacagac cctggtgtgt gatcttcccc tttctgtgcc catatgttct  113415
cagtgttcag ctcccaatta tgagtgagag catgtggtgt ttggttttct gttcctgtgt  113475
tagtttgctg agaatgatgg tttccagctt catccatgtc ccagcgaagg acatgaattc  113535 attctttta tggctgcata gtattccatg gtatatatgt gccacatttg ctttatacag  113595
tctatcgtgg atgggcattt gggttggttc caagcgttgc tttgtgaata gtgctgcaat  113655
aaatgtacgt gtgcatgtgt ctttatagta gaatgactta taatcctttg ggtatatacc  113715
cagtaatggg attgatgggt caaatggtat ttctagttct agatccttga ggaatcacca  113775
cactgtcttc cacaaaagtt gaactaattt acacttccac caacagtgta aacaagttcc  113835
tatttctcta catcctctcc agcatctatt gttccctgcc tttttaatga tcaccattct  113895
aactggcatg agatggtatc tcattgtggt tttggtttgt gttactctaa tgaccagtga  113955
tgatgagatt ttttcttat gtttgttggc cgcataaatg tcttcttttg aaaagtgtct  114015
gttcataccc ttaacccact ttttaatggg gttgtttatt tttttcttgt aaatttgttg  114075
aagttccttg tagattctgg atattagccc tttgtcagat ggatagattg caaaaatttt  114135
ctcccattct gtacgttgtc tgttcactct gatgatagtt tattttgctg tgcagcagct  114195
ctttagttta attagatccc atttgtcaat tttggctttt gttgcagctg cttttggtgt  114255
tttagtcaca aagcctttgc ccatgcctat gtcctgaatg gtattgccta ggttttcttc  114315
tagggttttt atggttttag gtcttacatt tacatcttta gcctccaact ttgttctttt  114375
tgcttaggat tgtcttggct atatgggctc tttattggct ccatatgaaa tttaaagtag  114435 tttttctaa ttctgtgaag aaagccaatg gtagcttgat gggaatagca ttgaatctat  114495
gaattacttt gggcagtatg gccatttttg agatattggt tcttcctatc catgagcatg  114555
gaatgttttt ccatttgttt gtgtcctctc ttatttcctt gagcagtggt ttgcagttct  114615
ccatgaagag gtccttcaca tcccttgtaa gttggattcc taggtatttt attatctttg  114675
tagcaattgt gaatgggaat tcactcatga tttggctctc tctttgtcta tcattggtgt  114735
ataggaatgc ttgtgatttt tgcacattga ttttgtattc tgagactttg ctgaagttgc  114795
ttatcagttt aaggagtttt ggggctgaga cgatggagtt ttctaaatat acaatcatgt  114855
catctgcaaa cagagatact ttgacttccc ctcctcctat ctgaatatcc ttcatttcct  114915
tatcctgcct gatttctctg gccagaactt ccaatactat gttgaatagt agtggtgaga  114975
gagggcatcc ttgtcttgtg ctggttttca aagggaattc ttccagcttt tgcccattca  115035
gtatgatttt tggctatgag tttgtcataa atagctctta ttattttgaa atatgttcca  115095
taaataccta gttattgag agttttagc atgaaggagt gttgaatttt attgaagacc   115155
ctttctgcat ctattgagat aattatgtgt tttttgtcat tagttcagtt tatgtgatgg  115215
```

-continued

```
attatgttta ttgatttgca tatgtttaac cagccttgca tcccaggaat gaagccaact   115275
tgattgtggt ggataagctt tttgatgtgc tgctggattc aggttgccag tatttttattg  115335 aggattttg  cattgatgct cctcagggat attggcctga aattttcttt ctttattgtg   115395
tctctgctag attttggtat caggatgatg ctggcctcat aaaatgagtt agggaggatt   115455 ccctctttt  ctatggtttg gaataatttc agaaggaatg gtacaagctc ctctttgtac   115515
ctctggtaga attcggctgt gaatccatct ggtcctgggc ttttttggtt ggtaggctgt   115575
taattactgc ctcaatttca gaacttgtaa ttggtctatt caggtatttg actacttcct   115635
tgtttagtct ggggagggta tatgtgtcca agaatttatt catttcttct agattttta   115695 gtttatttgc atagaggcat ttatcgtatt gtttgatggc agattgtatt tctgtgggat   115755
cagtgatgat ctccccttta tcaccttta ttgtgtctgt ttgattttc actctttct    115815 tctttattag tctagttagc ggtctatttt gttaatcttg taaaaaagtc agcttctgga   115875
ttcattgatt ttttgaagg gtttttcatg tctctatctc cttcagttct gctccgatct   115935
tagttatttc ttgtcttctg ccagcttttg aatttgtttg ctcttgcttc tctagttctt   115995
ataattgtga tgttagggtg ttgattttag atctttcctg ctttctcctg tgggcattta   116055
gtgctatgaa tttccctcta aacactgctt tagttgtgtc ccagagattt tgatacagtg   116115 tgtcttttt  ctcattggtt tcaaagaact tatttatttc tgccttaatt tcgttatta   116175 tccagtagtc attcaggagc aggttgtcca gttttcatgt agttgtgcag ttttgagtga   116235
gtttcttaat cctgagttct aattaaattg cactgtggtc tgagggactg tttgttacga   116295
tttccattct tttgcaattg ctgaggagtg tttcacttcc aattatgtgg ttgatttag    116355 aataagtgct atgtggtgct gagaagattg tatattccgt tgatttgggg tggagagttc   116415
tgtagatgtc tattagatct gcttggccca gagctgagtt caagtcctga atatctttgt   116475
taattttctc ccttgatctg tctaatattg acagtgggg  gttaaagtct cccactatta   116535
ttgtgtggga gtctaagtct ctttgccggt ccctaagaac ttgctttatg aatctggatg   116595
ttcccgtatt gggtgcatat atatttagga tagttagctc ttctcattgc attaattcct   116655
ttaccattat gtaatgccct tctttgtctt tttgatctcg gttagtttaa agtctgtttt   116715
attagagact gagatcgcaa cccctgcttt ttttgtttg ttttgtttt catttgcttg    116775 gtaaatcttc ttccatccct ttatttgaa cctatgtgtg cctttgcaca tgagatgggt   116835
ctcctgaata caggacactg attactctat ttaatttgtc agtctgtgcc ttttaatagg   116895
ggcatttagc ccatttacat ttaaggttaa tattgttatg tgtgaatttt attctgtcat   116955
tatgatgcta gctgtttatt ttgccccatt agttgatgca gtttcctcat agtgtcgatg   117015
gtatttacat tttggtttgt ttttgcagtg gctggcaccg gttttccttt tccatatta    117075 gtgcttcctt caggagctct tctaaggcag gcctggtggt gacaaaatct ctcagcattt   117135
gcttgtctgt aaagaatttt atttctgctt cgcttatgaa gcttagtttg gctgcatatg   117195
aaattctggg ttgaaaattc ttttctttaa gaaggtcaga tattggcacc cactctcttc   117255
tggcttgtgg gatttctgca gagaaaccca ctgttagtct gatgggcttc cctttgtggg   117315
taacctgacc ttttctctg actgccctga acattcttcc ttcatttcaa ccttggtgga   117375
tctgatgatt atgtgtcttg gggtttctct tttcgaggag tatctttgtg gtgttttctg   117435
tatttcctca atttgaatgt tggcctgtct tgctaggttg ggaaagttct cctggataat   117495
atcccgaagt gtgttttcca acttggttcc attctgcctg tcactttcaa ggacaccaat   117555
aaaatgtagg tttggtctt  ccacatagtc ccatatttct tggaggtttt gttcattcct   117615
```

```
ttttattctt ttttctctaa tcttgtcttc acgctttatt tcattagtca atcttcaatc   117675
tctgatatcc tttctttcac ttgatcgatt cggctagtga tacttgtgta tggttcatga   117735
tgttctcgtg ctgtgttttt cagctccatc aggtcatctt ggttcttctc taaactggtt   117795
gttctagtta tcaattcctc taactttta tcaggttctt agcttccttc cattgggtag    117855
gaacatgctt ctttagcttg gaggagttcg ttattaccca ccttctaaag cctacttctg   117915
tcagttcatc aaactcattc tccatcctat tttgtcccct cactagcaag gagttgtgat   117975
cctttggagg agaagaggca ttctggtttt ggatttttca gactttttgt gctggttttt   118035
cctcatcttc gtggatttat ctacctttgg tctttcctgt tggtgacctt tggttggagt   118095
tttgagtggt catcctttct gttgatgttg atgctattgc tttctgtttg ttagtttttc   118155
ttttaataat cagggccctc ttctgcaggt ctgttggagt ttgctggagg tccactccag   118215
accctgtttg cctgcgtatc accagcagag gctgccgaac agcaaagatt gctgcctgct   118275
ccttcctctg gaagctttat cccaaagggg cacccaccag atgccagccg tgctctcct   118335
atatgaggtg tctgtcgacc cctgctggga gatttctccc agtcaggagg catgggggtc   118395
agggacccgc ttgaggacac agtctgtccc ttagccgagc ttgagcaccg tgctgggaga   118455
tcctgctggg agccagcagg caggaacgtt taagtctgct gaagcttcac ccacagctgc   118515
cccttccccc aggtgctctg ccccagggag atgggagttt tatctataag cccctgattg   118575
gggctgctgc ctttctttca gagatgccct gcctagagag gaggaatcta gaaaggcagt   118635
ctggctacag cggctttccc aagctgccat gggctctgcc cagttcgaac ttccctgagg   118695
ctttgtatcc acggtgaggg gaaaaccgcc tactcaagcc tcagtaatgg cagacaccca   118755
tccctccact aaactctagt gtcccaggtt gacttcgac tgctatgctg gcagtgagaa    118815
tttcaagcca gtgaatctta gcttgctggg ctccgtgggg ttgggatttg ttgagctaga   118875
cttggctccc tggtgtcagc cccctttcta gggaagtgaa tggttctgtc ttgctggtgt   118935
tccaggctcg actggggaat gaaaaaagcc tcctgcagct agcttggtgt tgcccaaag    118995
gccgcccagt tttgtgcttg aaacccaggg ccctcgtggt gtaggcaccc gagggaatct   119055
cctgatctgt ggattgcgaa gtctgcggga aaagcatagt atctgggctg gatagcacca   119115
ttcctcctgg cacggtccct caaggcttct tttggctagg ggagggtgtt ccccaacccc   119175
ttgtgcttct cgtgtgagag gacaccccac cctgcttctg ctcacccacc atgggctaca   119235
cctaccgtct aaccagtccc agtgaaatga acctggtacc tcagttggaa atgcagaaat   119295
caccggcctt ctgtgtcggt ctcactggga gctgcagacc ggagctgttc ctgtttggcc   119355
atcttgccca ggagccccca gtggtacttt tttcaatgct taaaagaatg gaaacaatct   119415
atttagaaag tgaacatgta ttatagattt cagcatgtcc attagaagat ggtttactag   119475
aactatttct ttttgcatat agaggaacaa acttgaacag aaaactctca gtctttgtac   119535
tgaatttcct tgtcttgaaa gaaatgagga ggtagtgacc agcatttta ttagaatgtc    119595
agaggtgcct ctcataaact acttgaacgc tgacttcaag agttgcaatg atcaaaaaaa   119655
aatgcagaaa atgaactagt agataactgt gggagatgga aggtgttgat ggcattcacc   119715
acaggtatgc acttgtccac ttatttttctt ggctggatta atgaaaggat gaggaacctg   119775
tttttatttt ttatttttttt aaggcagaaa gatcttcgca actatcaata tggtgaaatg   119835
aaaaacaact acccattttc ttgtcctctt ttatccttga ttgtagttat gtaaaaagct   119895
ttactcgtta aaaaaaatta aatgtttggc caagtcatgg gatcaactca ggatttatt    119955
```

```
ataacccaga tcttggctaa ccacattttc ttaaaatgtc cagtagactg aattgcaccc 120015
gtggcttcta acatgaacgg ctggagccaa gaatgcttgc gtgaaagcag ccagccacca 120075
aaacacaatg ggatttattc cttcattctg ggtttaaaga aaggatctta aagatccaac 120135
cttttagcct agaaagcttt gtaaaccttt tcaaatacct ctgaggaatc tgcatacttt 120195
gtagctcaac ttattagtct atttcattca cacgaggaga ttctccactc taaacactct 120255
gacttgcaga ggatggaata ccaagtaggt gtactctgga ttggggcttt gataaaaacc 120315
tttcaaagaa gaaccatagt acaacagttt ttgggataca gtttctggaa taatgtaaaa 120375
tggtgaaatg taggcagatt tttgtaaccc tgctagtaag ctaattaaga gtatgtattt 120435
ctgtattggt tgaagaagtt ttatttttc ctttaagaaa tttctatgaa atgcaagcta 120495
ttataatgag aaagaattgt tcctttgcca attttaaagc ctttggagac attagtgtat 120555
taaccccaca tggtatctga agggagcatt gaactggcag ccagaattcc tgagttctgg 120615
ccttgaaact ggtatgtgct actgatatta tcttgagcat attcattcat ctgtcctgga 120675
agagatcatg aatgctaatc aaatattcca tgtgttcatc aatatttgca agcatcccct 120735
gtggctatgt tggggtcatg tgacaagtgc aggacataag tccaagggat gtttgtcttc 120795
cagtttgaag gagttaagtg aaccaggata aattttcaat aatctttgtc atctgcaaag 120855
cagcaaacaa aggttttaaa atggccaagt tgcaagatgg gagcaaggag atctctgagt 120915
tgtaaaaaga agaggaaagc catttgttca ttgcgacatg aaaaggaaat aaatatttgc 120975
tgtatcaagc tacgtgaatc tgggggttgt tttgtgccac agcatagcaa atcctatgtt 121035
gactagcgtc tctccaggag tcatcataag ctgagggggtt tggagacttc ttaattctgt 121095
tccagtttgt attcctgaaa ttgtctttgg gcatatgacc ttcattttac aaaagaaaga 121155
acagagaagt ttggagataa ctgactaaag tcacaaagta agtttgtggc catgctgcac 121215
gatgtatttc tctgggaccc tgtagattca tattccccag gtatatttct ccacaaccta 121275
tgagattaac tgtgggatca ttcaaattga ccattaacaa aatgctagat tgattctctt 121335
cctgtctact aggttttgtt cacttagaca tgatgtaatt ctgtgatgca atggataata 121395
cggcattcaa catcctgacc ttaataccag agacttatct atcagattat ggagtctgat 121455
agtatacata ttatgtctat tttcaactgg ggaaaaattc tacctctgtg tttagttttg 121515
aggtggttat tgaacaagaa cctatgatag accccaaagc tattttcaca aaacttgaat 121575
ttagaaattt aatgcagggg tccccaaccc tcgggccatg gactggtacc agtccttggt 121635
ctgttaggaa ctggccacat agcaggaggt gagtggcaag caagcaaagg aaggttcatc 121695
tgtatttaca gctgctcctt atcactggca ataccacctg agctctgcct cctgtcagat 121755
cagaggcagc attagatcct cataggagcg tgaaccctat tgtgaactgc acgtatgagg 121815
gatctaggtt gcacactcct tatgagaatc taatgcctga tgattgtcac tgtctcccat 121875
cacctctgga tgggaccatc tagttgtaga aaaataagct cagggctccc actgattctg 121935
catgaaggtg agttgtatta ttctttcttt atatattaca atgtaataat aataaagttc 121995
acaataaatg taatgctctt gaatcatccc gaaaccatca ccttagtccc agtccatgga 122055
aaagttgtct tccaggaaat tgatcccagg tgccaataag gttggggact gctgaattaa 122115
tgcatttgta actacctggt agtttcttgt ctttggcatc cgggatggat ataattgtcc 122175
tcccaattgt caagtgtcaa aatgtaaaat atagtacaca taaacaaata ttgatgagga 122235
taaaatgagt taatatctgt aaagtcccta ggacagagcc tggcatagaa ttaacaatat 122295
acaggtgttt attaagtaac acaaaggtga ttatgatgga tcatgagaca ctgtgagcta 122355
```

```
ggatctagtt gacatctcct ttaattttcc tcttatagaa ccccagatac atgtcatccg 122415 atttctattt aaccatattt ttgtgctagg aaatatgatt ttgtagtaca tggtaaaata 122475 tttttactta ggacccatca ttatctcaat taaaaataag aaaacaggct aagaggagtt 122535 aagaggttta cccaagttta caaagctgtc aatgtccttc actatctgcc taggaagttc 122595 ataatctttc ctaggcagtc ttctatatca ctgtctccat tattagtagg agtagcagtg 122655 ccatgtgatt tgagcatggc agcccacaag ttccactatt aactttctgc agggtaggaa 122715 tcacttcagc caagatctgg agctcaagca atttccctct gggtgagcag catttattat 122775 tcaaatacac ttatttaata aacttaatta ttacatattc aactatttaa taatctgtgc 122835 tagcatttta tcatggtttc acatttgttt tttctctgac cttttttgaag cttttttcct 122895 agcagctaag gtgtgtcaca ccaaccatct aaagacaag gccaggcaca tggtaatat 122955 ttgttgattg tacagttgct aaaaggagac aagttcaaat gagtcactta tagaagcatt 123015 tggacttcaa cagatcgtca agtgtttgaa aactcttatc actaccatgt cttgtttctg 123075 ggacattttg gttttctgca ttaggaaaac atcagatacc tcagtttgaa cactgtggag 123135 cttgcaattt actcacacta ttatgtcact tatgttcttg tgatcattta ctggaaatta 123195 tgtcattcta cttctctctg cttcataggg gaatcttaat tccaatccat ccttctacat 123255 tacttctaat aaatctaatt tttgcttttgt ttttgttaag gagtatcctg ccaccattgt 123315 actctagaca taatctcatt catagcatca gagatactct gcagattgtg tatttgcctt 123375 attttaaaaa ttgaagtttt ttaaaagact ctatttaaag actctaaaga ctattgtatg 123435 cattgctatt gttaacaact gaaaccatat cattcttgcc attattttaa gataagacaa 123495 atcatttgtt ccctgggatg gaaatgagct ccttttcttg taggtttgtg tattttttcca 123555 acccatatat gattataagt ttcttccagt aaccttcaaa attctttatc tccttagggt 123615 taatatagtg aaataattac ttgggaaaat gggaggcata gctttgcttt tgaagtctag 123675 ctttactact tggtacccac gtaatactga acaacatatt taatctccct gatcctcatt 123735 ttccttttgg gtaaaaggag aataatgtgc atatagaata gggattaaag gcatggactc 123795 tcaagctatt ttgcctagtt tgaagcttca ctgtgcccta ttttgcctat gatatcattg 123855 gcaattactt aactcttcgt ggtgcagttt tcacggtaaa aaattaggga agcaattgga 123915 tcttcttcgt atggtgatag aaatattttt atatgtgctt tttctttcag attgtaatgg 123975 aggttcgaaa taaagcttgc tcaagtccct cctatcaagt ggcatagtat ttgtatataa 124035 cctatgcaca tcctcccata taccataaat catctctgga ttacttataa taactgatac 124095 aatgtaaata ctgtgtaaat acagtcaggt gctacataaa aacttttcac tcaataatgc 124155 tccacatata tgatggtggt cccataagat aataatatag ctaaaaaatt tctattctct 124215 agtgaccttg tagccatatg cattattcac atgttggtgg tgatgctggt ataaacaaac 124275 ctacacatac gattacacac ggtacataat acttagtaat gatagtaaac gactacgtta 124335 ccggtttatg tgtttagagt actaaacatt ttatggttat tttgagtgta ctcttttac 124395 ttaaaaaaaa aaagttaatt gtaaaacagc ctcaggcagg tccatcagga ggtattccag 124455 aagaaggcat tgttaccata ggggatgaca gtttcattgg tgttattgtc cctgaaaacc 124515 ttccagtgag aaaagatgtg gagctggaag agagtgacat tgatggtcct gaccttgtgc 124575 agggctagtc taatgcattt gttgatgtct tagttttaa gaaaacatt taaaacataa 124635 aaaattaaaa tcataaaaca agtaaacgaa gaaggaaaat attttttgtg tggctgtaaa 124695
```

```
atgtgtttgt gctttaagct aagtgttgat tcaagagtaa aaaagcttaa aaattaaaaa   124755
gtttgtaaca taaaaaagtt acagtaaact aagtttaatt tattattgaa gaaaaacatg   124815
aatttagtgt agcctaggtt cacagtgttt acaaagtcta cagtacatac agaaatgtcc   124875
taggccttca cattcactca ccgctcactc actgacgcac acagagtaac ttctaggctt   124935
gcatgctcca ttcatggtaa atgcctgtat taggctgttc ttgcattgct ataaggaaat   124995
atctgagact gagtaactta taaagaaaag aggtttaaat ggctccaatt ctgcaggctt   125055
cacaggaatc atggtgctcg catctgctca cctttgggtg aaacctcagg gagctttcaa   125115
gcatggtgaa aggtgaaggg agaataggca tgtcacttgg cagaagcagg agcaagagac   125175
agcaagaggg agagagagac gcagacagag agacaaagag acagagtgag tgagaggagg   125235
tgcacatact tttaaacaac cagatatcac aagaactcac tcactatggc aaagacagca   125295
ccaagccatg agggacctgc ccccatgacc caaactcttc ccaccaggcc tcacttccag   125355
cactggggat tacaaggcaa catgagattt agatggggac aaatatccaa actgtatcag   125415
tgctctagag aggtgtaccg ttttatctt ttatgcctta tttttagtgt tccttttcta   125475
tgtttagata cacaaatcct taccatgtgt tgtaattgct tatcgtattc agtacagtaa   125535
catactgcac aggtgtgtgg cctatgagta acaggctatt ccatatggcc tagatatgta   125595
gtggctacta tctaagcttg tgttaataca ctctatgata atttcactga cagaatcacc   125655
tgagcacaca tttcttagaa cgtatctttg tctttaagct gtgcatgatt gtagttgttg   125715
tactgcattg ttttaaaat ttgtatcatt tttacagcta tattgttatt ttttatggct   125775
tcatttttt ccaagtgttt tgatccaga gttggttgaa tttgtggata cataaccttc   125835
tgataaggag ggctgacggt atgtcttagt gctttgatta tacttcagag gtctgtaaac   125895
tttctataac aggtcagata gtaaatttt aagactttg ggacacctat acaagtctgc   125955
cattgtatag caaagtcat tatagataat gtataaacaa attggcgtga ttttggtcaa   126015
taaaactgta ttcacaaaaa cagccttagg ctggctttgg cccatcagtc atactttgct   126075
gaccctgat ctgactgttg gttaacacaa atttgatccc atcaggcaat tttgcctttt   126135
cttccccaga ttacagatac tccgtctctg tagctctgaa tttgtacttt atttctcttg   126195
ctcatctaaa agcattcaat tttcaattgt ttaactaaca agcttttga gctgcgtgcc   126255
agagcagaga tcaattttag tgttaattcg tagtcgttaa atagaattag gaataaattt   126315
ttagaatcaa atatactcag aatagaggaa attttctact ttcatctatc tctcttgatg   126375
gactaaggtg agaatataca tcctcaactt ctccccatag gtcccctaata gatacccaaa   126435
cttgcagtat acaaaatcaa actccttatt ttcaccctct aatccattcc ccctgcaatc   126495
ttcttcttcc ttgcagttct tcagttcaaa attttaggt catccttgac cgtttgctct   126555
ttgacattcc acatggaatt caacagaaac tttctctggg actgtcttca gcatataccc   126615
agctctggct actttgcaca accattgaca ccaccactga gtgatgggga agaaacaaaa   126675
tatttccaca agtaaccttt ttactcagta actcaggatg ttttcaatt tgagagacga   126735
tgaagtataa ggctaaaatt taaaccatat caagatcatt tattattaag attattctat   126795
atatagtatg tttattgtcc ttttgagtaa gttttgtttt gtattttcca attgggttgt   126855
gttgtctcat gaaatggcta tttactttgc tgtgtcatgt atttaggcca ttttactcaa   126915
cattgaaaat aattttctta gtgtctttgg cattttggga gcataagtct ttcttcaaga   126975
tgaaattttc ttttcccctc caatatagcc atttcttgtt ttattacact ttgctctatt   127035
gcttagcaga tattgtggat tatttttttc aaattgaaag tttgtggtga ccttctgtca   127095
```

```
agcaagtgta gtgtcattac ttgtcttctt ttttaaatgt atcttttaag ttcaggagta  127155
catgtgcaag tttgctaagt caacttgcgt catgggggtt tgttgtgcag attatttcat  127215
cacccaggaa ttaagcctag tatccattta ttatttttgc cgatccactc cctccttcca  127275
gcctacaccc tccaaaggac ccaatgtgtg ttgttcccct ctatgtgtcc atgtgttctc  127335
accatttagc tcccacttat aagtgagaac atgtggtatt tggtattctg ttcctgtgtt  127395
atttgctaag gagaatggcc tccagctcta tccatgttcc tgtggaggac atggtctcat  127455
tctgttttat ggtgtaaatg aactacattt tctttatcca gtctaccatt gatgggcatt  127515
taggtcgatt ccacgtcttt gctattgtga atagtgctgc agtgaacata catgttcacg  127575
tgtctttata agagaatgac ttatattcct tgggtatat acccagtaac gggattgcgg  127635
ggttgaataa tatttctgtt tttaagtctt aaaggaatca tcacactgtc ttccatctgg  127695
ctgaactaat ttacacttta atcaatagta gttttgattt gcatttcttt tttttttttt  127755
tctttgagat ggagtcttgc tctgtcgcca ggctggagtg cagtggcacg atatccgctc  127815
actgcaatct ctgcctccca ggttcaaatg attctcctac ctcagcttcc cgagtagctg  127875
ggattacagg tgcacaccac cacacccagc taattttgt atttttagta gagacggggc  127935
ttcactatgt tggacaggat ggtctcgatc tcctgagctc atgatccacc cacctctgcc  127995
tcccaaagtt gagttttttt catgattgct gactgcatgt tatattgtcc tttgagaatt  128055
gtctgttcat gtgctttgcc cacttttac tgagatttct tgttttgttt tcttgtaaat  128115
ttgtttaagt tccttataga tgctgggtgt taaaaactat gttttgtcag atgcatagtt  128175
tgtgaaattt tctcccattc tgtaggtttt ctgttcaccc tgttgatagt ttcctttgct  128235
gtgcagaagc tctttagatt aattaggcat catctatcaa ttttgcttt tgttgcaatt  128295
attttggcat gttcatcatg aaatctttgc acattcctat gtccagtaag gtattgccta  128355
ggttggcttc caggattttt atagttttgg gtttaacatt taagtctttta atccatcttc  128415
aattaatttt tgcatatgat ttaaggacag gatcctgttt cagtcttctg catattgcta  128475
gccagttact ccaacatcat ttattgaata ggaaattttt tcccaatggc ttttttttgt  128535
cagggttgtt gaagatgaga tagttgtagg tttgtggcct tatttctgtg ccctctattc  128595
tgtcacattg gtctaaatgt gtgtttttat actgtaccat gatgctttgg ttaccatagc  128655
cctgtagtat agtttgaagt cagataacgt tatgcttcta gctttattct ttttgcttag  128715
gattgctctg gctatttgag ctctttttg gttccatata aatgttaaaa gagtttttt  128775
ctggttcttt taagaacatc aatggtagtt taatagaaat aggattgtat ctataaattg  128835
ctttgggcag tatggccatt taaacaatac tgattcttcc tgtccgtgag catgaaggt  128895
tatttcattt gtttgtgtca tctctgattt ctttcaacag tgttttgtag ttctcataga  128955
gatccttcac ttccctgttt agctgtattc ctagatattt tattcttttt gtggcagatg  129015
tgaatgggat tatgtttctg atttggctct ctgcttgact gttgttggtg tatagaaatg  129075
ttaatgcttt ttgcacattg attttgtatc ctgagacttt gctaaagttg tttatcagct  129135
taaggagtat ttgtgctgag actaggggc ttttagatg taggagtatg tcatctgaaa  129195
acagggatag tttgatttcc tctcttccta tttagatgca cttatttctt tgttctgcgt  129255
gattaccctg gctggacttc taatattatg ttggatagga atgatgagag aggacatcct  129315
tgccttgtgc cagttttcaa ggggaatgct tccagctttt gcctattcag tatgatgttt  129375
actatggggtt tgtcatagat gtttcttatt attttgaagt atattacttt aatacgtagt  129435
```

```
ttattgagag ttttttaacac gaagggggtgt taaatttttat cgaaagcctt ttctgcatct 129495
attgggataa tcatgtggtt tctgtctttta gttctatttta tgtgatgaat catatatatt 129555
gatctatttta tgttgaaaaa ccttgcatcc taaggataaa gcttactgga tcatggagga 129615
tgagcttttt gatgtgctgc tatatttggt ttgccggtat tttatagagg attttttgcat 129675
tgatgttcat caaggttatt ggcctgaagt tcatcaaggt tattagcctg aagtttttctt 129735
ttttgtttcc gtctgtcagg ttttggtatc aggatggtgc tggcctcata gaatgagtta 129795
gggaggagtt cctcctcctc attttttttgg aatagtttca gcaggaatgg taccagctct 129855
tctttgtaca tctagtagaa ttcagctgtg aatctgtctg gttctgagct tcttttggtt 129915
ggtaggttat ttattactga ttcaatttca gagctcatta tcggtctgtt cagagattca 129975
gtttcttgct ggttcagtgt tgggaggatg tatgcatcca ggagtttatc tgtttcttct 130035
aggttttcta gtttatttcc atagaggtgt tcataatgtt ctctgatggt tgtttgtatt 130095
tctgtgaggt cagtgataat atcccccttgt tgtttctgat tgtgtttatt tgaatcttct 130155
ctcttttctt tattagtcta gttagcagtc tatttttattg atttttttaa gcccctggat 130215
taattgatct ttcaaatggt ttttcaggtg tctatgtcct tcagttcagc tctgattttg 130275
gttatttctt gtcttctgcc agctttgggg tttgtttgct cttgttcctc tagttgtttt 130335
atttgtgata ttaggttgtt aaagtctttc ttacttttttg atgtgggcat ttagtgctat 130395
aaaattccct cttaacactg ccttagctgt gtcccagaga ttctgatatg ttctatctttt 130455
gttctcaatg gtttcaaaaa tttcttgatt tatgccttaa tttcattatt tacccccaaag 130515
tcattcagaa gcaggctatt caatttccat gtaattgtat ggttttgagt gaatttctta 130575
gtcttgttttt ctaatttgat tgcactgtgg ttcaagagat tgttataatt tcagttcttt 130635
tgtattattt aaggagtatt ttctttccaa ttatgtgatc attagaggat gtgccatgtg 130695
gcaaggagaa gaatgtatat tttgttgttt tagatggaga gttctgtaga tgtttatcag 130755
gtccatctca tccagtgctg aagtcaggtc tgaatatctt tgtgaattttt cagtcttggt 130815
gatctgtcta atatcgtcag tggggtgtta aagtctccca ctattattgt gtgggagtct 130875
aattctcttt gaaggtgtct aagaacttgc tttatcaatc tgggtgctgc tgtgttgggt 130935
gcatgatgtt ccctcagtct ttgaaaattgc tgacctttgg attattttttct tttttcttttta 130995
ttatatttta tgaccttgag ggtttgattg tggtgtaggg tggattctgc caacttgctt 131055
catttccgga agatcctagg gggccagtgg tcagctccca accactggac tgtatgctat 131115
cttttggggga cttgtattgg gccctgactt tgttctccgg ctccttgagg ttaggaatcc 131175
actgcgcggg aggggctgag gggtcccaag atcagtggtc actacacttc aatgagtggt 131235
gtcagccaaa gcatttcaaa gtgtggggac agcgggattc atcctccttt gcgaatgccc 131295
acagcagcag tagcaacagc tgtggcagag tactagcggg tattgtggtg cctgcctccc 131355
tgtggatgtt taccacggtg gcaaaggcag tgcagctggg gaggggtgg ggcccctgct 131415
ggtgactgtg tgcagggtcc tgctggaggt ggtattggct cggggacagg gtgcctgcag 131475
gcacaggtct aggtgccttt tctgtgcccc gcaagcagga gcgatccctc agggcagggg 131535
agaattctgc tgttctttgt tcagtgttag tgcaaggtca gggagctggc aggggcaggg 131595
atggctggct ctgtgcctgc aaatgttcca tctgcaatgg tggtccgtcg ggggaggtgg 131655
ggtggtctgt actcccatgt gctggcaggg caaggaaagc aaaatctgct ctcacagatg 131715
tgagccagca aagtaatgtg aggagttgcc ttggcctgg gagaatctac agtatgtggg 131775
tgggagagtt tgtgggctgg tgtgtgtctg taggggccac cccattggaa ctctccacca 131835
```

```
gtcagacatg gcccaccagc acagaagcta tgctgtgagt ccccagggca atcgagactg   131895
ctctgccagg aggcatggcc aggctgggc cctgaaagag ggcagcaagc caaggggtgc    131955
tcaagtcgta cttgttatgt ctgatgttca aggctgcctt gcagagttca ggtctgacag   132015
ttcctctagg gctaaagtct cctaaaggag caagtcaagt ctaggggtg actgtccttg    132075 gctgtgctat gttatagatg ctctcgcatc aaactctctg ggttccacat cagctgtctt   132135 gttgcccta ccacttctct aagcagctct ccctgccaac tcaaatgccc ttgatggtcg    132195
agggatttcc tcctgctgga gtcccagagc cctgcggtga gggtgggttg ctccttgcca   132255
gttcaactca tccatttccc tggagccatt gtgagccaag aatgagtcct gctgcatggg   132315
agctccgtgc caaggttccc agttttcttc cccttcagct tagcttctgt gtcttccctc   132375
cactcttggt gccttcgctc tgcagatctg ttaggaacag atctgtctcc gtccctaggt   132435
gggagctgtt tcacctggct gcgtctagtc agccatccta ccctccctcc tttcttggca   132495 ttattttct aacaacatgt gcttactttg tgtctctgtg ccacattgtg gtgatttcct    132555
caatatttca aaccttttta ttgttattat atctgctatg gtggtctttg ataagtgatc   132615
tttgatatta ctattggaat gttttgggg caccatgaac ctcctgcatg taagagggca    132675
aacttaattg ataaatgttc tgattgcttc atagcctagt cgttcccta tctctttccc    132735 tttctttgct cttctctatt ccctgagaca caacaatatt gaaattaggg caattgataa   132795
ccctataatc acttccaggt gtttgagtga aggaagagt cacacatctc tcacttaaag    132855
agctagatta agctagatta atcttaacaa ggaaggcatg tcaaaagcca tgacagactg   132915
aaagctaggt ctcttgcacc aaacagtgtg ccaagttgtg agtgcaaagg aaaagttctt   132975
aaaggaagtt aaaagtgata ctccagtgac cccagtaatg ataaagtgaa acagatttat   133035
tgctgatatg gaagaacttt agtagtctgg atagatcaaa gcaggcacaa cattcccta    133095 aaccaaagtc taatccagag caaggcccca actcttcaac tttttgaaga acgagagaaa   133155
tgagaaatct tcagaaaaaa agttgaaagc tggcagacag tgattcctga ggtttaagga   133215
aagaaaccac ctttataaga taaaagtgca aggtgaagca gcaagtgcta atagagaagc   133275
tgcagtaact tatccaaaag atctagctaa gagcattgac gaaggtggct acattaaaca   133335
acagattttg aatgtagatg aaacagtctt ctattggaag aagatgacat ctaggatgtt   133395
tatatctaga gaggagaagt caatacccag cttcaaagtt tcaaaggaca ggctgaccct   133455
cttggtaagg actaatgcag ttggtaactt taagttgaag ccaatgctca ttgaccattc   133515
tgaaaagtct tagtgacatt aagaattatg ttaaatccac tctgcctgtg ctctataaat   133575
gaaacaacaa aacctggatg acagcgcatc tgtttacagc atggtttact gaatgttaag   133635
cccactgttg agacccactg ctcatgcaca gagaaaagat tccatttaaa atatttctac   133695
tcattgacaa tacacctggt cacccaagag ctctgatgga gatgtatgag gaaattaatg   133755
gtattttcat ggctgctaac acaacatccg ttctgtagcc catggatcaa agagtaattt   133815
caactttcaa attttgttac ataagaaata tattttacaa tgctatagtt ggcatatatc   133875
atgattcctc tgatgaatct gggcaaagta aattgaaaac cttctggaaa ggattcactc   133935
ttctagatgt cactaaaaac attcataatt catggtagga agtcaaaata tcaacatagc   133995
aggagtttgg gagaagttga ttccaatcct catggatgac ttgaagggt tcaaaacttt    134055 ggtggaggaa ataactgcag atatggtaga aatagcaaga aaactggaat tagaagtgga   134115
acatgaagct gtggcagaat tgcacaattt catgataaat ttgaatgaat aaggtgttgc   134175
```

-continued

```
ttcttgtgga tgcaaagaaa gtcattttg agatgaaatc tactcctggt aaagatgctg  134235
ttaacattac tgaaatgaca tcaaaagatt taaaatatga cataaactta gttgataaag  134295
cagcagcaga gtttaagagg attgattctc attttggaag aagtttact gtgggtataa  134355
tgttatcaaa caacattgaa tgttacagag aaatctgtca tgaagagaag agtcaatcta  134415
agtggcaaac ttcacggtct tattttagga atttgccaca gacacctcaa cctttggcaa  134475
ccaccagcct gttcagtgag cagccatcga cgttgaggcc ccctgaggag gtcccaggct  134535
gtggcagggg ttcaggctgg tggaaaagtg ggagagaaga gtcaggggac aattgggaag  134595
tgtgatgata tggggaaaga gggatggagt ggaagccaga acccattgct tccagtatca  134655
atcttttca ctagcaaaaa ggttataact tgttaaagcc tcatgtgatt gttagaatat  134715
gttagcaata aaatatttt aattaaggca tgagcatttt tttaagatat aatgctattg  134775
cacacttaat agactacagc atactgtaaa cataactttt ttgtgcactg ggaaaccaaa  134835
acattcatgg aacttgcttt attgtgatat ttgctttatt gcaatcgtct gataccaaat  134895
tgacaatatc tctgaggtat gcctgtattt tatctttatt tgtgataagt tcttacacat  134955
ttgataaaac aagttattta tattgaaatg catttgatcg tatctcttat ttaagaagaa  135015
aatttggaat tttccgtgaa aaagcctgct gaagtaatca ccctctgcaa tttataaata  135075
ttagaaacat tggtcaagtt ttagaatatt ttattgccta ttaaatgtta tgtgactgtg  135135
ttaaattatt atatattatt tgcatagtgt gaaagcttac ttttgcttca cgaattattt  135195
taaatgaaa aaattctcag ttatacttgg aagagaaaaa tcacatgtcc attttggagt  135255
gcattttaaa ttgtgctaca aagaatgaca aaacactgca gtaaatgtga cgtttgaaat  135315
tttataagga gtatgatata aataccactt tttaatagta tttataaaag tggagccatg  135375
atacattctg gctataacaa ccataacaat attccatatt tttaataata tgaatgtttt  135435
taaaaatatt tttccatagt tcttagaaca actttagaat tcctcaagta cttgtttaca  135495
tttaggtgtt ctggtatttc ctgtttacat ttacccttg cgaaaggaca aaatcaagac  135555
tatgataccc ttttctcagc acacctgtct cgtgttggat ctgtcttccc ctggaaatgc  135615
ttctttttt tttttttt tttttttt tttttttt tgagacggag tctcgctctg  135675
tcgcccaggc tggagtgcag tggcgcaatc tcggctcact gcaagctccg cctcccgggt  135735
tcacgccatt ctcctgcctc agcctcccaa gtagctggga ctacaggcgc cgccactac  135795
gcccggctaa ttttttgtat ttttagtaga cgggtttt caccgttta gccgggatgg  135855
tctcgatctc ctgacctcgt gatccgcccg cctcggcctc ccaaagtgct gggattacag  135915
gcgtgagcca ccgcgcccgg ccgaaatgct tcttatttgt tagtgtggca gcgatgataa  135975
cagcacccc agacacctg gtaaatcgct tctctcgagc gctttgttgt ggtcttcgtt  136035
gagttctgag tgaggtgtga aatctgagaa gacagaattt gttttcattc ttcagtaagt  136095
aagttagcat gtggttgtgc ctagcagagt atctggcact tagcgggcca gttaaataaa  136155
cctggattta aaaccagact tcacaaaatt tgctgggaat ctttttttt ttttatactt  136215
taagttttag ggtacatgtg cacaatgtgc aggttagtta catatgtata catgtgccat  136275
gctggtgtgc tgcacccatt aactagtcat ttagcattag gtatatctcc caatgctatc  136335
cctccccgt cccctcaccc cacaacagtc cccagagtgt gatgttcccc ttcctgtgtc  136395
catgtgttct cattgttcaa ttcccatcta tgagtgagaa catgcagtgt tggttttt  136455
gtccttgtga tagtttactg agaatgatga tttccaattt catccatgtc cctacaaagg  136515
acatgaactt ctcattttt atggctgcat agtattccat ggtgtatatg tgccacattt  136575
```

```
tcttaatcca gtctatcatt gttggacatt tgggttggtt ccaagtctttt gctattgtga    136635 ataatgccgc aataaacata tgtgtgcatg tgtctttata gcagcatgat ttatagtcct    136695
ttgggtatat acccagtaat gggatggctg ggtcaaatgg tatttctagt tctagatccc    136755
tgaggaatcg ccacactgac ttccacaagg gttgaactag tttacagacc caccaacagt    136815
gtaaaagtgt tcctatttct ccacatcctg tccagcacct gttgtttcct gactttttaa    136875
tgattgccat tctaactggt gtgagatggt atctcattgt ggttttgatt ttcatttctc    136935
tgatggccag tgatgatgag catttttca tgtgtgtttt ggctgcataa atgtcttctt    136995
ttgagaagtc tctgttcata tcctttgccc acttttgat ggggttgttt gttttcttct    137055
tgtaaatttt gtttgagttc attgtagatt ctggatatta gcccttttgtc agatgagtgg    137115 gttgcgaaaa tattctccca ttttgtaggt tgcctgttca ctctgatggt agtttctttt    137175
gctgtgcaga agctcttgag tttaattaga tcccatttgt caattttggc ttttgttgcc    137235
attgcttttg gtgttttaga catgaagtcc ttgcccatgc ctatgtcctg aatggtaatg    137295
cctaggtttt cttctagggt ttttatggtt ttaggtctaa cgtttaagtc tttaatccat    137355
cttgaattga tttttgtata aggtgtcagg aagggatcca gtttcagctt tctacatatg    137415
gctagccagt tttcccagca ccatttatta aataggaat cctttctcca ttgcttgttt    137475
ttctcaggtt tgtcaaagat cagatagttg tatatatgcg gcattatttc tgagggctct    137535
gttctgttcc attgatctat atctctgttt tggtaccagt accatgctgt tttggttact    137595
gtagccttgt agtatagttt gaagtcaggt agtgtgatgc ctccagcttt gttcttttgg    137655
ctcaggattg acttggcaat gcgggctctt ttttggttcc atatgaactt gaaagtagtt    137715
ttttccaatt ctgtgaagaa agtcattggt agcttgatgg ggatggcatt gaatctataa    137775
attaccttgg gcagtatggc cattttcacg atattgattc ttcctaccca tgagcatgga    137835
atgttcttcc atttgtttgt atcctctttt atttcattga gcagtggttt gtagttctcc    137895
ttgaagaggt ccttcatgtc ccttgtaagt tggatttcta ggtatttat tctctttgaa    137955 gcaattgtga atgggagttc actcatgatt tggctctctg tttgtctgtt gttggtatat    138015
aagaatgctt gtgatttttg tacattgatt ttgtatcctg agactttgct gaagttgctt    138075
atcagcttaa ggagattttg ggctgagaca gtggggtttt ctagatatac aatcatgtca    138135
tctgcaaaca gggacaattt gacttcctct tttcctaatt gaatacccttt tatttccttc    138195 tgcctaattg ccctggccag aacttccaac actatgttga ataggagtgg tgagagaggg    138255
catccctgtc ttgtgccagt tttcaaaggg aatgcttcca gttttttgccc attcagtatg    138315 atattggctg tgggtttgtc atagatagct cttattattt tgagatacgt cccatcgata    138375
cctaatttat tgagagtttt tagcatgaag ggttgttgaa cttttgtcaaa ggcctttttct    138435 gcatctattg agataatcat gtggttttttg tctttggctc tgtttatacg ctggattaca    138495
tttattgatt tgcatatatt gaaccagcct tgcatcccag ggatgaagcc cacttgatca    138555
tggtgaataa gcttttgat gtgctgctgc attcggtttg ccagtatttt attgaggatt    138615
tttgcatcaa tgttcatcaa ggatattggt ctaaaattct cttttttggt tgtgtctctg    138675
cctggctttg gtatcaggat gatgctggcc tcataaaatg agttagggag gatttcctct    138735
ttttctattg attggaatag tttcagaagg aatggtacca gttcctcctt gtacctctgg    138795
tagaattcgg ctgtgaatct atctggtcct ggactctttt tagttggtaa gctattgatt    138855
attgccacaa tttcagatcc cgttattggt ctattcagag attcaacttc ttcctggttt    138915
```

```
agtcttggga gagtgtatgt gtcgtggaat ttatccattt cttctagatt ttctagttta 138975 tttgcataga ggtgtttgta gtattctctg atggtagttt gtatttctgt gggatcggtg 139035 gtgatatccc ctttatcatt ttttattaca tctatttgat tcttctctct ttttttcttt 139095 attagtcttg ctagcagtct atgaattttg ttgatcttat gctctcagtt ttcttgtgca 139155 taaaatggga ataataactg ccttctggaa ttgtagcggg aaataaatac aattgtagct 139215 ctcgggtgct aagcacaggg ctgggaccta gtaaatgctc agtaactgct cattactctt 139275 ttttcttatt ttgcttcctt ttttttttct tcactgttgt cttttttattt tctattttaa 139335 ggatattggc ttagtaaaag aaactaaaat acatctgcat ataaattaaa taaatgcctc 139395 attttttaaac attctgtgag tgtctatgta tagctggtac cttaattgta gttgttcaat 139455 aaatgattta tcttactttg ggaactttct taaaaagctt aaatccctca atgttaataa 139515 tagtgaaaat cttatgtttg aaaaaatgct tttgaaaaac atatattggg ttaccctttt 139575 aaagaaatat acttaatatt gatatgagta attttttaaa agtaatcaaa gctttagaga 139635 gtaagagaag aaataaaaaa aaacaaaaac attatgacag tgtttatatc cctacttatt 139695 aaattcaaca tggaaaacaa ggaagtgaaa agtactttgt aaaataccta aaatgcctga 139755 atataagaag tatttggata ttatagataa cattttctat actacaatgt cacctcaaat 139815 agtgtacaca cacagttatg aggatatgat agtcacttag aggattcatg ctgggattga 139875 atagtaggac cacacatttt aggaaatttt aagcagaaat gctttagaag aaatagtctt 139935 tatttattta ttttttttaaa agagctttta aattactgag ttcaaataca gaagaaggcc 139995 taagtttgaa ttcatggcgt attgctataa tgcactatta gactaatcct tcattttctt 140055 gtcaattaaa gacttacctt tattcactga ttcacttatc agtaattcgc tcggtatttt 140115 aaagctggct gttaaaaatc cctttgttta tggcaataag gcaccattca ttttgtgaac 140175 tttataaaac caacctctgc caattttgct ctttgagaat agctctaaag atgtgttccc 140235 acagtaatta ctgattccag agatgttcat taaagaatga agtcagaggc aagtgtttga 140295 aacaattgta tcccaccaaa gccagcttta ctgcgcacct tcccagaatc tacagtttct 140355 ccacgtttaa gaaaatcact gaacaacttc atacaaaatt tgtactttttg agtgctttta 140415 cctgcagtag cattaaagat gagtattatt ttttacatat ttgtattgaa atcagatgca 140475 gggaaagatg gagggaaagc taggatgctt tgaatgtggg cccagttgtc cgtcatatag 140535 cttctgtgaa tagtatgggt caatcttgtg ttcctgctct atgttgccca cttacccaga 140595 gtgaccaggg tgagaaaaga aaaggagggg agaaacttca gtgaagccag ccaaatctta 140655 gcagagaaaa ataaataaat aaataataaa taaataaata aataaataaa atggttgtgg 140715 agttgaatat ttcttttaaa atggatttgt tattgcagaa gagtaggaag aaaagtttaa 140775 ttcttttatt agcttattat cagaacctga aatgctggag tgtgttttag gtactgcata 140835 gctatcctgc agttacagcc caacctccca ctgagccata atgggcaaag gaagagagaa 140895 aattcacagt gagagagcag ggagagagag attttgctat cagcctgtca gtgacagatc 140955 tgaatgataa acgccttaca gaaatgaagt tacatttatt tttattgcat gaaaatatat 141015 aacagacaaa ggaaggaagt cagaaaacgg gattaggtat attttctaaa tctttaggtg 141075 ttaaacagac tagagaccag tcacttgtaa atgaacacat tccttgtttg gatgcaaaca 141135 acccagccaa attagtttcc taagtgcttg gaaacagctt tctgtttttg gcttccagac 141195 ctgagttctt tcattcatac tattttttttt ttcttttttgt tcaatcctta ttaatcacca 141255 atatttcaaa tactttgtaa atatagattg gtttcattag agttaatgta tttgggggcc 141315
```

```
aacaggttga atgaatgatt ttattttaaa attccaagat cctgcctgat acctggagta    141375
taatactgag catcctgagg agaaatgttg caatagcagg cttttgtgaa ccatatccca    141435
agaactgcag atccttgcac tgtggtgact gggaacattt actcaggatt cagcctgcta    141495
gcatttgaac actgagagat tgtggaatct ctgtaggcct cagcttcttc atctgtaaaa    141555
tggaaaagct aataatacct acttcaacat ttttgtttat tttttgacag agtctggctg    141615
tgttgcccag gctggagtgc agtggcataa tctcgactca ctgcaacctc caccccctcag 141675 gttcaagcaa ttctcctgcc tcagcctccc tgagtagctg cgactgcagg ggtgagccac    141735
cacaactagc taattttttgt cttttagta gagatggggt tttatcatgt tggccaggct     141795
ggtctcgaac ttctgacctc aagtgatctg cctgcctcgg cctcccaaag tgtttgggatt 141855 acaggagtga gccactgcac cgggccaaca ttttttgtttt cataaaggta gattaaatga   141915
gatttcctat aaacaactgt gagatcattg cctggtgcat agtaagtgct caataaatgt    141975
tagcaattaa tattacatac tgatgactgg agcaccttt taaaaaagtt atgcttattc    142035
ctaaataaaa aataattcac atacctatta ccaaaaattc agaaaaatag aactatagat    142095
ataaaccgta tttagaaaat aagaatccag tgttatctta ctacctgact gtatctatcc    142155
actatcagta cagctatcag atgcctttat taacatgatc ccattcaggc tgggtgtggt   142215
ggctcacacc tgtaatgcct ctctttgggg tgctgaggca gagcagattg cttgagctca    142275
ggagttcaac aacagcctgg ccaacataga gaaacctcat ctctacaaaa aaatacaaaa    142335
atgagccagg cgtggtggca tgtgcctgta gtcccagcta cttgcgggca agaggatcgc    142395
ttgaacccgg gaggtggagg ttgcagtgag ccgagatcac accactgcac cactgcactc    142455
cagcatggat gacagagcaa gaccctgtct caaaaaaata aataaataca taataaaat     142515 gaaataaaga aaaagaaag aaaattcctg ttaaaaaaca cttactgtgt ttattacaag    142575
ttaattattt actgccagtt catagccatc tttccatcaa taaatataga tgtaccaact    142635
gattgatgtt agtgtcttca tcatgctcca tgctccatag tggtccataa tttaagtagt    142695
cacccctggc atcttaaata ttttttgtaa atatagataa taaaaatgcc ttcagtcagc   142755
acattcttgt ttgctgtccc tggagtgttt ggatgaccat taaaaatggc agaaggctga    142815 cttggtttt aggcctgaat tacagccctg ccatctacaa gctgtgtgac tgtgagcaag   142875
ttacataacc ttactgtatc acaagtattt ttttttctcat ttataaaatg atgataataa  142935
gagtatctag ctgacatgat tgctgagcag agaaagatgt taagcacat aaagctttgg    142995 agactggttt ctggtctatg attttttactc aggaagtatt agcttgaggc tatgtaaaat   143055
cttggcattt ctcccaaatc atcaaaggta aattatgtta ttcctttgaa ttagctaaat   143115
tgtattgcta taaaaattta cttgcaatct taacatttca ctgcaatatg tatgcatact   143175
ttgggatgtt tacatgtgaa aatgcacatt atcctacaca cttcaattct caaaccatgt   143235
tggttagaga agagattaat agttatttct agacacacta tacacagaac aatttggaga   143295
aaaatcacca ttggacagta gcaactagtt taatatttgg cgtcttttat tttctctttt    143355
aacatttcca aggaataggg gacgctcttg tcaatgactt ttttttttttt ttttgagac   143415 tgtgtatcat tctgtcaccc aggctagagt gcaatggtgc tatcttagct tactgcaacc   143475
tccgcctcct gggttccagc gattctcctg cctcagcctc ctgagtagct gggattacag    143535
gcatgcacca ccatacccctg gtaatttttg tgttttagt agagaagggg tttcaccatg    143595
ttggtctggc tggtctcgaa ctcatgacct cataatccac ctgtcttgcc ctcccaaagt   143655
```

```
gctgcgatta caggcatgag ccacggcacc tggccagtga ctaaggttta ttacaccacc  143715
tggatagatg cagggctagg ggcatgaaga caggaaggta ctcccacttt tcaaggacag  143775 aatgtgggc gggtggtaaa atctgaagag atcctgaaaa attgtcctcc tttaggtgtt  143835
gtgatgtatt gcttctgcaa tggccatcca atcttaaata cctaagtcta gatatggcat  143895
ccttattatg taattctgga acaaaagtta ccctaataaa gagcttcaaa cccgctagga  143955
cccactcaaa atagggtaat aatactccaa gacattcaga aatttcctct gttcccagtg  144015
ggctagtcag gacagggcag tgagagccct caggctagct cccctggcct cagcaactcc  144075
attcacttcc cccaaaaggg tcctaaataa atttaaattt ctctatgtac ctcgacatga  144135
aatagttgga aagcacactc ttaaatgcca ctttactgac tgtactggct aaaacaatga  144195
gctgtgtacg tatgaaaaag aatgttcatg tgttttcttt gtcaattaca ttaatttata  144255
cccttgctag tgtttctgaa agagactaat agttccctca aatacattta atgacccagt  144315
ttgagaaata ctgttctaga aattaacact agtaataatt ttgtgctcat atgattacac  144375
atacaaatat aaattcttgc aacttaaact ccatagaaaa acttggatgt aacctggcta  144435
tgtggatgaa aaactgctaa tgttaatatg tcttttagca gatgatcaaa ataaaaacaa  144495
tacaatctaa taattcccat aaacatctga aatcctctaa aaacatgtct atgtagacca  144555
taaggtaata ttattctaaa gcaatgattc ccagaatgtg ctcccagggc agtagatctg  144615
tatcatctag aaacttatgg aaagctaatt cttgtgaccc actccagatt tactgaaaca  144675
gaagatgtgg aggatgggac ccagtcaact gtagtttaag aagctcttca ggtgattctg  144735
atgtgctcca gtttgcaaac cacataatga ggctgagtcc ttttcagtca ttccacacca  144795
aatgagcact gtcgtatgtt taccttagga aacataccct caattgagtg gggctgctga  144855
tatttcaatt cctttttaaag agtttgtctc agagccaatc tgtaacaaaa gagaaattca  144915
gtttcattat tttatagtca aatctcatta agtagttgct gagatgtttg tatgaaactc  144975
agatttgact ttgccctgca ctgtgaacaa agacgatgaa acattttcac atttggaatg  145035
attagtcatc aggagatgca gtcacaaaat tttattgaaa gcctaatatt tattcaaaag  145095
cctttgatag actgcttttg gaacttctgc gacattctcc accataatat tgtttagcct  145155
ctaactctcc ctaaattgcc tttggtcaga aaagttaacg tggttactgc tttgtttatt  145215
tgactttcct acctcctgat tcagagtaga gttagctttg gaaggagact aagagtcaag  145275
cgcttgcctg agtaaaaacct attttttggcc aagagaactc aaaaccaaaa ccttatatat  145335 atccaccta ttgcccagct aacttggcta ctaatttctc tgctactatg aaattctctt  145395
tcaaattcct aattcatagt caagtctcat cttgttccag agcaattatg gtggttggga  145455
agcccaagat gagaagggta acacaggaac aaggaagctg aatcctaaca gtcaatcctg  145515
cttgttccta ctatctcata ccttaccagc attccatcct gaggacttaa ctaccaactt  145575
caagctagcc catgtctcat cttgtggttc atcatgtctc gtcattttgt ggcaaactgt  145635
ccaggatgac ccccattttt tgcaaaaaaa gaagacacag aggggggaata atcttggttt  145695 ttctccaaac cctagatgta gctcatatct gtgtttcctg aagttttctc tctagtactc  145755
ttgcagcctg aggcttttc cagaatccaa gggagtggga agaaaaatg agggaaagtc  145815 atggtccctg aagaaagagg gacgctcagt aaagtccagc agacagagca ccagccaggg  145875
atgtggtggg cggagccaag gacattaagc taaagaata tgaaacttaa atctattgcc  145935
atgtcccagg gaaagtggt gatgaaattt caatgaacaa agcttactgt tatttatcac  145995
tttgtatgta cctttacttt tttacacaaa tgagatcata tcacatattt cttttgaaac  146055
```

```
tgctttttttt tatttaaaaa tttatgacag gctgggcccg gtgggtcatg cctgtaatcc    146115
cagcactgtg ggagccttag gtgggcgggt catctgacgt tgagagttca agaccagccc    146175
ggccagtatg gtataactgc gtctctatta aaaatacaga aattagccag acatggtggt    146235
gcatgcctgt agtcccagct acttgggagg ctgatgcagg agaatccctt gaacccgaga    146295
ggtggaggta tcagtgagcc aagatcacgg gactgcacta cagcctggga gacagaggga    146355
gactctgtca aacaaacaaa caaaaaaagg agacaaatat tttttaggtc ataaacttct    146415
tcttcttcct cctcttcttc ttcttcttct tcttcttctt cttcttcttc ttcttctttt    146475
cttctttctt cttcttcctc ctcctctcct cctcctcctc ttcctcttcc tcttcttctt    146535
cttttcctta ttcttccttc tttcctcctc ctcctcctcc ttcttctcct tcttctcctt    146595
tcttagtata tctttttcta agccttcaca gtataggttg agcattcgtt atccaagata    146655
ctagggacca gcagtgtttt ggattttcga ttttggaata tttgcctatg cacaatgagc    146715
tatcttccag atggaaccca agtataagca caaatttcat ttatgtttca tatgcacctt    146775
atatacatag cctaaggtta atttttatcca atattttaag taattttgtt cattaaacaa    146835
agtttgtgtc aagtacttac atgcggaatt ttcttttttt tttcagatct ttctttttt     146895 taattttatt attattttac ttcaagttttt agggtacatg tgcacaatat gcaggtttgt    146955
tacatatgta tacatgtgcc atgtcagtgt gttgcaccca ttaactcgtc atttagcatt    147015
aggtatatct cctaatgctg tccctccccc ctccctccac cccacgacag gccccggtgt    147075
gtgatgttcc ccttcctgtg tccatgtgtt ctcattgttc aattcccacc cgtgagtgag    147135
aacggaattt tctacctgtg gcattgtgtc agtgctcaaa atttcaaatt ttggagcatt    147195
tcagatttgg aattttttaga ttaggaatgt tcaatctgta ttctcttgtt gtataagata    147255
cctataaaaa ccatcttcta tacttattgc tttcatttttt tttgaccaga ctctttttaa    147315
tgttttccca tgagtactta gaataaaacc ctaaaatacc agcatgagca tttgcactgt    147375
tttatttgtt aattttaata tttatttata acaatgatac tttaaaattt ttcaaaacca    147435
agactatata caaatatata ctgagatgtt ccctttccac catttttatt tatttattta    147495
ttgagacaga gtctcactct gtctcccagg cttgagtgca atggcgcgat ctctctgcct    147555
ctcgggttca agtgattctc ctgcctcagc ctctggagta gctgggatta caggtatgca    147615
ccaccgtgcc cagctaattt ttgtattttt agtagagatg gggtttcaca tgttggccag    147675
gctagtctcg aacttctgac ctcagatgat ccacccacct tggcctccca gaatgcttgg    147735
attacaggtg cccagccaat tcattttttt tctgtaaaat taatgctact ctgatggccc    147795
ctaattctga ctaaactcct ttcagaatct aggattatta atcatcttaa tttttttctg    147855
aattataata agtagataa taatctgggc atctcaaatg ccatttctca tcctataatt    147915
ctgaaaaata ttgtttagtt gatgccacac aattcctggt aattctttgg aaaaagttaa    147975
tatgtgggac aatataattg tcaaaaataa acctgggatt tttcttccat gatcttccat    148035
aggtagcaaa ggagaattag tacaatttaa atgtaggcat gtttctgaaa tttaggttgt    148095
tcacccatgg atacatagtc ttactaaata tcttatttca tattataaca ttaaagggat    148155
ttataaagat tgaatattat attcttactt gaaccgatat tttactgctt ttttcttatt    148215
ttaattagca tgtcagtaac tgtagaatgg tatcagataa cctttagtct tgtttatttc    148275
caacaaaact tttctaattc ttgaaagatt aacataatct tgcactaatt tgcattctag    148335
tacgatgctt ttcaaccttg actgcacatt agagtcacct ggggagagtt aaaaaattcc    148395
```

-continued

```
aatgccaagg gcaccacaga ccaattaaat ataaatattt gatggtagga cctaggccac    148455
agtatgtttt aaagctcccc aggtaactcc aatgtgccgc caagcttgag aaacactgct    148515
cctgggaaag aaataattat ctagttttt tttcatttttt tccaattaga atttatttca    148575
gcatgctttc ctggaagtat ccgttttgtt aaatttggca ttgaaaacca aaaactaaaa    148635
taacaattct ttgtttttag atttgatgtg aaaagaataa attctcagta agagaaatca    148695
tattgtgtgt agagtttcag tctacatttt ggagtgttgg ggagagaagt tcatagcttt    148755
cttcagattc tcagtgtgat gtttctgtgg taggtaggga attgactgca ggaagaaaca    148815
tgttttgtta ctggtttgta cctgacccct gtccatgtaa acacagaatg cccctctctg    148875
aagtggttat aatgtaatct gagtcgagca ttgaattctg tgagtgatga ttctccgctc    148935
acactatagc aaactataaa acttccatgc acacttttaa tgaaacaaac tagccacatg    148995
caaaagaggg caaatgagtt gtgattcaaa agacaatctc agaatgtggg tagagctggc    149055
attatttctt ccttatgatt gaatagctca ttattattca tgggtgaact aaaaagtaaa    149115
atctagtagt ttggagaagt ttttatccag ctgtggaaag tagctcagtg ggcaaaaact    149175
ctcctctgtc ctgttaaaga agaaatgggg gctttctagc atagggaaaa gatggttgtc    149235
atcagaagtt ggggctactt tgtctttaaa tataattttt catgtgtata cttctgagag    149295
aagttatgta gtagaaaatt catagaattt taatttgaaa agacatgatc cagtggctag    149355
tgagaagaag gagatcatta tataaaaatt ttggggtggg gcttgagggg agaacagagt    149415
tggatttctg attctcaatt ttatttcctg ctattgaata agatactaga taatattcat    149475
tggattactt taatatttat gggttttta tataatagaa agtgttttt tcccctcaga    149535 cttttcttgt aaatcctata ggccattgat ttttccattc tttgtgaatt ggatatttta    149595
ctaggaatat cctggtaaaa gtctaaagat ttatgtggta gtctaccact atcgtatggc    149655
ttcactcact gaggtttcag ctactcaccg ccgaccagag tttgaaaata aattattaca    149715
gtaaaataag gtattttgaa atagagacta catttgcata ccttatatta cagtatattg    149775
ttttaattct tctattttat gattagttat agtgtatata gggattgata ctattttatt    149835
agtagtcatc gcatatatag ggtttgatac tattagcggt ttaggtattc gctgaggatc    149895
tggaacattt cctccacaga taagggggg ctattgtagc attcttcctt aagctactgc    149955
tttctcatac actctcccag agtacatgta tatttctct tcttttcttt tcttttcttt    150015 ttttttttt ttctgggagg gagtcttgct ctgtcgccca ggttggagtg cagtggcgtg    150075
atctcggctc accacaacct ctgcctcccg ggttcaagcg attcccctgc ctcggcctcc    150135
cgagtagctg ggactacaga cgcccaccac catgcccggc taattttttg tatttttagt    150195
agatacgggg tttcaccatg ttggctagga tgatcttgat ctcttgacct cgtgatccac    150255
ccacctcagc ctcccaaagt gctgggagta gatgtatatt ttcattacaa agcaattat    150315 attggcaagg tgatgtattg aatcccatga tagttattct ttaatttaga ggacataatg    150375
ttactgattt ttgtctggag cctcaaacat acccaattac aggacaacct gcattgttac    150435
ttttaatgaa ttacatttga taccaggatt ttcttccttc agacttctta aagcatgctt    150495
tcaaatatac tggcctgcca gtaatttcac ccaatttgtt cccttagata gggtaatttc    150555
atcaaagttt tcccgcatgg ccagaatctg tattagctat ttggtgtgct ataaatttaa    150615
aagctagtag tattcttccc actgcttata tacaaacaaa aaaacagatg ttgtgattac    150675
actgtaatgt tcctgcctaa agtaaattta gatgtaagaa tatcgtcttt ataggtattg    150735
tagcaaagta tgtcattctt tctcatttag cttaaatgga ggtttaataa aattgctact    150795
```

```
tatcaaaaga gaaactccag gggaagacta aataaatgag gtgatatttt aaaagttaat   150855
gaatgaggtg ccttgatctg tggttccatt atactctttt cattgcttca cagagctctt   150915
aaaacataag atgtgatgaa aagagtaggt aagctaattt gaacattgcc ttaaaacgta   150975
ggcagtgaaa cactcttatt atgcctacca aggggctgag agtagaaagt ccattattct   151035
agaaaacatt aggaggcaaa atgtaaaatg caaattaatc ttctttataa tataatgaaa   151095
attaaaagtg aactgtgttt aaagtgagta aagctgtaaa aatttggtga aacaaactat   151155
aataaaacat atttttaaaa tttactttaa ccattacttt gatgatatta ctgataattc   151215
tactttacaa gactcatttg tgttatatat tatgagcata gttttataat cagtatagat   151275
cacactacta atgccaactt atttcacatt ggtgattctg aaacttcttt attttggatg   151335
tctatatggc tggttttaac aaaactacta aaacatcctg tacttaatta ggactctttt   151395
ttcacaagca accaattcca atttgagcaa atttaaacca aaatatatg tattaaacag    151455 ctgctggatt atctcatgtc atctaatagt aaaaaaaaaa aaaaaaaaaa aaaaaaaaa    151515 aaaaaaaaaa aaggcttgtt ctttaggaga gacagaaact ggatccttaa tgtctgctga   151575 aatatttct ctgtgctcgg tctctgcttc tttctgtgtg tctatctcat ctctgtttct     151635
atgccagctg ttgattccaa tcctcagaga agctggacta gggttcctcc acatttatga   151695
atttacgtct atttccaaag acttggatta agctgaaaaa gagtttctca attttaattc   151755
tacattcctt ggagaaagag tgtgattgat ccagctacat caagtcagct gggattagag   151815
gaaagagttt cacttgctcg tgggcaccca tccctgtgga tggagaaagt agttatgaca   151875
gaagaggaac tgacatgaaa tcccaggaaa tgttcattac caccccgtta gataactaag   151935
aagtgtcagt ttaatgtttt cattatttta agtgaattag ccaccagaga aaatcttagt   151995
ttttaagata taagataaat taatatagtg ttttttcat tgaataaccct tttcttgtac    152055 taaataaact agttcatact atcagaaaat ccttaaattc ttatatcagt attctgtaac   152115
ttgaatagtt gctctttaat tttttatat tcttgagtat gcttatggac cattggagaa    152175
gtggaaaagt aaattttgga tttggattac caggtaaaac ttatcctcgt tctgatatga   152235
attaggtaat tttaaagtgg cattaagtaa actacaaagt gtatagtaca taaatgccat   152295
ttagaggtaa aatattattc agaatatgaa tacttagaag gagaattaga aattatcaca   152355
tcccaaacaa tttaataggt atgaataagt aagtaatgct cagaagggta cagagtcttt   152415
tattcaaagt tacaaaaact gtttagagaa aacttttaac gaagagccct atcttcagat   152475
tctcaacttt acgttagttg cttagccata tatgaaaacc aaatgaacca atctgaactg   152535
ctcctgtcaa ggagatgcac tctctttcca taaaagagaa actctaggac cttaggagat   152595
agtaatgcaa tgtttatcct catatgaaat ttaaataatc gtctgtttta ctgattcgga   152655
agtttctggt cagtattgca actgagaaag atacacaaag gcatattagg gatatacta    152715 ttagagtatc aggtagtctt ctcatagagt ccatgttttc aactcattca catctctata   152775
ttacttaaga agatgactta agaagattgt gcgaagtgag ttcacagaat aaatagctgt   152835
caataaggct cacccagacg actgggtgtg tgtgtgtgtg tgtgtgtgtg tgtgtgtgtg   152895
tgtgtgtgta aaactgttat ggtaaggaat atgcaaaact ttattttttc tgataaaatc   152955
ttaagataaa tccatttctt ttcaggactg gtaattatat ttctagtagg atttacttat   153015
tcataattgc ctttaattta gattttgaag tcttccatta cagtgagtta ataaagaaa    153075 tgagagttgc aatatcttca tgttagtaaa gagttttct gtttatgctc tttatttag     153135
```

```
gcataaatga tttgtaatag tggccatggt ttcagtaatt cattggcact taagggggcag   153195 tattaagatg ttatggtgat tagtaaactt ttctctgtaa cttcagtgct gcttagaaaa   153255
gtgatcgtgt taatgaagga cttgtatagg attagttcat ctgtatattt atttttaaca   153315
actcaaatta tctgcgtaag aacatttaag tacccttata tacaggtgag agcctgcttg   153375
ttgggaaaaa ataacgtgag attaggtata tttagctctt tctctactac tattttgctg   153435
tgtaccattg aaataaatga ctttatcttc ctaggcatta cctgttaaat gtagagttta   153495
acattaaata tccagggtat tttctagctc tgtttatgtt tctataataa atgttaattg   153555
tacatataaa cataaatcca aatttcatag atgatgatat aaacttaggt ctcattgttt   153615
tgaaaattta aaataaataa ctatgtagca atcaattgcc tcctattatt aactatcttt   153675
attctctcct tagtatcatc ccactttggg taattccaag aactcatgaa aagatttcac   153735
aaaccaataa tcagcattga ttttaacac actagaagct atagttaccc aatgttattt   153795
tcaattcctt tccatatttc atactcatat tagtattctg aacttcaagt aataagtatg   153855
gaagagtcaa aattaaaaag aagagaaaag gggaacataa aacattattt ttaactgtgg   153915
ggaaggccat tgtttccaag gagaaaataa aatgctgact cccaacattc tggggcatag   153975
atgatctcct cccttcctcc acatccattt agatttgttt tttatgaatg ggtgcatgaa   154035
aaaggaacta ataccatatg gcattttcag gttcagcaat gaaagtaag gaaggcaaaa   154095 atgaaatatt ggaataaaca ctcagagctt aggaaatggg agttccagat ctggtgcctt   154155
gtaccaaatt tctggtgatg tttattaaat ctctttattt ccctaccctt tctttcaata   154215
tctgtaaatt gaggagtttc agctacactt actctaagct cactttaaac tgtaaacata   154275 tttatttttag gatgtatttt ctttatgtgt ttataaacaa atactttttct tcatgtagtt   154335 gttagcttt taatccataa acatttttca ataccttta ccatatcatt tggaatatgt   154395
tcaggggata caaataattt aaatatttt aagcaaatat ttcaaatgta aatattttcaa   154455 atatttgttt aagcaaacta tagagagaaa tgtaaagttt tgatggcact ttcttttttcc   154515 tgtgttatct tctatcctta ctaatgcatt ataagcaagg tttgtttttt agatagtccc   154575
tcaagtcagt ttctaccaat ggattaaggc ctaacagaag accattgctc cttaagacaa   154635
aacaaataca aatcataaaa ctaacaaaca caacgcaaga aaattctgca ttaaaaatta   154695
gttggagtaa taaatcacaa taaatgaaaa ggcaaacatg ggaattattt tcacaagatg   154755
ataaataagc caagattttg ctcttttaca atctcattta agctgtaaca tacactcttg   154815
caaaaaaaat cgtcacgaat agcctacagg caataaagag ggtgggccta cttagttaat   154875
tttaaattgt cagctctttt tttcctattc tttcagtaaa ataaactgtt ttgctgaata   154935
agagggttaa gaaaaggcct gagtgagtca ctccaatttg tttccacatt ctgaacagtc   154995
aataaagaaa tttattgcct cattaggcat tttgagtaga tttctggaaa cctgggtgac   155055
gtaagacaga aaagtaacct cgtaagatgt tttaaaagtg attgcagctg aatttgtttt   155115
tgaaattgca agttgcctgt tagactggaa tggcatcatg atttgtttca agaaatggtg   155175
ccaggcagtg ggctggtttc aaggagagga ggaggaaact tgtgttttca gcaagaactg   155235
aaaaatactg taaatactgg ttctgaaaaa tactgtaaga tgagagaagt gagatgatta   155295
gaagagggca aggtctcagt aatcagatca agagtaagct tcttatgagg aaaaaaaatg   155355
aaagcaatga aaattggaac attaaactga atgggaagca aaagccagca atgtacccac   155415
tgcatgttgc atcctaactt ctgcttagct gatagttagc tctctgttca aatgtggaca   155475 cttaaaaatcc tatgtgtccc tcagatcaag tcatctctaa tcactttgta tctagttttg   155535
```

```
ggcttcaaag acttattagt agccgaatga aggtagctac tttccccaca ctctatgctt  155595
gtaataatct tgaggcaacc tgtcttaact tcttttaaaa tgactgaagg ttatactggg  155655
ggttggttga taaagtatta ttatttttg aatgaaggaa tgttgacttt gctccaaaat  155715
gtaaacaacc caggaggcaa aattcataga acaaatgact tattaacaag tagaacacaa  155775
tgggttgctt gcctaaacta actttctttt tattcttttg gcaggtaaac acattaatca  155835
taatcagtct gatctgtatt aaaaaataac ttaataaatt aatcacaatc agccatagaa  155895
caagtaactt tcagggaatt tttcagatac aaggaggtaa aatattggtt tcccaaaatg  155955
aatatatata ttcatgtgtg tgtgtgtgtg tatgcatgtg tatacacatg aatgtgacat  156015
tctatttaag agatttgttt tcataaagga aaaggaaaaa aaaggaata aaaagggaaa  156075 ataaagttt aatcagaatt ctcttcctgt tagtcaaaga cagatttatc agcactgttt  156135
cattctctta ttataaaata ttctaacttt aggagagatc ttgaaatgta aaaagaagga  156195
aatattttct ccatcatcca ttctttcaaa cctctcaact gataccttgc tactgttgtt  156255
ccattgaata tccggagaat aaaatttaag agagaaaaaa atgtggtgac aggatacaaa  156315
gggagaggca ttgggagaag aaacctagta ctcatctcat ctttgcaaat ctctctagaa  156375
agtgtcttca tctgcaaaat gtggggtttg aactggatga cttagattg cccttgaatt  156435 ttaagggcaa tgatgagtct aacttggtag cctggaggag attaaaatct acttaaaacg  156495
ttagagaaaa agttaagagc ggcaaaatgg tgctgtgttt cattactccc ttttaatta   156555 acattataaa agttccagat ctgagatcct gccaaattta aagttctact tttgaccta   156615 tccagacata gctcagagat attgtgggtt tggttccaga ccactgcaat taaacaagtc  156675
acataaatgc tatgtttaca ctatactgta gtctattggg tgtgcaacag cattatgtct  156735
aaacaaaata tatattttaa ttttaaaata ctttattgtt aaaaaatgct aatgatcaac  156795
tcagcctgca atgagttgta attttttgtt agtgtaaggt cttgcctccc tgttgatggc  156855
tgctgactga tcagggtggt ggttgctgga ggatgggtg gctgtggcaa tttcctaata  156915
taagacagca acaaactttg cagcatcaac caactcttcc tttcacagat ttctctatgg  156975
cacgcagtgc tgttcggtag tgttttactc actgcagaat ttctttcaaa aatggagtga  157035
gttctctgaa acactgccac tgctttaccc actacgtcta tggaatgttc taaatcctct  157095
gttgtcattt caaccatgtt cacagtatct tcaccacgga tagattccat ctcaagaaac  157155
attttccttt gctcattcat aagatgcaac tccgtaggtg ttcttatact atcatgagat  157215
tgcagcaatt ctgtcaccgc ttcaggcttc acttccaatt ccaattttct tgctctttct  157275
accacttctg cagttatttc ctccctgaag ccttttttt ttttttttt ttttgagat    157335 ggagtctcac tctgttgccc aggctggagt gcagtggtgt gatcttggct cactgccagc  157395
tccacctccc aggttcacgc cattctcctg cctcagcctc ccgagtagct gggaccacag  157455
gtacccgcca ccgcgcctgg ctaattttt gtattttag tagaggcggg gtttcaccat  157515
gttagccagg atggtctcga tctcctgacc ttgtgatcca ccagcctcgg cctcccaaaa  157575
tgctgggatt acaggcgtga gccactgcgc ccggcctcct ccctgaagtc ttgaacgcct  157635
ccaagtcatc catgagggtt ggaatcaact tcttccaaac tcttgttaat gttgatattt  157695
tgatcttctc ccatgagtcg tatatgcttt aatagcatct agaatggtga atctttccca  157755
gaagattttt aatttacttt gcccagatac atcagaggaa tcactatata tggcaactac  157815
agcattataa aatatatttc ttaaatactg ggctgcagaa tggatgttgt gttagcagac  157875
```

```
atgaaaataa cattaatttc ctcatacatc tccatcagag ctcttgggtg accagtacat  157935
tatcaatgag cagtaatatt ttgaaaggaa tattttgtgt gtgtgtgagc agtaggtctc  157995
aacagtgggc ttaacatatt cagtaaaccg tgctctaaac agatgtgctg tcattcagat  158055
tttgttgttc catgtataga gcatagggag gatagattta gcatggttct taatgacccc  158115 aagactttc ggaacggtca atgagcatta gcttcaactt aaaatcacca gctgcaaatg  158175
cccctaccaa gtaagtcagc ctgtcctctg aggctttgaa gccaggcatt gacttctctc  158235
tagctatgaa attcctagat gacatcttct cccagtagaa ggctatttca tttatactga  158295
aaatctattg tttaagaaaa ccgcattcac caatgatctt ttgaataact tacttcagct  158355
tctccatcag cacttgctgc ttcatattgc atttctatct tacaacgatg gcttcttttcc  158415 ttaaacctta tgaaccagcc tcagctagct ttaaactttt tttcctgcag cttcctcgcc  158475
tctctcagcc ttaatgaaat tgaagagtta gggccttgct ctagattaga ctttgggtta  158535
agggaatgtt gtgttgttcc tggtttgaac gtctatccag actactaaaa ttttctctat  158595
atcagcaata aggctgtttc ttttttttcgc cctgccccgc ccgccccca cctttttttt  158655 tttttttttt tttttttttt tttttttttt tttggcggag tctcgctctg tcgcccaggc  158715
tggagtgcag tggctcgatc tcggctcact gcaagctcca cctcccgggt tcacgccatt  158775
ctcctgcctc agcctcccga gtagctggga ctacaggcgc cgccaccac gcccggctaa  158835 ttttttgtat ttttagtaga aggggggtttt caccatgtta gccaggatgg tctcaatctc  158895
ctgacctcat gatcctcccg cctaggcctc ccaaagtgct gggattacag gcgtgaacca  158955
ccgcgctggg cccaaggctg tttcttagca tttgtatatt cactggaata gcacttttaa  159015
tttccttgaa gaacttttct ttgcattcaa aactttcctc tttggcacaa gaggcctagc  159075
ttttagcctg ttttggcttt tgacatgctt tccttgctaa gcttagtcac gtctagctct  159135
tgatttaaag tgagagacgt gttaactctt tctttcactt aaacactcag aggccattgt  159195
agggtattca tttattttg agatggagtt tcactctttc gcccagcctg gagtgaagtg  159255
ttgccatctc ggctcactgc aacctctgcc cccggggttc aagcaattct cctgcctcag  159315
cctcttgagt agctgggatt acaggcacgt gccactatac ccagctattt tatttttattt  159375 tatttttttg tatttttagt agagacaggg tttcaccatg ctggccaagc tggtgtcgaa  159435
cttccgatct caggcaaccc accctccttg gcctcccaaa gtgctaggat tacaggcgtg  159495
agccaccaca cctggaccat tgtagggttt ttaattggca tcattgtaat attattatgt  159555
ctcagggaat agaacagcct gaggagtggg caaaatttgg agaaaccatc ggtcagcata  159615
aaagtcagaa cacacacaac atttattaag ttatctgttt tatatgagtg gtttgcggtg  159675
cccccaaaca attacaatag taacgtcaaa gaccactgat cacagatcag cacaaccgat  159735
ataatgaaga aagtttgaaa tattgagaaa aataccaaaa tgtgtcgcgg agacacaaag  159795
tgagcacatg ctgttggaaa aacagtgctg atgataggct tgcttgacac agggttgcta  159855
cggactttca atctgtaaac aatttaatac ctgtgaaggt cagtaagtga agttcactaa  159915
aatgagttat gcctgtgtat ttttccacac gttaattatt gcttttgag aaagcataag  159975 gtgttatctt ttaatgatta tttattgatt atgatgttta ctgaggctct tgtggatggt  160035
tcggttcaac aagtatttga ttcatggcta ctatgtgttg agaagtgagc atgggaatag  160095
aaagtaactc tcccgcccca aatcaaaatg acaaatagtc ctaggtttag ggagtttaga  160155
atatgcctgg tatataatag gtactcagca tacattgttc aatgattgaa taaatgcact  160215
aagggaaaca attagagtat aatatctgtg cttaagtata tatatatatt atctatatat  160275
```

```
ctctctatat aaacatttat atccagatat taaaatgcca atactttcta aatatttcca 160335
tgacccccc  aagcaaatct  ttgcctactc  ctctatctat  ctgtatagag atctctatct 160395
atatagagag  atatgtagat  aatatatata  cttatttgtt  acatctatct atatataata 160455
tagataataa  atctatatat  aatataatct  atatatgata  tataatatat catatataga 160515
tatataataa  atatattatc  tacatatctc  tctatataaa  tacatagtta tgaagagaag 160575
taggcaaaga  tttgcttggg  gagtcatgga  aatatttaga  aaatattggc cttttaatat 160635
ccagaagtta  gaatacatat  atttacagta  aagatggcaa  ggaagcatat tagttgatgt 160695
atttttaagaa tgggacagat ctgccagaaa aaattagaaa gaacaaaagt taattgagga 160755
atataatcaa  taaactggat  tttttgggta  tgtatatatg  taacacatgt gtaataattt 160815
tacacatatg  tagagaaaac  ttcatactct  ccaaatactg  catattcatc ttttctctgt 160875
gttcataaaa  tatacatatt  tattgaagaa  caaaaaaata  aaaaaacaaa gaaagtatta 160935
acatttgagt  tggcattcca  acaacaaatc  agatttaaa   cattcatttt aatcagagaa 160995
agcattctag  tttacagcat  gtttgggaac  aattaacatg  tatataatga ggagtggtca 161055
cagatcacag  gaagtgaggc  tggaaaggtg  gctggggcaa  aattgccaag acttttaat  161115
tccaggtgaa  gtggtttaaa  cttcatgcta  tgaatagtta  aaactccata ctataaataa 161175
tggcattttg  tgtgtcaaga  acagagtgaa  atgacccagg  tttgtttttg tgactcctga 161235
tcctttagt   gtgcccagcc  tgtccggatt  aaacttttaa  agaactcatt gacctatgct 161295
ctagcaatct  aatggagcca  gtctttaact  tctaaagtaa  tgtactttct gttagtaatt 161355
tatgatattt  aaactatgga  actgaacata  ttgagtaggg  cttttcaaat ggtacatcat 161415
ccttcaaatt  tctgaaaatt  ctgttgtctt  ccttctctcc  ctagtccctc ccatcccctc 161475
atgcctttct  acctctgcat  tttttaggct  tggaacatat  taaatggacg caggtgttgt 161535
tcccactta   acacaaacct  tagaggcaca  aaataataac  caattttata aacaaaaata 161595
aagaaaataa  taataccaag  agccaggaaa  caataacaat  gcaatgtaag ctctcgatcc 161655
agatggctga  ggttcaaatc  ttggttttgc  cactgattgg  ctatgacctt gaccaattta 161715
cttaaactcc  ctgcagctag  attttgagga  ataatgttac  cttctctcct agcaatgttg 161775
gaggaataaa  agagttaata  gagattatgg  cctgatgtat  agtaggtggt gcataaatat 161835
tgtagacgtc  attgttgtta  tcgtatagca  ggggaagttg  gtataatttt tgtttgtccc 161895
ttatgttgtt  ttctgacctg  gaaaggagta  acgctgctcc  ttttaggaac aaccttagtc 161955
ctcacttcat  acataaatca  catgttcttc  tctttgccaa  cacctatatt tgataagac  162015
tcaatatctg  aagctaaaaa  cacattcaaa  tctccttatg  ttactactc  ttgttctaac 162075
caaacaccaa  cattagtact  tattctattt  tcttgtcctg  tctattcata caatagtggc 162135
ttttctctgt  atctgctttc  tgcttgtata  ttgagtcaag  acttttcc   tcgaaggcct 162195
gttttgtgtg  tagcagttca  aggactatca  agtcagtcct  ttatctcaac atactccaca 162255
atttgaaaaa  ataaatctca  tttttattag  tgtgattta   taattttttt ataagacttt 162315
gttaaactt   atgaatcttc  tctagatttc  tttatggttt  acatttcctt gtaacttgtg 162375
aagaccagat  ggaggttcag  ttaagttagg  gggattggag  cattgcttag aacatcaagt 162435
cccagactgg  gccaagagtt  ctgaaaacaa  gctggctttc  tgcttatcca aatgagtcat 162495
ttgggaagcc  attgcctcct  ttgctaaaga  cactttcttc  atcatcaact tgattgtgg  162555
tttcttttca  gacctatttt  gactataaaa  taaatctgaa  aaatgcttta gacagaatat 162615
```

```
cactgcaaaa tgtaagctat tcttcacatt aggctaaatt taacaatgat cctgaattta  162675
aaaaccagag ttaaaaatga caaaaaaaac tgtgatggat ttattattga cattactgaa  162735
ttgacatggt cagttaggat taaaatatta tgagtaatat gaatgttacg ttatttaaaa  162795
taaagagata ttaagagact atttgttttt atcattttat gagaatagct agtagcttcc  162855
cctctacccc ttcttcaata aaactaagca gttcaggaca tcttgtatta atgcaagaaa  162915
gttagattaa tattaatgat aatatagtgt tttcatgttg tagttgttca tctgaactga  162975
gccttcagta ttctttaatt ttactcagtg aaaataaact ttgtttatct cagctcttta  163035
aaaataaatg gcattgcagg attgggtaga accctgggca ctttgtttgg tcttatatta  163095
ctctgaatac caaaattatt tttttttcaag ctagttaaat catcatttga aacagagctg  163155
caagactaac atatggacta caggagagta atagatgtgt catataccaa aaacagaaag  163215
atccattacc ctaaatgtga aattgtgaga gggaaggaga atacacaaag taggatgtct  163275
ggaagccttt tttagactgt attaccatcc atctagaaaa atgttatagg taaataaaat  163335
atgttcttac tgaataataa gtataatatg cgcaatttat cctcattaca aagagatttt  163395
attgtgtgtg aagaattcca cagagagcca ttacagatcc attatagtgt ttttagtgat  163455
ctgctctact tcccaaaccg tggttgtttt atgcagtatc agatgtataa tgtgcatttc  163515
tatttttttc ctgctccaaa ctcgctatgc ttacaaataa ttaggcagga ggggttttgt  163575
tgccttgttg gccacttctt aaaagcatag tataatttat tggaacaaaa tatagtaatg  163635
cactttaagg aaagttctct tatgtaaaag ctcaatctca aattgaatga agggtaaatt  163695
tttattcgca agaattgaca catttccaat aggaaaggct tcatagttgc agtatttat   163755
tatgataatt gaattttata agaatagcac catttacttc tatgaaaatt tattctcctt  163815
gttctgctcc agagctttat tagcttccca gtatttcccc actcttccac ctggaattca  163875
tgggccaggc cccaacttac attgttactt cttttatata taattacttt tgcacataag  163935
cattttcttc cactcagcct ccatcttttc aagaatatgt gtgttccttc acttcttgga  163995
ttcacgcttt tactttctct acttttccta ctgctccaat ttttttttctt gttctaaagg  164055
tctttaaaat ttttcccatc tctataacgc tatttgtgga tgtgtgggtc tttttctttc  164115
aaataaggta cacatctgct gtgctgaact gctcatctat ctgtagagca gaaagggagg  164175
gtacacctgt tgaatgtcca gagttctcca tggattttc taggtcttct acgttatgta  164235
cctcatttaa ttctcttaac aaccaggcaa tgaagaacta gcatgcctgt ttcatgggcg  164295
aaaaaactga ggcttaatga gtccaagcag cttctctcaa gtttctttgg tagaaagcaa  164355
aagaggatag attcaaatcc gtctttttca ccaaacctgt gtttgtttgt ttttagctt   164415
tccctatgtg tgtgtctatt tcattttccc atctcctgat ggcaaggact ctatcatggg  164475
caatttatc ttttaggtag ccgtcacata tctcaattct gcatttacct ccttgtgtag   164535
ctcaggtgcc acatttcct tcacagtgtt tttccgattt ttacttatta aaatgatttg    164595
catattcata agtagaaatg gtatattttt ccttgttagc aaaaaaaaaa agaaagaaa    164655
agaaaatagt catgtgacta atgaaaactc tttcaagttg gtctatagtt tcaagttggt  164715
caagaacata aagaacata aaagagtttt ttatgttttc caagtttgat ttctatcaac   164775
tttatattct gtgtgtggtt gataatattt ctcagtttat acagctttgt gttctcttaa  164835
agaataatac ccacttttca tagactattt aaatcttcat tgggaaaaaa tatcaaaatt  164895
tataaattat atgaatatat ttaattagca catgtgcccc aaaactatgt acatctatta  164955
tacagcaatt ttaaaatttt aaataaaagg taaatgtaaa aaaagtacat gaactttgaa  165015
```

```
ccaaatttag acatgcttaa taaagcctat gtttatcact ttgaatttgg tattatttat    165075
ttattattat tatttattac tttgaatttg gtattattta aaaaggaatc cagtttttaa    165135
aactttaaat gaaataacat gtctgaagag agtttctaga tgcagcttac tcatctatat    165195
agggagcaaa ttacaaataa agtctttaaa gaacccataa atgttgagat aacgtggaat    165255
tactgataag caactcaaaa gctgctcctt aatattgttc acctatttat caccttattc    165315
taagccaaac tcctaaacaa ctgaaaaaga aagcttagat aattggataa tatttcttca    165375
caaagtcagc ttaaatttct gtctaaatgc attataatac atgaagaagg cttttaatat    165435
tacttatgct aaaggaaaaa atatgctggt tcttttgtca accttctttt gtactaattg    165495
tgtaagtttg aagcgagggc tgtaggaaat taaaacagaa aatagaagtc ctgattgtgg    165555
ggcctgttga atttgcagtg taacacagga gataaggcat cagtttaaac aaacatagac    165615
acacacatat aacatctcaa gatcgcataa tacagccgcc aagatggggt cacagatgag    165675
ttcagtaaat aaagaatgtc atggactagt atggtcagag aaattgttac caaggaggtg    165735
caatttgaaa ggacacttca agagggggca ggattttgtt agttggaaag caggtgacac    165795
agcaatttgg gcaggaagga aatcaagttg cagaagttgc ttagggaaag taggtttgaa    165855
ggaaacatca gaacaactaa aatagaagct ttgctcaaat aacaaagtct cgttttattt    165915
ttatctgttt tttttacttt acctctatca gtttgtcact cttttcaggc tagtacaaac    165975
tgtcatgttt taaatctct gtacttttat tagttgtagg atgtaagctt gaaataagc    166035 tttgcaactg tggagattag tgtcccattc ctttaagggt ctggccaacc tagggatcc    166095 acagatatta gctgctaggt ggtcgatcac cttgaaacac catcctgtta tgctgtgtcc    166155
taatagcttg agaagctgaa ccagaagtat gcagttcact tctacacatt ctgcagctct    166215
tcctgaacaa cttcattttt catctatttc acgatgaaca gaaatattct cagaaattct    166275
ttttttcttt tagctaccaa gatttgggcc tgcttttta ttggttattt cgtgagggta    166335
atggggcatt tgaccattct aatccgcttt tctgagaacc agcacattct gaaaattgtc    166395
tgagccctct ctccttttgac tatcaataag gatcactttt agataagtcg aagaagaggc    166455
cagactgaaa caggaacctg tgaggctccc tgttgcatgt ttttaattca cacacccaca    166515
tggctacatc aacagaggt gacctgaatt ttactccttt gatgttgcat accataaatt    166575
cccatagcag gtttgcaaca aagggggtat tttaaagctt ttttctaaca tcgccttagc    166635
agatactgac tgatccttc ccaggaactg agagggtccc acccatgctc ctgattttag    166695
aatcataaac atcagtagga ccaagatgct tttagaggga taaagtgact ttaatttatc    166755
ttgggtggtc aaaacacagc atgtgcaata ttttacaaa ctatgattca gaaagcacat    166815
agttctagag cgttttgttt tttgttatgt tggtgtcact ggaaacagtt gtgcttcctg    166875
atgtcttact gagatggcct ttttggtcat tttgggccac tttcccaagg atactgcatg    166935
ttgcctgacc tgtattcctg aggaaataag gaggacttag attgatctgt tttggacagc    166995
gtactttctc taagaatggc gaaaggaaaa acatcagact aggatgctct ccagaaataa    167055
taactgagaa tctcatcctg ttgtgtaaac tctccttgta ctttgctctg tgtgtgtttg    167115
gtggaaatat tattttaaa cagccattta ctctgaaaaa atatgatttt gcattaaatt    167175
agttttaaag ttaagggata tatataagac cttttttatta acaagttgat gagatgagca    167235
ttagtatacc tataggaagt ttttgaatga gtgccaattc tgaatttaca aatcaacatt    167295
tcttctctcc ag ctt tct tta gct tgc cca tgg tga tgt gaa gat gag aag    167346
              Leu Ser Leu Ala Cys Pro Trp     Cys Glu Asp Glu Lys
```

|  | | | | | | | | | | | | | | |
|---|---|---|---|---|---|---|---|---|---|---|---|---|---|---|
| | | | | 60 | | | | | 65 | | | | | |
| aaa | tag | caa | ggc | cca | acc | agt | tct | tca | tct | gga | gac | agt | tca | acg ttc | 167394 |
| Lys | | Gln | Gly | Pro | Thr | Ser | Ser | Ser | Ser | Gly | Asp | Ser | Ser | Thr Phe | |
| | | 70 | | | | | 75 | | | | | 80 | | | |
| tgc | aaa | cca | ggt | aaa | aat | aat | aca | gac | gat | ttt | agg | aat | gca | ta | 167438 |
| Cys | Lys | Pro | Gly | Lys | Asn | Asn | Thr | Asp | Asp | Phe | Arg | Asn | Ala | | |
| | 85 | | | | | 90 | | | | | 95 | | | | |

```
gtcactttat aaaataaact attttctttc tcaagtttga tctacagatt tttgcagaag  167498
ctatatttat catctaatgt ataacttgtt aataaacatg acattgtatc aatttcgatt  167558
atctgtgaag agcagagtga ctaaagcatg catttgtgca ttgactcatt aataaagtta  167618
tagttgtagt ataacttact tttataaaaa tattttaaag aaaaagagg acatgtggct  167678
atttgatttg cttgttacaa ttctaaacaa agtaaagaga ggtatgggct aaataaattt  167738
aatatttctt taaaaagtaa cttttaccaa atgaatacat gtgcatatat ttaaaattca  167798
ggtaaattta aaggctagta actaaagaaa taaacctttt ggcacaactg caggaaagga  167858
accactttca aactctttaa tttttatttt acttttgtgg ttttaaataa catctataaa  167918
tctatctcag gattttagga gttagtgctc taacaattga tttcttgttg ctatagatgt  167978
ggatttaaac ttccttaaga cctcaaaatt cttgattctc ccaatatagc tatatcacta  168038
tttttattgt tttaatttaa atctgtatct gaatttatag ttagtaagac tatacaaata  168098
atgtttactg ctgagactgg tgatgtgata tgattgcatt ctctttactg tagtagaatt  168158
ttcattttct cttgaagtca gtgcccttcc ttccttcctt ccttccttcc tccctccctc  168218
cgtccctccg tccctccctc ccctccctcc ctccctccct gcctccctcc atccctcctt  168278
cctccttctc tctctctctc tcttcctttc tttttttga tggagtctct ctctgtcacc  168338
caggctggag tgcagtggtg ggatctcggc tcactgcagc ctctgcttcc tgggttcaag  168398
cgattctcct gcctcagcct cccgagtagc tgggattaca ggcatgtgcc acaaagtctg  168458
gctaatgttt ttggtatttt tattagaaac agggtttcac catgttggcc aggctggtct  168518
cgaactcctg atctcaagtg atctgcccgc cttggcctcc caatgtgctg ggattacagg  168578
cgtgagccac ctttattctt cttttgctca gtttctccct caccatctcc ctatctccct  168638
tctcccctcc ttcctttttc cctccttcc tcctattctt cttcttttta tttttttct  168698
aggtcttccc gaaccctcca ttatcttat aaaatgcctt tctattcaat tttctacaat  168758
gacaagctgg tcaaataatc tagaaaggtc cccttcccac tacccttgga gaaatctctc  168818
ctgctaccct ggctccttcc agataaaagt agaaagagac aggagacttt tatctccttc  168878
cactttacc ttccactttt atctctagtt gcgctcgaag gcttcttata aagagatgtc  168938
atttagggtt ttgtttttgt ttttattttg gctgtcgccc tagtttattc ttccatttta  168998
tgatgtggta ggtgtttttt ttgttgttag ttttgtttt tgttgttgtt ttttgttttt  169058
tttctagaaa tcatgtcctc ttttacttg gctctgccaa aaagcttgat tttacccag  169118
taaaactgat gttaagtttc tggcctccag aactgtaacg gaagaaatct cagttgtttt  169178
taagtcagca agtttgtggg aatttgttat acaagaaaga aacacaattt gcattagagt  169238
ttcttttct tcctcattct ttgcaatgat ttttggaagt agaaagttat ggaaagatta  169298
tttattttac cttcttgaaa ttggaatcct ttagttatct gatttaagat agtttctct  169358
ttctttgcta taaggttat atccacctc agaacaatga tgcattctca gttgtggaat  169418
tttaatagag tcttcattcc tctcctcgtc ttagtacgtt atctcctgtc atatcattct  169478
ctcctcttct cccctcccct cccctcctgt actctccctg cctccctc ctctccctt  169538
```

```
ccctcccctc cacccctgc cctcctctcc cctctcctcc cctcgtctcc cttcctctcc 169598
cttcctctttt tctccttttc ctttcccagt aatccagcag ttgcctactg agtgctagat 169658
gttgtgacag gctttggaaa tactgaaacc aataaagcag tttgatgcct ccatgaggtc 169718
accatctatt ggtatagagg agggacaaaa gtaacatttg tttcgtgcaa gacataaagc 169778
caaaagcaga aataaaatca acaactaaaa tactgtacta aatacaaaat caggccagga 169838
gcagtggctc atgcctgtaa ccccagcact ttgggaggcc gaggcaggcg gatcacgacg 169898
acaggagttt aagaccagcc ttgccaagat ggcgaaatgc tgtctctact aaaaatagaa 169958
aaattagccg ggcatggtgg tgggtgcctg taatcccagc tactcgggag gctgaggctg 170018
gagaatcgct tgaacccagg cggtagaggt ttcagtgagc cgagatcgca ccactgcact 170078
ccagcctggg tgacagaatg agactctgtc tcaaaaaaaa aaaaaaaaa aaaaaaaaa 170138
aaaaaaaaaa aaaaaaaaaa aagaaaggaa gaaaagaaaa gaaagaaag agaaaagaa 170198
aaacaataaa aaacccaaaa aactaaatta gatacatgaa caaaatattg tgacctcaca 170258
taacatttag caaatcgctc tgcttggcag agactgggat aatttattga agagtgcttg 170318
tgcagcatct taggagatga attagcattt tagaaagaac taaatgggag aaaggcatt 170378
tatggcaagg aactggctct gtggaaggca cacacatatt aaggagcaca cgtttcttga 170438
gcatggccag atatttaatg tgcccagaac atagattaag agtggtagga gtgtgggcta 170498
atgagactat aaaggtcaaa ttatgatgaa tattattatt attattatta ttattttgc 170558
tgtgttaaaa gtttaggttt ttattatttt ggaaatgagg gaaactaaag gtgttgagca 170618
gaaaaatggc atgtattta ggaagaaaat tctggcaata ttttgattat tgagctgctg 170678
gagagaggct ggaaaccag ggaagggct ttgtaagaaa ccaggtgagc agtagatgac 170738
aattacctga gtcaaaacag tagaggcact gggacaagat cagagaatgg aatcaagaga 170798
tatttctgaa accaaattgg cagagggatg aaatttctac cttttagtga aagacagtaa 170858
gtgcaatgct agcagtcaca gagagcaact ggatgccagg ggagagggac tcaactgggt 170918
ctgggcagaa gcagaggagg tgacatctaa gataagtctt aaaagagaga agaaacaagc 170978
tacatgaaaa agaagagaag ccagaaaaag gagagaaagc agattgtggc tgcagggctc 171038
tccaaacacc aaagactctc tagtaaaagg catggccatg acaaacagag tggctgctgg 171098
ctttgcttta attagcatat aattattggt ggagaaagtc tggtgggagg taaggtggga 171158
aggaaccagt cactggaggc ttctggttaa tgtccccatc cttctttcc ctaaacatca 171218
ctcttacccct gtgtagctgg gactacaggt gtgcactatc acctttgt aactttattt 171278
ttttgtagag ataggatgtc actattgccc aggctagtct tgaactcctg ggctcaggca 171338
atcctctctc ctcagtgtcc caaattgctg gtatttcagg tgtgagccac gtgcccagcc 171398
ccttcttaaa tgtataccag tctttaggcc taaaacaatc ttttatcaac tgctaagact 171458
tccttctttt aaagatatga tcagagcttt tgtctttcac agcaggcatc ctagtttcat 171518
gttttcttgg gaaatttgta tagattcaca ctcactacaa atgttatttt cagctgtttt 171578
atagatgtat aatgcaccat ttattcattc agtacatatt tagcaagtaa aagggaacaa 171638
ccaagattca ttctatgcct tcttttgttg gaattcaagc acactaacaa tgtgctctct 171698
tgttggacaa gcatgaaaga aaaagatacc ctccttgtca ggtcttcata gttctctgtg 171758
cttacaagaa tcctgcaaca tttgacgatt tcttctcaag cttttccttcc tgaaaggaaa 171818
aagggcaaga aaagaataaa ctttgtaaca tgtaatctgt ataatatatt ccaaaatgct 171878
```

```
ttagctcaga tattttggat acctttctga tcacatgcta tagttagaat caattttctt  171938
tcttaaaagc ttgaaagtta attaattgag ctatgacttg gggacaaaat gaaaacaatt  171998
cccccatcca attcaacaga aagtgggatc tgtaaaaata gctcttcttg aaaattttag  172058
aactagaatc atagaacttt atttgctttt atattcatta tcccataata tcctcttata  172118
aatgaaagtt tagttctgat catttggata ttagctcagg gagctcagga aagtagtatg  172178
ctgccgttga ttaactcttc aggatgctct aactcaacag gcaaagtttc agtaacagca  172238
taggcaccca cagttttagg tactagtgat ttagggccag ttgtttaaga gtattaactc  172298
aaattcggca gccctgctcc tgagaggctt gccttctttg ccaacatcct ctgattcaga  172358
atatcctaat ctaaagcctg aagacagtca taaggaggtg aatacgatct ttacatgtac  172418
tatattttat ttttgtagaa gttccagaga tagtatttta cccatataca aattagtgtc  172478
ttggtatggt aaggattttt ggcaccaaaa tctctaaggg gatttttaga actaaggagg  172538
gctaaaggga aagataattt gataggttg gcctttccac actccttgag ttgtggcatg  172598
tgacatgctt ttcactatct gctgaaggaa gccctggttt atctcagaaa cattcttgta  172658
taagtgccaa atacagtctt gtttcttgtt cttgactctg ccactccatg tggctgtaat  172718
atgctggagc acatttgcct aatgcctccg gtatcttttc cttggttaaa attgttatta  172778
attccacact atcttcctag gtctgtctct ggggcccaag cagatttggt cacccaacag  172838
ctagagcaac cacttgactg ggtgaactct attggcaatg aggcatatgg gggccaggca  172898
gtatcatcca cgatagatga aagacaatct gggtatcagg accccagtta agcccaggcc  172958
tcacacacaa acgatcctcc cttgaggagc tcaatagttg cccctcaaat agtttcccat  173018
aggattagac ttcagctttg acctgtcact attgtagaca tgctacctgt gcttacttac  173078
ttacattaat gtagcaacac cagtgaacac aagaatcaat tatacatgtg catttcataa  173138 caccctcca ggagccattc ttcctcttcc ttcccagctc ccattctaat catttattca  173198 tttttaaaa ttatgggaga tcatctaata ttctctctct ctctcacctt catatttact  173258
ttctttattt gttttagtgg gttttttttgt tgttgttgtt gttttaacaa gagctttgaa  173318
aggcaacacc caggcagtat gctttataga tttatcaaaa caaaacttgt tgaactgggt  173378
gctcttgacc accctgctct ctgattctca acatgagatt tcacctgcac attctgatac  173438
cttgctgagc tttcactttt cattaatgac ctaattgtat agttttctct gtgttggcat  173498
gcttgttctc ttcccttcc ctttctcctt ccttcctcct ttccttcttt cctttctttc  173558
tttcttgctt ccttccttcc ctccttcctt ctctttctgc ctttctctct cccttttcttt  173618 ctttcttctt tttctttctt tcttttctct ctctttttt tttaaagcaa cctcactcaa  173678
ctcccagttg ctcacccatt tggctacatg tatcctcggc tgcagtaaga tactttcttg  173738
cttcccaatc ctttgggatc tgtacagata gggagagtct cagacatgag ttatttaga  173798 ttgtctgaga agatctaatt aagggtcaaa gtagtagatg ttgtgggagg gcatttgtca  173858
ctggatgaga tgactgtcac catatgctct cgaaggagaa aacaaaggct atagacagag  173918
atgaacatga ttttatagat ttatttttaa aatcttcctg tgaatctaag caacagagca  173978
gaagcagtga aattgaaggg aaggggggaaa tttccattcc ttaaaaaaga agaatcattt  174038
caaattctaa ctagatttgg gaaagtaaaa tatttgaaaa aattaaggc tttaagatgt  174098 gtgataaaga gaatgctgaa attaatgata cagcaaagtt ggaatgtctg cctctccttt  174158
gtttaatgtt tttcttttat taaaaaagat acttatatgt tttttaatt tagaaaatat  174218 cagaaagtaa atccaatatt ctactataca gagatgatag ttactgtcaa cattttgata  174278
```

```
cctgatcttt taactatatt gaaaaatact cgtcttacaa aattggaatc atacattatc    174338
tgcagtttgt ttctttcccc ctgcttttgc ttacctaaag tttacatctc atgactcttg    174398
aaaataccat ttttaaccaa tatctaatat atcataagaa ttgatatact ctattttcag    174458
ttttcctggc agttataaac aattttgtac aaaaatggtg cacacattac atacccct     174518
atctcactaa tgaatttctt acaaaagggc cctcaaagta tcactgagaa tcgtgcccca    174578
tcttagagcc tttcactggt acgtccctct ccacaagtgc ttttctccca tatattacgt    174638
tagactccca tattcactc agattattgc tgaaatgtta ccacaccaga aagacatttc     174698
cctgaacccg tatgtaaaat gtcgtatctg ctgcctccga agttatttgt cttatcctgc    174758
gttattttg tcttaacgtt cagtagtact aatatgtaa tgtttatttg tctacttgtt      174818
atctctacct catagaatcg aagataaacg aggcagaaat tttgttttgt aaatgctttt    174878
attcctagca tctgaaacag tgcctgagac atagtacgtg atcaataaat acttatttgt    174938
tcaacaaata aatacataaa aacaaaaagt acaaaacttt tggtacatat aaataagttg    174998
ccttccagaa agcctgtttt aatttgtata ctcatatgta atgtatgacg atactcattt    175058
tacaacagaa taacccactt tgaatattag ttttaaatg ataaaaaat aaaaatgtac       175118
actatatatc aatgttgctt caggttttt tgttttgttt tgttttttgt ttttttttg      175178
agatgcagtc ttgcactgtc gcctgggctg gagtgcagtg gggcgatctc ggctcactgc    175238
tacctctgcc tctcgggttt aagcagttct cctgcccaca gcctctcgag tagctgggat    175298
tacaggtgcc tgccaccacg cccagctaat ttttttgtat ttttagtaga acgggtttc     175358
actatgttgg ccaggctggt ctcgatctcc tgaccttgtg atctgcccgc ctcggcctcc    175418
caaagtgctg ggattacagg catgagccac cgctcatctc ttcctcttct ttatccattc    175478
tttttaaatt aaagtgtttg ctccttttt tcctttaaaa taatgtgcaa gagctgttat     175538
gcattaataa tgttgaagtt attcacattt ttatagacat gtttctctct ttcataatat    175598
catttttaag tgatatcgta atatcatttt tattttagat tcggggagta cacgtgcagg    175658
tttattacat gggtatagtg tagcatgctg agttttgtgt atgaatgatc ctgtcaccca    175718
ggtagtgagt atagtaccca atacgtttag cccttttcctc cctccctctc ttccccgtc    175778
tagtgacccc ccgggtctat tgtttccatc tttatgtcca tgggtacctg gtctttagct    175838
cccacttata aatgaggata tacagaattt ggttttctgt tcctgcacta attcgctgag    175898
gatagtggcc tccagctgca tctatgttgc tgcaaaggac atgatttat tattttttcat    175958
gactgtgtag tattccacgg tatgtatgta ccatattttc ttaatccagt ccaccactga    176018
tgggtatcta ggttgattcc atgtcttgt tattatgaat agtgctgtga tgaacacaca     176078
agtgcctgtg tcttttggg tagaacacag aatatacttt taagttttcc ttatgttttg     176138
tgacattta gatttaaaaa catgtgaaat caaatattag aagatttctt ccagcaagct      176198
tacctatatt gttgctacag atttcaaaca catctcttat tttttaaagt ttgtcattga    176258
tttcactgtt gtaatttttcc agtgtcattt atcatcctta cttcattttt ttttaaatcc   176318
attatggttt ctttctttc ttttttttat ttttaagtgt atacctccgt ttcatttct      176378
tcctttatt ttaagccatt tcctccttct tgtcctgtat gatagggaac atggctttgt     176438
gaattttatt taaaatccct gttttcacct gttttaatag tagtatattt acttattgct    176498
ctccttttaa aaatgttctt atcccatttt ctctgtagta tttgtgtata ggctccacct    176558
ttatatttgt tttttttattg gctcaacact ctggattagc ttagatctat ccaatgtcat   176618
```

```
gtttacaacc agataactcc tgttgttttc ttactattca cttcttgctg gttaaatccc 176678
attcatgctg attaaatcca cttcatgttg ctccagctgg gtgacacgtt ggtgtgtgga 176738
cctcccagca gctagagacc aggacacatc tatgcaatct gactttgctc tcaatagtaa 176798
gtaggtctct tatgtcccaa accttgttat atcacaagga tgaaaagcta ctattcctag 176858
tacagtaagt tcatttcttc accatcttcc tctctctcct actgtataac tcattttaac 176918
taattttggg gggatgtaat gtgttacatg ccagccctcc ctgccccgtc ctcccccaac 176978
tccacctcgc tgcaactttc tgttttrggg tactaatgcc aaaataggaa gagatagtga 177038
tataaggaca ccgcactatg taccctaaga accagcacct tctattgata cctgatgtaa 177098
ttatggcagt ccaagttttg gtggaacagg ccataaatat gactgcagtt aatcaagaat 177158
tgttaaaaat accttcttaa ttttcagatg gataggacta atctttctac aatgcagacc 177218
acctgttttt cttagcccaa catcattagc tttagaagaa tggtaaagat attaccgcta 177278
ttaatcttag tttttagaat tgttgagaga tgtacttttc agtttaagta ttttaacaaa 177338
aagttagctg agaccacctt gtgatggtgg actgctatcc agatgtcatg gaaaactaaa 177398
atttttatgg caatattttt caggtctttg attttagttc aactcttcct tcatcccaaa 177458
atgactatct tccaagacat tccaaatgat tggacaaatg catagatgca taataggatt 177518
agagtagaaa atatcaacat gacataataa gtagcaagta ttttctttta ttatgtgatg 177578
ttttgaaatt atgtctttgt aacttcatat attattatta tgtcatacca ttttgaatgg 177638
cctttttattt aattaaaata taattttaat tattttcata tttattctaa cttagcatct 177698
ctaaatacac atcataggg tttagtggta gaattatcta agctattgag atgttttttca 177758
agttagatga acttagtgaa aaatgttctg caatgtttga taaaatcacc acggcatcta 177818
gagcagtgga caatatcccc gtgaaatgat ggtggaaacc gaccaacttt tttcaatagc 177878
atcctggtag tgatcttttc agtcactttt aaaatgggat ttttttctgt aacccgtatg 177938
taattcagaa tgtctgtggt tgttttagtc aactggccat taaaaaaaaa tacattatgg 177998
actgtgaact caccaaggcc ctttcaagtg ctgatgtatg ttttatgttt tatgtaggtt 178058
attagtgacc ttttttgcac ttttatcaga aagtcctttg ttttgtgcat gtagctctgt 178118
cagaatagag gccagatctt caggtgttta attgcagact tctaatgcat aagacctgct 178178
ggccttgttg acttttagaa gttatttgtt agtctcaaat gaaagaaaca agaaaaaaaa 178238
aagcttgctc tttttataac agagtaagat gaaacatgca atgatagggt ggtgctgagt 178298
tgtagaaatt tctaaaaact aggtattcct caaacagtaa ttagaatttt tgattttcta 178358
catatctatt ggctaaagag ccaaaaatgg ttttcaataa tgcctgtttt caatatataa 178418
aacgtccata acagaatcac taaaagacat caaattatta ttatttaaaa tttattgaga 178478
ggcaatgtca atctgttttt tcaaacctat cagtgactct ctattgtata ttgggagaaag 178538
tagaaactct taatttctgc cctaaccccc acccataact gattttaaca ctcctattac 178598
cacattattt gttactgcag tttttaaaat tgactctatc catcagacag tattatttgg 178658
ccgctgtttt tttacacctg tcttatttat tcttgatttt tttttttttgg tttgtctgtt 178718
ttatttatgt cactgtccac tttgcagaca atttagttgg ccaggtatcc atgaggaata 178778
ttgccattcc tgcactgtgc tgagtcagac atgccttgtg gcatcatcaa gtaacaaggt 178838
tgagaaaacg tgggtgtggc aaatccattt ctgagtaaca gccttttggg agggaagaga 178898
ttggctaatc caatcagtat caaagcctgt gcttcttaat tgggttgtat tattcaaaag 178958
catggattta atttgaaata aaattgcctg atgtttctgt atcattgatt tattgatggt 179018
```

-continued

```
ggcggctact attttttagt gttttcaagg aatatgaaaa cttacagtat gaaatttaca 179078
caaatctgta gttttaaaat attaccttt  cctttagtgt ttctcctatt ttccgttagt 179138
ttgagttctc attttaaaaa aatgttaaag agaaaaaaca tttgtctgac atagagctca 179198
aaaggaaatt ctcattaaaa caactatgag aatgagagaa atcatgatac taagatagta 179258
tgtaatcttt agagtttaaa atagttgttc ctagccccta aagtgatatt attttgactt 179318
ccttaagcat agagaacttt gtttacagta gttctactct gcagttaggt gtaataaacc 179378
agcattcttt acaaaactca aatgagacct tggaacctga gctatatgag taacacatat 179438
atgatcctgt gatctatatg atatattatt tgtcatttct ctattcccag cttgaaattt 179498
aatataaaaa aaagtttcac tgcttcattc taaatcctgt ttgatccaac atggaaaaca 179558
ttgttttaga tttcttaatg taaaaaaaaa aaaatatat  ttgactggat tagatagtag 179618
ttactgcaaa aagttactgc aaaaaaaaaa aaaaaactc  ggagtttacc tttagtcaca 179678
tcttcagtac attttctatt aaagtatttc tagatttag  tgtctgcttg gttttggtta 179738
tctaagctgt aataagtagc cttgggaccc ctgaaggcac gccccacaca cttatgctgt 179798
gtgacctaag gtcacaagta atggctgcaa gctaattgat tgagaaaggg ttgtctggcg 179858
gggcctcttt gcgtcctccc tttacattcc taagttctgt gaaagaggca ctagtagctc 179918
aggctagcaa ggaaggaaaa aagaggaagt ttctctctgc gttctgatta cactctgaat 179978
tcccttgtag tgagcttact tctctccacc cacttcttac caagaactcc ttaacttgag 180038
ggtgaacaac ttaaagcttg atcctacagt tacctgaaaa gtgatttgag tattcattga 180098
actgaaagaa caaatcgcct acttcaggcg gtggcaagcg tatggaaatt atattagaac 180158
ttcagcaaag tgcacagctg cataatagag aagccggcac tcagattgac aggcaaataa 180218
gccagcttgt ggaaggggcc tctgggtggc agctctgggc ttttgggtgt tggacaacca 180278
taggcaaaac tgaaatggaa caggggcaga aaatagcaca cttttactct acgcaactgt 180338
tgcttttca  tggtgagtgc agatttaaga tattatattt aaaatatact ttctatgttg 180398
taaaacaagt taagaaatct gttgtgcttt gagggaaatt atagcaaaag catttcttag 180458
aagttcttag acgatgtggt tttgtttctg cttgatttca cactaacctt ggtgatgcaa 180518
acagaaaaat acaatatttg tattgtctcg tgtgtccttt ttctgaaaat tgtcctttgg 180578
tttaaatcat gcttctcttc aacttgaatc agcattgttt taggcaaatc atgtgtggga 180638
tagatgatga aggaacaacg gtgtgacaga atatatgtaa acatttcatt tagttcgact 180698
ttgtgtcact tctccacggc ttcatgtttt gccgccttat cttaggaata tatagcgcag 180758
tctgcatgaa aagagctttg tgtgagaatt cctggccagt tgaagggtca gggcctgtgc 180818
gttatctgac tgccagcaag atcactggtg tgtcctctta ttttaactt  aaaataggaa 180878
aaaaaaagt  gcatctttac atattaaaaa gtaagtgtgt ttgatttcaa cagttccctt 180938
cttgtagtat gtggatgtta ttcctggcaa agaattgttt aaatttcttt taggaagcgg 180998
catgcaaact tctttttgttt cttttttgtct tgtttgctca tatttcattg aaactttaca 181058
cactttaaaa aaatttgaaa tggtaccaag tagttttat  tttggtgcaa atattttgaa 181118
agttgctagg cttatgtttt ctggagaaca atgtctcaga gtgtaaattt tgtttaactc 181178
cccgtgtagt catacttata actctacttt aaatgtgctt cttattttaa aaatatcaga 181238
gcctatagag actattccta gaaatgttaa tagaaatgtt tttctttggc aaaaattgca 181298
gattcagttt tacaatttat taagtgccaa gatatcattg ctgttgttga ctttgctaaa 181358
```

```
aaagcaattt tattaacaag gtgactgcat tagatgttac caactgagac gaagtgaaac    181418
atgtgctttc accctgttga tctgatgaaa tatagaggtc tgtgtggtta cttcgtgcgt    181478
cacattcatt taaactttt aaagagcagc tgcgtaatac aaattttgta tactcactta    181538
aaaaataaaa tttactagag taggctcttg ttttggaga cttatacatt ctgtttgcta    181598
aagtaaacta agaaactgaa aaatatatt ggagttagaa gctccaaaac tcttcaaagg    181658
gaagaaagct tttaagaaaa aatgaatgt gctttcagtt ataaggcaat tttgaagcat    181718
tacttagctc tcttttgcaa agatttaagg aaaaatcaac tgttgtggaa ctaagtaata    181778
ggcttgcctt tatacaaaaa ttatgtataa aagaataat tattttccga actgtttcta    181838
tgatttgata caagcttcct tcaacaattg caaaatgtga ctgacaaatc cttttctaag    181898
agaacaagtt cattatgctc tcgtcacctg ttacattcat tctcccttgc ccacatacac    181958
agttcctagc tgtttattag tgctgcagga aagtgaaaat attttttttg aaagaaaatg    182018
tcaaagattt tatttgcatg aatcttttga gctttaaaaa attgtggtct tatcataatt    182078
gcccaaagtg ttttgttaat aaggtctttt gttattatct taatatgaat agtcaggaaa    182138
ggacatataa atcattttgg attttctttc actatatctc aagtaaagtt aaggtgtggc    182198
tgagggtttt taaaaggcca agagattaga cctttgaaag tttatccttt ttgtataaag    182258 atgtttaaa aaatgtttac cacttaccta ttccctccaa atgaatgtaa agaccaaaaa    182318
ttaaagggaa ctttattatt ttacttggtt ataaagtcta accacaaggc aggaagttac    182378 taggcttgg agagacgcta caaaagaatg agcttccctc taatgaaagt acataaatcg    182438
tgaaaaacta agacctact tcttagttct cctaacattt aatcttaaac tagtaacgcc    182498 tgtctttct ttgtatattt acttattgat ttgctgctga dacagaggca tcttttaaaa    182558
actgaagtca accacataat tttaataccca tgattttaag aaggtgtata ttttcttatg    182618
taaagctagt cttccataga tgtttagatt acgtatttga ttactaggaa acagtggcta    182678
tatggtcaca gattaatata tgctgatctc tcttatctat atataaaaca tatattcaca    182738
tacaaacata aacacatatc ttgtgctag gcctctaaca tcttaaggca atgtcttttc    182798
ctcctagtta tgcacttagt tttgaagaca tgtgtagatg aaataaaacg aaagagtctt    182858
ctgacaagtg ttctgaataa aacaagaaaa aaaaatgctt caccaatggt gtgaagcgta    182918
acaccaagcg cttgttacag aatatatcac tagtgggttt gttgcttttc ttatgtattt    182978
attaccatat tgatgattac ttctcctttg cctatagacc aggttggtgg tgtgtgtgtg    183038
tgtgtgtgtg tgtgtgtgtg tgcacttatg agctcacata gggatgagag agtagcctgg    183098
acatgtgcca gggttatgac actctttgat ttacttcttc agttctcttg gtcactaaat    183158
ttcaggctct tctgtaccct tgtagcagtt gacagctgat acagtgaaat cgtgccttct    183218
ctttaagagt acatattata tcagctgcat tctttcaaat ggattgaaca atttatgtta    183278
aagatgattt attccatcaa aatatagaaa ataatctata ggactagatc ctatcatccc    183338
agacaaatta tgggtcctta aagactttcc tagagagtag cagtatagtt ttattcttct    183398
tcttactggg tagagagcat agagtttgtt catctttcta gacactttga tcttcctgaa    183458
attatttcca caattttgat cccacaaagc acaaatattg cttttttttt tttttttttt    183518
ttttttgaca gagtcttgct ctgttgccaa ggctggagtg cagtggcggg atctcggctc    183578
actgcaacct cccctcccg ggttcaaatg attcttctgc ttcagcctcc taagtagctg    183638
ggactgcagg cacccaccac catgcccggc taatttttt ttattattat ttttagtaga    183698
gacggggttt caccatgtta gccaggatgg tcttgatctc atgaccttgt gatccgccta    183758
```

```
ccttggcctc tcaaagtgct gggattacag gcatgagcca cagtgcctgg cactgcttct  183818
tttaacatta gctctaatct cttttttctgg aactccataa tagatatatg ttaaagtttc  183878
ataaataca tatttcttaa attctctttc acactatttt atatatctat ctgtgctgca   183938
cttttggtga attactgaga catcttccca tttactaatt cttttttga ctatgtccac   183998
tccagaattt attttttga caatgttttt cttttctgga aatttaatt gattctcatc    184058
gccacttcaa atgttttatt tctacttact ttgttacaca ttgtattgat gttatttctt  184118
gtctcttcca aaatcctagc atgcttattt tgaagttatt ctgaaaccgc tctattattt  184178
tcatgtcttc tggaataact tcactgaatg ttgtttttaa aattttgctg gtgcctttt   184238
atatcattct ctcatggctt agaattttgg ttttcaggct taactggaat gagaaggatt  184298
taaaaattct ctctctctct ctcattgcta gcccttctgc accattccta ttgtcttagt  184358
gttggctctg taccctctcg tttcccagtc tataatctct gctaatgggg atatcaaaaa  184418
cctagtcact aaatcaaaga gcagtctgtc ccaggatgtg actgtgagat tatggctgct  184478
tgctttggcc tccccaagaa agcagctcta tgcaagccgt ggctccagga aaagggaggg  184538
gttagtcagt tgttcggctt cctcttgtct taccttcagg ttttaatcag taagcttggc  184598
actgattatt actccctgtg ggacacatgt ggcatccagt tactttgcag atacaaggat  184658
tggcttgctt ctcattctag acaccatctg gtgcagtgta cctcactttg tgtttatagt  184718
ttatttctgg tatgtttatc ttgtttttga ctattacttt tctttatat cacctctttt   184778
aaaacttatc tattattgtt acatgttgga agcaaaggca cggggctcaa accatatat   184838
tgcaatgcca tcttgacaag agttttcaaa gccgtgggct ttggaatcag aaaacttggt  184898
ttcaaattct gactcactta tgatctatgt gttaccataa gcaaagtctt taatctatta  184958
taaacctcct tttcccttgc aaatattgat agtaatgcct acttcgtatg actgttgtaa  185018
gcattgaatg tgaaaagatg tggaaagtag ttaggcctgt gcttaaacat tctgtgcgtg  185078
caaattctgg aggtggagaa aaagcaatta aaaccaaaac aaaactagat gttactgatt  185138
atgtaattaa caaatggtaa ttggagtatc aaatagactt gcttcttgta ttctgagtga  185198
aagtaacact atcatttttg atatctaaag cacatttcta aagatgactg ctgactgcat  185258
gagtttccac aggtggatca agctctgtt acactatcca cctacaccat tcacctaatt   185318
cagagaatct taataaaatg aaaagcattc ttcagaatga cccctttaggt atggttctct  185378
aaatccatgt cacttaagac agatggaaaa gaagagagaa gtggcatgag aacatgcttg  185438
tggcttgatg aatagtaata tatataccac ccaggttggg tttctgtaat agtgaaaatg  185498
gggaggaggg tggtgatctt ttgtaagtgt ttcagacagt cttgttttgt tgctttgtag  185558
ctactttgta atattgtctc ttttaaaaac atatattttg atgacctagc attcaaattt  185618
atagcatcag caaagggtcg gtttagttga gtgggaaatg aaattctgaa acaaaaagt   185678
tttaaaaata agaaagatgg ggatgaagat aaagaagcag tagtagcaac ttggaatttg  185738
tcttagaatt tgaaaataga aacaggtttc taagaatcag tcttagtcca ttttctgttg  185798
ctataacatg ataccacagg ctgggataaa ttataaacca tagatattta tatggctcat  185858
ggttctggag gctgggaatt ccaagagaat ggcattggtg gaagcaagaa tgtgagacag  185918
atgacagcag agagcccgag gggtagagtc ccttttttaa aaaactttttt tctattttaa  185978
gttctgggat acatatgcag gaagtgtagg ttttttaaca taggtaaaca tgtaacatgg  186038
tggtttgctg cacctgtcga cccataaccct aggtattaag cctaacattc attagctatt  186098
```

```
ttgcctaatg ctctctctcc ccacacccca tcccccagca ggccctggtg tgtgttgttc   186158
ccttccctgt gtccatgtat tctcattgtt cagctcccat ttgtaagtga gaacatgtgg   186218
tgtttggttc tctgttcctg ccttagtttg ctgaggataa tggcttccag tctctgcaaa   186278
ggacatgatc tcattccttt ttatggctgc atagtattcc atggtgtata tgtaccacat   186338
tttctttatc cagtctatca ttgatgggca tttgggttga ttccatgtct ttgctattgt   186398
gaatagtgct gcagtgtaca tatgcatgca tgtgtctttg caatagaatg atttatattc   186458
ctttgggtat atacccagta ctgggattgc tgggtcaggt ggtatttctg gttctagatc   186518
tttgaggatt caccacactg tcttccacag agcttgaact aatttacatt ccaaccaaca   186578
aagaatattt aaagaataag cagaagatgc tcctacaaat ggaaatgaaa ggaagaagct   186638
aacctggtgg aaggaaagcc agtggtttgg ccatactgcc cgaagtatgg ccttactgcc   186698
caaggattcc cttttacaac aacccgttct tacaataact aacccagccc agcaataaca   186758
atccatttat ggaggactcc accctcatga cccaatcact tcttactaag ccccacctct   186818
taatactgtt tcaatggcaa tttagtttcc aatgtataaa ctttggggga catatttaaa   186878
ccataacaga agctattgtc aatatgtcct caggtaggac atttatgaaa taagcatttt   186938
attttctttt cttaccactg ggtttccttc caccagatta gcttatttct ttcatttcca   186998
tttgaaggca catcttctgc tcattcttta aatattcatg aacttcactg cttttttcctg   187058 ggttgccctc tcttactttt ctttctcctt tgttcatctc atccatctcc gtaacttcag   187118
ataccattat aagcccatct ctagcctgtt tcttgctctc aaactttaag ccagtatatt   187178
cagttagcca caggcacttc atcctcaaga cgtctgaatt caaataatca tcttttttgcc   187238 agaatctttt accatgtcaa tccatcatcc acctggttgc acaaaacaga aacaagatac   187298
gaactttgtc ttctctcttt ctgtctctac aacatttaag gcttttgaaa tattgatttc   187358
taaccatttc tattttttaat cattttttta aatcacagct acacatttct tactatatga   187418
ttaatggtgg accacttcag agttgtatca cttgaggaca aggaagctgg ggtgtgtatc   187478
tgaaactcct ttctgtcatt ggttgaaggt tactcctgtg accatgaatt ctagaatccc   187538
agcccatctc aaggcaaccc tagcatgttc ttggctagag aacaccctca ggcagagagt   187598
ggcaggtgct tgcagtaaaa catcctcaat gtgtaaggaa aatataagtg ccaaggttat   187658
atgagaacac cgaaaacatc tgcattgcac atttcagagg catttaagtt gtttctatgt   187718
gtttgctatt tcaaacagca ttgcaaagaa cacaattata tatgcaccct tgtgaacatg   187778
tatcaaattt ttcttaggat aatacccaaa gtggaattta tatgttgtga gatatatgtg   187838
gtctcaattt taccacttt ccaatcactc tctaaaatac tgaaattcct ctccaagggt   187898
agtggacaaa tttctatttc catcagcagt tgctagcatt cccatttgcc tcagtccttt   187958
ccaattcttt ttttttttt tttttttgaga cggaattttg ctcttgttgc ccaggctgga   188018
gtgcaatggc atgatctcag ctcactgcaa cctccacttc ccaggttcaa gcaattctcc   188078
tgcctcagcc tcccaagtag ctgggattac aggcatgcgc caccatgccg ggctaatttt   188138
tttttgtagt tttagtagag acggggtttc tccatgttgg tcaggctggt cttgaactcc   188198
tgacctcaga tgatccgccc acctcggcct cccaaagtgc tgggattaca ggcgtgagct   188258
accacgcccg gcctccaatt cttaatattg tccaatgttt taactttat ttgttgggta   188318 aatgatattt taaggctttt aaaatttca tattttgat tctaaatgaa aacagaaaga   188378
tatctagtaa atctctgaaa tgaagtgagc gatggagacc ttatatacaa aatgcaatac   188438
attcatcatt tttattataa atgtatcttt atttattcaa gtgttctctt cagtgaagtg   188498
```

```
cttccttata actttgacaa tcttttattaa attgtttatc ttttttttatt gactttttgg   188558 catttgctat atacattctg agtgctgata ctttgtctta tatgtttcaa ataatgtctc   188618
caaggctatc ccttgatttt aaacttttgt tatgtttttc ttataaagaa ggtgttagaa   188678
attttaatta tttttaagat aaacatattc atgttgaaat cacaaaagta gacaatatat   188738
agagtgaaaa gtctccccac catccttgtt tctcatccac tccgctccca ctggcccctt   188798
gtggggttct tgactataaa ccaaataaaa gcatacaatt tacacctcct tcaattacat   188858
acagtgtttt aaaccctgct tttgtcatgc aatgtactgt ggagatattt caagatatgt   188918
aaggaactgt gcttcattct atgagggatg aaaatatgaa cacaatacac agcctatcca   188978
ctgaaagatt agtctgtcat accatgttga gagagtcata aaacactggg aattccaagg   189038
ggagatattt ctttccaact gaaagaatat tcttcagaac agttgagaat catgcatcaa   189098
ggagatacag tttacttcaa caccagaatt tttttttaatc caacatcttt cctttatttt   189158
tttctcttga gacagtgtct ctctctgtca cccaaactgg agtgcaatgg cacaatctca   189218
gctcactgca acctccgcct cccaggttca agcaattctc ctgcctcaac ctcctgagta   189278
gctgggatta caggcacgca ccaccatgcc tggctaattt ttttttgtatt tttagtagag   189338 acagggtttc accatgttag tcaggctggt cttgaactcc tgacctcagg tgatctgccc   189398
gtctctgcct cctacaatgc tgggattaca ggcatgagcc accgtgtctg gtctccagca   189458
tcttaaacat taagctttct atagctgaga aaagtgtagc aaatttataa ctgaagaaaa   189518
tatatattaa gaacctagta catatcaaac actgtgagag gtatgaggga tgtaaaagtg   189578
aacaaggcag atagtccttg attttgtggg aggtaaaggc tgagagttga actgcaatga   189638
agatatggtg gataaagtgt gttaataaaa aggtattggg ggtgtagcat gtggacaggg   189698
tgcatgggtt tcagatggag tcttgttgaa agagtagaga gatatgtaag tgagagtaag   189758
caatgttcca ggcagaggaa agagatatga aatattataa aattgagagt ctggtgagct   189818
tgagaaactg caaaaagttt aaattgtatg gagcaccgag tgctgggagt ggcaaagggc   189878
tgagaaggag gtttggagat aaatactggc tccctcctga aaggtctagt ttggattatc   189938
ctaagggcac tagagacaaa tctaaagggt ttaataaggt tggcaaatgg ttgtatattt   189998 tctttatttta gataggaaaa tatcctggaa catgagtggg agttaaacca agataatatg   190058
tgccatttct caagaatttt ttttaatgct gttactgtag ttacttagag gattcgaaga   190118
taggcttcag agttattaaa aactaccagc gtttatatgc tgtataagca ctagtataaa   190178
gaagaatata tgtacatatc ctttattaaa ttctcaaaca tttcattgat tgaaacattg   190238
aaaaatcact agattaaatt aagaacagtg gttgaccaga aaagtaccct taagaaccttt   190298 taagaaaaga accttttaaga aaatctttaa gttcagagaa ataacagaga gaatcatgga   190358
agccaagtgc atgaaagaag aaaaagattc caaaattaag tcctttacat aaaacagtta   190418
aattccctca tggtacaagc cagcctttct gtgctaatgg ggccgttctg ctcctcaagg   190478
taattcagga gcccaggttt ctttcacctt gttgctctct catcccacaa tatgttgcct   190538
tttaggttgc agacatcact gagttcacat atgaagagaa aaagagccaa gtttcggaga   190598
ccacagcctg tctttaactt gaagacagcc tagaaattaa acacagtatt tctattctac   190658
tcatctaatt gtagttacac agtcacaact gcatatgaga aaagttggga aatgtggttt   190718
ctagctggaa agtcatgtct ttaagaagag ggacaatgaa ttttaggtga ataacaagca   190778
gttgtcacac caaccttttta agtttcaaaa actattgagt gattaaataa gtttacatac   190838
```

```
tcattaaaca agtatttatc aagtgattgc tgtatttggt tgattattct atgtgatagc    190898
aatatagact ttttttttt aagaaaatca ttaccaagtg gtacatattt tagaaaggag    190958
agataggtgt taaccaaatt accaaataaa tatgtggata aattaagaag taataagtat    191018
taagaaaaaa ataaatttaa agaatagagg ggctgttttc agatagaata gttagagaag    191078
ggctttaggt taaaaattgc aaaacgttct ttaaaggata caaaattgag atctccctcc    191138
ttggtcgaga ttttgcagtt gagttgcaag cttagaacag tagttgaaat agggcaggga    191198
gcgtagctca ttggaaggag attcagagtt aaagtccaag gagtgttatc tttttaatga    191258
gtttgggggc cgtgattaca gcttaatgaa caaatgcatg cagaaatgag attgttgaga    191318
tacttgtgct gacaggaagg agggaatgat gggtaaataa gaagttagca aagctactga    191378
gagtgagggt tgtgtggact gattccagtt ccttgatgtag tcacataaag gcacggagtt    191438
gttatggaaa ccctccagga agttgagaag tccgagtcta gtaggggagg tgtgtcatga    191498
gactgaacct gtgctagggc ttctctagct gtgtgcactg gaagggtacc tatactaggt    191558
aaagaggagg tggcaatgag agaggtttaa gtgaggaatg taatgtctat tctacatagc    191618
aaaagaaata gtcttttcaga agagaactga ctgggaggcg ggcatgtggc tcatgactgt    191678
aatcccagca tttttgagaag ccgaggtggg tggatcactt gagctcaaga gtttgagacc    191738
agcctggcaa acatggtgaa acccccatctc tactaaaaat acaaaaatta gctgggcctg    191798
gtggcgcatg cctgtaatcc cagctactgg ggaggttgag gcaggaaaat cacttgaacc    191858
ccgaagccgg aggttgcagt gagtggaggt ggtgctgttg cagtgagctg agaatgtgcc    191918
actgtactcc agcctgggca acagagaaag actctgtctc agaaaaaaaa aaaaaaaatg    191978
tggcagaaga gaactgactg gaaccacatg ctccagttct agatgatgcc tgaatttgta    192038
aagagactaa aaatgtgttc cagattatat ttttcgtgac aggttttttt cttttaatt    192098
taatatttaa aattctaaac ttttaattta gttgactctc ttgattttgt tgtgtgggga    192158
ttgttgtgta gagctgtaaa ttcatggtca cagttataaa gttaggtaga taagtcataa    192218
aaaatattaa gaaattaaaa ccctcagtga atctctatta tattctgcat tttttttgt    192278
taacatcagc cggttcctag tggatttatt gattttattt catgtaataa ctagggaaac    192338
atgtattcct gaaaaaaatt aaataatgtt taaaagctat ttattgatat agttcattta    192398
gcatcatatg catgatcttt tatagtccat tcctccgtag atactacatc atagagcaac    192458
cagccttctt ggctagtata tttttcttga taacttggtt tcaatttttt tttcgtcctt    192518
tatgtgtgga tatttgcata ttcctatttc tacttccatc tttgtattag aaatgacttc    192578
agatataaag aaactatggc cagagctata aggattttg ccttttgaag gtaataccctt    192638
gatatcatga cattttctat gatttttaagc ttttttagttt ttatcatttt atataaagta    192698
ttaatcattt ctgtttattt gctggttctt ggattactcc aaaaatatct aatatagacc    192758
ttttgaggca ttgctattgt tgtttacttg tttctaagca agcccatttt ctctagtatt    192818
tatttttat tagttatttg ttaaataact aataaaactg ttatttatta tttattagtt    192878
tgtctttcct ccaaggacat gaacatgtct ttaatatttt ctcctgttct tttttcagtt    192938
gcattaactt gtcttatttg acttctctta ccttttctttc tgcaaagtgt agctgatttc    192998
tgcattcacg tctcataatt tgttactttg gagtgaaagt cctgtttgcc ttcagctctt    193058
agcaaaatct gtcttttcatt accctatttg tattgccact tcttggtgct ttaaaattct    193118
tctacactgt tcccccattgc tgacacagtt cctctcctca gcagaaattt tactccactc    193178
tctgtaaaat atctgtctca acaaagaaga ggtaaacgtt ttaaatcttg aagctcaata    193238
```

```
tggtattctt tgacatcagt ctcttctatg ttaagttttg atatcttata gcaacattta 193298
aatgactttc ttattgttct catcttctca atcaatattt tcttgtcagt cagatttaaa 193358
ttagcaagat tagatttcat atattcttga aggcaggata tcacaaaaca atttagcaag 193418
ctgtttgcaa tcaatattat ttatatattc acacactaga gattacatag ggacaaatat 193478
aacaggaata tggcccaaat catctagatt tagagcccct taatcaacat ttagaattat 193538
ttacttctgt gggtagaaga aattatcgat atttactaaa tgttattaac ttttttaatca 193598
ctgttacgcc tttagcaaat aaatttattt atgtattggg tgattagaaa tgactagcta 193658
caaacagata tgtagaaaag ggacattaat actatacaca tacacacaca cacacacaca 193718
catgcaaaga ctaatagtga cagatacatg tacatagaga gatatacaca tatcatactt 193778
tatggaatgc tatattccat atttcatctg cataagtcac tgatatactt taagttaaat 193838
catgacaaaa tgaattgtat ggtttgaaag ttccagaatg caccattaaa aaggaggaat 193898
cagagtgtgt attcattgga attcttattt taaagattaa ttattaatga atcaagtaat 193958
ttcaaagtaa tattaatcct ttttaggaaa atttgagtgg gctgactttc tttaatatct 194018
ttgaagccag ggaattcagt tttttaacat agggaaaatt ttgtattcat catcaatttt 194078
ggagcttcca atctttccct ggtacttgct agttataggg gctcacagat aactaagatg 194138
gttgtatctt tttagtccat ttcattttga agaatgtgtg actattgctt ttcatgacac 194198
tgtgtctcat ttattttaa ttttttcaaa taatgacaat ctagatgaac ttttttgggat 194258
tagtgggtgt ttaaatttgt tttaagaggg gcaatgctac atgttgccta tcagcaatcc 194318
agaattttt acatgtctaa tcactttaca gccactatgg aaggtgcttt gggatctaga 194378
gccaactatc tgagctataa ttcctattca cacattgctg agttgcagta gggagggtta 194438
actaagagag cttccttaat gctttataga aaaagcaga atataaatag gtttattcag 194498
aggataaaag attccaaat gaatgttaga gatgtaggaa gcaaggcaag aacattctgg 194558
attgactgat aataaacaat gtatgtgaga gcaaataatg taagagcaaa acatttgttt 194618
gactttgagt gatggcaaag attggaatat atggctagga gtttaaaagt ttagtcaaat 194678
ggatttagtg gtcagtgaga aggtctgaag aaccaattcc atacagaggt agcaaatccc 194738
agaagagtaa cagtgtccaa atggagaaat tgttaaatct aagcagcagc aaaaggctgg 194798
gttcagcatt ggaggaaaga cgagatggcc atgccagcca aggtaaagtc gttccagcca 194858
agttatccca gactaaaacc aggagaaaac agaagtaaga tttagttcta agggacagga 194918
ttgtagggaa cagttatgac ccctgttata tataaagtat ggactgggga ccttctagtt 194978
cacagacatt tttgccaaat tggtaaaagt tctcttataa aatctttaac tctaggaaaa 195038
tataattctc aaacacatga gggtaaattc ttctgttcta taagatgatg gacatagaaa 195098
ttatgggaag ccaaggccag gtatggtggc tcatgcctgt aatcccagca ctttgggagg 195158
ccgagatagg cagatcactt gaggtcagag ctcgagatca gcctgggcaa catggtgaaa 195218
ccccgtctct actaaaaata caaaaatcag ccacgcaagt tggcgaatgc ctgtaatccc 195278
agctcttggg aggctgaggc aggagaataa cttgaaccca ggaggcggag gttgcagtga 195338
gccgagatcg cgccactgca ctccagcctg ggcgacagac taagactctg tctcaaaaaa 195398
tgaaataaaa taaaataaaa taaattctgg gaacccaaaa gagatgggta gaataggaag 195458
attcaccttt taaagtgca ttctgaggga aaggaacgtg ataacttgac agagatgttt 195518
gactgctcct ccttctgaat cccctgctaa aaacttcagc tgacagtttc agtctcaccc 195578
```

```
agttcaaggg caaaggctac tgggccagtg gctcatcgac ttattgtttc caggggagac   195638
gtaagacagt ctggaggatg aggagttagt ctggaaaagt gaagagggcc tgctatagat   195698
acagaaactg atgggtagca tccatagttg gagcacaggt gcagagggtg tgttcctctg   195758
acacagggca acttgtggtg gagtttgact tagaagtgag attgtttggg ggatgaaaag   195818
ggaaagatag atatgaaaag aaaatttcca aatagcaaat atattggtct tctgctgaaa   195878
atggctagaa cggacatata aactctgaga aacaggaaat tcaggaaagg agctaatggt   195938
agagagacta gaggagctta gtttgggaaa taataagttt gtgaggggtg ataagaaagc   195998
cgagaggcaa gtccttttgg cagttgcaag caatgaagga gagaagtcaa acctggagat   196058
gcgtatttta agagcctatc tcaaatgtgc agatcatact ggttttcata tatgatttta   196118
aaaaaagtta agaaaacata cgttctttaa aatgcaataa ggttgtataa tattctctct   196178
ggaccagtaa ttcacacagc catcacaaca caagtaaaac atgctaatat cttctggtaa   196238
actacctttc acaattcaat tagataggta ttgtaccagc tccatttctt aatgtgttcg   196298
tttatctcaa atgcaacagt gtggtaggat tgtatgtgcc tggagaccct gagcatagaa   196358
acaggggaga agagaaatgc attaataagt acaaggctta aactaaatat aaagaatttc   196418
aatatcacga acatataata gctttaatca tgcttgttct caaacattat ttatggcagt   196478
ggtttatgtg attttactta attaaaaatt aggtaaactg attttttaaaa atgtatatat   196538 aaagaaagca agctattatt tctttgaaaa ctgagctttt gctttggcaa gtcttgataa   196598
aagtaagtct ctaagaagta tttccattgc ataaagtatg gacaatacaa atgtaaaaga   196658
ctacacaaat tataaaaatt cagatgtctg tactgaaatt tttttctcta gtgactaaat   196718
tctccattca tttaaaaata tattaaaattc aaaattattg atggggcagt ttatacacaa   196778
aaagcaatag caataaaatt atgcttgatg ggcacacagg taaagaaaac tttaactata   196838
taaatataca catatataca tatgtctaca ttaataacat tatttattat agtctccatt   196898
gtaataattg gctgaccaat cagcagactt gctgtgttat aaggatatat cagctgatgt   196958
aatagataaa accccagctt cttagaggtt cagagcttgt tcagattaca atccacgcag   197018
tatgccttgg acagtttttt actccctgat tcaaagactg aagttctttc catcttgtag   197078
ctccaccaat agcaacttcc acagttgcta ttgaagtatt agttcacaca tgggaaaatt   197138
ttatggtctg gacctggagc agacccatat atactccact cttcagtgcc cagccacatg   197198
gccataccct gctcaggtga atctgggcaa tgtcatctct ctgtgtccct catgagagcc   197258
agataacaca cgtaggataa ctttggttgt atgtacaaac tctgagccag gcactgtgga   197318
gagcacttct acaaccagta tacattttct accctctaga ttcttagtag ttacggaaca   197378
gaactttccg taagtcagtg ttaatgcaag gctggattta ttagcttata cagtagaggg   197438
ataaagactt tctcataagg agaaactttt tgcaaggggc agtattggaa cagagcttga   197498
agcataggca gggactcgtc atcagcagag atagaggcta cagcatgaaa agtgacatga   197558
caacaggaaa ctataaaatg gccagagatg agattctatg atagggcag agataaagat   197618 atctgaaaga tatttgtgga ctatcacatg acaggcctta agcaccctat ttatagttca   197678
ggagtcactt caaaatcttc agcaaatgct tgagaaagaa agcagtgttc agaacaagta   197738
gaatggaaag aaattaggaa tgggagtagt gcagagcagc ttgaactaat gcactgggaa   197798
tggaaatgag agaacaggca aaacatttga gaaagtcgat ttgaaaaggc agattgttta   197858
tgttggtgag taatccagag attttgtatt tcactgacag agtgttctca atcgttaatc   197918
cttgggaatt atttgatgag ttccaaaggg cactaacagc taacagtcga tctcattaac   197978
```

```
taaggatctg ttaaaacctg ccaaggcaag aattttttct gggtttgaca atgacgtctc   198038
tgaaagcctt gaacttgaag agaagcacag taaaaatatc ttctgttata gccacaagtt   198098
accacatttt gcaaaacaaa actgaataat aaattatata ggatagacca tgcccccacc   198158
tttttaaaaa ctcattaaaa agtctttttt atctttgttt ttccttaacc aaaattatat   198218
ggctctaatc ttctttctac attctcttct agagttatgg tcagggtata gatattttt   198278 gaaatgatac tgaaaggtaa catttcagag agtttgaagg cattatgagt cttgattctg   198338
ctagacttca gtgaaggaaa aggtaatatt ggagttcttc ttcaatggca cctgtaagtc   198398
tcatctgcat aatcaagaat actgtattca caccataaag ggcactcttg aaatagggtt   198458
ttgagggcca ttcttttctc attttatga tgcaggggaa gtatttaaac gtttgaggag   198518
taaaatagcc tcttctattc ccattagacg tagctgcaat ttaccacaat gtaaaacatc   198578
aaatagtgtt gatgtagaat atgtgaagtc tcattttcag gtatttgact taagaatatt   198638
tttcactggc aactgagact gttagtcctc caagaagata gcctaagtct tgccaagttc   198698
aaaatgaaag atcctcctca actccgtcag agaaggggta acaaagttta gatgacagcc   198758
atagagtcat aattaacatg taactttag attgataatt taaattattc caactttcag   198818
aaaaattgtc ttactaccct caaacatatt atgtgctatg tataattgtt aagcttagaa   198878
tggcaattgg aaatatagtg tggtagcaga attcaagtgg aagtgcatta attgtaataa   198938
aaaattgtat ctaatcatgt ggtttcctgt tataatgggt agtagtattt atgtgctctt   198998
taaacacttt gatctaaggt gtaggtttcc tttcaataat ggatacattc caaaaatatt   199058
taaaagggaa gaaaaagaca tattaaacgt gtttgaaatt tactttatt atttcctact   199118 cgttgatggt attgagagag tgaagaaaat tttgattaag caagaggaaa aaggactaag   199178
ttaccagaaa atatgggttt tagcttagtt tccctcctta ttggccatga aacttgtctg   199238 agttttagt ttttatccac ataaccattc tatccacttc acagagttat tttgagggcc   199298
aaattattac atgttttaca tacacaaaca gtgtataaaa tcatttccct tctgaggtca   199358
ctctagtatt tttataacat catggcttaa ctccactgac ataaatccca tggcctattg   199418
ttgcgacttt ctgatcactc atgagtctgt agaggagtct tggtcctcag cctaccgatg   199478
agtctgtaga ggtgtcttgg tcctcagcct accagtctcg gcttttaaca cctgggagaa   199538
tgatacaatt ccagcaattc agtaaggtaa aatattaggg caatgactga gataaaaaaa   199598
aaaagaaaga atataagttt taccctataa ttggttgctg ccaaaggatt attttttctac   199658 attgcaattc ttattacatc acaccactct acttaaaatt atctgttaat gttttttcaa   199718
gtctcttggt ttttgatttt ggcatttctt caaatctatc tcatgtacta gaatctgtga   199778
tttgagaatt taggctgaaa atgtgtaaga atcaggtgct cttgttaaat tttgttgagt   199838
tggaataaaa ccacaacaga atactttga gttttaaaa aataaactcc cactgatttt   199898
taaatagtat gcacttggag ggaaaatttt tattttgttt tgctatgcct catcaccatt   199958 tctttttgctc tgcaggacag tactacgaaa ggactaagta tataggaaac ttgacttatt   200018
taaataaggc agtgaaaaaa atagaatatg gggagtaaaa caacctctga agctaagtct   200078
gcatatataa taactgggta agtctttcag tgagtttatt gattagtaac aggggtttga   200138
tacgtaaaac agagcaaatt gcatataggt atgatttgaa tgggctaaca tacttacaat   200198 taatatataaa tatttccaga ttaagaatta taagcacaca ttaaaataag aataaagaaa   200258 cttttttcagg tgtcttgaag accctgaagg atttagtgag tcatcagtga gacatattaa   200318
```

```
taaggatgag tatatgtatg agtacctgtt gggtttgttt tcctatcgtt ttttcactct 200378
aagtagtagc atgtattttc ttttttcttt ttgaaatgga ggtttgctct tgttgcccag 200438
gctggagtgc aatggcatga tctcagctca ccgcaacctc cgcctcccac gttcaagtga 200498
ctctcttacc tcagcttccc aagtagctgg gattacggcc atgcggcatt acgccgagct 200558
gattttgtat ttttttagt agagacaggt tttctccatg ttggccaggc tggtctcaaa 200618
cttccgacct caggtgatcc acctgcctcg gtctcccaaa gtgctggaat tacaggctga 200678
gccaccgcac ctggcaggta ggatgtattc tctagttctt ttacaaaagg aggattttca 200738
tttacctgca cttttttgttc cccaaagagg gagtcctgga gtctcttggt gtgtatagaa 200798
aggcttaaat attttagcca gtcctttgta actttttcct tgcttgtcaa aagcaataat 200858
attgccatca ttgagaaatg gtttcaatga tggcgacact tcacagataa gaacaagctt 200918
attaatcttg ggaaactcac aaatgattat tgagtctcct agattgctaa aaacaaagaa 200978
gaattaattt tttgtcctga agatttaagg taattgtcca cagcttaata atcatcagga 201038
agaggataaa ctcaatcaca ggaaatacaa cgtagtagtg aaatttgttc aattacagag 201098
gaaagttcca tcggaaatgg tggaaatcct ggcacttgga ataagcaaaa ccaaacagga 201158
caaagtacta aactacaatt agtaaggttc taatacagct ctaaaaagga atgcttccta 201218
tattgatgat aattagttga tgatagatta ctgagctgaa aacttgacat ttgattgcta 201278
cttttaagtg ttaggcaaat taagaggtat ggaaaattgg acatatcata gtgtaaatga 201338
atttattttc tccatggcag gatttggttg cttgtgaaca tatagcagat tctctaatac 201398
tcataaggct ccctctttcc tttaatacga aggatgtagg agaagttcag caagcactta 201458
tttgttaggt tgaattctaa atatggacac agtgcagtct taaattatgt tagaaaaagg 201518
acatttggct tagtgagaca cattaatcat agtgcagtct taaatagatc tgaggactta 201578
caacagtgca tagatatgtc tttaaatcag cagaaattca gaagaacatg gcaggttaga 201638
aatgatagga tgataacttg gatttgatta tggcaagatt aactaagcag ctgttgagat 201698
tggataatga tatgtgaggt tctcatcacc ctgtaacttg tttccactaa tacagattaa 201758
gaatgtctgg aggaactata attatctctg tggctcgtgc ataacataat tatgttttgc 201818
cagtgcaaag cattttatta agtggaaaat gatttttaaa aagttataca agtggctaca 201878
agaacaaatc aactaagaac agaaacattg gcacttcata atagtaatgt gaaaaatact 201938
tatctctttt tgttatatgg agttttcaga atttaaagcc ttgttatatgaca ga tataca 201998
tgagggatta tttcagtgat gttgaccctc ttactgaagt ttgtgcccca ggtgtccaga 202058
ccacaaaata gaaatgcaa tctttgtctg ccttacataa atacagtact gagatcagct 202118
tgtcttttaa atgtctgatt gctatttaat tacaaaaaat ttgtctttaa acagagcacc 202178
caaaacaaca aaaaaacagt aaagaactca tttcggagcc ttgtaatcca ccctaccaca 202238
taaaagagg gtgatatgtc tgacaactct ctgtataatc aggttattta agtgatagtc 202298
attatgcatt ttataaacac taccctaaaa tatgtaatgt gaatgtatct gttaatcaga 202358
aaaagctaac taaaactgaa tgcaatgtac tcatttccat tctggtggca ttcttacata 202418
atgattttaa agcaactgtg atgagataga aagagtgtta aagctgtagt gaacaaatgg 202478
gaattcaaat tccagctctg aagtgttccg gctggctgag tttcttatac tttctgagcc 202538
tccgtttatc cagtagtaaa atgcagctat gaatttctac cccagtgggc tgctgagaga 202598
attaaatgag ataattttatg tgaacaatct tcttagaata tgtttatttta atctgacctt 202658
gaaaaataat tcacaaaaaa tgtgtcagag taagttttct ctcgtctcaa aggagagaat 202718
```

```
atgaagtaga ttaagtgaca tttttgaaaa aagttccaca tttgaaactt ttatttataa    202778
aattgtgaat ttatctttag ttatagaata actttcctct tcctttgatc tttttaagcg    202838
taatatttag ccctctcttt attactctga gagaagatga atattttaaa actatttata    202898
tcacatgtct aaaagtattt ctcattttt tcttaagctc tttttgaat atttataatt     202958
tctttccctt ttattctcat atttcacacc tagtatttct gctttcattt cattaatctt    203018
tttttaataa cttggcacct gggcctgttt tgcagctatg tgcagcaatc ttaagtacta    203078
tgtatagttt agttttcaat cagttccttg ctgttacttt ctgcaaataa aaactagctt    203138
agctatgcat gtgattaaca tggcccaggt attcctatta ctaggtcttt ctattactag    203198
gtctttcttt ccttctgtgt tatttaatat aaggcaaaat aggaccctgc cgcttaccaa    203258
gctttcagga tcctccatct tccatcttcc actaatccct tcctatgtct ctatgaaaaa    203318
tatatctcta agatggtggt tgacaagagt gtgagagtca aatggtaagg aatattgctt    203378
ggaaataagg ctgaattaat aattccagag aaacattgtg aaataactta taggtacata    203438
aattcactat atttagatct gcctcatact tttaaaccag cagcatgata attcatagca    203498
tggacttatc atcataccat atattgaaac attcctctat tgttggatgg ttatttcatt    203558
tcctctgctt cattgttttg aacatcccta taataatcac cactgtatat gccattttt    203618
gcagaagtgg aattcctagt taaaagttga atttcaaaat tgttcttgac agtttatact    203678
tctagcaaca aagtctctaa gtcttactat taagagaaaa tgcaagactt agaacaatac    203738
atttttataaa tgacatgtgt attaaaaaag atctattatg tgaatgtatc atataacttg    203798
aatgatatac actaaacact taacctctgg ggaggaaaat aaaattaaga aaaggtgggg    203858
aaggaaaatt tacttcaaat acatttgtat tgttcagatt ttttacagga aagatgagtt    203918
tatatactgc tatgtgtgta tatatatata taacatatat atatctatat atatatatag    203978
atatatatag ataaattttt tttttttttt tttttttttt tttttttttt              204038
tttttttgga gacggagtct cactctgtcg cccagactgg agtgcagtgg cgcaatctcg    204098
gctcactgca agctcctcct ctcaggttca tgccattctc ctgcctcagc ctcccgagta    204158
gccgggacta caggcgcccg ccaccacgcc tggctaattt ttttttgtat tttagtaga    204218
gatgggttt cactgtgtta gccagggtgg tctcgatctc cagacctcat gatccacccg     204278
ccttggcctc ccaaagtgct gggattacag atgtgagcca ccgtgcccag cctactgcta    204338
tgtatttta aaataaaatt aaaatagaga cacaaaggta ttactatagt ggtatcaaag    204398
taaacagtgt gaaagcatcc aacctgaatt tcatagctgc agtgtgatgg cattttatt    204458
cagctatttc taggcatatt ttaaggtctg agactcacca tatgcactat catgtaaatt    204518
tattttata ggtaaaaact gtaaagtaat aaaacagtct cagtttccag agcaaatcat     204578
atccatctgt actgctgggt aaatgtagtt ctgattcaac cacatgaata agattacacg    204638
tgttttgaa aatcactatt tgctgaagat cataagcaat tcacatgctt tgtctatggt     204698
taattttggt aataagatgc aagacagctc acagatcttt aagctatatc tagaaatagt    204758
gctgattgaa tttaagctga ttatgcagct tattttggtc gtttgccctc ttcctaaatt    204818
ctaaagttca aagtttaacg tgaaatagtt ttctcaagtt tagctctagc caaagtccat    204878
gaaatggctt atgtctgtca atagttgacc taatagattt gtcctatgtt gacactttgt    204938
tcttttcata ctagactgtg cgtatcatgt aggtatgtta ttttcagtgt gctgtgcttt    204998
aaaatgggat tagaaagtca tggagaattt tttgaaaatg ttttgatgtg ttagtgtttt    205058
```

```
ttggtagggt tttgggatac atcatttatt tattaattaa ttcattattc tgtatttatt   205118
ctagaatgtc atcagtaatg tattgaacta ccaatcatgt tagtggagat aacaaggcaa   205178
gaccagtata gtgacattag aggcataaaa tcaatgggtt ctataaaata tttgagttgc   205238
tttataagaa ctgtgtatca acaggagtaa agtcatcaag aagaacctct tctaccagtg   205298
ccatcaagaa agggttcatt tatatgggga agctccaaca gaatctggat agacagaaat   205358
aggattcttt ttcacaggca gggatggaga tatgttttag acatgaaaca tttgagagga   205418
taaaagaagc atgaaaccac atgtctggta cctgtgacta ctaaggcatg taaataaggc   205478
atgctgagag atgagaatga aggtaaggtg gtaaagcagg ggtaagattt tggaaaccat   205538
taaaaaccat gccaaagttc atgaacattt tcctttaggc agtgaagatc ttttaagggg   205598
ttttcagcag gagagcaaca gagctgtaca ttttagaaag agccctctgg cagaaatgca   205658
ggggatgaat ggggaatgca caataagagg cgttaaatga ttccttctgg taatattggg   205718
acataaaata aagcctgaat ggtggggata gagaggaaag gatttgatgc agtatatgtt   205778
aaggaagtag tagggtgtgt gtgtgtgtgt gtgtgtgtgt gtgtgttttc tttctttctt   205838
tcttttttt ttttttttg acagtttcac tgtgttaccc aagctggagt gcaatggcac   205898
aatctcagct cactacaagc tccacctccc aggttcaagc aattctcctg cctcagcctc   205958
cagagtagct gggattacag gtacatgcca ccatgcctgg ctaattttg tatttttagt   206018
agagacgggg tttcaccatg ttggtcaggc tggtctcgaa ctcccggcct caggtgatcc   206078
acctgcctga gccttccaat gtgtcgggat tacaggcgtg agccaccacc cctggccaga   206138
agtagtatta acaagtcaaa gtcaatgata aaatttggat gatgtggaag aggcagtaga   206198
ttcccaagca tctgtcttgg gttaatgggt agatggtgat gctgttcacc aataggaata   206258
ggaaaagagg tttgggaggc aagagtgaga agtggttagt gttcagtgtt tagctatgtt   206318
ttgtttggag tgtttatgtg gcagccaggt ggagattcca agtatgcagt tcaatatgtg   206378
ggcccaaagg ttagaacaca gggacgaatt agagatgtag atttgttggt cattgacgtt   206438
tcataaatgt agtgttaata tcgcacaaag caaaatgttt agaggaggaa gaataacatt   206498
aggaatagca acctgccata tatatatata tatatatata tatatatata tatgatgactt   206558
accaacataa tccatagggt gtcacaatta ggagtttatt agggacgttt gtgagaccag   206618
tctcagtaac atagtggaag tataagtgga gcacccactc agtgcatagt agaataaaat   206678
acaaatgaaa gagttaaaat gaacaggttc atgttctttt ttgaggagct tagctatgta   206738
gggagggga ggacattaac tggaggaatt cacagggtag agggatgcat taattaatta   206798
gacaagagac acaaaggcat tactaatagt ctatgggaaa ataactggtg gagtgagaga   206858
ctgaaaatgt agaagagata ggaattactc acaaggcaca gatacagcaa ctctcaacac   206918
aatgcagcag aaaaagggca aactggctat tcttattatt gagaaaattg tggatgataa   206978
aatagaaatt atggtatatg aaaggacagc ctattaacca cttatatagc aatgttttaa   207038
acctgcatag gtaaaacggc cgaaatggta gtctttcttc caaatctctt tccctccacc   207098
atatgctaga cacacccttt taataaacag caccacagtc taccttgttg cttcagctga   207158
agacctgagt tgtccttgat tctcttttcc acagtttatt ctccagacat ctcaacttcc   207218
tatgttcctg tcaatttcta ctactgcatt ctaattgaaa gtatagttac gttatcccca   207278
gactacaaga gtagcctaac ttttctctct gcttatctag agccactcca gccccactct   207338
tccatctgtt ctcccacttac cagccacaat aaatatcataa aaaagtaaac caagtcatgt   207398
cactctctgg ttcaaactct tcaataatgc atagtgggca tgtggtaaat tatgactatt   207458
```

```
ataatcataa ttagaattttt cctttctctt tctctttctc ttttggtttt ctctttacct 207518 tcatttaact ctataatagc aaagacattt aaaaattggc caatctattc taaacatatg 207578 attactggta gatttataga aaacatattc agcactaatg tgacttattt ctgtcataaa 207638 catttgactc cttgctgttg ccttatttga aaatgacaaa tgacaaataa gtaaaacggt 207698 gtttctgtta cttgtgtttt atttgacccc tcaattccca gtaataagta agataatact 207758 ttaaacaatc tttgacattt ttttctaatt agatgacaag caatctcaat gcatgcacca 207818 cgtgtttcaa ggatataaat tagagtgaat actttaaaaa aatagaataa aagcgggaca 207878 cactgatatt tgacattttt gaaaatctcg aatctcacat ccctgattttt tataatgaca 207938 gtgattagga aaaaaagct taatgtaaga caataagctc tgagattttt cttagaaatg 207998 tactaaattt gattctagga ggagaaggca cttgagaaga gcctgttgaa gtctcatctg 208058 ctggagaaaa tttactccaa gaaaatagga tgaaagtgtc aaagacaata gttacaagcc 208118 ttggtggtgc aattgattat gatcttgtaa tggtataatt ctgaaacgat gacacagata 208178 gtgtctttat atgatggagc tggtccctag aagcagaagg cacagttttc aagttcagaa 208238 atttctaatt aaatcatgt atatggtgaa ttacatatat atgtaataat atgtaatata 208298 aggttctgta atatatgtaa ggagttttat tttatgatat ataccataaa atgttcctta 208358 tgtcctaagt gtatgacaaa gaataaaaca cttcatatca tagctatgac gttgtggaaa 208418 agacacagaa ctagtagtaa aggagcatga accagattcc attctatcaa tcaccgacta 208478 tgtgcctggg tttgtctcct ctttaaaaca tagagaatgc ttctcctcag gcgttctctg 208538 atgggtccat tctatgagct gattcttttt ggtgaaatca gtcactaatt cagtatcctg 208598 aatgccatat taaggaggtt tagagaaaat ctgaaaggta actatgctaa aacagaggca 208658 tttctaagtg aatcaagttg gtagtcacat tcagaggctt tggactcggt cacaaggaag 208718 cctaaccaat aatcacttca cactgagtaa ccattctaca tatctttctg ttgttataat 208778 tttaggaaca actgtaattt taggcaaaac ttggcaactt ggccttatgt ttagtaaatt 208838 attttgggct ctttgttttc cagatttcaa ctgatgtttt tatagtgaca aaaccatccc 208898 aatttgcctc atgtgaaagt cattctaaaa taattgatat ccaaagtcat taagataatg 208958 caactaaaca ggaatgtagt tacttatatc ttattggtag ggagcataaa aatgtaggca 209018 cgagaaaggt gttttagtga tctaaagatc caatctgtta ttttttaaacg atgccattct 209078 attttgcaaa tgcctactat aagcagaaca gctgaactca ctgccaaata tgaaagagta 209138 gttaagaaat gatttgcaga atggatctca aggtctttat tttgctcttg cgtgtggaat 209198 ctatttgctc atttgcacgt gtggaaattt taatctctac agcatgtttt taagcgtcac 209258 actgagcctg gaagttaaca cagaatcaga tcagtaagta aataaagcat atctttgaaa 209318 acatgaaatg gaaaaaaaat acttgttttt tgaaagtttt atctttgcac aaaatgtcta 209378 tctacatgtc aaagatattc agatgttcag ctaagcactt tgtaggtcaa aaaatatatt 209438 ttttgcattc tgaactcttg gcatcttggt taaactttca ttctatatta attatacgga 209498 tggaagagtt tattcaatac tttaatgaac caagattatt agaattaagc ttcatgaaat 209558 caggttcttt gtctatcatg ttcattactg attccccagt gctcagttag atgcttggaa 209618 tatattacag ctttaataaa tatatttcaa aataatgcca tggaaagagg cataaaataa 209678 agctttgaga cttagcctgg ccatagcact gcttctaagc ttagatctta gccaagccat 209738 ttctcttttcc ttgagtttca ttttcctcat cttctaaaaa taaggatttt tttaaattga 209798
```

```
tgagagttct ctggtcttat aaaagtactt gacaattatt ataccatgtc tgaaataacg 209858 tgctaatcac aatcttaaaa taaatatatt tccagaggtg atataattgc caaacataca 209918 aattagctca cctagtatat agactcaaaa agttcagaat gtagatttcc tctgatcaca 209978 cttgaagatt atagtgcaat tttctcctac agaaagtttg tgaagtacca ttaaaaatta 210038 tgagtgtagg ttgtggggaa gatagccaaa taggaacacc tctggtttgc agctcccagc 210098 tagatcaaca cagaaggcgg gtgttttctt catttccaac tgacataccc ggctcatctc 210158 attgggactg attagagagt gggtgcagcc tatggagggc gaaacaaagc agagtggggc 210218 gttgtcttac caaggaagca caaaaggtcg ggaactccct cccctagcca agggaagccg 210278 tgagggactg tgccgtgagg aatgatgcat tctggcccac atacccacag accaggagac 210338 tccttcaggt gcctatacca ccagggcctt gtgcttcaaa catgaaactg gcggctggt 210398 tgggcagaca ctgagctagc tgcaggagtt ttttttcatg ccccagtggt gtctgaaatg 210458 ctagcaaaga gaactgttca ctcccctgga aaggggctg aagccaggga accaagttgc 210518 cttgctcagc agatcccact ccacaaagcc cagcaagcta agatctactg gcttgaaatt 210578 ctcgctgcca gcacagcagt ctgaagtcga cctgggacac tcaagcttgg tggaaggagg 210638 ggcatctgct cctactgagg cttgagtagg cagttttctc ctcacagtgt aaacaaagcc 210698 acagggaagc ttgaactggg cggaacctac tgcagctggg taaagccact gtagccagac 210758 tgcctctcta cattcttcct ctctgggcag ggcatctttg aaagaaaggc agcagccaca 210818 gtcaggggct tatagataaa attcccatct ccctgggaca gagcacctgg gggaaggggc 210878 ggctgtgggc gcagcttcaa aagacttaaa cgttccttcc tgccagctct aagagagga 210938 gaggatctct taacacagca ctcaagctct gctaagggac agacttcctc ctcaagtggg 210998 tccctgatct ccatgcctct tgactgggag acacctccca ccagggtcg acagatacct 211058 catacaggag agctccagct ggcatctggc aggtgaccct ctgggacgaa acttccagag 211118 gaaggagcag acagtaatct ttgctgttct gcagcctcca ctggtgatac caaggcaaat 211178 agggtctggg gtggacctct agcaaactcc agcagaccta cagcagaggg gcctgactgt 211238 tggaaggaaa actaacatac agaaaggaat agcatcaaaa tcaacaaaaa ggacgtccac 211298 acccaaacac catttaaaga tcaccaacat caaagaccaa aggtagataa atccacgaag 211358 gtgaggaaaa tccagcacga aaaggctgaa aatgctaaaa accagaacgc ctcttctcct 211418 ccaaggatc ataacttctc atcagcaagg gaacaaaact gcacaaaact ggatgagttt 211478 gatgaattga cagaggtagg cttcagaagg tggctgataa caaactgctc cgaaataaag 211538 gagcatgttc taacccaacg caaggaagct aagaaccttg aaaaaaggtt aaatgaattg 211598 ctaactagaa taaccagttt agagaagaac ataagtgacc tcatggagct gaaaacagc 211658 acaagaactt cgtgaagcat acacaagtat caatagctga atcgactgag tggaaaaaag 211718 aatatcagag attgaagatc gacttaatga aataaagcag gaagacaaga ttagagtaaa 211778 aagaatgaaa aggaatgaac aaagcctcca agaaatatgg aactatgtga aaagaccaaa 211838 cctacgtttg attgacgtac ctgaaagtga cagggagaat ggaaccaagt tggaaaaaac 211898 tcttcagtat attatccagg agaactttcc ccacctagca agacaggcca acattcaaac 211958 tgaggaaata cagaaaacac cactaagata ctcctcgaaa agagcaaccc caagacacat 212018 aatcatccga ttcacaaagg ttgaaatgaa ggagaaaatg ttaagggcag ccagagaaaa 212078 aggtcaagtt acccacaaag ggaagcacgt cagactaaca gcgggtctct ctgcagaaac 212138 cctacaagcc agaagagagt gggtgccgat atctgacctt cttaaagaaa ggaattttca 212198
```

```
acccagagtt tcatatccag ccaaacgaag cttcataagc gaaggagaaa taaaattctt    212258
taaagacaag caaatgctga gagattttgt catcaccagg cctgccttgg aagagctcct    212318
gaaggaagca ctaaatatgg aaaggaaaaa ctggtaccag caactgcaaa acataccaa    212378 attgtaaaga caattgatac tatgaagaaa ctgcatcaac taatgggcat aaaaaccagc    212438
cagcatcata atgacaggat caaaatcaca cataacaata ttaaccttaa atgtaaatgg    212498
gctaaatgcc ccaattaaaa gacacagact ggcaaattgg ataaaaagta aagacccatt    212558
ggtgtgctgt attgaggaga cacatctcac gtgcaaagac acacagggc tcaaaataaa     212618 tggatggagg aatatttacc aaacaaatgg aaagcaaaaa aaaaaaaaa aaaaagggt      212678 tgcaatccta gtctctgata aaacagactt taaaccaaca aagacaaaaa aagacaaaga    212738
aggacattac ataatggtaa agggatcaat gcaacaagac aagctaacta tcctaaatat    212798
ataagcaccc aatacaggag cacccagatt cataaaggaa gttttagag acccacaagg     212858 agacttttac tccaacacaa taatagtggg agactttaac cccactgtc aatattagac     212918 agatcaacga gacagaaaat taacaaggac attcaagcct tgaactcagc tctggaccaa    212978
gcaaacctaa tagacatttta cagaagtctc tactccaaat cagtagaata tacatttctc   213038
cagcacattg cacttattct aaaattgacc acataattgg aagtaaaaca ctcctcagca    213098
aatgcaaaag aatgaaaatc aaaacaaaca gtctctcagt ccacaacaca atcaaattag    213158
aactcaggat taagaaactc actcaaaact gcacaactac atggaaactg agcaaccttc    213218
tcaatgacta ctgtgtaaat aatgaaatta aggcagaaat acataagctt tttgaaacca    213278
atgagaacaa agacacaatg taccagaatc tctgggacac agctaaagca gtgtttacag    213338
ggaaatttat agcactaaat gcccacaggg aaagcagga aagatctaaa atcaacaccc     213398
taacatcaca attaaaagaa ctagagaagc aagagcaaac aaattcaaaa gctagaagaa    213458
gacaagaaat aactaagatc agagcagaac tgaagaagat agagacacga aaaagcctta    213518
aaaaatcaat aaacacacga gctggtgttt tgaaaagatt aataaaatag tagacccta    213578 gccagagtaa taaagaagaa aagagagaag aatcagatag acacaataaa aaatgataaa    213638
ggagatatca tcattgaccc cacaggaata caaactacca tcagagaata ctataaacac    213698 cttttacgtaa ataaactaga aaatctagaa aaaatggata aattcctgga cacatacacc   213758
ctctcaagac taaaccagga agaagtcaaa tcactgaata gaccaataac aagctctgaa    213818
agtgaggcag taattaatac cctaccaacc aaaagagccc aggaccagaa ggattcacag    213878
ccaaattcta ccagaggtac aaagaggagc tggttccatc ccttctgaaa ctatttcaaa    213938
caatagaaaa agagggactc ttccctaact cattttatga ggtcagcatc atcctgataa    213998
caaaacctgg cagagacaca acaaaaagaa agaaaatttt caggccaata tccctgatga   214058
acatcgatgc aaaaatcctt aataaaatac tgccaaaccg aatccagcag cacatcaaaa    214118
agctcatcca ccacaatcaa gttggcttca tccttggcat acaaggctgg ttcaacatat    214178
gcaaatcaat gatgaaaaac acatgattat gtcaacagat gcagaaaagg cctttgataa    214238
aattcaacac cccttcatgc taaaaactct caataaacta ggtagtgatg gaacatatct    214298
caaaaaaata agagctattt gtgacaaacc cacagctaat atactgaatg ggtcaaagct    214358
ggaagcattc cctttgaaaa ctggcacaag acaaggatgc cctcgtgctc aaaataatat    214418
tggaagttct gggcagagca atcaggccag agaaagaaat gaaggatatt caaataggaa    214478
gagaggaagt caaattgtcc ctgtttgcag atgacatgat tgtatattta gaataactca    214538
```

```
tcgtctcagt acaaagtctc cttaagcaaa taaacaactt cagcaaagtg tcaggataca   214598
aaatccatgt gcaaaaatta caagcattcc tatacaccaa taatagacaa acacagagcc   214658
aaattatgca tgaactccca ttcacaattg ctacaaaagg aataaaatac ctaggagtcc   214718
aacttacaag ggatgtgaag gacctcttca aggagaacta caaaccactg ttcaaggaag   214778
taagagagga cacaaacaaa tggaaaaaca ttccatgctc atggatagga agacccaata   214838
tcatggaaat ggccatacag cccaaagtaa tttatagatt cgatgctatt cctatcaagc   214898
taccattgac tttcttcgca gaattagaaa aaaactact ttaaatttca tatggaaccc    214958
aaaaggagcc tgcatagccc agccaatcct aagcaaaaag aacaaagctg gaggcatcac   215018
cctacctggc ttcaaaatat actacaaggc tacaataacc aaaacagcat ggtactggta   215078
ccaaatagac caatggaaca ggacagaggc ctcagaaata atgccaccca tctacaacca   215138
tctgatcttt gacaaacctg acaaaaacga gcagtgggga aaggattccc tatttaataa   215198
atggtgttgg gaaaaccagc tagccctatg cagaaaactg aaactggacc ccttccttac   215258
accttgtaca aaaattaact caagatggat taaggactta acataagac  ctaaaaccat   215318
aaaaaccttag aagaaaacc taggcaatac cattcaggac ataggcatgg gtaaagactt   215378
catgactaaa acaccaaatg taatagcaat aaaagcctaa attgacaatt gggatctcat   215438
taaactaaag agcttctgca cagcaaaaga actatcttc agagtgaaca ggcaacgtac    215498
aaaatgggag aaaattttg caatctatcc atctgacaga gggctaatat ccagaatcta    215558
caaagaattt aaacaatttt gcaagaaaaa aaaacaaccc cattaaaaag tgggtgaaga   215618
atatgaacag acacttctca aaagaagaca tttatgcagc caacaaacat atggaaaaaa   215678
cctcatcatc actggtcatt agagaaatgc aaattaaaac cacaatgaga taccatctca   215738
tgccagttag aatggtgatc attgaaatgt caggaaacag cagatgctgg aaaggatgtg   215798
gagaaatagg aatgcttta cactgttggt gagagtgtaa attaggtcaa ccattgtgga    215858
agacagtgtg gcgattcctg aaggatctag aaccagaaat accatttcac ccagcaatcc   215918
cattactggg tatattcctg aaggattata aacattcta ctataaagac acatccacaa    215978
gtatgtttat tgcagcactg ttcacaatag caaagtcatg gaaccaaccc aaatgcccat   216038
caatgataga ctggataaag taaatgtggc gcatatacac catggaatac tatgcagcca   216098
taaaaaagga tgagttcatg tcctttgcag ggacatggat gaatctagaa accatcattc   216158
tcagcagact aacacaggaa tagaaaacca acaccacat gttctcactc gtaagtggga    216218
gtggaacaat gagaacacat ggacacaggg aaggggacat cacacaccgg ggcctgttgg   216278
ggcgtggggg ggctagggga gggatagcat taggagaaat aaatgtacat aggtttcaca   216338
aaccactatg gcacatgtac acctgtgtaa taaacctgca cgttctgcac atgtatccca   216398
gaacttaaaa tataataaaa aaaattatga gcataatggt acagtctctc tattttgttt   216458
aaggggagta tcaagtcaga gtttagagtg aattatttct tttaactgca cagtgtgatt   216518
cgtgaaggtc agagttgagg ttcagtgcag tcaggctgga aaggtagctc ctggcaataa   216578
gaagagtgtg tgaataaata aaagacgtga gctgtttcct aagtttactt aatattcaga   216638
ttaaatgaaa attatgagcc tgaatgtagg agtctggaat gaatatgagt caaagatcac   216698
atggaattaa tgtattataa aatgatatac aag a tag gtt taa tta atc ttc     216750
                                       Val Leu Ile Phe
                                                    100
ctc aat cat tct tat ttt tca gat ctt cag gaa ttt tac tgg gat aat     216798
Leu Asn His Ser Tyr Phe Ser Asp Leu Gln Glu Phe Tyr Trp Asp Asn
        105                 110                 115
```

```
tat cca aat aaa ttg caa gca ttc tat cca aat gg taagcagaac      216843
Tyr Pro Asn Lys Leu Gln Ala Phe Tyr Pro Asn
        120                 125 atcttattat gtaatcatat tgtttatcc ataattaata taactttctg agtattgaaa  216903
tgagaaactt gatttactct tcttcactca tgttttaatt ttttttataag aaaaactaga 216963
atcactaaag aatttctttt tattttattt aaaaattata atcctgagat gcaaatatat 217023
gccatgtaag cctgggaact atttaatcac tttactctaa aatctggtaa aaggtaaaat 217083
ttctgaaaat aggtgactgg caaacatttt gtaaacaata tataagaaga attgtatatc 217143
aaaatataca cataaaacta tcttttcaga taattatgta tcatttattt tcttatagcg 217203
aaattataaa aatacaacct atagccttcc atagatacat aattaactat gttttgaaat 217263
gatatccaat tcagtaccct catacatttg aaactttgat aagctggtct atcttcactt 217323
tggggatctt cttcattaag agtttgtttt ctcaagtttt gaggtaggat acatgaagtc 217383
attcttcttc tttataatta tgtggcagga actatctccc tgaaaacttt atgcttaagt 217443
ttttgacaat cacactgtca gtcagatggt gcaaagtctt ttaatacttt ttaatataag 217503
agagttgtct aaaatacaga tagttctcca tctgagctca tgacccaagc aatgtgcttc 217563
aaaattgcat ttattgtatt tttcttatta caaatgatac tatgttcata atggatagat 217623
aaattagata cacataaata caattaaaaa gcatattctc accacctaat gtaacctgtt 217683
aaccttttgt ataaattggt gaatggtttc agtatatgaa cacacaacct actgtaaaaa 217743
ttcaagaaat gagtgtgatg atgatgtaaa atgcaggttc accttctctg tccccacttc 217803
ctctgcagct tgggtataaa tgcctgctcc accacctgtt ctctgtgtga actttggcaa 217863
atcctttaca ctctctgggc tgtcctttct catctgcaaa atggagctaa taatacatac 217923
ctagctgaag gggttgtctt gaggatgaaa tatgttaata caagttaggt gtatagaaca 217983
gtgcctagct cataagtgtt agatattaca aaattaccta ttgtatttga attatttttt 218043
agaattctta agatgtgcct attttgtata cttatatctc atttagctct ttattaatgg 218103
caattattct tcagttagtt attttgtggt tccagataga atatcatatt ttctaaaaac 218163
aataacaatt ttagatactt ttatttttt cctttttagc atcatacttt tttctatttt 218223
gagttcacta cttattgcct tggctatgtc tttcggtgca acatgaaata actgaataat 218283
tctttgttct ttctgatttt attaggaatt actttcatga ttataatttg agtactgtgt 218343
tgactatttg tataagtttt attcttttc ttaagaagta attatattct taattaacta 218403
tatttgatga tcagaagttc ctgttgatat tctataaatc tcaattaaat ataattaat 218463
gttttaaaat ctgttgagaa gatgacttgg ttctcctctc taggtcagca gatttgctaa 218523
tattatgtta ctccttgcata gctggaagct tacttttatt atatacccta gctcaattcc 218583
tttttgttta cttgagaatt ctaaagaata ttccaaagta agaatgatat atactatttt 218643
ttattgcttg atatctatgt ggtactatta aggacgttat atccacattg aacttcacaa 218703
tatttctgt ggagttacat atatgtaaaa attacaaata aaataaaaac cttactggta 218763
gaatattcag accacagaat ctatttttgga ggtgaaattt agaaaaaatg ttttattaat 218823
tgttctttga attttgtagg aattctacct tcattgagtt aatttctagt ctgacattta 218883
aaaagtattg ctcatttttgt taagttttc attttactgc cacatatta taaactatag 218943
tcttttggtt tgcaaagtta ttgttgaata ggtttgatag actcctcatc atttctaatt 219003
tttatgtgtt tttcttcatt tttcactgat atttgtgtca gaagttccc tgttttatag 219063
```

-continued

```
cttctctcaa aaagccaaaa gtggaattat gtacttgttt gatatattta tcttcctgat 219123 ttattaattc tgcttaatac ctagtgtgtg tgtatatata tatatatata tgtatgtatg 219183 tatatacaca cacacacaca cacatatata tatatttatt tatttattat ttttttttgag 219243 acgaggtctt gctctgtcgc ccagattgga gtgcagtggc gcaatctcag ctcactacaa 219303 ccttcgcctc ccaggttcaa gcaattctca tggtgcctca gcttccttgg tagctgagac 219363 tgcagatgtg taccaccatg cctggctaat ttttgtattt ttagtagaga tggggtcttg 219423 ccatgttggc caggctagtc tcaaactcct gacctcatgt gatctgctca ggttggtgga 219483 tcaaagtgct gagattacag acatgagcca tcatggctgt ccaaaaccta gtctatttct 219543 aatgccattt tttaaattct gagatttatt tctatgaaaa tatttctaag tgtatcaggt 219603 tgtatacacc agggtttgaa tatgattgat tttttaaatg ttttggaaat atttgaaaac 219663 agtatgtaat ccttgtcata gacttatttg gatatagttc tatcagttca gcacaattca 219723 tcataatatt caaatttcat gttcttatat tctatttgct ggacagagat gaggctagtt 219783 tgtgcaaatt cttaaaatgc ccaagtgatc catttggatt tatacagtag gcataaaact 219843 attgaatata agctggtgag ttatatgagt agaccctata taggaagatg aatctttggg 219903 ggtatgaaag atcaactaca gtggcgtaca actaaggcca aatataagat ttaaggatct 219963 gtttatttca gcatttctac ttttaggaat ctgaccttag aaatatcttc cagtctttga 220023 aggaagggtt tagtgttctt aatctttccc aagccaattc ccgccatctt ctactttttcc 220083 ttcatccagt ccatttcctc catcagcttt ccttctcagt ccttttgtga ccttctgtga 220143 catcaacttc ttaaatgtaa aatataatga ctttcttgtc tcatgaattt tatcccccac 220203 tttatttttt agaaactttg atatagcttg taaaagccaa gacaaatttc taccagaatt 220263 agagatatgg cattcatcca gccagccatc aaacattttt gaaaaccaac tatctgctag 220323 gcaccatgct aagaggtaga aaaagctgcc tccctacaag agatagaacc tttaacctcc 220383 atacgaaaga gctcttaatc ttttgcttga attctccaaa gttcagcatc tccaactgac 220443 attaatatat ttttgattcg atgacctgaa gacaaccaaa actttaatga gctcagtctt 220503 tatccctaac ctacctctcc tactatttcc tctcctggtt gatggctgat attaatctgt 220563 gctagaaact taataggctg tcaatatata atctttattt aattaatatt ttatgctgta 220623 tctttactct gtcctatcct taaccaaact tcataaaagt cctattgatc acatctttac 220683 atgtatccca aacttctctt tacctctgta tttattacct cagttttagg accacaacat 220743 atgcttttttg attttttata aaccactaat tattttttata tccctacctc ttttgtccgt 220803 cagctacact cctaccagaa tttgcatatt atcatgacag tcacccattg aaaagttttt 220863 atgattttcg tttgcttaga ggaaaaaacc aaaatcctca ggatgcattc agttttcttc 220923 acaacccagt accaagttta tctcttctca atttattccc tttctccatc tccatcatcc 220983 tcattcccct gaatttcatc acatctaatt aatgtgcatc atggcttctt catacttaga 221043 ccatgttctc acacatagtg ggtattcaac caatgtttgc tggtcattat tttgaaaagg 221103 caaagggcta gattaagcag gagcatatga tcaatcacct gagtgggtca gactgagaag 221163 acagtttagt tgtttagttg ataacttatt ggaactcttg aagttttata ttagaatacc 221223 atggaaatgg aattcataaa tacaacttag aaatgaccta gtctaagcta tgtttcctga 221283 atgttgagac ctgaagtatc agggacttgt tcagaatgat agttgcagct gtttaatact 221343 atgagattta ctgctcccga atctgcggca actgaggtaa acaatggttt gagtcctgag 221403 taggaattta agagacatga tgaactgtaa ctattattga tagaagtaga ttattctgac 221463
```

```
ttgattccaa actgattgca tacatgtaat ttacctccaa gggtgtataa ttatgatttt 221523
gcctgaggta tctatatgga agtatttatg aggatgcaat tttcagggtt tttttttaaaa 221583
gcatgtaatt ggatatttga tttgtaacct ctaaaattaa ggttagaaat agagtcatga 221643
gtgcttcatg gaagacttca aatggagaga gagtgaatta atttagtagc tgcttcatac 221703
aacttggctc aaatagagat tgtagtcttt ctcctagtct ttatcatatg aaaagcagcc 221763
aggatagatt ttccttgtta tattttttgta tagttgaaag ttttgaatca aatttttaagt 221823
ctttacaatt gcctttttaa aattttaact gtttgttctt cgttacttct ttctaaatgt 221883
caaggtatat ttatttactc ttaataatgt gatatgtagt attccacaaa cattgtcagt 221943
gacaaatctt ttgaactaaa gaatagattg tttgaccatt ccagtaatta aggaaactag 222003
attaaatata caatggttgc actggttttt caaacattga tgaagtaaac attattctca 222063
attgacttag tagccagaca ttcttctccc aagtcttgaa aaataaaata ttcaactttc 222123
tgttcaattg agtggggaga gctataaatt ttgtttcata gctttgttta tattgtctgc 222183
attttctctag atttatagt tttagaacat tataagcctt agaaattcaa atgccgtttt 222243
gcatttaaac ttatgaaaaa taatttaggc ccacactgaa gatctgtgaa cacttttctt 222303
ccaaagaggg gtcgtactgt ttaagtttga gaaacactgt atgaaactag tagcttaaaa 222363
tatccctttt ctaaatgtta agatggttcc tattgtacaa gggcaagttt ctgaatatat 222423
agttataaag cctattgata tattgggtag tgttttttttt tgtttttttg agtgcatcta 222483
acccaatgtc cacattgtat aaagtgccag agagattgaa tgaattatca agttcgtgga 222543
ctagtcagtg actgacagga cacaactata gtgataaata tacaaaata aacatgacaa 222603
agtcattcat aataacttta attataacga gagagtcggg tctaatcaaa ttacatacag 222663
gaagagttaa aataactatc tgaatattaa aagtaagata aattttgct tgatgtaggc 222723
tttctggaat atttaaataa acaaaattct gaaatacccct ctaataagta tttctctata 222783
gagaggtaat tatatttaac agcaaaatta acattgatct atattcactg tgatatattt 222843
taaatattgt tttgaaatac tattgtattt atacaatgca aaggaaagat cgctatttt 222903
attaaaagaa tgttttcaaa aaatatttta aattttttatt tcaaagtgac agttattcaa 222963
atgttgaata tgataagtgt tttgtcatat aacaatgttg taaaatataa atgattttta 223023
tatataaata gaaatatgtc attcatcaag ttatatgtaa ttggccacag ctaactctaa 223083
gtgggaagat tttttttctca tcctattact tttttcctga gtatctcaag acataatgct 223143
tgtttctgta tttagactt tttagttttcc cttgtatttt agttagaatt atctaattgc 223203
tgctctcaca caaatgatgt tatgtgacta gagagaggaa tcacgactta cctctttatc 223263
tccctgtagc cccctgtttc tcaactttgg ctgcatgtta gaaacactgc agaagattaa 223323
caaataatca tgtatgggtg ataaatcttg atttttactga tagctttaca tgtatccaca 223383
acttctcaaa ttatacactt taaatatgtg cagtcttaaa aaaaaaaag gaaaacatac 223443
acttatcata tgacccacta atcccccctac ttggggggtgg gaaggggaaa agtgggaggg 223503
ttcaaatact caggtcccat ttgcagatat tctaatgtaa ttggtcttaa gtgaggctca 223563
ggctctgata tttattagaa acttcccatg agatcctaat gtgaattcag cattgagagc 223623
ttctagtgag tactttgcat ataagttctc aaaaataatt gttctcatgt ttttatatat 223683
ataatgtgta tatatatgtg tgtgtctata tatatatata cacatatata tgagaatata 223743
tatctatatc tatatatata tatgtgtgtg tgtgtgtgtg tgtgtgtgtg tgtgtgtata 223803
```

```
tatatataca tacattttttt tttagacaca ggttctcact ctgtcaccca ggctggagtg    223863
cagtagtcag accatggctc actccagcct caaccttctg gtcccaagcc atcctcctgc    223923
ctcagcttcc caagtagctg ggattatagg tgtgatatga tatcacatct ggctaatttt    223983
tattttttgt atagacaggg tcttgctata tttcccaggc tggtcttgaa ctcctgtcct    224043
caagcaatcc tcctgcctta gcctcccaaa gtgctgggt tacaggtgtg agccaccata    224103
cctggcctgt cctcatattt taattgaata tgttttttct ttaattacaa gtaatgtaac    224163
ttgggcaaca tggcaaaacc ccatctctac aaaaaataca ataattag ccaaccgtgg    224223 tggtgcgctc ctgtagtccc agatacttga gaggctgagg tgggaggatc acttgagcct    224283
gggatgtcta ggctacagtg agccataatc atgccactgc actccagcct gggcaacaga    224343
gtgagattct gtctcaagaa aaaaaaaatt acaataaagc cttgaataca tacattgaaa    224403
agccttgaga tgtataaatt atgccagagg aagtccagta aaagaagtac tcccaaatag    224463
ctttttgcaa atatagacat gccacagcct tataggcata catctttact aagcacatc    224523 ataaaaacac atctgtgtgg tacttttggt gcattttgaa taaggactga aaaaagttca    224583
caaagattgg tcagtttgaa gtatggaatt taaatcacag ttgtcatctt attaatggct    224643 actattttc ttgaaatttc catttatat gatatagtag tttgcaaatc actttcattt    224703
acatagtata cggtcatttg agtcatattt atttgtttg aacatggact ttgatggaga    224763
cattcccagt ttttttttaat ataaaattca tttctttaaa catcagttta taattgaaaa    224823
tttcagtttt attgaagttt ggttccagac agttaaggtt tagtagtgtt tgcatttttg    224883
tctttgtaaa aatatttgca catttaattt atgattcaat ttaattttc tgttatgaac    224943 atgagtgggt agcagaaaaa aattagagtg tagacattgg tagttagaat tgtgggtctc    225003
aaaaatgggg tataattgag ttgacaatct catactttgt atctagaaga gaaactgtgg    225063
caagaaacat tttatattta ttttttgttc tttgggtata acctttataa tgttaacctt    225123
ttggaatgta tatattttgt gagtcagaat actatagact atgctgtagt aataaaccat    225183 ccccatatttt cactgattta tctcaacaag ggtttacttt tcctttcttt ctttctttct    225243
ttttctttct tttttttttt tttttctgac agtcttgctc tgttgcccag gctggagtgc    225303
agtggcatga tcttggccca ctgcagcctg tgcctcccag gttcaagtga ttctcgtgcc    225363
tcagcctcct gagtagctgg tattataggc gcctaccacc atgcccagcc aattttata    225423 ttttagtag aggcagggtt tcaccatgtt ggccaggctg gtttcgaatt cctgacctcg    225483
agtgatctgt ccacctcggc ctcccaaggt gctagattta caggcgtgag tcaccacccc    225543
cagcaggttt acttttcatt tatagagcaa ggggtactca gcatgttata gttacttgga    225603
gcccagactc agggaggcac cgtattgact catgtgacag ggaaagggac actgatgaac    225663
agcagttcac tgttaacaca tgtcacatgg gtacttctca ttcaaaaggg gtgagaaagt    225723
acattcctac tatgtgcctg ggaggagagg agaattggag tgtttgtaaa cgagtcctag    225783
agagacccac aaacgtcttc tgatggatga gataccggat gacagcgtat cttttcttc    225843 tcaacataag cctgtattgt aaggaaggta gaatcttatc attgcacctt tcagataggg    225903
aagttgagaa tcagaatgcc tggacagcgt cactatacac ccacagctag tgagtagagg    225963
gatcaggttt attatgtctt tacagcataa ttatgtctcc atatatttca ttgatatgaa    226023
acctgtactg tgttctgcta ctttacattc tatgatcctt ttatataatt gctactttat    226083
tttataatca aacaaagagc cagttttatga taagcataga ttcttaggtt taagtgtgta    226143
aatttataac tattaccatc ggttgtcttt ttatactttc ctttaaataa tatttttag    226203
```

```
tgttaaaaat tattcctacc ttcagtccac ctttacattt tcgctaaaaa atattctgtt   226263
aagttgaaaa acgaagcaaa tcattgccac tggacaccat atttatatca ctgggaatga   226323
tgttgtttct caataggatt tgattttatc tgaaattcca atgtttccac cgacaatata   226383
aagaaaaaac aaaaacaaga acaatctgct aatgaacagt ttctgaaggg acagaaggga   226443
agttttccaa atgcaaagct cagccaaaag ggagaattta ttgttgttgt tgtttatttg   226503
tttcctgaga cagagtctca ctatgttgcc caggctggac ttgaactgct gggttcaaat   226563
gatcctcctg cctcagcctc caagtagct aggattctag gcaggtgcca ccagaccagc    226623
tcaatgggga ggtttactaa tgcaattttg ctacaccaaa atggtggcat ctatttattt   226683
acttatttta aataggaaga agtcagaaga cttaatgaat caagcattac ttataattat   226743 atttttaat  acaacgcttt gagcatggac ttaaaaatgc agagatgaaa tataagagct   226803
tcttggaagc aaacattgtt ggacagactt ataatgtgtc aggattttca aactcatttt   226863
ctataacttt ccaaagatgc tgtcaaatga aggatgagtc aggttttcca taaaaacatc   226923
attctaattt tgtaaaacgg tgtggctcaa aactataaat tgggctgcca aactatttct   226983
ctcaaatgtt tgatggtttg ggaacatgta gaatccatta tattttcttc attaaaggac   227043
tccatataat aaagtgattt attgtgacaa tttaatttat tgtgataatt taatgtttgt   227103
gattcaatgg aaaaacatca ttcttttcat aaatgtgatg taataacata atattcatca   227163
ctgggtgcac aaaagaagtt tatgatata tgactctgct gctaagctat cagaaggatt    227223
cgtgcccctg tcactccaca cacgctttag aaagataaca gccatgattt ttgatatgta   227283
aagtcccaac cattgtgtgt tcaggaatct gtctgcatca tgacacaacg gtggaactaa   227343
gccataatga atgatttagc tctgtttcct cttcttcac aatgtgccca tgattctcat    227403
accaatatgc ctttcttgga cttatctctg aagtctgtag gagataactt cctccccatt   227463
actagccagc agggtggcct gagtttcctt gtctggagct gcaggatatt tgttctatcc   227523
tgtttacagc caatgggggg ccctttttct tccctacagt gagccttttc atctgcacag   227583
agggagatac aaaatcggaa atgatcttaa ttaaatgttt tccgtccaga aacaactagt   227643
ccactacctt gatctggcgg accttcttgg aggtgcccct tcccacctcc ctctgtggtg   227703
agattgcagg taatagacct tatgacaaaa gacaaggata aatatttatc agggcaccga   227763 agaattttg agtatctaca attatttaca ttcattcctg tgaacacatt taaccatgtg    227823
aggtgttatt agtactcccc gctgacattt ttttcctttat aatattttca ataaaattg    227883 tatcccctga acaaattaca aaagtgcctt taaatatcca gaataaatat tttgagaata   227943
ttcattttaa ggttcaagtt tctaaagtac cctattcgat gctaagttat tgcaatatct   228003
gtcgtttaga ggaacttgta ggtttattag ctctataatg tcaacattcg cagatatgaa   228063
gcattttata tttcttagtg atgtatataat gtatgaggaa tacatgaaaa tgcaacaaga  228123
ttttggttgg cttaataatg agtttctttc ttaaagatca agataaaaat tctgaatttc   228183
tattgttctg tttttaaaat tataaactta aatgtatcta gctccaatgt aaactctaca   228243
ttgccaactt tttggaatat gaatataatg aaagtttata tctggttagt tgtgaaaaaa   228303
attattattc tatcatgtaa agaacataga atttattaag gagatattac ttaattggta   228363
gattattcac aagttttagc tgaattgatt tttttaagga aaaattatg tgaggaattt    228423 aacatatttg ttttggtaga aacatgtttt gacagaggaa ttttatactt agataaaata   228483
tcagtttcat ataaacaaat cataacttttt aaattataag tacatcttat aatttttatg  228543
```

```
ttttcacgtc catagattat ttattgatag ataaatagat ggatagaaaa atttgcaaag  228603
ttcagatttt tttagtgata atctaattttt ttaaataaaa tgatttaata tttgcacagt  228663
aaatgtgatg aaaactttgt gtacagatat aaggtcctgt ggtttggggt ttccttttg   228723
tccaaaaggc attgttctat gtgaattaga cataccgatt taatattcta attcaatgcc  228783
tataaaacca acctttattt aattctctgc tttctgcaat tcctcaagga gtgaaaaaat  228843
agactgtgac ttcttaaaa gaggcatttt gttaaaagaa taaaatgtct tttgaaatat   228903
tagtgaagta ctagtatttt aatacccttt tttaaaaaa acaattaaag aatcctatga    228963
ttatttcttt tccctatctc aaaaccaagc atattttcaa gtaaaattaa atatatttga  229023
atctacactt tataatatta caataaagga aagaaatagt tatcattact acatttggag  229083
attttttaa atgtagtttc tcgttgaaag aatttacttt caaccacaag aagttgatta   229143
ttctgtgtgt ttttatcaga taggctttat ataatttctt gtatctcata aggaagtcca  229203
tgcataatag acaaagcatc caagaacaca aacttaatga aaaaccagct tttgttgaga  229263
tggtttcact ccagtaacct tggaagtgtt ggcgagtaat ttgagtttta gtgacaagat   229323
tctgttgctg ctagggatgg ttttggccat ttgataggct gagttttac aagaataatt     229383
tactgtgttt acagacagct taggtcttat tagggaatat taaccccttcc cccaagttta  229443
ggttctatgt gtgcgtaaat taagagatct attctgtttt tggaaagcac acagtatatt  229503
ttaaatataa ttttaaatg taatttttaa agaaaggct ctattttagc cttctaaatt      229563
atatcttcta tatacacttg gtattgctga ataaccaaaa ttagcttcg cttttcttgc    229623
tggaaatttg taattttctt aacatattct ttctgttctg agtaaaagta aataaaggta   229683
attaaaatac agtatttttt taaaaacttt tgaaaaggtt catcttttaa attcttcaat   229743
gatatgtaaa agtttctacc tatgaattta ttttttgtta ctgataaatt tgtattaaat   229803
aattgatgcc taaaatatat atttagtaga ataagaaat tagctataaa acaaaattag    229863
aagagccaca aactagacag ggcactgtgg ctcatgtgtg taattccagc actttgagaa    229923
gccgaggcag gtggatcacc tgaggtcagg agttcgaggc cagcctggcc aacatggcga   229983
aaccctttt ctactgaaaa tacaaaaatt acccaggcat ggtggcaggc atctgtaatt    230043
ccagctactt gggaggctga ggcaggagaa tcactagaac ccgagaggtg gaggttcag    230103
tgagctgaga ttgtgccact gcactccaac ctggtgacag agggagactc tgcctaaaat   230163
aaaataaaaa taattaaaaa aaaaaaaga gccacaaact aaagtctggt tgggttgggt   230223
tccattgcct ttgctcagaa tgtaagctgc tactatctag gtacatcagc tgtacatatg    230283
tcttgtagcc ctttagggtc tcagaatttg tctctgaaaa taagaggatt ggataaaaaa   230343
aaaaaaagc tcagtactat tttataattc cagatgacaa gctgaaggat caagtctta    230403
gcttcttaaa attgttatag aggatattga aaatgttatt actaaatttg gagtgaacat  230463
acatgaaaac attgattctt tttattttg ttttgaaaat agttaaaaat aaaaacaagg   230523
ggaatttatt atgtcaatct cacaatttat aaagcttgat attttgagtt gcaagtaaaa   230583
ttaaatataa aaatctttat taattctgtc acattagtag aggtctcaat gctgtgaaag  230643
tccatgtcta aattatgaca aaattatttt caaccatatc agcattgttt cagaagaaaa  230703
gatcacaact aaatttactt acagcaatct tacaggttta agtttttattg cgatttcaaa  230763
aacaaaataa tttcactatc aaattaaaaa caattcattc ttttatccag aaagatagac  230823
attaatttga attaataaca tatttctgtt ttttatgttg caatttcttt cctaaagata   230883
taaaatcttg tgccaactgt cagaaaaagg aaggatgaga ttattaatat gtgcaatgtg  230943
```

```
aatcaaaaat gattcaagag aaattatatg tatatcagga aacttcttgt tctttcttat  231003
tgatgctaaa gcagggtggt gatgacttga ggtataattt agttaacact atttagatat  231063
atattgtcaa atttagaaac acatttgtag taatataata tatcatatat gacatgcttt  231123
tctgagggat ttgtgataat agtaggtttc atgaaaatct ctcaagaaga cattgatttt  231183
tttaccaaaa ggtaaggctt tatatctata gtatggggat gtaaacataa ttatcaaatg  231243
aatatttgat tcgaatgatt tatttgatat tcacataaat caaatgattt atttgatatt  231303
tatgaatgtg atattcatat tcatcaaata aatttgatat tgatgaatat caaatcaaatg  231363 gcaaagaaaa tatttatgat gagatgaact tttttttatt cacatcagat gttctatacc  231423
tagtattatt accttttgtc actcatcaac aaaaggtagt attgagttgt tttcttactg  231483
gcactttaaa atattatgca ctattaattt tcttcagtaa aatttaatct acttaatctg  231543
ctcttataat tatattctgt gatgttttcc aatacaaata gttattccaa ccacttttag  231603
aacttgtttc ctttccaatg tcctttcata gcatctttta gtataaaaca acctttggga  231663
taaatattaa taacatcaag tcaacacaca gagtgcctat tcatctttgt tcattatatc  231723
acttgctcta tttagatgaa aatcatataa tcaaaaatgc caatatattg tctgtgtgac  231783
aaagtgtctc caatgacaca tttagtataa aagccatgtt gtactaatct gagaataaga  231843
tagatctata tctcattcta ataataattc tcaatgaata gtgtggctct ttcaactgat  231903
gcattaaaca gataaagata tttcttggag agttcagtca gttggctatg ccgccagtta  231963
taacagaaac caattttcaa gccgtgagtt cttgtttttt gttttttacc aaaggtactg  232023
tttccgtaca ctggtattaa aaaaatggat tattcttttt gatataacta agatgaaaca  232083 tttttttcatt ttttcctgtg attttcagtt tgtcatttat tattatattt accagttttc  232143
gtttctatgt gccttacaca caactctcac aaactttgtt tctccatttg ctttactctt  232203 ttttaatca atctgtctag tttgtcctga tgaaaccaag taccatagac agggtggctt  232263
ataaacaaca taaagttatt tctcacagtt ctggaatcag ggaagtgcaa gatcaggta  232323 ccagcatggt tggattctgg tgagggtcct cttccaggtt gcagactgcc atctgctcat  232383
tgtattctca catggcagaa agaggactgg agggctctct ggggtatctt tcataagagc  232443
actaatccca ctgacgagag ctccactttc atgatctaat tacccccaa aggcccaac  232503 tcctcatatc agcacattgg aggttaggat ttcaacatat acatttctgg gcaatgtata  232563
caattccatt ggacagtctt acaatctttt cagtgtttac atgcataatt tactgcaaga  232623
cttggaatga aacttcttag ctttgcttgg tctatataat atgcttcatc ttaagcaagc  232683
tctacattac tagtgatgtt aaatttcagt aaatggaaaa attccttgag aatactatat  232743
tctctttcat tatccaaata cctctaattt tacaatttga tcagtgttcc tgcccgtgta  232803
caacccaatt gaattacatt ggatgtaatt gccagttttt aaaatatatc tttggattaa  232863
aagataaata ttatgaagga ccctgtctca ttgtgccatc agtatatcat ggctgagact  232923
atctcagata agataatgta ttagtcgtct gcttcctagg aaaatgaaca ctaaaatgaa  232983
atatggaaga aatggattct gagtgttaaa tgtgagaaac aaggtttata ctgaacattc  233043
taagccattg ccaaatgtca actttaaaact tcagatcaag agattcagaa ttctacagtg  233103
tcaggtatgg tagatgttct cacaccaagg tgaacacaag aatcaaccga gtgatttatt  233163
taaaagagag tcctgagtgc cacccccaga aattcagatt tttaaatttt taaataaatc  233223
tgagtgtgtc ttttaaactt acattttgta ccagcaactc caagttattc taatataggt  233283
```

```
aatccacaga taaaaaatat ttgttagaac gtattttttta aaaatattgt ttagaccata  233343
aatattttag cctttctttt ttttttaacaa aatataaatt tactttttt agacagcaaa  233403
aaaaaaaaaa aattgtttaa agaaactctg gccgggcgcg gtggcacacg cttgtaccca  233463
gcactttgga aggccaaggc gggtggatca cctgaggtca agagtttgag accagcctgg  233523
ccaacatggt gaaaccccat ctctactaaa aacacaaaaa tcagccggcc atggtggtgt  233583
ccgcgtgtaa tcccagctac tcaggaagcg gaggcagaag aattgcttga acctgggaga  233643
cggaggttgt ggtgagtcga gatcgcacca ctgcactcca tcctgggcaa cggagagaaa  233703
ctcagtctca aacaaaacaa agcaaaaaca taaactctaa attccattat gtatgtatgt  233763
atgtatgtat gtatgtatgt atgtatgtat tttttgaggc acagtcttgc tctgtgttgc  233823
ccaggctgga gtgcagtggt acaatctcag ctcactgcag cctccacctc ccagattcaa  233883
gcgattctca tgagtagaat gcctcagcct cctgagtacc tgcgattaca ggtgtgcacc  233943
accatgccca gctaattttt gtattttttag tagagacggg gtttcaccat gttgaccagg  234003
ctggtctcga actcctgacc tcagatgatc cacccacctt ggcctcccaa agtgctggga  234063
ttacaggcgt gagccacctc acccagccta aattcctttta aaactatatt tatttcttaa  234123
gaacctgatc actagtcttt ctgtcagctc tttctctttt ttatttttat ttttggtcat  234183
ttctggttta tattttagaa tgtgctacta tagatttgct gggatgattc tgattttaat  234243
caattttttt tccttcttgt accataaaaa attgaaatgt cccagaaatt ttgaatacat  234303
ctagaatcta gactgtatct cccagattcc tattcatata aaaatttttca ggcaaattgt  234363
ccctctttgg ggttcacaaa tcatgattgc aagagctaga agtaaaccac tgtagaatat  234423
tttagaggct aatagtttag aggctaaaga tgtctcagag aatattggtc taccctgtc   234483
ctatggatga attcactgtt tagcaaagca ctggacgtgt attatgtcct agagtatccc  234543
aaaagggtat actgaatcat ttctaaaaac agtcagtgta ttaggaatcc atgtgcaagt  234603
aacagaagtc cttagtacag gagcataaat agaagcatat ttacttgtct catactacaa  234663
ggagcctgag attaggccac aggctaatat agacactcaa gagtgccttc aagatttcgg  234723
gctcttttttt tttttttctgc tctgtattgc gctgactact attaccctca tgctaactcc  234783
ttcttaggta gatgattgct acacttctag gtcccatatc ctcaggataa ctacctggga  234843
aagaaggaaa gaacaaatta gcgaaaagca atgctctgtt tttcaatttg gaaagagatg  234903
gcccttttcaa cttcatgtta ttacccaaaa ctgtgtcact ttatctgctc tggctttatg  234963
agaagctaaa aaattgagta atttttacctg ggtacattga tgtcccaaac taaatcaggg  235023
ttctgacagg aaaaaagtag gaatacatac tgtatcagaa actggaattg tttgctacag  235083
atagtatatc tataaagaaa aatgtgtaag aaagactcag aacaattaat gtagacataa  235143
agatgtagat tattatttgc ctgttacatg tattaaccgt ttggtagact attttttggg  235203
agacatcgtt gtgagtcttc ataatgctca tctcactcac ccatgacagc aaaatggggg  235263
ttggtcgcta attattaggt aaaacattct aaactaacag gaaaaaggaa tccttgagtt  235323
aatcttggga ggataacagt gggtgaaaga cgatgataaa tgcgcaaaac tgctaaagtt  235383
taaatgattg gcactttcag gatggtagca gtcaataaga atatgactgc tgtgtagtta  235443
acctctgcac ttttttttctt ttttcttttt tttttctttt tctttttttt ttttttgaga  235503
tagagttttcc ctgttttcac ccaggagtga tctcggctcg ctgcaacctc tgcctcccag  235563
gttcaagtga ttctcctacc tcagcctcct gagtagctag gattacaagc gcccaccacc  235623
acacccagct aattttttgtg ttttttagtag agatgaggtt ttgccatgtt ggccaggctg  235683
```

```
gtgttgaact cctgacctca ggtgatctgc cccctcagcc tctcaaagta ctgagattac   235743
aggcatgagc caccatgccc agcctctgcc ctgtttttat cagtttacct ttatgactga   235803
ctgaggaagt cctgaagttg cagctgctcc acttctgagt gatcctggtt tttttatttc   235863
ttgttgtccc acagcagaca gttattaaaa tattgaaata atgagaatcc tcaacaactc   235923
tagtcacctt tggcacctgc aaaatagaag ttttgctata gtggtctagg gtgagaggta   235983
ccccaaagag gtatattgaa tcagttttaa aagcagtcag cttgttagga tttcatgtac   236043
aaataacaga aatctctgct acagtggctt cagtagaagc atactcactt gtcttatact   236103
ataagaagcc tgatattagg ccacagagct aatacagagg ctcaaggatg tcctcaaaat   236163
gaaaggtttc agtgttcact ggcagagttt cctctggcaa gcctggaggg gatgggcaga   236223
ggctggagtg gaattcagat tactcagaat taatcaggtc agaattaatc ctggttatta   236283
ctttatacca tggttcagtt acttttatag gtgaagatgt attttgtgcc taatcctaca   236343
aaaacatcca ccccataata tgtcaagagc ctgcatttat tctgggaaga ataaccataa   236403
aacctctcaa gagaaatttt ccactataaa atacaaaagt aatttatgc gatacacaga    236463 tcaatattac ttgataaata tattacacaa tggtcttgaa cattgaaata tatgttaata   236523
atactttggt gtacataata cctgtatttc ccatatgtat taacatcatt ttatagaaaa   236583
gatcataatt ttaaaaaaag ggtttgcagg aaggtacagt tgggacctgt gcacacattg   236643
catacataca gggtcttaat ggaaagataa ttcaatacct gctgaaacca taacagatca   236703
ttaagaactt ttaaaaagac ccgtgtctgt attgaaatag agaacctagc tcctacttca   236763
aatttacacc agaaaatgga acaattgata ttattttttcc attctttaat ttcttttgc   236823 ttaattgatt tttgttttgt cttagttatc agtttgtcag atagcatgtg gtttgttatt   236883
tttagagagc tcagattttc caaaataaga gtaagcttct tgtcattat tttatattac    236943 catatatata tatatgcata tgcacataga tatatatgtg tgtgtcttta cacatatgtt   237003
tactataaaa taaagaaagc aatattttac ataatagttt taaatattct gtaagtacca   237063
tttggactag aattggtaag attttttttgt ttttgttttg ttttgttttg tttttttgtt   237123
tttaatttga gacagagtct tgctctgtcg cccaggctgg agtgcagtag tgcgatctcg   237183
gctcactgca gccttcacct cccgggttca agtgattctc ccgcctcagc ctcctgagta   237243
gctgggttac aggagtccac caccatgcct ggctaatttt tgtattttta gtagagatgg   237303
gtgataagca ttttaaacat attttttaaaa aattatataa atttaggggt acaaatggag   237363
ttttgttaca tggatatacc gcatagtggt gaaatctggg cttttaatac aaccctgtaa   237423
tatcagtttt gtcaaactct tatcagtccc acagtttatg aagagttttg aagttttgtt   237483
atggtgtgga ttacagaatt gtaatattgt cgttaacacc tatgggtctt ttcaatgacc   237543 ataaaaagt ttggaacctg tattcattaa ggaagaattt cactaacctc agaaggaatg    237603
agatatggtt ctgagacaga gagaccctga tgaactctaa tacacaatgg tagttccagc   237663
ataagcataa tcatatatgg acaagctaat ttcattccac ccttatggaa atctgccaaa   237723
ctccactata ctttcaattg caataaaata gcttcaggca aatctgactt tttatctact   237783
tctttgtgta ctgtaaaaat aaaactaaaa caagttttta ctctgaaaag cttgtcgttt   237843
caaaatgtat agtattaata actatgaagc catacagtta tcactaccat tacttggtgt   237903
ttattttcat ttattttttc ctgggtattg attttgcata gttggaatca tagcacaaaa   237963
taattttgtc cattttata taaaagggct attaaccttt gttaatttca ttccagtttg    238023
```

```
gtaattggct tccacttcat tactgttata tggatgttta tataactgtg ataattgctt    238083
gcgtgcaagg acagagtaaa gaaatgagaa gttttacaaa tttgtaaaat ttgtgtcagt    238143
gattgagcct aaaatggaat ctttacttca gcatatttga cccttagact ttttaatgtt    238203
tatgaaaaca attactaaaa ttatccccat tttctacttg atccagtgta cctcatggaa    238263
agttaaatat gtttgaaggt agtgaaagtc tcagcaagac aaatgccata aaatgattct    238323
aatattgcat tcaaatgttt ctatcatgta tatagatatg tatgtgggtg gtctgaatgt    238383
atgtgtatgt atatggaaag agagaaatga ttcataatag attttacatt gaaatgtact    238443
aagcaaaata atagaaaagc atgctgcaga atataaaagc aatagagaca agcaataaaa    238503
aaaaaagaaa atgtacatat cagaaataaa acccactaca tgcttctgta tatttgtgaa    238563
taaccagtac tcactgtcat gtaccaatta aaaataatag gaaattttat aaaccctata    238623
aatattgtgt ttaactttt ataatatagg acttcaatag aaaatagact gcataaatta    238683
ccttttatag aagtttagtt gttaatgatc atttttaggg tctcatccag agaggttcaa    238743
cacattgtta tggctgattt aaattatgat tacaattatg aaatattgtg tctgtgaagt    238803
tcaaaaattt acataccaca gtcagcagtg aaatctatta gaagctctag tgcgtttgta    238863
ggtctaatgt gaattgatat actggttcaa ttttaaaaca tgttaattca gtcccctgtg    238923
ccatgccact gggattaata ttattataat atgtcatatc acttaaaatt aaattatggt    238983
atactctttt gtgataaaaa ttaactaaag tgcatgaaat tgtttctgag tctctaacaa    239043
aattacacat tccttcgttt tacgtaattt aaaataatat gaaaaatgtc aatatttgga    239103
gctaacctca catcattcaa attatagcta aaaacataga attgctacat tatttcttag    239163
attaaacata ctttttcctta atgtgaaatt gatattgaaa tgtcatctag acaatgctat    239223
ggatatctac agcttttttaa gtttgcatcc gttctaatag attatttgaa atgaataatc    239283
atcagcttct ttgagacagt aggggaaatc agaaacttca cagatgttta gtgatcttcc    239343
aaggacaaaa taatagaagt aatttaaatt gctaacgtat tggtctgttt tcgtgttacc    239403
ataaagatac tacctgagac tgggtaattt ataaaggaaa gaggtttaat tgactcacag    239463
tttctcatgg ccggagaggc ctcaggaaac ttacaatcat ggtggaaggg gaaggggaag    239523
caggtcacac cttacatggt ggcaggagag agagagaaaa agacggcagg gaaacctgcc    239583
atttttaaaa ccatcagatc tcatgagaac tccctcatta aaggagaac agtatgggg    239643 aaactgcccc catgatgcaa ttaccttctg ccaggttgct cccttgactt atggggatga    239703
caattcgagg tgagatttgc ttggggacac agagccaaat catatcaact agtttgtcat    239763
ttggattata gcactcattg ggaggcacag tatattatgt aactttgaag tataactttc    239823
agttaatttt ttttttttatc attgcatttg tacacatttt tgccagggag gctaaaacat    239883
aggttaggta ccaatattta aatctatgga ctgctttcca ctgggggata cgtattttca    239943
acggtaaata aaagaaaata attttcattt catagtccct taaatttac ttggagaata    240003 gattgcctgg taatcactct atcactcctg tctctttct tagaagcagg caaagttgcc    240063
cagctaccat agtgtggacc ttatgggaca gctctggata tgtatgtcac tgatacccct    240123
gttcactgtc aggttgacag acctgatgga ggtactctgt accacctgta tcacaggatt    240183
ttcctgcaaa ttgatatcaa tctatcaatt gaatagaatt gaatattgaa tatccaattc    240243
ccctccctaa cataataaaa tacactagta acggaatttc agtcccctg gaagagagaa    240303 gacattttgg ggctggtatt atacttagga ccttccacca atgagtccct ccacgttaaa    240363
aattgtcagt aagagtatca aatagatcac ttatattagc atttcttctt ccttctactg    240423
```

```
tgtaaagtca tcaaagatca tttttgaagac tgattcatat attattaaat gtagtattat   240483
tttactattt tttactaaat ttgggaaatg actcagaact ctttaataat tttgagaggt   240543
atgaaaaata aaagttttt  tccccatatt tttgtgttgg tagccctctt taaaatagaa   240603
agtatgaatt tatttaagcc agatcaaccc agcaaaaaac aacaaaaaaa gacttttgac   240663
tttatcttgt gttattttg  ttactgctgg tggagaattt gtttctcaat tcttccactt   240723
atttttataa acatgaataa attcctcatt gaaaaagtt  cctgtatttc tatttttag    240783
tgctaccacg taacttattt tgagtgtgac atttgccaaa ataaatagtt ccaataaagt   240843
tccaatgaat acttgttcac aagtatgtcc agcatgtcat ctatgctaaa tagtttcttt   240903
aaatgtcatt tcttctccaa tcatactagg tactaaatca tctctatttt ctactgccac   240963
tggaataagt tacatgtact tcagtttaca tctatctggt atattattaa tggcaattga   241023
tggcttagga atgaaaagtt ttgtgattaa aacttaggtt tagcccgata tgagaggcac   241083
caacatgagt gttaatacaa tagataggtt atcataaatt attgctctta aaatgtcaaa   241143
tttgttaatt ccatcgaaag aaatagcttg aaaaaaagaa agctagccaa ttgcctttca   241203
ctgaaatgta atggtttatc tgtagaataa acagaattag tttcccttcg tttgaagatt   241263
ttgtgggaaa tacatttcat tcattgtgtc ccatcctgaa gtatgctagt ctatgatttt   241323
tattatgcca ccttacagaa attatagaat acaaacaga  tataatctcc tttttgtgca   241383
gagaataaat agaaatgcat atagaaatat aaatattaaa taatccagaa ctacataaaa   241443
agcaagtcca attcattcaa catacttgtg tattactcac tgataatatc catgaattgg   241503
actatttttc tccaactcac ctgtctcatg ctacacagga gcctattttg aatgtttccc   241563
gtgggaaaga aacctcatgc attcatttca attaaggcag tgattctcaa ctgggggatt   241623
ggttgtatag tttataatag taatggtaca gagaatttct actatacaga aatgttagtg   241683
atagaatcct taatgatgtt aaactgttga tggaagtatg tcatgtctgt caggattctg   241743
agatggaaaa agattggcaa atactgaact ataatattgg tcactggtag tagcttggaa   241803
aattctcttc taggaatttt gcatttgata gggaatcatt gaatatccaa ttcccctctc   241863
taacataata aaatacacta gtaagggaat ttcagtcccc ctggaagaga gaagacattt   241923
tggggctggt attatactta ggatcttgcc acccatgagt tcctacatca ggtacatgtt   241983
tacttgacat tcagtcatga gattcctggg ccaatctcca cactaacatg cacagttgtg   242043
tgtatagacg agacacatac atagtaggct taagagcaaa tgtctacctt ttcctctgtt   242103
ttcaactcaa agtgttggtc ctgggtaaac aaaagttttg attatacagt ttttatcagt   242163
agatacccccc aatttttttt ccatctcatc tcaaatgatt cattgcctac caataaaaat   242223
agactgtcca ctggcagtaa cttcagatct aatatttatc aattgtttaa cagtgttgtg   242283
ggataattcc gccgtattgt ttactatttc tcttttcccc aagatcagat atgtttgtct   242343
ctagttgcat atatttaaaa cttttctagtt tatattttca atacgaagac atatttaaat  242403
acattaattt ccatagcctg aattagagta gcatttgtaa tagcattttc atctcagttg   242463
atattgattt tctaaaatac atttgcctca gaaacattct ttttttcatt tggcatttc   242523
tttacattga aaattgaaga aatgcagtca ttaaattatc atttttcattt aactggatct  242583
tgttcaaatt tcaatcaggt gttctacaaa aagttaatag tttaccagac attttcacat   242643
ttctactgta tgcaatgggc tattagttttt tttttaaaaa agagaaagct tacacttttt  242703
ctctctatga tttggcttca tttattgcaa aagattgcaa agtaattgaa ggaaaatgaa   242763
```

```
aactaaatga aataattaaa taagcaatct aatttctagg tgttaattca attcttttc    242823
taagcaattt tctgtatttt aaacttcatt tgctttctat ctacttttg cctgcaggct    242883
tagatgtctc aaattatggg atggatacat cccttagtac ttagcatgat gacacagggg   242943
aaaatgccac tcagaggact agactaacac atttaacagt tatttcatta tttggtggcc   243003
tcaaactcca gatggccata tctagttgat tttattgtct ttgtcgatta aatacctgta   243063
ttgtaaaatt gtatgactat aaaaggataa attttgattt actaaggtg atcttctgag    243123
atattttgag ggaaagaggt agtataccaa aatggaaata ctacgcaagg taagtgaaaa   243183
cctttttaat gtatcttggt cagtaaatta aaccaagttt atattgatgc cgttgccaaa   243243
tttccatgtc ttttaccaac acaggttcaa atctggaaaa acatttact gaagaattca    243303
ctgatttggc ttgtaaaagc cttttctata aaccatagga tcaattgtca gtcctgtctt   243363
gaatgattac ttatctctaa agctaacaga gttgctattt aagctgaata ccttccttaa   243423
aagcaagaaa gataagtagg agtacacagg acactgtttg ttagcattat aacaaatatc   243483
ctccagcata agtgatcagg atgttaaatt tatggtaatt gaattcaaga attttgtca    243543
gaaaagtatt ttcagatatg aataggtaaa ttcttagcaa gctagtcttc tttggaaggt   243603
gcttatattt gaataaaaag gatttcttta aaaaaattgc ttttaggatg ccatttaaaa   243663
gaaataggca aacttcagaa gccttaatgg atttcttaca gaaaacaaac cctccataaa   243723
attccacctt agcttcttgc agccctgaat tcatgagatg ttaactaaat taaccttgac   243783
tgtcttttat tggtctgttt aaaaaattag aaataattaa tttaaattgt cattgcttgg   243843
ttctaaatat ctttgctggc catgtctata gagagtaggg gagcattttt gaagataatc   243903
attagcaaat ttcctagatt cttccttact actgattgct ttattataaa gctaatattc   243963
atagtttgat tatattaatg cgatcttgtt ttcttaatct aactgcatga aaacatacat   244023
ggaatgacag atctacctgt catttacaac atacttagga gattgaccaa tttctaaata   244083
gtggcctaat taagaaataa tggacattaa atcaaactgt gtgtatatgt atcttcacat   244143
gtttgtaaat tatcactgtg gcaagttctt tatagcacat caaagatcta gttctttatc   244203
actcctctgc ccttggagtt tttatgcata cctttgcttc tctgtggcta agcacatacc   244263
cttaaattat atgattgcat gtggcagcag tctctcttat cgacatcttg aagacggatg   244323
aagtgaagct ggatttgtgg attttgcctt catttgtgtc agaaaccaat gccctctctc   244383
ctttgggagc caatgccagt tatgaacaaa aagccgtaag cagttgtgtt tccccactcc   244443
catattctaa gtgatcagaa tgtgggattt caatgattta tcgtcttcca aggataggta   244503
catttcaggt ttttaatca tgttgaaaac ttccaaaacc cattactgct gtatgatatt    244563
tacacggttc tttactctga tagggcctgt tttataaggc taccgtgtct aatagtaagc   244623
ttgcttttaa ttgtgacagt ctgaaagctt actttgaaag ctgcttctag agaaacctaa   244683
ttattcctgg ttgggaatgt tcttctggtg ataccactag cctcctgggt actaagcatg   244743
tctgatgata ggtgattcat aagctcaatg tgacatttcc caatgagttg ttttgtcacg   244803
ggttatccat tttgtcagac atgttatttc atcctgagct ttaatgtgac tatcatgttg   244863
ctgggcaagt agctgagagt gtcatatagc ttgtcaaaac cgtaacacca tttgaaccag   244923
aatatgtaat tttaaaatca gagctgtgaa atttaaacga ggatcttgct aagtcacagc   244983
taattccttt cttacttggt aacctggggt ctaatgtaag agtattaggt tgccgtcatc   245043
agcctttgta aataagttaa atcaactgaa ggacatagtt tctggctagg gcagggtctg   245103
tcacctgttc tgggttaagt tactgtgggg tgcatttgaa gatttgaaga aagcagtctg   245163
```

```
ttgagatgac gaacttcttg aatcaactgt gacaaatgca aaaacccatc tgtgtttttt    245223
tgagtatcat tctagtagtc atgcctctag tgttgcttta cttactctcc aaacatgaaa    245283
gttagcacat ctattaaaaa gcaaatctgt aatattagta gaaatcattc tgatatagta    245343
actttgcatg ttctataaat tcagaggagt agaagattac aaaattccaa caccaataca    245403
gcatagctat caaagctgtt cttaaaaata gtttgttaat atgactacat tttaaaataa    245463
aattagaagt tctttgtcca catagaattc cctttagtta aattattttg aaattagcta    245523
gtaaaaaggc atttacagaa tttgaattag ttgacagcac aattttaata cattcctttg    245583
tgttggtatt tggagtttgt ttccttttaa aatgtttata aatatataga tatacacaca    245643
catatatata cacacacaca tatatttaca cacacataga taatacatta tatttactat    245703
atatatgtat atttgtgaca gttacaaact tttctgaaac atgtatatat atatagtagt    245763
ggtgcctgag tgtttctaaa atcattgtaa caatacatta agccaattag tagttgaatc    245823
aaaataaaaa aggcagaaaa agaaagactt cataaaaaaa tagtaagctt tgcaaatatt    245883
taaatataaa attaatactt agcaatcaag ggtaatattg taacagaggt gtacaaatgt    245943
ttaaacctaa agaagataag tataagaata ttcattttaa aattagaaag tacaagagaa    246003
tgacgtaggg acatgtgaac tgctgatgtc ttcatatttt acagaatcct acagaattat    246063
accctgtatt atagagttttt aagatggaaa atgcatcac ttcttaatat tttaaataat    246123
ttcttaagca aaaaggaaat ttaaagaaat catatctttg ttggtaaaga aatattagaa    246183
attcaccact atctttagtg ttacttcaga tttattttgt tataatctat aaaaattaag    246243
tttaagactt aaaaaagtgt ttataatgat taaatattca taaatgtatc atttaccatc    246303
catccatcca tccattcatc catccatcca tatctacgca cagaaaaatg cctgaaatga    246363
atttcccctc atatcaattc cagttatttc tttgttagga ttttgtgtgt ttaaaaatat    246423
tttgctgtac ttaaataatt ttttgaggtt tttttttttt tttttttttt tttttgcag    246483
tgaacatgac tcctagtagg aaaagcaagg aagaacacta ataaaaatat gctaagatat    246543
tattgatggt taactctaga tggtaagaat atgtatgata tgggtgccct tgtttacttc    246603
tttaaacatt tttagtatct tttcaatttt aggaaatata acttttaaaa ttaagagaga    246663
caaaccatgg tagaacctat tattagcaaa gtatggtatt tagaagaaaa aataattgaa    246723
taaattgttt tcataatgtg gagttatgtg ctgcctgtta agacagcaat cccaataatg    246783
tttccattcc tttaggaaac acattatgaa ccttataaaa tcgggtggga ttttccatag    246843
ggatgaaatt cattagagca atgtctgcat tctatgaaaa catctggtgg ttttggtcat    246903
tctgtcttgt gttttggcct aattttctac cacgttgtaa ggcacagttt taagaataat    246963
tcacacattt ttccatctag agattttttga ccaaaaaaag tatatttata ctgatggact    247023
aaacaagttg cattataatt gtgacagtta caaactttttc tgaaacatgt gtatagttttt    247083
tttttttttt aattttaaaa gtagatgtca cacctaaaat gggtaggtcc atttcatttt    247143
ataaggaaag cacccagaag ggtccatatg tatttgtgct cgaaaaggaa gtaattgtgt    247203
gtgtcatttc cgcccccttt ttatcaatat tgcctaatat caaggagaat cagtaataat    247263
agaattatta atagcagtaa tagaatcagt agaataagag tggtagagtt agtactcatc    247323
agtgaaaaac taatcaacct tattactttg aagggaaatc tgggaagaaa gagaatgaaa    247383
tgaggtacat gttagaaatg gaatggcga agtaagtaat ttttctgatt ttcataattc    247443
tgtttcacta gttaaatcta ttttccactt ttctttcctt cctttatctg gctcggttct    247503
```

```
cactttagaa ggcaaaattt tgattatttg caagagtgct cccaactcaa gtctcttagt 247563 caacatttcc ttccctcagg cttcagtcta tgatatttca tgtaataatt tgtaaaatat 247623 agttctcatt gcgggactcc tcacttctat tttaagatat ttttcttaaa ttattttatt 247683 tctattgctg catgcattca ttgatttgag ataaaatttt ataagtttgt ggaaatcatt 247743 gaataggaac ttctcagtca gcgctgaaag aaattttatg aatgaataat acaattccct 247803 cctcctaatg aaagtattgt acatctcaca tttagtttat attgattgct ttctgacatg 247863 gaaataaaac aatctttata ttatgcagag ttcctgttag tggtactatc aagaatataa 247923 atctgcccctt gtgacttcta tttctatgct tttctccaac ctgaagtaac cccaaccagg 247983 tttttaatta agtaatgtg agtcactgag tgtatcaccc cttttatgca tgatcaagtt 248043 accatagcat aaatatattc caactctttt gtaaacttga attttatgga taggtaatac 248103 aattcttctt tccaaagttt gcagttttac ttccaccttt aaaaaatgtt gtagtctctt 248163 ggcagtgctt atataaaaat atgtgaagtg tgggtaatac tagatatagt atatagatgt 248223 actagatatg gtttgcaaag gtggacttgg aagccatttt cattttttggc ctatttagaa 248283 aattaaatga tactactttt tcctatacaa cttatatttg gtgggatatt tttatttact 248343 taatttgaaa ttttagactg aatagtctta aatttccagc ataaatattc tatattttaa 248403 tcaatgtttc cttgtatgta gcatttgtac agttagtttt ttgaagtttt taattttttt 248463 tttgtttgag acagtgtttc actcttgttg cccagactgg agtgcaatgg gcgacctcgg 248523 ctcactgcaa cttccatctc ccaggttcaa gcgattctac tgcctcagcc tcccaagtag 248583 ctgggattac aggcatgtgc caccacgccc agctaatttt gtatttatag tagagatggg 248643 atttcacccct gttggtcagg ctggtctcaa actcctgacc tcaggtgatc cgctcacctc 248703 agcctcccaa agtgctggga ttacaggcgt gagccaccat tctcagcctg aagaaggtct 248763 ttaagaatat caatgaacat taataccagt aatatcaaat gttagccaca catcatgaat 248823 attaccatat ataagcacag atggtaatat cgggtagggc ttaagagtgt ggtgtttgga 248883 ggcagaccaa cttccaacac ttactggcgt taggacctt aacaagcctt cccaaacctc 248943 agtttattca tctgtaaagg tgagaataat tatattactg cctcttgggt ttgaggagat 249003 tagagataat gcaattgctg cagggcctga ctcaaagaaa ccactctaaa atgttaacta 249063 gtctcattag ttattcattc atcaaatgac aaaatctgtt ttgctcagtt ctaaatagga 249123 ggcctcaaaa cttttagagg atggtttagg aacttgagta tagtacacta accaaagttc 249183 ttggctatgg tcttatacca attgaggatt cttcagaagg gcttcaaaaa taggcaggtg 249243 tctatgacag gtctgtccat agctcaaatt atttcaaaaa aattccttgc gttttccttt 249303 tgttctgcca tagaagatga ttattttttt tctccatgat gttgtcttgt ttttctgtta 249363 gagggctgtc atgtggtgtg ctaaactttt agatagccag agattagcta tctaaaagtt 249423 tcagaatgac tgaaatagtt attttttctt tctttctgtt tttattatgt gtctttgcaa 249483 aggtttgttg agggaaaatt accaaataaa gtttgaaata gtattagtac ctttaaatgt 249543 tttctttaaa atatcttaac gatagataga tagatgatag atagatagat agacagatag 249603 acatagagat atatggaatg cttcattacg catactagac acttgttgat ttttttaaaag 249663 gaaatgaatt tagaaagcaa ttttcctcga aaccagtttt tttcttctttt ggtaaaggat 249723 aagtcattct tacaactctc aatgatgcaa ggtgaaattt atccaatttt aagtagggat 249783 gctaaataat gtagagaaga cacaagcact tgttttggag acagaatatt tgccctctgg 249843 gcccagatgt gccatttaaa attgagtgtt ctttcattca tttattcatt cttgcccttg 249903
```

```
tttggtaaag ggtattggga aagatctgta attaaagata aaagtgtaaa aagaaagaaa    249963
aattgccttg aaaacaaaac aaaagtgcca gcaacggggc taaaaagata acataatgtt    250023
atatgccctt gctataaata ggtcataatt tttgtttcaa gatttctagc agccaatgca    250083
aaaaaggaaa tcctggtgaa attacacaag tttaggatat cttccagacc acgaatcaac    250143
cagtcacaaa gaatatgaat acttatttc ttaatattag gaacagaaat ctcccatggg    250203
tcctagtaag gagaacatgg aaagtaagtg attacgtcaa ttgtagtatc ttttaaaagc    250263
agtattgagt tttataagga agtcacttct tcttcagcct atacacttcc ataatttgga    250323
gatgtttggg cttcctttaa ggttcctttc agtttcaaca tacgtgactc taagctggaa    250383
cccgatgaga tcagtgagtt gttaaatgtg aacatgatca aactgaatta aaagctgtt    250443 aagaaattag atatctcatc ttcagttttt ggactttatg attttctttt ccattcctaa    250503
tgttttttct atcacagaaa aaaagtctca tggtaactgc ttttaatttt gactattttc    250563
tattcttcca agaaaatcat ttatttaaa catacaactt atctttttta gcatattctg    250623
attgatgcaa atactcttgt ataactttca atagtcaatg aaatattgga taaaatgtat    250683
ttctaagaag atagccatat atgtgtactt tttcaaaatt gctgcttttt gcctattatt    250743
gtttgctcgt ttgtcttttg gttttgcctt actataatag aagacttatt agttatattt    250803
aactttcctc ctttgaggaa ctaatcatta tccaacttaa ttcataaact tcacagatgg    250863
catttcttct taacttagaa ctattttgt cttactattc tgattctttc ttctataaga    250923
cagcctcatg aaacctaaac acccaacatg gaaatattag atggcaaata tgttttccat    250983
tttgtttggc cttaattta ttcaggtaaa taattgggtt gtgcttaact tacatggaat    251043
actgcagttt atatgatgtg tcataacatc aaagctaaat taaggaacaa gggagagagt    251103 tgtgctttt tccaaactag tacaacttat aatgttatgc tgtttttaa aattattgtc    251163 agtcttgttt ctcttatagc acaaggtctc tcttaattat gtaatttaaa aaatgtatcc    251223
ttctcttcaa gaccagcctg actaacatgg tgaaacgctg tctctactaa aaatacaaaa    251283
attagcctgg tgtggtggca cacctgta atccgagcta ctcggaggc tgggcagga     251343 gaatcacttg aacccaggag gcagaggttg cagtgtgcca agatcacacc actgcactcc    251403
agcctgggtg acagggtgag actccgtctt aaaaaaaaaa aaaaaaaagg tatccttctc    251463
aacatttctg agactatatc tcttaaattt gttttgcagc tctccaagga ccagttgttt    251523
ctcaaataac tggtccttgg ggagctcagt ggattgcctg aaaaactctg attgagttgg    251583
ggaagatttc taacaggatg gaatatttga gatttacata ggaattttcc aggtgaagaa    251643
ggggaatatg ccattagatc tacaaagact gtaatccagt agttgggtac tagaagtaga    251703
gatgaaaatt tcattggctg ttaagttttc agcatcaata attagaagca cactgataca    251763
gcctgaaaca ggtaacaagg acactcacat agagtggatc aaacaagata gaaatttact    251823
tctctttcct atcatgtctg gaggaagata ggccaacgag agcaggcatg tggctcatca    251883
ccttaaagat atctaccgcc tcagattctt tctatcttat tatcaaccgt ttttacatga    251943
atgcgtgaag cttcctgaac tgtctgtata ttatggcagt aatagactat aagcagaaat    252003
taatgatcat ctctcttttt ttgttcacac aaatcagatt ttgaaacttt aaggtttctt    252063
agggaattta tagttctaca aaacacttag aaatgctgcc ttcggttacg gtatctccat    252123
taggttccaa ttctttggtg tcaggacaat ttcttacgtg ttttggagcc cctctgctat    252183
atagcagact ctcaaaaata tgtaataata agggagaaa gaaagtaag gaatatgact     252243
```

-continued

```
ttcatgtaga tttgaagttg taatttcatt gatctcgaag agttggaagg atttaggtaa    252303
tcttatgcag ataatggtaa ttttaaagaa aaggtctcat tatgtcatag tcactatgtg    252363
gactaaataa aaggaaataa atgaaaaggt tgtgttacag ttatcattca aaaacatcca    252423
aatgaaaaaa gtatttttta aatcagatat gcatttattt tggggtggat tttggcatta    252483
tgcacaagtg ttctcttgaa aagcaattca taggaccctaa actgaacttt tggattataa   252543
cagaggtaat gtcattctgc caaaacacac tgaaattagc aaaagccagt acccttacta    252603
atttgattct tattaaggga atccaagtga ttgaaaacct gagatgagat ttaactatttt   252663
ccgtcatcaa attcataaca taaggggaa gcataacatt gccagttagg agagggtaaa     252723
ttcaatttgg aattttccag tagtaggaca aaaaataata aactcattat tctcttcaga    252783
ttattaccat tattgctgct gttgttttga gtacaatgac tgcttacttg tgctctctga    252843
cagtatataa ccaattaggg gatttgaaat atagggagtc attttttgaac aaggaaaagg   252903
cagcatagaa tctatctatt tgcatatctt caaaaggatt tattttttata gctagtttac   252963
ccattgccta tttacataca tgagtttgga ccaaataatg ttctaaaatc tatccaagtt    253023
tttaaaaaat tctgtttgga aatcaaattt tgtactaatt ttgtcaatta ttgttgtaaa    253083
aatctgaaat gccagacctt ttatttaaaa tatcaacatg ggtatgaaaa ataataacat    253143
gggaagatgg tatctatcat ttgacgggct ttcatcaacc ctgtatgata cactccaatc    253203
ctatcatgag ctcttgaaa aggatttagt ctctttttgt cagatgagga taacccaga     253263
catttaagga gctgatgttt tctcaattcc agaaaaagaa ttggaactca aatctgtgag    253323
gcacgaaagt cccgaagccc tcattctcca ctgttacaaa tttgcagaaa tctgagtgat    253383
atgaaaaata tttattttta ttgatgcttt atacacatat ccatattact ttacatacaa    253443
tgaatacttg tgtaaaatta tttaaaataa ggtgcttcat atgttcagtg ttttgttttt    253503
gactaaataa aatattttatt gaatgccatt taagagccct gctacatgtt gggaatacag    253563
ttgtaggcac aaaaaggcat gattcttact tttggggagt aaatggtctt tagggatcat    253623
ttggtttttg caccataggt gagcagaaca cccaaagcaa tgagtcaaag tggatgatat    253683
aattttctt attcccaaat gcaaataaaa tgtatcttca ataagtaga tctgtagtat      253743
ttccaaggaa agtgttattt tcattgaaaa acacatacca tgctttctgt agactcttaa    253803
atatcaatct tcaaattaaa aaaaaggttt tacttccact gccctcccca accagcccat    253863
gaacatgtgg cgcacacacc agcagaacac atacatacat agaatctgaa ataaacctac    253923
atgtgaaatg accaaatggt gcatctggat tagagtttta gacagatctg tgctattatt    253983
taatttgtta gcataattat attttatgtt ttattttctt acacttagga attttttaaac   254043
tgtaaaaacc ttatattata tcattacatt attaccgaca tacctcatta catttatcaa    254103
ctggtttttt tttttcagaa ttttttcaagag ttgtagcaca ttcataagat tttgtgcctg   254163
ttattctgtc ttgaatattg gtgcaaattt tgtatttca ttgcaaaatg ccagcctctt     254223
aagtaactgt aactcatcat atgacaggtg gaataaaatg gctaccagta atgcagagtt    254283
aagctaggaa atagtttagc ttttagtgtt aattttactt caaggaaatt agagcatttt    254343
atacatttat aaccatcagt cttggctgaa atacttaatg gaggcatgat aacatatctt    254403
gtacctttat agatgttgta gctcaaaatt atgtttaaaa gttgcttttc caattaggag    254463
atcctaactt cgttggcaaa gaaataatac acggtaaaac aaacaaacca ccaatatagg    254523
cattatgaaa gaggaaaaac ttaataattg gcattgcaaa tgggtaatta tctaattatc    254583
tacagaagaa aatgttaaat gacataataa acagaattag aaaaactggg caagatacaa    254643
```

-continued

```
atattagctt tcaggtcag accatagcac aaaaggagat agcaaagtaa gatttcagtt 254703 tgggattaaa acctcttaaa aaggatttta aaaagatcaa ttaaatttgg gcttcaattt 254763 ctccatgaaa tgctacaatg tatgggatta aatatataca ttattgatat gactagttta 254823 aaactgttca tgacatctta cctgaagttg tatccctcct ggaagacaag aatgtaacaa 254883 atattctgaa aaaacttcag aaagtatatt attattggaa ttataattat ttgatgaaat 254943 tcaattagtg tttattaata atgagcttga catagaatgc attatataga cggtcaccca 255003 agtgtctaat cttacacact aaaatataca tgctgggaaa tgaagatagg gaaaatataa 255063 tgatggcaga acataacatt accaaaatat aaattgtctc tagagattat tgtatcttcc 255123 actgttccac agaaagaata attttgtatt tctattgcac attgatagtc atgggatctc 255183 ttcaggaatt ttttttttctt atgataatgc ttgtgttctc gtcttacaaa attttaagaa 255243 aatttcttgt gaaaatgtgc tactctctaa gacaggctac tgtctaattg ttgccaagca 255303 caagctataa ctatgataat gagattggct tatttccttt gtgtttgtca ttcagacctg 255363 ttttaaaatc ttgcagtttt agatgtcaaa tagtctgtga tgtaaaatca cctgatgac 255423 atgtttccac acttgtcatc aacatgaaat aatcatattt cagcacagct cctctgtcat 255483 atgagaatta tgtgccacag aatccagatc ctggaaaaact acaggaccct aatgtgtgtg 255543 ttatcagatt aaaacacctg aaaatttaga atttatgcat aattagccat ttcaaagact 255603 tcacagaatg aaaataatct actgggcaaa acataatata tatatatatg aaatcaaaca 255663 ttgaatgaac acatgctttg tgtcaggcat tgctctaaat actttaaata tattctcatt 255723 taaccttca aattctttat gggttgagta ctattatcat ttctatgtta tagtttgtaa 255783 atagcttcca gaaggtaagg tctaaagtca cattgctagt ttttggttga aagggactct 255843 gaacccaggc aagccaactc cagggtttgc acactaatgt atagctatac ttttaagaaa 255903 actatgatta ctagatattt caattatatt tcaaaggtct taggtaagtt aattgtagaa 255963 ttgggataat gtcttgggtt cttggagtac actgcaatca ccatgttcag ctctttagga 256023 taatatgaca aattctagcc tgtgcacaac tgtttctctg ccgggtacat tttcagctgt 256083 ttctctcctt aacctctgca atagtaatcc aatcaccctg agattcctca taggtattat 256143 agcacagcat taaacactag ccagtttcac cagggcttta caattcttgt tatgctctat 256203 ctaggagaaa acagaaccag ttttttttttc ttttaacttt tcatcactga tagaggcctg 256263 gtctgaaagt ttttatcat ttgaacctac agaactggat tctagaattt atagtgcctg 256323 ccaagttgtg tgtaaccctc gtgctggttc ttgggttcta attgctgctg cattcaaccc 256383 aacctcctgg cacccatttt ggacattcta catggaacaa tcaatttccc accttagaat 256443 ctaaattctg attattttaa tccgtgttgg ctctccttgt ccaggctccc cctgcccatg 256503 gttctgatgt cccaaaaggc tttcatacag aatgctgcta cgtagcaaaa taactttat 256563 aatagttctt gacttggatc tgctatttgg ctgtaggtct gtgaaccta acattacctg 256623 caacattata tgcatgttca taagcacatt ttttttttc tgagcagggc ctagagtttt 256683 aatttttttc tttcaaaggt gtctgtaatc caataatact taaaaccact gctactaaca 256743 gatacaaagc aaaagagaag ggtggttct tgttttgaca cctgtgttag tccatttttgt 256803 gtggccataa caaaatagca caaagtgagt aatttatgaa gaacagaaat ttactctctc 256863 aaaattctgg aggctgtaag tccaagatca agactccagc aggttcagtg tctctgacgg 256923 ctgctgtcca tttccaagat ggtacatcct tgctgcatcc tccagagggg aggaacactg 256983
```

```
ggtcttcatg tggcaggagg ctgaagggca agaaatccta atgctacatg aagcgttaat    257043
ccccttaatc ccatttacaa ggggaggagc cctcatggcc taaccagttt ttaaagtccc    257103
tacctcttaa tacatcacat taaacattaa gtttcaacat ttaaatttgg aattttgggt    257163
agtatatatt caaaccatag caaccccctga attaaattat ttaaacataa agcaatatgt    257223
tcctgaaatt actatttcac atgtttaata tgtgcatgtg actagtggct aacgtattga    257283
acagcacagc ttatagcaat aagtgatgtt gtgcaagttt aaaatatggt ggcagagagt    257343
aatattgcaa ctgggctttt gattgtttgt gagaacccag tattaacagt catatgaaca    257403
gtagagtatg cctactaaga aggtatagtt aaacattatt gtacatgttt gagtctaaga    257463
aatgctagct gcatttgatc tatatcaatg ccatatgggt ttttaaaaat catgtattga    257523
atgtgatttt caagtggttc aatgatgtaa cagtgttggt agggtgatac tttatagaaa    257583
taaagtaaat tgtgtaattg aattcagtag gaattcataa gttctgaaaa tgtggtaata    257643
gtctacaaac cttgaaataa agtgtaaaat atcacagctt taaacaatgc tggaattggt    257703
aaatattgtt atgaagacag taacaaaaca tactaaataa ttgataaagc tataaaaaca    257763
aatatgaata tagtatgtta taagtagtgg ttactagaga gcagatgata atatacatta    257823
tatttaaaca tatctctata gagtcaacaa aataaaataa acattttggt aaaaattacg    257883
taagcaacaa aatgaattag agtgtatctc tgcctcatta caagtataac aataaatatt    257943
ttacaaacaa ctgttagaaa tcatgtgata aaataataga cgttaaggaa ctgcaatatt    258003
ttcatccata ttagtaaatc aggagcatca ggaaaaaaga gaataagtgt taatcaaact    258063
gatagatcat tggatatcct tatgaaggtt gtatttgcag catcaggtag agttcagctc    258123
ttcctgtgac gggtaaagtc tttatctcta ttttctccc aagtgttgac cttccaagat    258183
attattctgc aaatctctta gcaagcacat ttctgacttg tacagcattg agcttaaatc    258243
tgtattggaa caacatttca accgtatttg agtcatagat tatgttagta aaatgtttat    258303
gtttaaaatt tttagggaaa agcaccattc tacttctaat tcacagtgta ggtgatgact    258363
tatatttgta ggaaaagtaa agctacagcg cggtgttttc tctagtattg ctctaccgtc    258423
agagagtatt accctattat tgttctcttt aaatacaggg taatatttgg ctgtgttcta    258483
taatgccaac aaatacttca ccttaaaggg cattttggaa aagttcttgt caagattggt    258543
tgacattatt ataatcaaat taaagttttc cttgaataaa aacatcatat actgagagaa    258603
aagaaaagga tatttgacgg ataaatgttg cttccatctt gttaaagagt ctttaccatt    258663
cctttttataa aaatctcagt attaagagtc atggtctctt tagaacattg ccttaaagtt    258723
atctgtaaca ataagcattc ctatgaacta ttagttttaa atagagtgaa aagatgtttc    258783
tttcaaataa tttttctttg ttgccaaatt cccaaacttt ctttcagtca aaaaaaaaa    258843
aaaaaaaaaa accacagggc aacacacaca cagagacaga gagggagaag agagacagag    258903
acagagagag agagcgagaa ttcacagagg gactgaatga atgtccaaga tcttgatata    258963
acgcaaggga aattgaactg ataatcttca cctgtttgtc ctgtcagttt acaaaaatat    259023
aggctttgag ctcaggcacc atggattggg atcccatctc tacctttac ttactgtcat    259083
ttaaccacta taggtctcag ttttcacacc ttttaaatgc agagaaagta gtaattccat    259143
cataaaggca aagatcttat gccttattta tcttttccta gaggtaagta ctctatctag    259203
catataatat gcatgaaata aacagcagtt aaataactga ataaagggcc gggcgtggtg    259263
gctcacgcct gtaatctcag cactttggga agctgaggtg agtggatcac ctgaggtcag    259323
gagttcgaga ccagcctggc caacatggcg aaactctgtc tctactaaaa atacaaaaat    259383
```

```
tagttgggtg tggtagcgca tgcctgtaat cctagctact cagaaggctg agacaggaga 259443 atcacctgaa cccaggagga ggaagttgca gtgagccaag atctcaccac tgcactccag 259503 cctgggcaac agaacaagac tctgtctcaa aaaaaaaaaa aaaagttga agaaaatatt 259563 atggatattt atgaatataa atattcataa taaaataaaa tgtttatgaa tgcaattgaa 259623 taacataacc aacagatgct aggacaacag ccaacaggtg actatttggt aataatgata 259683 gttaattatg cttccactta ctaagttatt cttgttaatt taagcatcgt ttaaactaca 259743 ttttgtatga aatgggtgta ttattttatt tcttacattc tacttcaact ggttatctta 259803 tatttatatt gttgtgtttc agctagatat gctgttgtgt tagaacatac actgttatac 259863 acgatatatc tagaacctgt attttagcaa acttttgtt tcagaaagat aatagaactt 259923 ttttcattat tatacataaa gtatgctttt tttctcctgt gctaaaacct aaagattctg 259983 ctttaatttt ggctaaatta tttttttccc atcactatct atatttagag cttacttctg 260043 agttgtagtt ggaagaatta aatgtgggag agtatgtttt gccaaaccca atcagaagga 260103 ctgcctggac tctgtacatg agcctgttgt gacctgattc tcatgtattc tcgacacaat 260163 gctgaaggtc caaagccctg gcacttctag ggagcaaata cctccagagt tgagtaaacc 260223 tgaatcagga acactttctc tgactgaatt ctacctcaac aatatgcata ttcaaaaag 260283 aaaaggtaac atccttggaa aatatgtgct gggaactgcc atattcaaaa tacttctaaa 260343 ataaatggag agtttttttt ttttttaaa ccaggaaaaa aactcttgtg aagaattagt 260403 ttctaagttt ttggtttcta agtagtttct aagttttctt tgtatttat tgatctcaaa 260463 tgttgttggg ttttatacat cacgtaactt ttgatgttac ttacagaata ctctaattct 260523 atcattagat gtgtttattt ctgaaaagtg agtgattgtt gaatagaatc ccattagcaa 260583 cattaatgtt acaatttaaa gacaataatt tcttgtagaa ctatgacgag gatacaagtt 260643 ttgcaatgtt aaacattttt ggaggtgtac ttcccttgag tgggcacagt tttagtcatt 260703 ttgatctatt tttaagcttc agtttgaaaa agtcatacct catttgtcct tataaatatt 260763 tatgtcatct tataaccaaa ttaactccta gattttcatt tgaaataact cactttggct 260823 gagtgcagtg gctcacgcct gtaatcccag cactctggga ggcctaggtg gcagatagc 260883 ttgagctcag gagttcaaga ctagcttggc caacatggtg aaacaccatc tctcttgaaa 260943 atataaaaac tatccaggca tggtggtgca tgcctgtaat cccagctact ggggaggctg 261003 aggcacgaga atcacttgaa ccctggaggt ggaggttgca gcaagccaag attgtgccac 261063 tgcactccag cctgggcaac agagcgagac tctggctcac aaaacaaaca aaaaaacctc 261123 acttcaatag tatacactgc aaaagcataa ctataaaatg gaataagact ttatatgttt 261183 tgcttgacat tttatatgcc ttatatataa ctttttttac ttaaatgaga atagaataca 261243 atatttaaac caatagcaag gatggactat atgtacaaat cttcactatg agcttcaaag 261303 gaatgtgtac taattggaaa aacagaaata aggctagaca tagaggattc tgttatgtct 261363 cctccgagtg actaaatggc ttcacaatat tacatataga acctgcagat gtagcccatt 261423 attgacaaat attatggtta ttttgatata aatatttga tattattttg gttattatca 261483 ttttggtatc atctttatgg ctcaaataag ttttccaatt ttccttgaaa catctttaac 261543 cctccttaaa catccatta taagcaaaga agcatatcgt ctcccattac catgttggtc 261603 caccttcaga acattaaaaa taactcatta atgtagtctt ccacctaaag agttcttctc 261663 taattttctt taaaaagttc tttaataagt tgaattactt caccagttaa attttaatgt 261723
```

```
atttgagggc gaaccccata ttcttctttt ttttagtatc tattatgatc aatgaaatgt   261783
ttctgtttca ttgattatat tagactttt gttcgtatgg tgcctattta aacactgtat   261843
taatagcagt taatatatat tgaatggtta acatttccca ataacgttct ggcatctgta   261903
gtaactgact taattctcac cctaatcctt tgagatcaca cctatttac agacaagaaa    261963 accaataaga aggattatta atttgcccaa aaccaatcag ctattaagtg gccatacttt   262023
ttttgacccc ctagagtctg gttccagggc cccatgcttt tcactgcctt agtgtttcta   262083
aattcatctt cctaaatata ggacaaaacc tgaaccctcc tgaaagagca gtataaagta   262143 caaggagag agaaaagatt gagcaaaggg aataaaactg cgagtatgcc agttgagcaa    262203
gccacacggt aatttaacat aagccacctg aagccagggt gaaaatcaag ggtggaagca   262263
cacacacttc ttgtgatgtg acaggatgat tcataccagt cacttttaaa gcactgtgta   262323
atgagcagag tccttagaaa catcttagca tcagatcaag atactgctat tcctcatact   262383
gattgatctt tactgatgtt ttagacatta tattttaaaa attctgtgaa agtgattcca   262443
cgagggcatt aagattgtgc aaatccaaat atatagactt ctgctgcctt tattaaactg   262503
aaagaatttt aggaagccta gagaaatgtg atgaaaatga tgatgttggt catggtcatg   262563
atgaagaatc ttgccagttt actagcatca agtataaatt acaatctttt gatgtcagtg   262623
atgttatttt agagctcagg aaactggatc ttggacaggc caaggggcac ataaggtcaa   262683
agagcaagta ggtccctgaa gctcaatcag catctagacc cttactcaaa aatctatact   262743
cttcatcctt acactataga ttttttctca aatcggaatt ttgaaggaaa ataactacat   262803
gagaaattaa ccattatact ctctagttta ggtatgtaat tgataatttt gattaaagac   262863
agatctacaa gctatccagc aggtgggtgg taaggttaac attttataac agaagcaggg   262923
acaaatattg aagtacttac ctacttcacc tggctctact ggaagggaga agataccaag   262983
caaaacaaaa ttatccttag aatgaagttc tggtttatt caacttgcta ttgttgttat    263043
tgctggtttt aacatgtgat aacattagtt tgtttgggct gctataattg aataccatag   263103
attaggcagc ttaaacaata gaaatttgtt ttcacacggt tgtagaggtt agaagtcatg   263163
atcaagggct ttggtttctg gcaagggctc tctttctggc ttgtagatgt ccgtcttcct   263223
atggcctcat atggcttttc ctccatatgt gtgtgcacag aaagaaaaag agtgaattct   263283
ctcttgtctg ttcttataag gacgctaata ctgttggatc agagtcccat cattatgacc   263343
tcgtttaacc ttcattactt ctttagaggt tccatccctg cgtatagtca cactgcgggt   263403
tagggcttca acatgtaaat tttaagagga tacaaacatt cagtccataa caatatgaaa   263463
acctcaactt gtctctaggt ttatcagagg ctctctaaaa gctttgttaa acctcgtagc   263523
atggagtcac attgctatct atattctcgt tgtaaataca cacatccaga ttcaagttgt   263583
caattgcttc caccctttac cacctccaag ctattcttgg ggccacattc tctcgctttg   263643
gctcccagag tttcaggcag aaaagagagt gctattggtt gccacttctc aagccctcca   263703
gtaacatcta cattcaactt tgcctcctcc tccaccttgt tatgaattgc aagaccccat   263763
gaaaatcaat ggaacacatc ccttagaaaa agaatgggga gccctactct agaacttcac   263823
taatattttg aagagcaaat tcttcaaggg aatggtcaaa ccataatttt ctgcttctca   263883
gaaaatactt gtcacaatag aaattgaggt ttgataatac agattctgtc ctaaaatatt   263943
atgattcctt tggtgattaa tgaaagtaaa ctatcacatt aacattttga tgtgatataa   264003
ctcattaaca tatagtctta tgaaaaaaat tattgatttt tacatagcca tactaaatat   264063
taaactcact actataaaat tagcttattg tttaattatt ccacaaaaga ggaatatata   264123
```

```
tttcagatca ttttccattt tctaaaatag ccctttcac atatttgcat aactgcaagt   264183
atgtcttcag catccattga tttactgatt ttatatattt aaaggcaaat ttttaggta    264243 tatttgaaga gccattggac tttctatgct ttcagaaaca gtagaatgca tattaattat   264303
aataataatt tatatcaatg ctgaataata atattgaact ttatattaca attatggttc   264363
caatatgtat ttcataaatt tctaaatctt aatacctaaa tagaatgcta tgaggcactg   264423
gaatgtttaa tacacaacta aatttctttt cttttgaaaa tttgtcaaat ttctgtgact   264483
caaatttgat agaagagaat tctttgacct actggttcct atgattcaca tacgaagggg   264543
gatacctatg ggtatagagc aaatgcgtgt tttatttata atagcaactt tgttttagat   264603
aaattcagtg aaataataaa tgtatatgac tttttatgt gaatggttaa ggaatgattt    264663
tatgtttctt ttattttacc tctttaaaaa agaaatcatg tgtttgagag tttgtgcatt   264723
tctatcttct aaatattaa caacatttct ggatatatgg ttatagaggt ttgcataata    264783
tttagtcaaa tcagatttat ttatatgtac tttagaagta ttctttttaa acagtattca   264843
actttctctg acatatgcag ctgcagcaaa aaacgtttac tgaaagatac cttggaatca   264903
tttgtgtaca gagtttaaaa gttaatgttg tcttatttac caaaataaaa taagaaaata   264963
aagatttgat agggccagaa tgttaattag actagaaaat gcaactttt attctgtaaa    265023 tagatcagag tgtgttaaag caatctgaaa atctgaagca taaatgtaga aaaaatttta   265083
aacttcttta ctctttgtta actcatcaag ttgaaatgaa agttaagtgc atttaaaggc   265143
attttcagta gaaaacagct tttctttggg agctgctggg caaacatcct ttttttaatg   265203
aaatagatat tgtatatatg ataaaggtaa ataaatacag ataaagcact tagatgaaaa   265263
aaatagactg caaacactgt tatacattca cttgtaggtt cttaagtcat ttttttttgtt  265323 cttttgttct gtaattgatt gctagcaccc cctttaaccc accttaaagg gcaagcagga   265383
aattcatgtt ttcgttcatc agcccatccc tctgaaaagc gttcgatatt aaaacagttt   265443
tcaaggagca aaagcagagg aaagaagagg cccagctaga ctgtagcaag gttagaagat   265503
acacgcaaga ttgcctgcca cacacatcgg gtcttgttcc tgtccagtat ttgcatggag   265563
atatcaagtt aattagggta ggactctgtt cttcgctttc tatgtgacct tttattatat   265623
ctgtggctct ctagttcata tggtgtcata aagctatggg aaagtctttc tagtgtttga   265683
cacaaactgc aaaagaaata agcattgata tttccctttg cctgaaggtt tttacagcag   265743
caaaatactg cagaggcaaa gttgatattg tggtagattt gctgtgggtg taagaatgtt   265803
tcttttgtct ttcggctccc cgcttccccc gatgatgatc aggtgcgacc tagagagttg   265863
tggagaggaa tggggtattg gttggggagg gggtgcgggt tagttcagga ggaggttaca   265923
tggcggaatt cccacgaatg ctggcgaagg atgaaaaaga tgaagaaatc ttgttttttct  265983 gaacgagagg attctctgca tgacttcccc actgttgggg tgatgagctt tcaggctgag   266043 atttttattaa caattcatat ggagattgag ggcagtggag gagcagattc tcacataaac  266103
ttgatctgtc catgaatgca gttctctgtt tgccctgacc ctgcatggct taagacactg   266163
cctgtgaggc cagtgtgcca gacacaaaga aagaaatgaa aagcaagcac attccaggag   266223
tctgcacaaa ggagcccggc cgtttctagt cgtctcccca gagaggatct tatctctgca   266283
cagccaaaaa cctctaaaat gtttatttgt gtacttaaag ttttaaaatc catgtggctg   266343
ttcattaagc aacagtcaat agagaggttt tgtgaggttt taaatgttg ttttctgaac    266403 ttgttgaaac tggaaaaata tttgcaaggg tacattttct gaagtttagc tttagaagtc   266463
```

```
actggccttg agttgttttt actttgtcaa ttggtaggta gcctgcaaaa tgagtccttt    266523
ccagctttgg gagaggccag aacaacatct taaatcttga tttgacttcg taatacatcc    266583
tgacactgca agctctgaaa cttgtggcag agagttaatg catgagacaa aactgacctg    266643
ggatcacaag tggacatcct cacgctcatg atcacagacc acagtgttac attagaaaaa    266703
ctacgggaga agcaagtgca gagaaaagtt tgagtgagaa gaaagagtga gagaaactag    266763
gaacttttat tataatgttt ttacaattat tggcagttca ctatctctag aagcattata    266823
acaggataat gacaagctct cacaagacat ttctctgtaa cttaatataa taggttttat    266883
tgtttgacaa atgcattgtc tgaaagtatg acatctttag gttcagggga taaaaactcg    266943
atatacataa ttctgctgct caaatacatg tttccacaga tacttaaaat tcagaaaatc    267003
cagatacaca ggcttttaa ttttgcatat gtgtttagct gttcaaatta cttcaaactt    267063
ttatggttca ttaattaaat aaccagtaga ggaatgtaga caaatgccat taattatgat    267123
aggttttgtt cctttcattt tatagtggtt ttatttccat gaaattaact gttgtactta    267183
ggctaattgt cagtaattgg tgacaaaatc acttcattgt ttttctatag catgatacta    267243
atgaggatat ttgcaatatt ggcccaacca tgtgtgtatt ttaccttctg tgtttagtca    267303
gtggtagata atatcaaatg caactttta agagaaccat gagataaaac atttctatta    267363
ataattaaac aagtctttta aacagcctgt cataaattaa ttttaaaaca tcgagattga    267423
aggaagcttt tattttaggt ttagttggtt tcatgaaata tcaactaatt ttcctgattt    267483
gaattgaatt gttttggaat catctatgca atatcgcaat tacaaatctc aactgcttag    267543
ccacatgtat ttttattatt ctatttgtgt aggcaatgct aaaattagca ttgctaaaca    267603
tgcttttgtg aggtatcaca gagctgagtg ggattgcctt tcttttcaca cctgatggtt    267663
aaattctcat aatatatagc aatattactt attcttgttt tctaacagta ttttcctgtt    267723
tcattttgcc acatgaaaat gttttttcaaa acattgtatt tcaaatgaat atatatgaaa    267783
cagttgagat catgaaagct tggttttatg tatttttttc aacattaaaa aaatatactt    267843
ccatgtaagt aatgggttat aaagagaaaa agcagtggga gagtattcca ttttgtgaag    267903
tgagatttaa tgccaatggc agaaaatatt gcaacactac ttatcccatt aaaacaatca    267963
cagccaatac tgctttgctc acttcgttcc ttaaaagaat tcttctcaat agattcccct    268023 atgatttta tgaattcgta agttacaaaa gttttctagt actttgaagt acagtctttt    268083
tgcttctttt tcttattcta agatgctttt accaatcaag tgccatttta cagtttatag    268143
cccactctgt ttgttttaaa tgcaaccata atgtatacct tagagctgag tgtctcccaa    268203
tcatcctgaa aaaagttttt acaaagcaat tagaaaaata attgcctatt aaaaggtgaa    268263
gattggtttg agtagggaga gcagaaactg aactctgaaa ttgaaagcat tcattgttag    268323
aggaaacata tgcaccaaat ccaaaattaa agaaaactca caaatacgt atcttggcaa    268383 ggggaattgt ttgaattttc taaagctgtc agtccatttt ctctactttt tttccggtaa    268443
agaaaaactt caaatggaaa gcttcacctt ttgtacaaag ttgaaatgtt ttattattgc    268503
agaattgttc tacactgtac aaaaccagaa caattcaata gcttccgggg ggccagggga    268563
tggggaaaca aatgagaatc tttccatcat tctagaatac ccatagcaga gcaaaaataa    268623
gtataaaaat ctatggtcat ttccttgaaa aaaagaatct tttgattaca gcagttattt    268683
gaatacccat tcaggctctt ttgtgacatg taataagtgc tcttctccca aatgaaaaat    268743
actcttaggg aacaaaaatc aaacataaac tacgttcaga tgctgcattt caataggtga    268803
ccccatagga ttaagcaaag gttatttttc ttttttgcat gtgctctaaa aaataaattc    268863
```

```
cccagagtta aattttgttt gtttgttttt catcttactg gtgtatttcc aatatgtttt  268923
cttgctttt  gtcagtttca aatatataga atgtgaaaaa taaacaaggc gggaactgac  268983
ttcaagtttt aagagtgata aagtattgtg aaagttactt agagaagatg attttctctct 269043
gatttatcct gccatattat agactctgga gaatacaata atatggaggt ttttttctct  269103
ttcttgagta ttctaactgt tcaaggaaaa tactagaaag aagtaggact ctggtaatac  269163
tatgagccat atccatgggc atctaaatcc tgtagaaaaa aataataaat acagtttgct  269223
tctcacttaa tcatacttga caaccatata gacactgctg gggccatcat gagtagcagg  269283
cggtatgttt gactgttttg gccccagaag tctttataat tgtaatcagt ttcttcatca  269343
gtccatgctg tgccaatacc cctaactagc catagtgtca ttttaaaaat taaaaataac  269403
ccacattcaa taacatcaac aacaacaacc acccctcagc ataaactatg ttctctgtgt  269463
gaactcacag tacggagcag ttgcatccaa cccctgggct ctgatttact tggcacactt  269523
ggggttaatc aaattccccc actgtgaggt gcacacacat ttagaggact ataacacact  269583
ctaatgctac ctaactctgc tgtcattttt aatattttca tgagtttttt ttaagtgatg  269643
tgcatagcag aaatagcctg acttttttctt actgctaaat agagtgccca ccaactaaag  269703
caaacaacaa taaattaaat aaaaaatgat cagatgtaga acatatttat tccaagatag  269763
ttttagtttc tgttgcccaa ataagtttca cattctatga aacttgcctt tcccagggg   269823
ttaagctcct gcagcacttg agatagtgag caatggcttc attaaaaaac ataaagcata  269883
acaaacgat  gtggtaaacc ttggggtgct tttgttttta cttattttag aatgtactaa   269943
caattttgta tgcctcacaa tagaggcatc catgtataaa gacttgtaac tactcttatt  270003
atattccat  tttctggggc cttaatttca tggtgaacaa tatcaatctg taactggggc   270063
aaatttacat gacatcacat acaaggccca gcaggtcaaa ggtggatgaa acaggttcac  270123
tgctgcatgc catgtgtctt acctggacag gcagccatca gctcctgctt caggtgacca  270183
ctgtctgcag gtaaaaccaa actctgtaca ttttgctctt agtgccttat gaccagttgt  270243
tttcactcat aaataatgtt tgaattgtaa gctcttttgc tctggaatcc agaagcaacc  270303
agtcactaat gatcattttg caaactacct agtcatctac cagctaagaa aataatggcc  270363
tctcactctc ttttgtgtgt gtgtgtgtgt gtgtgtgtgt gtgtgtgtgt gtgtgtgtgt  270423
tagagctgtt agcattcatc aacaaccta  gttgtcccta ccaacatagg cttcatcaga   270483
aacttttctt tttttttttt tagtagcaaa gataggctac ttaagatttt atctccaagt  270543
atgaacatag aaaatataaa atattcaagc tctaaatcat actttggata taccttctaa  270603
ttctcactt  gaactacctg tgataagacg tgacatttat gttttgtcat attattcaac   270663
atataattta aaaataattt aaaatcacat ctaaaatttt aaaagaactt aggcactaat  270723
atgttttgta gtcttacatt attatttaaa ataataaaag agtaaaattt tatagagtat  270783
atttgtaggt acatatttttt ccttgaaggg ttacatgcaa tggaagaag  atagattaag   270843
aaagaacagt cacctatatg taattaaatt tcaaaatgat atagaaaaaa tttactggaa   270903
tgaagaaaaa aatctgcctt ttagacaact acatggaagg tttatttta  ttttgtaata   270963
cggacttttg ttcccggata acttgtaaca agctcaagat gtggagtatt aaatgaatta  271023
ttacaacata tagcctagaa gtaggaccgc attgtaaacc atcaaaggta taacacacta  271083
aaacaggcca tgtgattgtg gttaacgcac tcatagcgag tgcaagcaaa ccttaacctt  271143
ctggattttt acatgttatg ttttactctt tggtttactt cttcctgtga tcaatacccg  271203
```

```
ggcaaagcca gagctcttca ggagaaggtt gagattataa caatgtcagc ttttgctttt 271263 agcggagtga tgaggttatc aataatgcat tggagatctt gggaaccttt gacatacaca 271323 tatcacagct gccccacgtt tatcgtagga cttgcaggtc tgagctgagt tgtcacctca 271383 tctgtgtttg agccagccat tgatgcagtc agtctcaagt aatcttgggc acctaggaa  271443 agctgttgag attatttaac tgaaacattg catttgagga agttatttag gagtgagaat 271503 acatctatga aatggctttt attaagaagc ttgttcaata ttcctttaat aacttttttgt 271563 ctccctagct cccttctaat gtttataagt cttgttgttt ctgtgacaag tttattcata 271623 tcctaacagc ttgtctggca gcagggttcg tgtttttttac ttgagctttc tggtcacggt 271683 ggtggctgag agtaatggag ggggaataag tgggtgtgga aatgcaaagc tgtctcttgt 271743 tacattttat cgatctcatt ctggtgtcat tcaattaaga cagaaatgtg atggatagtc 271803 tctgcccaga ttcctgggtt gctctccatc ccttgcagat acagcttttg tgttttattt 271863 tgggggaagg gatggggaaa gggcacgggc aagtgagaga aatcaaatat gctatgtgat 271923 ctgaattaca aatcagtgtc tctctaagga tgctccaaaa tgtcaaacat gccatgttta 271983 tattttcaca tacacagagt acttctgttg atgtatgaga tgggttacta gaatttaagt 272043 tggggttaat tattgttgat ttattttcaa agacctgtga gctaacatca ctcttctacc 272103 agctcaagat aattaaaaat gagccacata gaaaaatact tgagtccaac tcatgccatt 272163 tttgaagttt gcaaatgaga aattattttc tcattttttt tttatgagac tgtgattcta 272223 agttgacctt tctgcaaata gactttcagg ctgataaaat gaaaatagta ggtatttttt 272283 ttttttagttt ataaacaatt cattctaatt gttgcctatg ttatcaagaa gtgtactatt 272343 gtgagtaaat ttcagaattt aggactgtgt gaattctgat ccttacccct gatgatgtat 272403 tttcccttag ctatatcact acctttgttt gctaccagtg ttataatgag ggttgtagga 272463 attcatggat gtgagaggct ctaaaagtaa cagttcatgt atgcaaagtt ttttttaaaa 272523 agacattaaa atcgctactg caagcacata taataaaagc aggatatgtt caacaaactc 272583 ccttgccctt ctcaaaacaa tgccagattc aaattgagca ttcagaattt tctaatcgag 272643 gttatggctt ctgataatta atccatacta aaagggagta tggaataaaa atataagcag 272703 gagtttaac attagatcaa tatgttaatg tccaggctcc cctatatact cagtatatga 272763 ccttgggaaa catgcataca gcctgtagtt taaccttaat ttcattatct gaaaaataaa 272823 tagcattgct ttgagaatta ggagactcag aatatgaaaa tgattgctcc atgcttatcc 272883 tgtgtacttg gcccacggga gacatccaac acgtttagtt ttattctgaa tccccttta  272943 tggttttgac actgagtaat ttggtcctat aataagcttg ctcagtcatt tgggaaagga 273003 atgtaagcaa agaaaaataa tacacttggg tcctaccact gtgagtcaaa atatattccag 273063 atcctaattc acagaagcta atttaccaat ctgtgtgatt ttttttagtg atttttattaa 273123 aaaaactaat tgtcattaaa aagttatcct aaaattttgt ttatggaagg cactccgtgt 273183 gttttgtctt aatccaaatt tatcagtgat tttaaactat catgctttca tcctaaaatt 273243 aaagagaagc tgctggttaa agcagttgtt tactaattt acaaaaatta tagggcactt  273303
ggaaatgatt taggtgggaa tttaactgat aacccacatt gtaacccact caatagtgta 273363 gaaaaacaca aaatcttatg ctgctggtat atgtcttgta ggtattgtta aaaactatac 273423 atatatatgt gaggtgggac ctggctatct ttattttttac tgtttccttc tgaggttgta 273483 aattttttaaa ttggatgttt aaaaaaatca tcttcatgag acaaggctta ccagatatac 273543 atcaaagtat aattgatatc tatttaagga aaatacatcc ataagacgta ggtagtaagt 273603
```

```
aaaaagttttt tctacatgat ccaaacataa gacataatta gagcatgtct gggaaaaaaa 273663
aggatgtatc ctaaatattg cacatgactt ttttcaatat atacttggtg tgtgctaaga 273723
ctgcttaatg catgctttat gaaaacacta ccaacacttt ggttgaagat gtaatgagaa 273783
caaatttcta cactcacata atcattgtac actcagtaag cattactgca taatgaacat 273843
atttgtgtgc ttgtgttggg aattaatgca aaccatttta ttcatttcac aaagggtatg 273903
aatagttctc cttgatgtgc taggataatg ttataacttt tcccagatag ggtaggaatt 273963
gcagtggtat gtttggtcat tctcttatcc tttgagatag ttcaggtcta aatctgggtg 274023
tggggtgctt cttcactctc ttggatccaa gaaggtgcta ctgaaaagca actttccaag 274083
ttgtactaca ttccacagct aactgatgga atttttaaata tttcataagg tagacttaaa 274143
aaaatcacaa gtaactatga tttacagaat ttatagaaac agaggctcta gtttggggtc 274203
atacctaata cactaagttt cagtgttcaa ttccaggaga atacataacc aaatcatggt 274263
gacaatattg cctcccctta aactcttaaa gaactctttt cgtggcaatt tacaagatag 274323
ttaagcacca gttgtcaatg atatatgttt ttctttttaa aaattctttg ctgcctgtag 274383
ttaatattaa aaactttgtt gttgtttgcg ttctatttct ttataggctt tctttccaat 274443
tagaatgtaa gctttgtaaa gtaaaaggca attggagatg ataaatgaag gttgaagtaa 274503
tcatgctgac catacttagt gcgctggaga aacagaaggt tcctatattc gccattttta 274563
ttttctgttc atcaaagagg atttaaagga agatgccatc ccttagaccc tggcagttcc 274623
ttctcttcaa cgtttaaacc tccactttac attattgaac taacaagatg ttctaggcat 274683
tctattgcag gcaaggtatg aacaatttca aatttatcaa caatcaaaat catcaacaag 274743
atgatgttaa gtttcataat cactctgcgc ctatctttgt gtttgcaaga ttctgactgg 274803
tatctacctc cattggtttc tctgtctttg tcttaatatc tttcctgcat ggctttctgg 274863
ctatagcagc atggtttgaa atactccctc agtagtccac taccatttat ctcaaataga 274923
ttgttctttt gaaacgtcaa agtattttt aatacctttt tgttacagt tacaacctaa 274983
gacaacttca agttgatatt ctccaaatga gactctgatt caatgaaatc tgttctctct 275043
attagctcat tttctctcaa tctctatctc tcttgctttt cacactttac tcatctcttc 275103
ctctctaatt gtattggaaa ctcttttagaa tcctaacatt ggagttttgg atatggcggg 275163
aatcttagtg gtcacagact tcatctctgt gctttcacag atgaaggtcc caaggctcag 275223
aaaacctatg ggagctcaaa tctaagagga agtctaggaa aggtctttgc cctgtggagg 275283
cctctaggtg tcttactgag ggtcaaccct atcatctggt cttagagttt gctgggcaga 275343
gttccttgtc ttatttatct ttctgcccac agtgcctggc accctggagg aggctaacgt 275403
atgcttgtta aaatagtcag aaaactttat gccatatctg aagatgtttt taacatatga 275463
tgagttaaat ttcatcttcc caaatgcaga tgctaattat gcgttctgag catgagaagg 275523
aatttgaatg ttttataact atatgttgat aatttttctct ttatagagat ctgttactcc 275583
agaggaagaa tttgggggtcc tgttttttctg tttctcctca gatcatttct agaaattagt 275643
attagcatta atattctcat aatttttata ttagaagaag gtacctccaa gcttgttttc 275703
tgagtaagat cctttttgag aataactggg tgtctgctac ataaatttga caagctattt 275763
tggtggtgaa agtttaaaca atactctgct aagaatagaa gatatacct caaatcacac 275823
attgaaaaag gtagtccaga tgaaacctag aaattcttca tgttgatcaa ccttctcact 275883
atattcccac cgtagcattt tatctttcct ctcatcaaaa tctgattaat ctcttatggg 275943
```

```
cttttttgttt tgttgtgttt tgttttcagt cattaatgag tataatgtca gccttttggc 276003 tatcacttga attacttagt tgaatatttt ttttttttg agacggagtc tcgctctgtc 276063 gcccaggccg gactgcggac tgcagtggcg caatctcggc tcactgcaag ctccgcctcc 276123 cgggttcacg ccattctcct gcctcagcct cccgagtagc tgggactaca ggcgcccgcc 276183 accgcgcccg ctaattttt tgtatttta gtagagacgg ggtttcacct tgttagccag 276243 gatggtctcg atctcctgac ctcatgatcc acccgcctcg gcctcccaaa gtgcgtggga 276303 taacaggcgt agagccaccg cgccgtgcc attatattaa atatggaccc aaatttgtct 276363 ctggccccca agcacagcaa gttttctaaa agattgcttt gcccagatt gaattacgag 276423 cgtgggacag ggcattggaa taatctgggc aagtgggcca ttgagaatag gggtaaagca 276483 acacagccat gctactttca cctgtcactt gggaacaata attttggagt gtttaccat 276543 aactaaagat gtctggaaaa tatagacatg cacttctttg cttgtttcct gtcatgttat 276603 attgtaaagc tcactgtttt gagctaagcc ataaaaatcc tcagctgggt ccaagtgttc 276663 cacgactgtt gaatttggtc aggaagctta tttggtcatt gtactcaagg gtgataaaag 276723 tccttgagga ttaactctca cataatcaag tttacaggaa atcaacaat agaaaaaga 276783 aaacaaccat ggataaatga aggatgtata tatttgttag ctgatcaaaa cattttcttt 276843 ccagtagaat agtgaattca ggaaatcata ttagtgctta tatgaccatt acagattata 276903 aaatcaaaat aaattgtata cattaatcct aatgattatc accagataac tatcacctga 276963 atttccagtc aagtgaggag gaatcaggag tctccaacat ggttggcggg aaactccttt 277023 caaatggact ctgccgtctt gtcccttttt tatcctcatg cgaattatca ttgcttatga 277083 gtaaaataag tcaacggaat gcttggtatc gttcaaaaca gataaaggta actaagcaaa 277143 atatcatcac aaaagaacaa gctagttagc aaaagaaagc atgccgctta tcagcataga 277203 tgtctgttct tgtcctcttt gtttatcgat ctgtctggtt ttattttagc aagtaacagt 277263 ttatctagca aagtttcaaa tgcaagtaaa aaaaaactgt gggattagag tacctgtaat 277323 tttgcttcca gacttcacaa atataagaaa aagtccccaa acaactctac gattttgcaa 277383 actttctata ttttggaaga taggttttct gattttcttt tatcagcaaa aactaatcaa 277443 agttgtctta ggtgagcact atgctcagta gagagtgatg tgagtgtaca aaagaccact 277503 ttttacctta agcagtttgc aatacagcta ggtagaaagc atcttgaaat ggagggaaga 277563 ctaagaattt taagtcagtt ctgaatgcta aaaaagtgat acaaatcaat cctcttcaga 277623 acttcaaaat agaattgggc atttttttt ctacgtagcc cagagcaatg agagaaagat 277683 atttggagga aatgtgattt gagaattgtt ctaaaagaaa gttagagaca gacaaaccaa 277743 cagagaaaaa aacatcccag agaactttgt atctctgctc ccaatctcag gaccgtggag 277803 acgtactcat ggatggagaa aatggaccca cagaagattg cctcaggaca tcacagggt 277863 tatctagagc aaaaaaaaaa ggactaacat tcattgcatg ttctctggtt gactttaatc 277923 agtggtttca tgatccaaat gaaattacat gtctcaatga ataaatatgt agctataata 277983 caaaacaata ggggcacttt tgtattttgg gcaggtgggt gagtgaaagt atgtaggaa 278043 acattatttt cacatcttgt atacattctt gggaggtacc tatctgccaa caccctttag 278103 atctttttg atgtagacta aaacattata cattcaaaat gggagagaga tgtataaatt 278163 gtcataagaa gtaatgacat gtgtgaaaca ggcctcatat tttcccactc atctactcct 278223 gaaatcctgc tcctttccaa tttcctgtct cagtaaatgg taccaacatt cacccaccca 278283 gtaactccag tgtaaaggca aggtgtgata gatttctctt tttttctgac actcacattc 278343
```

```
tttctatcct caagtcttgc caactttact ttcaactctg ttccagtaca gtcaattccc   278403
cataccccca gaactaccgc ttttctgaa gccactgtca tctgctacaa tagccctcta   278463
actgatattt ctgttttcat tcttctcccc ctagagttaa ttttgctcac accagttaag   278523 gtgattttc aaaactgtaa attagataaa gcttttctat agtctctcat tagaagaaat   278583
tttaactgct taccctcgac tgcttgagcc tacattttga agctgctgcg tatgtgtctg   278643
gcttcatttc ctaccactct cccttgcata tcatgtccta aagacactgg ccttgaagat   278703
gttcctctaa cgtgccttaa tccttctaac ctcagagact ttacacttac tctatctgcc   278763
tgggacactc agccttcata tgggtttctc tttgttacat tcaggctacc actaaagcat   278823
ctcttcctca gaaagacgtt atccagcctc ccaaccatta cttccaactc attactctca   278883
tctcattatc ctcatttgtt tagcatcatg gtacttgtca atacctggac tcacattata   278943
tatttctgta tttgtttgtt gtccttttcc taacataagt ccaataatag caaaggcatt   279003
gtctctttta cttaaccccca ggatctagaa gaattcaggg cacaaaagaa gtatttgata   279063
agtatttgtt gaatgaattt attaaggaaa gtgggacata gtttgcaaga ctttatctga   279123
aggagtgaaa agttattttg tagccaggag gacctggatt ataatctcat tttagacaca   279183
tgctttcctt ctggacttgg agaaatcact aaacacccca gttttatcct ataaaaatg    279243 gaaattacct ataaggctgg tttgcagagg gaattagaga taataaacat tatcaacaca   279303
atagttggcc aataggagat gtttactgat agaataataa tacaatagtg aatataagtg   279363
taataacccc aggaggctga gacatgagaa tctcttgaac ctgggaagtg gaggttgcag   279423
tgagtcaaga tcgcgccact gcacttcagc ttaggtgaca gatcgagact ccatcacaca   279483
cacacaaaaa gagtaataac tcagtgcccc gaattgtagc caggatactt caccaaagaa   279543
acataaaata taaacaccca ccccccaact cttcaactca ttatcagtga cttctatcag   279603
actcttgaat atgcaccctt gggaaatgga gtaagaacca tagcttaaat cgtttaaact   279663
catatgggac aaaacgatga aaatatgcaa gagggaacaa tcttacattg gaaaagaaat   279723
caagccaatg acccaatata tcttttatt atttcttggg agaacctgta tgtttaattc    279783
atggaattct tcactgtttc tatgttgaaa tacacttatg tgaaaattgc actcctatta   279843
ataaaatagg actttaaaaa gcccaaggat tttagtatcg aaatgttcct gtgcaatata   279903
ttaacattca ttgactatgt gaatccccac ctgtacttcg tgtaaattac caaaggtgcc   279963 cttcctctg tgcacatgac acgtgtgccc ttgccggtgt aattggactc atgcttaggg    280023
cttagtgaga agagcctggg ctatatttca atctcactca ccaccctggc caatctccct   280083
ttcacagggc tcagtccaaa caaccatatg caacatcctg taaatgttag ataatgaata   280143
caaagacaga ataagattcc aaatagagtg aactgaagat agacaaacct cagctatgcc   280203
tttcttccat cggaaattt gaacagcatg tagaataaaa gagacatgta gtttctctga    280263
cagaaaaagc aattacaagc atgtcacatt taaatgtgga tcactgatta ttattgaccc   280323
aaactctaaa aaagcactat tgtccaagta gcatgcttgt caatatttta agcctaaaaa   280383
ctaatttgac aaagttgtag taagcttagg gtaggaaagg gaggagttca tcaggaactg   280443
agtaatccct gctttttaga gaataccttt ggttttaaac ttaattctaa tgatttact    280503 gagtatcctc tcctctgttg gacatttcga gttgtagaaa aatgtatgca agcagttttg   280563
gaccttatgg aagcaacact taggagcacc atatcagtgt atgagtcact gtaaaacaga   280623
acacagaaat acagaagcca tgacaacaaa gaaagcaggt ccaaggagga aaaacctaca   280683
```

```
tatcggcagg tggatcagaa aagttgcatg ggaaaagtgg actattgcat tggaagcctg    280743
taaagggcag gaccactctg tcatcttaac tagcttggta agcagatcct gggtttctgt    280803
attaaagctg gtccttttgaa tgaatgagag cactaatatt ttcagctgga ggaaaacaac   280863
atgaataaaa gtaaaaatgg aagagtgtag ggccttttta gggaaagtag acaatccact    280923
ttggcaggag tgcagggtgt atacatggaa agatgggggtg tgagttgaga ttggaaagat   280983
acgaaagtgt tcacctgtag actaggttct aggggagtgt gttgttttc tattttccta    281043
ttgttttcca gataatatat ttcttttgaa gtcttttgac cataatcaag cctataatct    281103
atgaagaatg aattgccata tgtatgtaga aggtatcatt tgagtcaagg agtgtgagaa    281163
tgatatgtaa gaggatgttc ttatgtaata tgtaagagaa gcaataagga cttaatgtga    281223
gacaaaagtg aatataatga agatgaagtt ttggcatgac ttaggaagtg tttgggtgaa    281283
acaacaacaa aaaaggaagc agaagggtta aagacaactg acattttgtg cctgagtaaa    281343
tggaaaaatg gtgtcgagtt aacagattag gtaaagctaa gaggttttcc tagaactctg    281403
gaaatttatt aaatattttt tcttaacgaa aagtgtaaac tggcccataa tgtaagcaaa    281463
ttttgactga gattcatggt agattcttag ctcttttata attatttaag taacattaac    281523
tcttgtttat tcattaagct ccaagtcatc ttatgtagtc atatatttgt gtatatattc    281583
ctgtcttatc ttatgtaatg caatcagatt tgatttgcaa atgtaaatga actcatgtat    281643
ttaatcaaga ataaagacat aacactgaat aacagcccctt aatgctggta tttgaatatc   281703
tttctctttc agagattttg tatacatata ccccttttaa atgacctcac attgctgatt    281763
tttaaaattt tttttttttt tttttttttt ttgagacgga gtctcgctct gtcgcccagg    281823
ctggagtgca gtggcgcgat ctcggctcac tgcaagctcc gcctcccggg ttcacgccat    281883
tctcctgcct cagcctcccg agtagctggg actacaggcg cccgccacca cgcccggcta    281943
attttttttg tattttttagt agagacgggg tttcaccgtg ttagccagga tggtctcgat    282003
ctcctgacct cgtgatccgc ccgcctcggc ctcccaaagt gctgggatta caggcgtgag    282063
ccaccgcgcc cggccaaaat tttttatttt gagataattt taggcttaca gaaaagttac    282123
aagatagtgt acacagtttt tatatacact tcaccttgct ttcctaatgt taacatatga    282183
tgtaactgca atccagtgaa caaaactaag aaattaatgt tggttctgct aattgacttt    282243
aatcctgttt ctcaatcact tttataaaaa tgaaacatat ataaaaatac aaaactagct    282303
ggtgtggtgg tgcttgcctg tgatcccagc tatttgggag gctgaggcag gagaatcgct    282363
tgaacccggg aggcagaggt tgcagtgagc tgagatagcc ccattgcact ccagcctggg    282423
caacaagagc aaaacaccat ctcaaacaaa caaacaaaca aaaacataa atacagagaa    282483
aaataatata gtctactatt tatgggcttg gaatgctatt ttaaactttc agacaatgag    282543
aactaacatg acggattgta ctctaaattg ttagctaatt actattaaca caacctacct    282603
caaatgatct tagcactctg taacagtctc cttttgtgct atttatttta aattccaaca    282663
actttgacca ttatagctga tgtaaatgtt ttaagtaata gattgcaaaa caaacaaaaa    282723
gaaagctaaa aaatctgaga aaatgtattg ctggatgtag aacagcaagt gtagtagagg    282783
ctggggatac tatcaagaaa atggtaatga agatagtaaa aacagatcat tggcaattag    282843
gaattgatgc aaattctttg acattattaa gggaaatagt catgtccctg gaggctgaaa    282903
agagtggcca acaattctgc aaggaatagg aaaggaaatt taggtttggg gaggactcgt    282963
acgttcctcg aatagaaaat tctgagatg ctgagtttcc ggcctggcat caacccactc    283023
ttgttggatt tccagcctta ttttactatc caccccttgtt aaattccctc atccacccaa    283083
```

```
ttgctcaggc cagaaaccca gatgtcatac ttgacctctc tttctgtaat tacccccaatc 283143
tcattgatca acaagtgctg ttacttttac ctcacaaata tattttttaaa ccatcccatt 283203
ctgtttatct ccattgctac caccctagaa tgcgacactc ttctctcaca gcagaactat 283263
tgcaataaca ccccaaatgt tcttcttcag ttttttaatcc ttctcttttct ctatcctctt 283323
tcccataggg caatcagatt gatattttta actcatagat ctgataatgt cattcttttc 283383
ttaaaacctt ccgaagtctt ttcattgcac acaaattgaa cttttaaaag aggtgcaaat 283443
gtcctgtatt aactggctgt tggtcatccc tcttgatacg gtttgtctgt gtccccaccc 283503
aactcgcacc ttgaattgta gtttccatga tccccacgtg ttgtggaggg gaccaggtga 283563
agataattga atcatggggc cagttccccc catcctgttc tcctaatagt gagttggttt 283623
tcacgggatc tgatggtttt ataagggggct tcccctttgg cggggctctc attcttctct 283683
ctcctgagcc atgtgaagaa gaacgtgttt gcttcccctt ccgccacgat tgtaagtttt 283743
ctgagacttc ccagccctgc agaactgtga gtcaattaaa cctctttcct ttataaatta 283803
cccattcttg ggtatatctt tattggcagt gtgagagcag actaatatac ctctcaactc 283863
atcactcctt ttgcctagat gggatctgct gcaggcaaga tattcccggc ctcagaagct 283923
gaggggagaa ccttctgttc tttccccacct tcggcttgca ttcctccttc agcatcttct 283983
taaggacagt ttctactgca cagtgatcaa agttgcagag gggtgaagtg tggatatcca 284043
ggaaccccca ttttactgtt actgtcttta ctgcactttc cactatccag ggagggtagt 284103
ttatgcccctt tgggtgcttt tgggtgcgta tcagaggaac ccactgggaa cattcgactg 284163
tacttcctat gtgttgggta atagagtttc ctctcattgt gtgtcatcct cagctcacct 284223
ttttagggat ctattccaca caactttctc ccttatgatg tccagtatcc ttccaggtgt 284283
tctgttagag agcttctttt catgcttggg aacacaaata tggctcacag gctatattca 284343
tctatttttg cactgacgaa ttctgggaat ttaagcagat tatcaacatt gtaggaagct 284403
cttcttgaat cgaaggctga agcagttagc taatccaagt gtgacattta cattgtccaa 284463
caggattcaa agtcaattcc actctgtctt caaacttcag ctccccaagt ggtcctactg 284523
aaatctcttt cattaaaatt gagtggaaag gcaggcccaa tgctccccaa agaaatcttc 284583
ctcagaaaac cctctcacgt ctcttcattt caggccttat atagtttcaa tgtgttcaca 284643
gccacctact ttgaaattcc tactttgcca cttaatacct cctatataat ggtactccaa 284703
ttaaacactt ttaatgtaat gcactgatat ataccccaaaa taaataaaat cttatataaa 284763
gtgacaactt taactctgat tttaaattag acttatcaaa ttgaacacca aaagagcatt 284823
tcagtatgta attattggta cagatgaccc atgtcaaaaa acttttaaat taaagccaaa 284883
gtatctaatg cacttagaaa agtggaccat cgcggggcgc ggtgactcac gcccgtaatc 284943
ccagcacttt gggaggccga ggcaggtaga tcacgaggtc acgagtttga gacccacctg 285003
gccaacatgc tgaaaccctg tctctactaa aaatacaaaa attagccggg cgtggtaact 285063
cacgcctgta atcccagcac tttgggaggc tgaggcgggt ggatcacgag gtcaggagtt 285123
tgagacctgc ctggccaaca tgctgaaacc ctgtctctac taaaaataca aaaattagcc 285183
gggcggggtg gcatgcgcct gtaatcctag ctactcagga ggctgaggca ggagaattgc 285243
ttgaatccag gaggcagagg ttgcagtgag ctgagattgc accacggcac tccagcctgg 285303
acgacagagc aagactctgt ctcaaaaaaa aaaaaaaaaa agaaaagaaa agtgggccat 285363
caatattaag tacaaaattc taccctaag tgtattaagc attctttgta gctttatttt 285423
```

```
catcttctac atgattaaac ataaatttcc aagaagggt  acatctgtaa attagacttt  285483
gtaaaggagc aagatacttg tttcgggaga agttcagtaa agggaagcca ccgttaaaaa  285543
tgtcaactat tgtatatcca tggtaagttt gaaacatgtt gcttttaatc ttgtgttcta  285603
atagccagaa tttacagtgc tgcaacaatt tgttttaag  tggctggaaa aatgtagtga  285663
aacttgttat taagtatctt atttagcaga aacaccttgt aatttgtctt aatagttgtg  285723
ttattaattt cttatcctgc ttgggccaca gcctattcag aatgatctga actgcctatc  285783
caatctttag agcatttaat gaatacattt tatcttccca aaagagatct aaacagttaa  285843
cttaaaaatt tttcttaaaa acataaatta tattataatt gaatattctt ggttgttaag  285903
tagaaaatag tatcatgtct aatcgtaaca taaagaagca gcatacatgt atgctactca  285963
attcgtttag ttgctagtat actgaaacta cttgagtcaa tccttttcat gtataatatg  286023
atgcccttaa attttgtggt tgaatactta gacaaaacat agaattaaag gaataatat   286083
cattggtgaa ttattttgcc gtataagtag gtaaactcag aggacacacc tgttcttgac  286143
tgagaatgtt aggtatatat ttgctaccag aatcacatac ctcaaccaat agccaaattg  286203
acctgttagc attaacctat aggaaggaaa tggtttcatt tgctcttgag aaaaaaatca  286263
taaaccagtg tccgaagtat gcaaattttt cagttaagca aaatgagaag accagattat  286323
tcaccaagta atgccacaag gattgtttat gatattgtta ataattattg cctaatatat  286383
tgggttgcaa ttgatggtcc tcaaatctaa ggagatttta aaaaatgtta tatcccacat  286443
ctcatttctg agagatggtg gtacctcggg tgtctaatgc cttgggaata agatcctagc  286503
ctctcctaat atgctgagtg cctttctgcc tttggtccct cacacaagct gttccatcta  286563
gtgcagaaac ctggtgtgtt ctgattccca taacgggtc  attctcattt taaaaactca  286623
tttcacgcat tgccttctgt tgccttctga agaccttttc tcctggcctt tcctgaccat  286683
tctgtctatg caagaactct ttctcttctt cattctcatt attctctatc atagcatata  286743
atcctctgat catttaaaat aatccatatt gcgttttag  aagcttgaac attgctaaat  286803
agatatatag aaaatatatg ttgaatgaac aaatttcctt caaacccagg atagcataaa  286863
ggcaattaaa aaatgttagt tcggccggga gcagaggttc ctgcctgtaa tcccagaact  286923
ttggaaggcc aaggtgggtg gatcactcga ggccggagt  tcgagaccag cctgccaac   286983
atggcgaaac cctgtctcta caaatgtaca aaaattaacc tggtgcggtg gtgggcacct  287043
gtaatcccag ctactcggga gactgaggca tgagaattgc ttggacctga gaggtggagg  287103
ttgccgctag ctgagatttg gcactgggca acagagtgag actctgtcta aaaataacaa  287163
taatatgtta cttgaatgaa tgattggatt ttagaccaaa ggactatttg atgtaaaatg  287223
ttgtcaatgt ctatactagt ttatgagtta cttcagaaat gtcttttgag agcaaggcct  287283
ctaataaaac atcatatccc ccaaagaaca gttgccaatt tattgcaagt ttttatagct  287343
tattatattt atctttcaaa ccatatatat ataaacatat ggttgttatc tgactgtctg  287403
gaagaaataa tgctctctag aaatattgtc atgttccaac tttcattcaa tgttttttaa  287463
agtaaaatat gcttagaggg caatagtttt ccatttctag aacaagtttc acaattatat  287523
gtataaattg aagtgtattg gcttttgata gcaaaagcta taatactaca aatgtctaaa  287583
ttgtatttg  acattattaa atataaattg agaagtgtga ggcagtgcac tgggctcaag  287643
atttgaactt gaggctttgc tttaaagaac aatataaact aagatagatt ttttttccta  287703
aaatcacagt gacatgtatt ttcttggatt agtgaacagt gtggctcata gatgggtttt  287763
tacttttagt ccaaagcaac aatgaaagca tataaagttt tcattgccta tttaggatat  287823
```

```
attataagca tattcagcat ggggctataa ttttgtgaca taaaatatta tttataaagt  287883
cttgacattt aaaaatagtt ttaaacactt tctttaaaaa aaacattaac tcaagctcat  287943
tacttttacc aaaatgtagt atagctaatg gaaaagtaat acaaaattat gttaattaga  288003
ttgttttaaa aatcccttca acatggaaaa gtatcatgtt ttatgatttg atatatgaaa  288063
ctgagcatct gtgaacaaat ttaattttaa aagaaaagt aaatcatatt tagccctctt  288123
tttttcaaat gttagagaaa aataaaaaag ctgaggaaat acagctagtg atttctgatc  288183
ttcctttagg aaatcctgac attccagaga aacttggata gactctgaag gattaaccca  288243
tttctgactt tcaggaagt ttatctttca tttaaaagga tatctgatgg ggtgggatac   288303
aaaacttaaa ataagaata tgttaaatgc catctcaggg atgcaagttt aacagcggtg    288363
gtattgggct ttagaaacat ataaaaacat gacattaaca taaaaaatt acaaaaaaat    288423
attaaaatga gcataaagt gttttttgtt tgtttgtttg cttgcctgtg tataaacacg    288483
aaagtggtac atctctcatt taagttatgg cccatgtact tgaaacaatt tttttgcttt   288543
ctaagtgatt gtataatgaa tggcctaagc taacatttac tttagcattc actctgtcct  288603
agtctatccg tgtgtcagct gagttactgt cagaggcttg cttggcttgt ctatctctga  288663
cctctgcatt ctgaatttgc tctgatgaag ttttgtggcc tagagcatga tttctgcaag  288723
tcatctgtga gtgtggcgcc tgctcagtct aaggactaga gtctgataga tcagagagag  288783
gcaagaatag actcagatgc cgtcagtttt ggaggccaat gaaaagaagg aaacaaaact   288843
gaacagcagc tgtgttgaag gctgtgcaag gccatcagaa attgggttct tgaggtggat   288903
tggaggagaa cagcctctgg atgtctgctg ggcagtgacg atgtgtctgg aggctttgac  288963
attggattca ttaggcattg ctaatgtaca caaaaaatgt agcaaaaatg atgcctgttt  289023
ctgggtgaga acatctggag caccatagaa gatgtgggag taccttcacg tctcaggcat  289083
tatccatagg cttcgcttga aaaagttca gtttacttct tatcactaga aagagagttt    289143
cactaataat agttattata ataaacagat tattaaaaga tgacagagaa atgtgacatt   289203
ataaggtttt gcagaaagaa taaaatatta aagcaaaatt tgaaattgtt tttctaagtg   289263
gataaaactt ttccaaactc caaaatttca ggatcatatg atttgcatta aatgacatag    289323
attttttta taaaaccacc aaattattta atttaaattt gaattattcc tcatctatgg    289383
aaggagcata ctgcatttta aataaggaat atatttcaat attataactc agagagctat   289443
aaattgtgat tttcttgaag acattcatta catgttggag aaaatcatga gactgtaaat   289503
tgaaatgttt aaaactgatg tgaaaaagga aaaatcctt atttctaaaa taaagtgagg    289563
gaggaatggg agacggtgaa agtatataaa gcgtaagaat gaatatgttc cggagatcta  289623
ttttacagca tggcaactag ttaataataa cgtattgtat tttgtactca aaaaatttta    289683
caagaataga tcttaaaagt tctcaccaca aaaataagta tgtgaggtga tttaatcatt   289743
gtacaatgca tttgtatata tcaaaacatg agactgtata ctataaatgt ataccatttt   289803
taaatttgtc attctatctt aataaagctg ggaaaaaata aaataaaggg aaaataaatc  289863
attgaaccac cattagtgtt ggtatacagt ggattatctg tgctttctaa taatttacat   289923
atatgaagat tatcttacgt ttagtgctta aaaagaattt aaaatagtga ttctattatg   289983
tgtaaatgga gtatacagtg ggcatatttc ttttgtttac tgggatatgc tttgtgcaag   290043
aaaaaatcta gaagcagtaa tcttggtcat tttgatgtaa agtaagagta atccaaataa  290103
agtcattttg ctgagagatg agaggaagct ggtattttaa ataaaggatt tcttatgcta  290163
```

```
atttcaaggt agaagttttg gtgtgtgcta attttgcttg aaatatcaaa atggctatgt  290223
catattagat taaaaataga attctttctc ctatggtttt tattgtttaa aaaggatttt  290283
ttaaaatgca gcttaaatga agagagtact ctccattttt ggttggatcc tacattgcaa  290343
tactcattta ggcatatttg ctttaaatga ccaggtacac taattaaaaa gaaaacaatt  290403
taccaggagc tgtatcaagt acagccctgc aaacggtata agcttttcc gagaatccat  290463 attgtccttg gacttggctg ttgtattata ctttaaacgg aattgattgt atggttgtaa  290523
tgaaagtagc agattgattt ttatccagtg ttacaaagag taaatagaaa aatgttcctg  290583
tcttgacctg cattcgtaac caatgggatt tgctggcttt agacccaatc tttaataaga  290643
gataacatgc aaatgtaata aaactggctt cgaagtttaa ggatcttttc aatgctcatc  290703
aaagatgttt gttgaggcat ttaaatgtgt tgtattgatt agatcacaat cacctaggaa  290763
atgttacttt ctttaaatgt tattcataat ttattatgta attagcattc atagagttgt  290823
gcctttatac acatattaag attattgaag tgcgggttat gacacaatgg tatacctttt  290883
aattgtcctt aaaattgaat tgtctttat tgttatttaa gcaaatgatg atggtttaat  290943
gactgattat ttgtgagtaa attttttacat tgcaaaatat tagagaaagg tgtaattggc  291003
ttactatagc aggatattgt agcagtgttt cttgaagggt ctattcctgc tgaattcaga  291063
gttattgcat tatttattaa aaactgaaat acttgttcc aatagtgaac tcagtctttt  291123
ttctccacct tttcttggta atttagaagt taaccaaata tgcgtgttat agttacattt  291183
tagattctaa ttttttaggac ttcatgagcc tctattcctg ttcatcattt tgtaaacaga  291243
actcaagccc acaaaacaag gaatttaaac tataaagtgc agttgataaa tttgctttgc  291303
tataaatgaa gggatgcaaa aaaaaaaagt aacaattcat ttgtaagcaa cagtttcttc  291363
acacattatg tgactttttt tggatttgtt ttatgttttg ggtaaaacag tttagtataa  291423
tgatgcctaa atgagacaaa acaaaataaa ttaaaaaaca aaacaaaaac aaaaactaac  291483
acatttgact gccgatgttt ctcagttgta gcttccaaga gctctctatt cttcccagcc  291543
cacttgatac cctgcaggtt gtggcagaca attcacagga aaagcttaga catcgagctt  291603
gcacgcttct tgactccatt ttaaaccttt tgttcacacc agggtggcat tttttcacac  291663
cgcatgtggc agttttgact cctatccaac ttgtcttata aaatcaaagt ctgtgatttt  291723
tacattcacg gggctgcttc ctgaaccgct actactgttt gtgtctttcc tagtgattgg  291783
tgcagaagtt tatagcaaaa tgtgttttag ggagagggag gaagaagaat gcaatatgaa  291843
aaatgttctg ggcctgaaac acaggaaata aattttgaat aaaacagagg ttgactctga  291903
aaagatcata cccgaaataa aatacactgg cctctatttc tattattttt tgcagcacta  291963
tgctgggtgt tcaggtaaat tctttatgga aacaatacaa tgcatcatt ttcaggttgc  292023 atgatgttat ttttaaaaag ctgtcatgta attgcaaaac aaagtcttat cctcagagcc  292083
gtacagttat tttcttatat aatatttat aatattcagt gagtgcaaat gaattttact  292143
tttagataaa accatttggt atgctccact taactatgaa caaaacaaaa cctattattt  292203
taaaaatcta tactataaac cacacattta aacaatttca ataacaacat catcattcgg  292263 aaactttct tctttcccct atgtttaatt aaaaatatca cttcagtcat ttatactttc  292323
taaatataag ttgtacagct atttcaaata aattacatga agaggatagt cataaaataa  292383
caacagaagt gaaaaatttt accaaatacc aaagtaggta aattggcttt cttctgtaat  292443
tattaggaag acataaaact atagatagga aatctctgca gacaatctga cagtaatcgc  292503
tatataaatc tttatatttt tcctttgaaa ttcttatttt gttaaaatat catctttag   292563
```

```
ttgtgttagc aaaaacataa cgaaagaata ttctaaaata tttgcaaggc atatgtttaa   292623
ttcagttatt tttttgtgta gggaggacag aggaggattt ctgctttcat caacaaatag   292683
aaaatcataa ttatattatt ttttatattt ttgcaagtta tagaataagc actcttattt   292743
ttaaattact acttttaaaa cattaacaat tcattcacca agaaatcagt caatagaagt   292803
aaatctttat gaagtaataa gtatttgtga acagtggtaa acttcaagat aaatattatg   292863
acgtatttaa tttagctttt agctacaaaa ccaacttaat gaaatcattt cagctaattc   292923
aaattgtata attggtatat caaaataacc aaattattgt atttaagaaa aaaataacaa   292983
atagttgtag attatagtct tattcctcct tccagggaat acctaattaa attaagtgca   293043
tttgaattat tcattacaat atttgaaata tgaaatggat ccaataaatt gagaaagact   293103
tcaatttaga atttagattt ttttttttaaa ctttctggac aagaacatag ggaaatagca   293163
ttttgttgta agtcttgtaa cagtaggcat actagcagac agaacaactg tacactttcc   293223 cttcacaga tagaaaacta tttcaactac aatttctata aagtattagg gaagaaaata   293283
caaacaattt tcaagaataa ctaaatccaa atggttaatg taagtaaaaa tctatttaaa   293343
acaaatgaat tgcaataaat gttatagtct gggatttctt tttattatgc acagatattt   293403
atcaagtaca agttttgcc cctcttttag ttaatttaaa aatttgacct cataagaaat   293463 agaaggaaa atatttttg tatttgcata tacaaatttt ataagatca aataaaatcc   293523 ttgtcattaa aagcaaaaca aacaattgaa agcaagtgaa atattcaaat aaacatatac   293583
gtatttaacc caagtttaat attaagccct cttataaaac taaacggcat ctagagatct   293643
cacaaagcat ttgaaactaa aaatatgaaa aacaaagaaa atcatctaaa gaaaggtaag   293703
tttatgaaat aaaattacc tacttttgca gctgttgtat ttgttgaaaa aagtatgac   293763 tttatttcat gtgcatgcca aagaatgtag aaatactgta tatttagttc atcatttctc   293823
attatctagt atagaaaacc cacaacttttt attactttaa atttcttatt ttctaccctc   293883
cccgcctatg ccctcgatgt cttcagagtc tcttctggcc agcatatctt ctgcttgagg   293943
tggatcaaaa taaagccccc aaacagacac acacaaaata accaccatcc agctgaggag   294003
aaatagtttt tctgccttg ccctatcctt atgtgttaat aaaatcagct catacattct   294063
gccacaaaat tcagcttgga agtaatcctc tgctacttag agctggatga aaagagtact   294123
cattgtgaat tatgtttcat ctgtcacaat aaccttcttt attctgtcag ggacctcccc   294183
tttgcctgtg gcaattagag aaaataggta tgcgttgaag tatgaaatag tgggttctta   294243
aaatgaaaca aaacaaaaca gaaactgatg acacatacag acagtacttg ctaagcaata   294303
tactgcagat tagtagagga ggcattttaa agtcattctg attttacaag aacacagtaa   294363
aagaatgctt tttagaatga gcaggtgtta tagttgctat tagttattgt caacattagt   294423
tattgatgac aagctgtgaa ttgtaattgt actaaaaatg aaatgtgaaa atctttttat   294483
attgtgtact ttctaattaa atcatgccat aagatatata tcataaatat atagtattta   294543
tttaacatat gaaatcgcca tgattttata tgcctttcac agatcataat gaatttatgt   294603
gcttttgagt ctattttaat gctccagaat aacattttg caaatttttt aatgggcaaa   294663
aacaaagaaa aactttccct tgaaacagag cttatcagac aattttgttt aatttaaaat   294723
caatgtgatt atttgattta cttactctta caaatcactg aaattacctg gaggcagttc   294783
aagttcacct ttctggaata aacctgttaa atgatagaca ccatctcatt atctccttga   294843
aagaacacct caacttttg gcttcatagg ttacagtcaa agttatacta tctctagtta   294903
```

```
caaatgaatt aatctagaag atcttaaaaa gcttaaaagg aaaacaaaca tagttgacag  294963 aaagaaaat  gctccttcta ataccaaaag aaagtcactg ctgacgaagt aactgaaacg  295023
gtcatcgtaa cagttggata aagacatata ataatttaa  gctaacacga aattcataaa  295083
gtctgaagaa aaaattcttg aggctaaaag gaaaaccttt tggcccactg cacaggttgg  295143
gcacaaaagt gcttgctaag ctatctattt cacacatgca acgacagaag gttcgatatt  295203
cattcgatcg atgagtgaaa aggcacaatg gcaaatcag  acagacttct tttcaaatac  295263
agatctccaa tgtcccctc  cagtctgcag atgcacggct ggtggtgtgg ctcagacgga  295323
gcaagggtta catcaaggct attctctgga ccgtgcaaac agtctagacc aatgacctgc  295383
agcatcatgt cctttgaaga agaggcaagt tcggtcatga tgaagaaaaa tcaaggcgta  295443 cccctttta  caatagggag cagctcgagg ctgcaaagag gtaagcaggg tgagaagaaa  295503
acggcatctg cttccatggt tacaggccaa ctatgagaac cttgcttttc aaggagtct   295563 gttctcaggc tccctcacag ggtatgtcat gcattataag caaaggcagg ttgagctgaa  295623
atccgcatag ttatttcaga gtaaaatgat acggagcaca tggctggcag aaaaaacagt  295683
cacatgactg ttaagaacca gacttgggct atttcagaaa agatttttt  tttttcttat  295743 atcagttaaa gaaagacagt aaatttgtat aaaacaaaca accatgataa acatgatttt  295803
catttctcag gcttttatgt gagcagaggt caagggtcaa gacacccctc cactccaatg  295863
gcaggaccat acagcttatt gttaatatag ctttattatg gatatcattt taaaatattt  295923
tcctcttttg ggcggaccat aacatagaat ttgtgttctt gtgaaatttc tctctctgac  295983
ctgattctct ttgatgtgct ccccaggatt ttctgtgttt tagatctcat gttcatttcc  296043
gttgttagat ctcatgcgga gaggtagaag gtttggtgag aaacttcctt gttgtgtggt  296103
tactcctcta agatagcgcg agcttgcctc tgcctcgtga aatctgctta tggataattc  296163
aaatctgcag caaaatcatt cgcctctgac aatcgtcctg tttctaattc atgcctttgt  296223
agtttattcg atgtgtaata catcaatgag tctatagatt ctaatatcaa tgtttttttc  296283
ttttctgcaa gataaagttg aatttcataa tatgatacac tagcagctaa tgttatctga  296343
ataaaatttt gacaagcatg aaatgtaaca tattctgtat tattaaggaa agaccatagt  296403
atatagtaac cacacaaaat gcacacatat ataaaattaa catggataag acattcctct  296463
gacaatgtac cacaactcaa tattagaaga attaatattg ggttatgttc taactatgca  296523
caattaacta cagatgttcc atgcagtgta cctttgagc  aattttttgtt tgcaagtata  296583 ttgttaaaat tagggagtga aaaaggaaag aatctttcaa aggacaaggc atgaaaacaa  296643
ctttcattaa atttattttt cagaatttat gtattttaat ataatgggt  accatatagt  296703 tttgtgtgta gatattcatt tcaaatactg accttgtagg aaaatatcct tatagcttcg  296763
caaaagcaat gaagtgttgg tgatcatggt agaaacaatt ttacgctttc aattaagaaa  296823
ccagagaaat atttgctggt atgtttctca tatagatgcc ttgatttgag ttgggttcat  296883
gggcaaacat atgcttattg tttggtttct ttgaatgtgt tgaggtacat tagtttctat  296943
tcttgcatgg tgagaataac ttaaggtcta aaaaagtga  gctattggaa tgtcactatt  297003
atagtataat aatctataca ctagtataag cactgaatgt attatcttaa agtagccatg  297063 ttctattgc  tttaaataat ttacatacta ccaaaacaat tcaacatcag agtttctttg  297123
atgtaacaac ggatcacact ttctcccaaa ggtcaagtgg caaatatttc tccaatgaaa  297183
aatctacctg tcagttctcc aaaggaaaac aaaacaaaac aaaacaaat  acacgaaggt  297243 ttatacattg catgataatt tgtgagttgt gattaaacgg aattgtgtct attacctgaa  297303
```

```
atctgttgca aaatagatag ttggattctt gttattttt cagttagcat ttagcctact  297363
cctgcttttt tgtttttcaa aaacatgttc agtgttagga atatttacat gtgaccataa  297423
attagatgaa cttgctaagt gtggacatgt ttaaacactt agaaacattc taatagagtc  297483
aaattggtgg ttcataaaat gctattattt aaacatttaa caaccaggta aaaatattta  297543
atattgagta tttagtggga aatgacagct tcttgccttt aaaaaattct ctatatctga  297603
gttatcaaat agctgtgtat tatgtacatc ctgcatatag tttgcaaaac ctccactcct  297663
aacatgtgtt agatttaaat attcctttaa attacatttt agattaatta ttgagttttg  297723
ccctcctcac ttcaaaattt gtttaaaaaa ggaaaactaa acttggcctt gcctaatgga  297783
gcatttatcc ttaaacgtga aaaaagagtc tgaaatgttt cagtgactta gtgtcccgat  297843
agtgctctga atatagtata tgctcaataa atacctctct aataaatgaa tacaactatg  297903
gttgcaccaa tgaaacaatt ttcagaataa tccagtctca tgaaaatcag gaaatagtcc  297963
cttctattta ttcatatatc gtttctaacc ttttcgtat gaccgttcta tatgcatgaa  298023
tccttcttgt cagtaatttg ctattagtaa atgactactt tgtgtccagt atgactagaa  298083
gtgtgtgcct acagccacat ttcccaaaca aggtcctgtg aagcattatt attctgaaac  298143
atgttggaag gtattctgag ggaaaaaaat caaagagtca aataaatgtg agaaagatgc  298203
tatgttaaac aatggaaatt aggtttctta tgtacaatag attttaggac atttaaaaga  298263
ctaatgtata tagtgcatac ctaagaaggg tgtatagttg acatcatttc acagaactat  298323
ttaatcaact ttttcagaa aatacttagt aatgtaaat gacctaattt cacagatgtg  298383
ctcaagctgg cttaagccag attgaataaa ccaattttaa ctatctcttc ttatattcca  298443
ttttcagtga catcattttc ttagcttgaa atcagttgtg gcaggagtat ttgcaccatg  298503
gaaatcagca aatgctataa atcagggctt ttttcttt tccttttttg agactggttg  298563
ttgagcattt accagcacag cattgcctca ttttgtctct gaatccattt ttgtaggtaa  298623
gctgtgcact aaaaggtcag taagttcaga ggctttctat tcatcagact gtctaaaata  298683
caaaacaatt taaagcaaat tgtgaacatt agacataaaa gaaagggata gcattaaaaa  298743
atattggaca ctcaattttt cttttaagat ttagcggtta tatcaggatt tcaaagagtt  298803
tatgtttctg atttctttaa attacctgga taaacatcta tgtttattca tttatccctt  298863
ttctatcaaa acatttacat acactggtat gtaattgtct aatcatattt aagtgagttc  298923
tcaacatgaa agctctgaaa atctccagac atcctttaaa agtgtctcta actcagccc  298983
acttcatacg aactttgagt tcgtataatg ctgagatgaa gcatctttaa tcaggatata  299043
cactttattg catatcatgt aatttacggc attttatcag acatgtttac ctgcctgaca  299103
tcttgggtga gattttagg agaaaaacaa aaatggaaaa tctatgaata gagaatttga  299163
aaaacacatt ttaagtgata aatcaattaa ttcccaacta atcttttacc tactaaattt  299223
ctgtgaatag gttaacaagt aaaatctgta aatataggta gcgtataagt atagatattg  299283
gctaaataaa agatgtaaaa tcatgaatgg attcttcctt ggccttattg cttgaagcca  299343
tgagttctat ggtgacatgt tttgaagggc ctctggaatc tactttgtga cagtatatga  299403
gatgatttat atgagggttc taatttacct tcccaaaccc aggaacccaa agcactaggc  299463
acttcagttt acagagccct caaattaatt aatccgagtg tctattttga gccaagtttt  299523
gtgttattta tcagaaacta aaacatgact aatacatggt ttctgtcgtt gtggagccca  299583
cagtcaaatg tgagaagaaa gcagctgaaa tgtgttatca caagagaaaa ttttctgaat  299643
```

```
ataacagaat atatatatat ttgatctaaa gtgatatatc tatcaaattt aaagtgataa 299703
atatatgtgt gtgtgtgtgt gtgtgtgtat atatatatat atatatatat atatatattt 299763
aactcccaga attcttctgg tttaatccca gaatctcata acttttttgg attctactct 299823
catcacataa taggtattgg tacatcacag agagctccat attcacaaaa cattaatgaa 299883
tagtacaacc aagatggcaa tgatatgatc cttaatatag tcttgagtga ggagtaagta 299943
caggttgcgt tacagaatct tgctgtccat cctgtttgta aacataggga agaatttcac 300003
ataacgtcaa gattctcaaa ggatacttca ctattaaaga taaatacaag caattctaaa 300063
cccagtgaaa attctcacag acattcagct tagataaatac tgtatgcctg tgtgtttatg 300123
tatgaaatac atatttgaat actcattgga taagatgttc tttgtatttg gaaaaaaatc 300183
ttttggacat actaacatta tacttctgaa aactctgaag ccaatataaa gttgtaaaag 300243
gctttacttt tcattatatc aaccacgctg gaaattcata cacaatttta tcactggaaa 300303
attttcttct ctgtgccata aaacctggaa ctcttcttc aaacagcacc tcccaaattt 300363
gaaaacgtat tactgtaaaa tatttatata tgaaaggttt ttaaatgaat tattgaatgt 300423
cagatattta ataaaaatac ttttgctatt tgatagataa atttataagc actattatct 300483
ttcaatttta gataaaataa ttttatatat ttttaaagaa catatctcac atatctctgc 300543
tcttgataac aaatagtgtt tttttttttaa gaatttctat ctagaaaatt taattcattt 300603
ttctgggcct agttcaacta ttctctcttt tgtatgtctc ttctcactgg actatcttct 300663
ctttctatct ttcccccttta tatatactca tctgctcttc acttctgttc cgcttatatt 300723
tttgctaagg taggaacaaa taatggtaat aaataggtgg caaagggaaa attttaaaat 300783
atatacagaa gatctttaca ttggaatgct gtagtaattg agtctaaaac tcagctctga 300843
actttgaacc acttttttaa aaatgctgtg tttgaacctt aaaaaatgta aaataaaaac 300903
aatctccctc ccttctgaaa ggggaaatga ccttcttact cctgtccatt ctttatctg 300963
agcaatgagg ggtgaatgtg tttataaaaa gccatgttta ggctctatat tgccctgctt 301023
tccaaaaatt attgtttgtt tttactaaca taagatcacc caaagcaatt tcctttaatt 301083
agcatgtcat aaccttccta ttttttgttga gtatcaaatc catttgactt agccatggtg 301143
tgtctctgtg tatgtgcaga ccccctaatg ttaacatgtg ttaaagtaag catcgctcaa 301203
tactttgttt ttacagatgg atgtcaacta ttgtgcttgc tacattactt tgtggcctct 301263
tttgtattct ttttttctca aatgattgac tccatcttca tttacttcca ccaggctgtt 301323
caatttgct tccattaaaa agaggctcaa tcctttaaat ttcttttttt ctttgagggc 301383
cacatccatg gacctaaaat atgttttttt aaattcatat tcattatcat atattttata 301443
taaatcatat tatcagttaa taatatatat tgagtattct ttataggata ttatttattg 301503
ctttgttaat tatacttatt taatatagaa atagttatat taatactcag tattaagtaa 301563
gaataattct atgtgatagt gttactactt tatatatata tatacacata tatcaatatg 301623
tatggtgtga tggttcttct attgctatat actatacata ctgctataca tatgtataca 301683
tgatgaaata tacagttttc tatatatact gtcaaatatt gtcaatata tttagtcaaa 301743
tacatatagt ttgactatat atagttatat tcatatatag gatatatgaa tatataaata 301803
tagaatatat ttattcatat atatcctata tataagaata tataaacta tatgtaagcc 301863
aaatatatat aaaagtaaca aatatatttt actatatatt tgaatatata aatgtatttg 301923
aatatatatg tatttgaata tataaatta tgcaaaataa aaacataaat aaaatatata 301983
tagtcaaata tgtatatata taagaataac atttctatgt gatggatctt ctattgctgt 302043
```

```
ctgtctatct agtcaaatat atatcatcat gatatatata tttgaaggca gataggttct    302103
ctagttttat accagttaag cagttaactt tagtaactct aagtgagagt aactcttcaa    302163
gtgaaacttt gaaagagtaa cagctcacag gagtgtaagt gtttctcctt gaattttaca    302223
gtgctcctcc ctcttctttg ggataaagga ttggagaggg tgattctttc tgcctctttt    302283
cgtcctcctt taaatgaatt attatctttt tactccagca ttccaggact cagggtgtac    302343
ttttttaacaa cacacctaaa agttgttttg ttttaccaat tcttttttaa aaaccccaaa   302403
tcatccagaa agcagttgct cctctttcat cctgtaatga acctgcagag taacctgggg    302463
atattgttaa tactcaatta agattcaggc atctggggtg gagtctgaga atctgcattt    302523
ccaataagac cccaggaggt gatgatgatg ctggcctatt ggttgaggtt agaatgtgag    302583
agttagaaga ctttgcttca agttttcgct ttgtcccaat tctgatctta acctagagac    302643
ttaacctccc tgatcctgtt ccttatctat aaaatgggtg gaatcatgtt tcttctgcct    302703
gcctacccat agaattgttc tgtacttcaa attaaattaa ggaggaaagc actttataac    302763
aaaagaacag aagagaaggt aatgcagcag gatatttcgc cttatttctt gaagagtata   302823
ttttataccca gtaacctaat ttcctttaga gtttgcccag ttagcctaaa atgatgaccc   302883
ctgttttaaa gttatcttca gtagttcttt atcctctttt actctcctct ttttgttcat    302943
ttattcattc atcagacact tattgtgtag ctactatgca caatacattg tgccagctgc    303003
tgtggttgca attgactctt tccatttact tctacttttt tctcattctt tcaaatactt    303063
tgatttattg atttcactct gtgctccatg tctcccatat cttttacttc tgccttcagt    303123
gggatgttga aatcactaat ttgaaggttg cattcgtctc tttgaatcaa ttgtatttaa    303183
tttcacaaat atttactgat tccccattat atggcagaat ctctacaaaa agaatacaga    303243
attgaagaac agtactttt tttaggaaaa aaagtttat atcctatttg ggaaataaga     303303
tttttaataa tttttcaatg aactatagta ccaggcagga gattttttggt gtcataagaa   303363
acactttaaa ggaggaagtc acagctgact tgaagggttt gaaaaagact tcttaaaaga   303423
tggctaaatt gtgacagaaa tagatgagag gaagaagagg atagatatta caggtggaac    303483
aaattatacc ttcccctctc tttgctttca ttcatggtga gtgacttggg aaaatggtct    303543
ggtgtaggca aaaaggtctt aaaagtatat gagggaaagc tggaagctct tattggagtc    303603
acactgtgat agccttggat ggaagctatg ggagtctgta cttaatttgg ggggcattaa    303663
gaagtctttg aaagttaatg ttactgttga ccttcctgcc atgcattcaa agtcaacctt    303723
taattcaatt ctgtggaatt taaatgtaag tcaactgtcg ggctctgggt ttgtacagag    303783
cagattggca acctccaggt agtcttttgc cagttttcat caaggcagca tatcataatg   303843
gacacaatat agtggactgc atgaggacgc ccggctgcta atcctggttc actaacttgc   303903
tagccttttg accttagaga aggcattcat ctgtctgagt cttcagttct ttcttataat    303963
gatgggaata acaaaatgcc tgttttcaaa gtttatgatg agagataaat atgaaagaaa   304023
aataaatttt gaaatgtaa actttgaaag agcaacagct cactggagta taccggtttc    304083
tccttgaatt ttgtagtgcg cctccctatt ctttgggata aacgattgga gagggtgatt   304143
atttctgcct ctttttcctcc tcctttaaat gaattattat cttttcactc catcattcca   304203
ggactcaggg cgtacttttt gagaacacac ataaaagttg ttttgtttta ccagctctcc    304263
ttcaaaaccc ccaaatcatc cagaaagctg ttgctcctct ttcatcctgt catgaatttt    304323
tgttcatggg aggttatatt aactacattg tcattctgac cttagcttaa atatcaccac    304383
```

```
ttaagatatc caccacccct gggcacagcc acagtgtccc tcatggaacc tctcaccatc    304443
tttttatttt ccttatggaa ttgccttcct catttatttg cttgtatatt gcatgtctct    304503
ttagccaata agattttatt agttcattat gtggcagaca ctgtcacagg aactgggaaa    304563
atgtgagtgg gtgtgtcctt aaagaaacag acacataaat attgatacta ataatgatct    304623
atttacctat gtgtataaat gccagtaagt aaaaagtgct ataagaaaa ataaagcaag    304683 ctgaaggatt agagactgaa ggttattatg ccttttttt tttttttttt tttggtcaga    304743 ggttcaggc atggttcctt gattaggtgc tatttactca aagaccaaga ggaagtaaga    304803
gagtgtgcca agcctgtacc tagagagaaa gtggtccaag cacagggaat tgtgagtgca    304863
aaagctttaa ggtggagtca tgtgtggtat gttgaaagac aaggtaggag gccagggtgg    304923
ctagagtgca gtgagccagc agacagcagt agacactgag gccagagggt tagaggacag    304983
ggcctgggca ccatcaaata agctttggag ttcctgttag ggtcggagat ctcactcagt    305043
gtgacatggg gagcctctcc ggaggctttg ggcagaagag tggtatcatc ccactcaagt    305103
cacgtcggct gccatgtggt gatgaggcta ttaggtggct agtgtcaaag aagggagaag    305163
cagcgttata tcggaatggg ctcctaccaa ctcagcagaa gccatgtgtg catctcttcc    305223
tgaaccatgc cctcatgtca cttgaaatta gccacggcga aggtaagtcc atgtggaaat    305283
ctgcaaatac tatagaggat ttcttctccc tcccttgtcc cttcccttc tcgtcttcc    305343 tgcatttctt cctttcttct tcttcttctt cctcctcctc cagttccttc ttttctcttt    305403 tttttacaa cattatatat acttatttat tgtttataag caaagttgtt gataaacact    305463
taccagcaca tctcagaaga gacttttaga agtgtattgc aaccatttat gtaaaagatg    305523
gtggtggctt agactagcat ggtaacaaag gaggtgatag gaagtggtga gattctgcaa    305583
ggaatcttca aaggaagcac ggacaggttt tactgaatga ctaagaaaac ggtggagaaa    305643
acattcctcg acaaaatagt agagaaaata atgagtgaag cctggcttcc aggttttcat    305703
cttagtatct aaaagaatag ttatcgtgga ttaagatgga aatggcttca ataaatgagc    305763
agtttgtgaa atgagtgtta aaaacctgat ttcagacata taaagattga catcttaagg    305823
tgtagccaag tggagatatt gagtagaaag ttggatatat gagcttcgta ctcaggaaag    305883
gagtctggat tggagatatc aatttgggaa gtatctgcaa ggagaatagt atgattctgt    305943
tctccctaat ttaaatgggg gctgattgca tatcagaaca gagaggcaat gccaccatac    306003
ttccactgca tcttttgcag actgctgagt caggtgtttt tttgatgctt tttataattt    306063
taatataatt tgagcaacca aatgaaagtt gctatggatt gattgaaccc ttactttttc    306123
tgcaattcat tttcatagtt atgcttcttg cttcctggaa ccaatcagct acagcatcac    306183
ttctcaaaat gtggtctcag tactgcctac atcagattaa ataggtgcat tgtaaaatgt    306243
agatttctgc attccagtgt cagacctatt taatcttaat attagtccag ggacccgaaa    306303
atatccattt tacaaaacaa atacgcattg tcttttattat gcaaataaca atttggcccc    306363
tcctgatgta atgtttaaat ataaagttta atatctatcg ttttgtaagg attcccatgg    306423
caaaaaaaaa aaattgttta tatcatttat atatttaaac ctgcctgtac atattctagg    306483
ttgttcagat taaatagat ttaatttcag tcatatagat ttcaatctta gttaaatagg    306543
aaaaccaaat ttaatcatct tttttttttt ttttttgagga aaagtgtaat tttagggcat    306603
actgtagata tactgttcaa aacaggaaac ctgagttttc aactgtaggt attggattgc    306663
tatggtaatt taaatagcaa atatttctga ttttctcatg ttttgggtga cagaatcgtg    306723
ttgcatttcc cagctctcgt gatttagatg gtatagaaaa gtaattgtga ccaagtgtgc    306783
```

```
ctggggccag agtatttaat ttccagtgtt ccttcatctt acttgtgtct ttctccacat  306843
ttgaggtgga agctgccctg ttatcctgct tagctaagat gctacagtca gcaaagcttc  306903
cctgctaacc tgtaatgaac gtttaatgtg agggagaaat actttgtgat tttaaactgg  306963
ttggtactcc agcataatct aaagcatcct gactgattgt gactttctct agcaaaaatg  307023
aactgctcta acctgagtta tctcctattt aacatgctga cagcgggaat tgatctaagg  307083
taattcattg ccccaacaaa ttagggattt ttttgtcaat attttgacct ttgacaaatg  307143
agagataggt aggaggtaaa ggtctcttct tttacaaatt tgctactaat taggttgttt  307203
caaaaacaaa aacaaaccaa gaaacaaatg ttaccgatcg atttctgcaa aggtagagac  307263
ttttattaac aatcaggtat gaaaccaaat agcttgttct gaataatctg gagggtgtct  307323
ctgttccttg tcttttttagg tatgccatcc agcactttgt agaaaaggtt cactgcagag  307383
caaatgcaac tgtattctag tagcaggagc aatgagcctt ctagtagtac caggtgaagg  307443
accctcctta tatgtccagg agtgggtagc aattcaaata gattttagat caaaggtacc  307503
acttcaaaga tgttagactc acaaccttttt cctggggtta ttttactttg ttcccacagt  307563
ggggagatta cccagtgttt cttgccaatc acatatcttc atcatcattt ttctcatcaa  307623
tgaaaaatta tttgtaactg tcttgtaaat taccaagctc ccatgggtag tttcacagtg  307683
caatatttgg agacttgaag catttgccac aggtgcccct agagtataaa ctactgatta  307743
ggaaatggta gatcttaacc aatgtaaaga gtggatctct aattagattt ctttaaatct  307803
tagctaactt cttctagtgt gtacattaaa gaaaaaccaa ggtactgtga aatctctcta  307863
ctggagcatt ttaaagtaaa gtataggcac taacagaatt aattacagat ttttgtttat  307923
tttcccctat gttctactag gactacaaaa accataaaac tcaccagaat cttacattat  307983
tttattcaac aaatgtagaa gtattgcttg atcaagtaat gtggtgcttg atttttaaca  308043
atttactgta gactttgtta tcaatatttta actagtttac ttcaatatta aacagatcaa  308103
taaccatttg ttatttaaac aaatgtttaa ccacaaacat acctatatgt atatggatgt  308163
gtgtgtttgt gtatgtatgt ataattgagc tgcttatata tcatgtagtt ttttaaacaa  308223
aaaaatagat aatagcatct taaaattaaa tcttgagaca ttgggttata agtttcaatt  308283
ttgcttttct ttctgcgtat tcatggtctg tagaggagac tagacttccc taatgtttta  308343
gtttccaaat attttgccaa gtatgaatga actaggtcaa cgaaggaaaa cattctttct  308403
gaagcctaca ttaatattct actgtttgaa aaactgggct aacccttcaa tcattttgtt  308463
aatatttgta gcttctcaca gagttgtaaa acctcataag taaacatagg tttttcaaat  308523
ctttacctca ttttaaattc ttttagttac tgttgtgaat aaagaatttc tggatggcta  308583
atatcagcta ataagattag taaggaatga attgtaaata gagcatataa aattacttat  308643
tttcaaatac ttcttaaaaa cttgaaatag tgtctctagt attataattt tatacatttg  308703
acttttatg atatatttaa tggtaacatt taaaataaaa ctgttttta aaagtagcat  308763
tttactagcc caatgactga aaaaaagttt gtaaatttat agattttaaa caaattgaat  308823
ggtgctagtt tttctattca cttttgtctc taaaatattt ttggtatttt gtaaacagca  308883
ataaaaatag caagagtaaa atttgacttc atggaaactt aactgtgact ggacctcttt  308943
taataatttt tattaatttt gactcctgtg aattttgatg tttggaggtt atatatttcc  309003
aaacttaaaa aacagaccta caataaaatta gattgattat tcctagtgaa gtactttact  309063
aatattattg atattattgt gtagtagtta ttagggagtc taagaggaag actattttta  309123
```

```
ttataggqag gatggtttca actgacaggt tttaaactaa aatgtttaag cattttagac    309183
attctatttt aataagtatg ttttagtttt aatttttta agaataaatg tgaaatgaat    309243
gatttggata taggttagtt tatggaaatt tttgatgatg actatgtatt gattactttt    309303
catttcaggt tattgattat aaaatggca ttataaagag atagctccaa aataacagtg    309363
tcttaattac ttgaaagaca tgttgtttta atattgcact gtaacatacc ataccatatt   309423
tggtgatttt ttttctctat tccagttttg tatgctactg tagggcatag aatgtgagta   309483
gcaccoctag aactcaaagt atatttttat gtgaagctga aatgttttta acttgactca   309543
gccagttaat aattttggga tttggcaagc ttcagtacgg tcctatttt gagaaaagcc    309603
aacaaaagta tttatcttct aattcaatgt cctttttcc cttaaagaga ttttgtgtg     309663
caaatgctta taaatgtatt gttattacag taacactaac atattctatt tctttctacg   309723
gtgctaaaaa taattaacat ttatggtaca tttaaacttt tgtcagtcag aagatctagt   309783
tattaaacca aatgaaatag gtataacaat accttctgta ttggagttag attatctctg   309843
aaagtaatac acacatcaga tgttatatgg taccaccgct acctcaaaac catgcatcct   309903
aatatgttta tttataataa aaattttaaa tcagtcatac attttcttct gaaatgcata   309963
catagcatat gcaatggact ggtggaaata ctgtaccatt tctcattact tattagaatg   310023
acttaaaata ttggttttgg ctaaacaact aatcagtatt ttagtggaac agatttacaa   310083
cctttcctga cagtaaaata cacttttgt atataacatt tcttacccaa agacagttgg    310143
cacagtagta aacttaataa tcacctccag aaataaaaca tggaaaaaca atgttaaatt   310203
aaaaacaatt ggcaacttta gatatacgta tatgcttgtg tgtatgttaa tgtgtgtata   310263
ttatacacac agagtttata caggcatata ataatatacc attatgtatt atatatatat   310323
ataacataga catataatat atatttaaat aaattatata agtatatata agtaaattat   310383
ataaatacat ataaatatgt aaacataatt atatagatat ataattataa aggcaataga   310443
ttctaaaact caaaacagac acatataaag agaaagttac taatcatttc ctcctgtcat   310503
cctgaggcag ccaatgtcag agtgtggtgt gtgtttcttt acctcactca tgagcttctc   310563
caagctcaga aagcacagat gcacgtttgt acatctcttt tgttagaaag agagatgtgg   310623
ttttgtttct gtggtttgtt tttatacaga aactatcaaa cacattgctc ttcattttgt   310683
tttttataga tacccttca aattaatata cagaatattc atattaaggc atgctatttt    310743
taatttaagg aaataaaaat ctggatattc attgtctttc ttttatcata gccatagtaa   310803
aaagtaccaa tattgtcatg gactgcaaat ctcagggata ttttaactcc agatctggta   310863
atcgcatgaa aatgactctg atgtctatgg gaaagcagga aaccaagatt tacaaagtga   310923
attgcaattt ggtagacaat gttcttttac tgatctactt gttatctagt gctatctatc   310983
tccaaaaata cctgatcctc atggtagaat acatgcttca ctatgatata atggttgtag   311043
ttttcagaca ccgtatttgg tgaaaaaat cacattataa aaccatacgt cagtagaaag    311103
gaatgagtta gggaatagat ttgctaagct tctaccaatg gtataaaggc ggatgcagga   311163
ttttctttag attaagacta ggtataatga agagagcaaa aataagttaa gccatggatt   311223
aatccaagtg aatacagttc aaggaaaata aacatgatac aatcatatgt aagagtaaat   311283
aatattcctc aatgaaaaca ttataacaat tttgttagaa atgccatagg ccatcagaaa   311343
gctgtatata tatatatgta ttatatattg tatacactca tctattacat atttaacatg   311403
tattacatac atattaatgt ttattatata ttcatatttc acgtagtata ctgatatagt   311463
atacctacca tactgttagg tgcatctgac ttttccatc ttaaattttg catgcacaaa    311523
```

```
gtatatttct tgttcaaaat ttaaatccta acaataatat agcaaaggta gatcatgctt  311583
ttgagaagct ttttaaatta acaagtgttt aaaagtcttt gtatatatgt ctgttacatg  311643
tgtgtgctat gtgtgtgtgt gtgtgtgtgt gtgtgtgtgt gtgtgtgtgt ttagcattga  311703
gcctaagttc caagcaacca gtgtgggtca ggcagattta gttcagctgg aacgtaagga  311763
gaaaattgac aagaatgatt caattcaatc tatcaacatt gattaaatgc ttactataca  311823
ctaggtactc ttctaaacgt tcaggtcata gtagtgatca caaaaagtcc caagcaaaca  311883
tggttcttat attctacagg tggtgctggg ggcacataga gaggaggaag acattaagcc  311943
aaaaaccaaa caaataaaaa gcatcatact gttttttgaca gtgtcaaata gtgtgaagaa  312003
aaataaagtt ggttgggtgt ctatggggag tgtttcttct atttttggtt gcagatgatt  312063
ttttgcagtt ggtagcatct gagaagagac ctgcaagaag tgaagaagta tgctaccagg  312123
catagcccgg gaaagggcag cccgaggcag ggaaaagagc cagtgaggtt ttcaaggaga  312183
gcagagtgtg gcatatttga gttataccaa agacaataaa atggtgaaat aaggccatga  312243
aaggccttgt tggccatatc aacaatattg gattgttttt cctaagtcag ttgggaagcc  312303
cttggaggcg tttgatcagt gacgtctcag ttcatatcat agataagtga atatgcatat  312363
tttaagagtt cactctgcgg ccgggcgtga tggctcacgc ctgttatccc agtactttgc  312423
gaggccaggt gggcagatca cgaggtcaag agattgagac catcctggcc aacatggcaa  312483
aaccccatct ctactaaaaa tacaaaaatt agccaggcgt ggtgacccac gcctgttatc  312543
tcagttactc gggagactga ggcaggagaa tcgcttaaac ctgggaggcg gactttgcag  312603
tgagccgaga tcacaccact gcactcccgc ctggtgacag agtgagactg tgtcacaaaa  312663
aaaaaaaaaa agagagagag ttctctctgc tacataaaaa ctagcctgag aggaaactgg  312723
gaaattggtt caacgcttat ggcagtactt tggaagagtg aacttgtaga cactaggtgc  312783
ttcaaaacag aatgatatta ataacataat atttgattta taatttatct acttctcaca  312843
acagaataga ataatatgtg tagagcttta aagcaatact agcatacagt aagttccatg  312903
gaaattctaa ctattaactt tatcctctgt atcatcataa tcaccatcat cattatccaa  312963
atccttaata gatgctcttg ggaaaaaggt cattttaaat gatattacaa atatgaccct  313023
cttttcctca ctaaagtcaa gcataagtta aaggatttga ggatgtgccc tattacagag  313083
ttgtttaaga attttacgtg taacatccaa tgttttttc atccttaagt tgttgcatga  313143
gttataatta aacctaattt aaaaaaacag ctaaactaaa ttggcattgt ttctatttac  313203
attttaaaaa ttaaatccta atcaaacttt tcctcttcat ttatatgaaa attttgtctc  313263
caaatgtgta catttatttt cagctgactt ttcccagcct gttcctctta gatagaaatg  313323
tcttctctgt actattgttt ttatatgatt ttttcaatg ctcaaccta cttgatatac  313383
atacatatac acaaccatgt acaacattca ctgtactctt tgaaattcat ggcttagcac  313443
atgaaaagta gcatattaaa cttaaaaata atacaaatat atttggttat ccttgaaaaa  313503
tataaacatt cgcaaaaaat atcaccagcc gcacatacat atattcatat aaaataatgt  313563
atattaataa aaaacttata taggcaatga tacaatcatt aagtgttagc ttggaagtag  313623
atggtatcag aaaattagaa aatagttctt gtgtaagtta ttcttctact aattggttct  313683
tagtttcctg aggactgctt tcttaaaaac agatttacat ggtatgcaga tcagttttgt  313743
gtagtgtttt tgttttgtgg ttactattat tttgttgtt ttatgtgtgt attttttaaa  313803
gtctgacaga gtgataaatg gtgctagttt taacttgagc ttcaaatact gattgatatt  313863
```

```
ttttaaacat acacctttga tacaataaca aaacaaataa aaacagagcg ttaagtcaaa 313923 tggagaaact agcacagata aaatgttcta gttttctgat ctatgcctgg caaataaatg 313983 tatgtactta gggaaatttg gtgtgttttc ctatgtgata cataaactgg ataattttaa 314043 tatattcccc attttggaca ttatattaga gtgagaaaaa cagaaaatat atttaaaatc 314103 ataaaaagta ttagtaaagt tctgaaatta aaataactcc atgagtattt ttttaagaaa 314163 atattttcaa tttagtgata aatgagtttg tatatatacg gccaaatcca aaatagtcta 314223 aagctaagat tgaggcctgt ctcagctaaa ttacataaaa tcaaatgata aaagttgaca 314283 cttaactcat cttggacttt ggatgtaaaa catatgttgc tgatgttagt ttgacatgtg 314343 tcaaacacct tcaaaatgta tgtatgaata tttatattct tcatacatac ctgtttatgg 314403 gataatattg aaattaaata acattcttag aaaattaatg tgacaatatc caaacagaat 314463 tgagatctca gacacaaaac atctgagttt aggcctattt gccattgacc tattactaaa 314523 gtgcttctga aaaatgtcct cacagaaggt tgtttggcct ttcatcctgc tccaaagtgg 314583 gtgagcatag ctcagctgat gtctacaaac tgtcagattc tatgagcaga gatcgtgttt 314643 ttccttctaa cagtataagt tgccgttgtt taatcttttg atgtggctct ggaagagaat 314703 atggtcattg gtactcactc tagggaagaa aaagagcagt tgggggtgga gggaggagga 314763 tgcagattga aagacgtaaa atagtggcaa aagacagtgt tccttctcca gaggtgaaga 314823 cctgagtccc agctgggaga catgtatcag tttctgtgcc tgggaacttc acatctttgg 314883 cacctatctt gtgctcagtg taagtccagc attaagatat atgtattttt cctactgcat 314943 agcatctaaa tggaaaccag tcatatcatt aactggttaa ttaacagata acaaagaagc 315003 caaattaaaa aacaaaaata aaattctgc ctttattaga ctaattgaga ggccccaggt 315063 tttcaccatg catggttgct ttagaaccta actccccagg aagatgtggc tccattctgc 315123 taggaagcag tctagagcag cactatgcaa agtggggtcc atgggccagg cccttctgag 315183 aacagtttga tacccattag aaaacatgga agtacaaaaa tagagagtaa gcctttagaa 315243 aatttcatag aaaatcaacc caacattgt ctgttgattc aagtaataaa atatgaatgt 315303 tttaatgtca gttttacat ttagtttctc tagttatcca cttttactgt aaattggaaa 315363 acattacttc atgatttagg aaaaaaatag tctggcttag accacagtta gtttgagaag 315423 cactggggta gcacttttag agtttcaaca cagatcaata taagacaagt gtgatcaatg 315483 gcaaagtat tttcaatccc ttgaaacatc aaggcaacaa tgaggttgca taattatatc 315543 cctaaagaaa tttacatctt tattaataag ctttgtcctc tctcttttct taagtattca 315603 tgtaaaaaca ttctgaatgc aaaaaatcat atttaaacac taaatagaat gtcagtagaa 315663 ttgcatttgt atgtgttaaa atcctattgt cattttacta taaacttctt ctctccttgc 315723 tgttattgcc taacttctac agggcatttg tatgtggcct tcttaaaaca tttactggaa 315783 agaaacttaa taaaaataaa tttatcaatc caagatgtga tttctcatga gaatcttgaa 315843 tatctgcatt tagaaattat atatatggtc atttatagaa aaaggaaag atctccttaa 315903 aaactggaat aagaaaatga tttatatagt catgctaaca aaatatctta ttttagcaac 315963 cacctgtcta tcactcttac cagtgaaaat tattcataaa atagctgctc cttataacta 316023 ggggtaagag atatgcaaac aagactgctt ttaatcttga aaagcatgca aaacaaaatt 316083 taaacataga catcaaaaga gaaaaactgt tctccaattt gtcaccaagt cattgctccc 316143 tatattaagt ccagcaattc acgaaaccct cactcattgt ttgcagtgcc ctgtagcaag 316203 ctggaagtgt ctttatatgt attattaaat tgccgttact gccatctagt gggaagaaat 316263
```

```
actccctgtc actatgtcag ggattgtaca taaagcccta aagttctaag tgtaaaggga    316323
aagccacagt ttgtgtgaat cgcagagagc aaaatggcaa actgaagaca caatctcatg    316383
acaatagaga cataatagac atctattcac cgaataagtt aaagaggtat gtaggacgaa    316443
aagaaagggt gtgggaatg catgcattca cgagaattca ttttgtgtac acccaaaatt    316503
acatctaaag tattatttct tattgaacac aggttacctg aaccaggaca ttttattaca    316563
tgtagactta ttttgtcttt accttttgaa tgtagatgga ttgttttgca tgtgcttatt    316623
aagtcttaaa aatgaagaca gcttagatct gttcttaaaa ggtaaggttc atacgaaaca    316683
ctgtaacgag ggaatcttgt tacaatgcag attcagactc cccgggggtc tgcatttcta    316743
gcagctctta ggtgatacca tgctcctgtt tatagtcaga tcatacttta ggcagttaca    316803
ggcttcgagt gggttaccaa agggaaggag tccagaaatg aagcaaactc ccccacagag    316863
tatatttcac cgcttgttat cttgttgtta taatgtaata gactagttca ttcaatggcc    316923
tatacagtca aattgccaaa ttcatttctt gagtttgtta cttaactatg taggtaaact    316983
tggacaagat atttcacatc tctatgactt agtttcatca tctgtaaaat aaaataaatc    317043
ataactaaat atatctaaat agacatacat aaataactat ctcatggttc ttatgggaaa    317103
taaatgagct aaaatctcag gatgagccat atgaaattgt cctctttata gatgaaaaat    317163
aaacatccac aattttatat agttaaaact aagtatgtaa attatttagt ataatatgta    317223
gcacctagtg aacaataaat gttagtatca gcaacaattg tcactgggta aattcataga    317283
cacatgaatg tactaacacc ctaaaaagtt tctttcaatg aagaaaattt tgacatcaaa    317343
tacacattat gcagtagcac atataaacca cgaggacata aaaaaaaaac aaagactctg    317403
gataaaatta ataatatgat aaacctgttc tggggaaaat aggccatgaa agtatctatt    317463
gttttctaaa ttattagagc aagcatactt catgtttttg aattctttgt cgttcttacg    317523
ctgtaaacat ttttacatga tttcaagcta tgttacattc cttagttgta tggtgaatca    317583
taaaatgtgt gataaattat ttatatttat aaagttttgc ctcaaataat agcatttagc    317643
actgtgcttt gatgaaggga cattcatttg tatgaaaagc agttctgctt cttttgagta    317703
catttagtca ctttgcttaa atgaatagat atttcctaat tttgaccctc aggttttaaa    317763 cttttgcttga agtgtactga ttttttgctct tgtgaagtat tgttggtgaa ctacagaaa    317823 gcatgtaaca tactataaaa ctataaactt taaaattatg agttagaatc tggttggtat    317883
taacttaaat tgatgttaat ggttacatat acaggctatc aactgagata tattgtaatt    317943 cttttctaagg agtccttctt tttctaaaat ttgaaatctt ttcaacctttt tgatgtatat    318003 aaaatatttg ttataaacct gttttataat gaaagtaatt tttattacca cgtagtttag    318063
agactaaact tgtaagtttc aaggttagtg gaagaaagaa tttaagccac tataatctat    318123
tccacatggg caacaaagta catttaagga ataaaactat tagactatat ttattgaatg    318183
atgaaactca agctggtgtt atataaagtg atgaaggaat tactgaattc tcttttttttc    318243 gttttttgag atggagtctc gctctgtggc ccaggctgga gtgcagtggc actatcttgg    318303
ctcactgcaa cccctgcctc ctgggttcaa gtgattctcc tgcctcagcc tcccgtgtag    318363
ctggtattac aggtgcccac caccatgcct ggctaatttt tgttaaattc tcttttccaa    318423
agatgcgata ctattattct gttgcagcaa caaaactgg gtatacacac aaaataattg    318483
aaaacatgat atttatacat ctaggctcat gtcagcatta ttcacaacag gcaaagatg    318543 gaagcaatcc agatgttcat tggaaaaata aaatatggtg tgtacagaca ctggaatgtt    318603
```

```
attcagctgt aaaaaggcat gatattctga tacatgctat ggcatcaaag atcattgaga 318663
acattatgct aagtaatata agtcagacac gggaaaacac atgttttgtg attttaatta 318723
tataaggaat ctaggataat taaatacata aaagcacaaa gtagatcagt ggctaccagg 318783
aactgagaag aggaggaaat gaggagttaa tatttaatag gtacagagtc tcagtgtgag 318843
atgatgaaaa agttctatag ttggactggt gatggctgcg ctttacactt aaaatgacta 318903
aaatgataca ttctatactg ttttgtatat tcatttcagt acaataagaa taatttataa 318963
aagacgctaa tgagctccta gtcatcatat gacacaaagg tgtcttttag gaaccatgaa 319023
attaatttaa aaaaaaagtc tactctcata cctacacagc tattttccgt ctgttatggt 319083
aagaaacaga agttaaggtt gttaacaaaa ataatttgga aagcaagaca ggagatcaac 319143
tgtttgcatc actttaggcg aagttaattg acactcaatg tctgtctttg tcttttcagg 319203
ctgctaaaac aaaacatcgt aaattgtctg gtgagggcct acattctggt tcatagatgg 319263
catcttttca ctgtgttctc acattggtgg aaaggaagaa ctctggtttc ttcacttcct 319323
tataagggca ccaatcttat tcacgagggc ttcaccctcg aaataatcac gtcctcaaaa 319383
cccccacctt ctaatattct aataccatca cgtgagggct taggtttcaa cataagaatt 319443
cggtggtggt ggggttgggg ggagagggaa acaaacattc agaccatatc aatgctttat 319503
ttttctcttt ttaaatctgg ccattgtgag aattacagga gaattaaagg catctgtcat 319563
catcccagac acatagtaag ttcttaatat gggtggttat tgttattttt tctgatgttg 319623
ttattgcttg aactttcaag atgtagggac aaaagtttta tataaataac aagaagttca 319683
actaaacact gtattgtaca tcctgtaaat atgtagaata tggaggcaca aaaatgagct 319743
ttaggaccaa aatacaaata tgttaaaata gtttagactc aagtgttaat gctagatggt 319803
cagtcctgaa ctttgccacc ctactattat cagagaagtg aaaaataata atttttttt 319863
cttttttctt tttttttttt tttttgaga cggacttttg cttttgttgc ccaggctgga 319923
gggcaacggt gcaatctcga ctcaccacaa cctccatctc cgaggttcaa gcgattctcc 319983
tgccttagcc tcccaagtag ctgggattac aggcacctac caccgggccc ggctaatttt 320043
gtatttgag tatagacggg gtttctccat gttggtcagg ctggtctcaa actcccgacc 320103
tcaagtgacc cacccgcctc agtctcccaa agtgctggga ctgcagacgt gagccaccat 320163
gcctggcctc taagaataaa taataatctt accaactatt ctatataagc attttttggcc 320223
cactgaacac tgtgatatgt aacttcattg caccttcaca tcaacccac caaaatatac 320283
gtaacaatag gctaacttta aaattcccaa ctaaaacaaa aattgtgacc agtaaattac 320343
aaagttaata agagacacag tcaaggttga acaccaggtc ttctgactct aagtcaaact 320403
ctctctttat tccctgttgt gtatcatagg ttgctgtaga ccaagtattg aaaatcttgt 320463
gttttcttca ttttgcattc ttagtttatg ggattattca gaaaaaatta ggagagaata 320523
cagtaattca aaatctacag attttttaag acacagattt ttggacatca gtgttcaaat 320583
caatagaaag tcatgcttcc cttcagcagc ctttattttg acaattttaa ggggcaggta 320643
cactaaattt ctgctgatta gatggaatga atcctatcct taaatcataa agagtgttaa 320703
tgaatctggt agcaaaagtt gattgcagac ttcttacaat gacaccatgg gatgacaact 320763
gtgttaacac aattttgaat atctcattaa acatttttc tctgcatgta tattttcct 320823
tttttttttt tttagacga gtcttgctct gtcgcccagg ctgagtgcag tggcacaatc 320883
tcagctcact gcaagctccg cctcccgcat tcacgccatt ctccagcctc agcctctcga 320943
gtagctggga ctataggcgc ccgtcaccac acccggctaa tttttttgtat tttttagtag 321003
```

```
aaatggggtt tcaccgtgtt agccaggatg gtctcgattt cctgacctcg tgatccaccc   321063
ccctcggcct cccaaagtgc tgggattaca ggcgtgagtc accgcgcccg gccttcttca   321123
tacaaatttg ttcatgtaat atattaattg cctgcctacc ttcctattac aggtttctta   321183
aactttggta gattctcttt tgtttctgtt caccaaggtc cttcttcata cgaatttgtt   321243
catgtaatat attaattgcc tgcctacctt cctattacag gtttcttaaa ctttggtaga   321303
ttctcttttg tttctgttca ccaaggtttt gccagaccaa gctacaggca gattttacc    321363 attaacagct ccttctaaag ttattcacgt ttggtcagta ctctgggctg aaattccaac   321423
catcagtact ctttcacttt gaaaaataag cttgtttgac tttatttgga aacatataac   321483
tggattgctg tgctggatgc tagtgagcaa tggtttaagg accccgttta ttgtaggaaa   321543
gtttattaca ttttgttttc atactgcttt acagggttgg aatttttgc agcattggta    321603 tatagacaac atgtcatttg ttttagttgc tacatgacac cttaaagttt attttttctc   321663
caaaggaaat ggcaactgta ttctttaaaa acacctatgt aaaatgaaa taactaaact    321723 tgtttttaga gtattctata ttctagatgg ataatgccgg aaaaaaaag atgcatgtgt    321783 acagcaaaac ttgttttatg aaacaactcc atgggccagg aaaaattagt tgcctaagaa   321843
agatgtatag ttaactgaaa attaaacaca tattgtcttt gaaatttata agacatttaa   321903
agcatccatt taacttatcg gtggtctcca tatctgtata gttgatgcca gaaagagaga   321963
ataaaagatt acctagagaa atggacttta ggtaagattt taagatatga acatatgaa    322023 caaaatttag ttttccagat gatttgtata aaatactgcc agataatttg ctaattatat   322083
ggcactgggg acaataacaa ggattaatga aaatgttcta actcaacaga tttttaaata   322143 atattttct tatacaaata ataaagattt attgtaaaaa atagaaaata tagataagaa    322203
agagggaaat tattcataat ttctgctttt taatataaac tatgcacatt tcagtatatc   322263
aacatccata cattttccta tgcatatata cactattgca tacttgaatt agtccatatt   322323
gtacacagtc ttttaaaatt cacaccttta acataaatat tgaaaatacc tttttcatgt   322383
cataatagtt tttgagaaat tgagtatcat tttaaaataa agcaatgtc cttattgtgg    322443 aaaagcctag ctcctccctg ttgattttca caaaaatct atgtttggaa atgatagaaa    322503
acaacattgt atcatagtgt tgttttccta gcaataccac ataagctcct ggtgtacaat   322563
ctaggcactt gtgggtgtaa cctttgagca tggcttcatg tgtttaagcc ttagggcctc   322623
gagcacgtcc tagaacaagt atggagaaat gacattgggt atgctaaggg gctgagacca   322683
tggtgaggtg tagaatatag aagggctcag gagtaggtct ggctcagaag tcagtgtatg   322743
gggtctagga agcagctcaa tgtaggaagg atgtccttga acaaaaaggt caaaaattgg   322803
ataaacacga attctctgaa tgagcacgca tccataaact ttaggataac aaaaggccag   322863
gctgcaagag actgtgaaat ggatatggat cacaataatc aattaaaaaa tctttgacat   322923
acattaattc cactaatatt tattaagcat aggatagttt tatacaccat tcccagctta   322983
agacagctta taacatacac aatatggtga gatgattgtt aagtaataaa aggcaatatg   323043
taattcatat ggtccaagaa taagtgctat agggatttgt ttattggaag gtttgcttct   323103
gacttttgca aagtagaaat ttataatgat aatagcggcc gatattggca agtattttat   323163
aggccttatt tttatgttca caacaacatg tgcataaatt attattttca ggaacacagt   323223
gcctatggtg gttacagtct tggagccaga ctgtctgagt ttgaatctca gccacttact   323283
ttgtggcttt tggcaattta tttaactctc tatttttcag ttttctcatc tatagaaaag   323343
```

```
aaataatggt agtatctatt tgatttagtg attgtaaata ctaaatgtgt ttatatataa 323403 tacttataaa tagctctaca aatgttagtt attgttatta attttatttt cgtggtatag 323463 aaatgaaggt ttggataatt aaggtgatat acctaagtta tgcaggtagt aaatgttgga 323523 gccaagggtg aatacagctc tctcttacct gaacctgagt tcttaatgta gccactttga 323583 tgtctcaaac tttaagcatg acaagagtga gtcaaagata gtttggattt tgattatgga 323643 tgactggaat cattcgtgaa atagggaagt gactaggaga ggttgttttt attgctattg 323703 ttggataaag gaaaggtcag atttaagatg tcttgaattg gaactggtga ggaggcattc 323763 agggtgaaat atgtagctgt gagatagaaa tcctggacca gaactctgtg gagagttgga 323823 gtggaagctg agattagggt agtatctatg ttaagttaat aataagattg gcagggagat 323883 aatattttaa gaagcaacat atataaaaag aaggactacg tcgagaagtc atagcattat 323943 taaccatggg gaagagaagc tattaaagaa ctcagaagca gaattgatag ggtccaacca 324003 gagtcagtga tagcctgtca gcatgcaaga tgaagtccaa gaactccact aacaacaggg 324063 tggaactctc aactatgtga gtagagagga aagattttc tatttttttg atcatgaaat 324123 tgcttatgag gtacaggccc caggtgttat gaagaatatg acttggttcg tttggggcac 324183 tgaaggtact gggggaggcg ctacttttag agcgctcaaa tatgccacga tttcatttca 324243 ttttgctttc tccaggcctg tgacatacta aggcagtttt tacttaggca tcgatatcat 324303 tttcaatttg gatcatttca aaagaaagag aaggacttct atgtgtgtgt gttatatgtt 324363 ttttggcttt tcttagtcaa gtatttccga ggatattcta ccattccttc ttttaattt 324423 cctgttttg tttgtttatc aaatgcacca gacaatttat ctttcccaga agttttaatt 324483 tttgttccta tctacatagg aaagagctgg gaaacagagt tttttttttc atatttagat 324543 tgacattaaa ggtatggcag gttctgtttg gggagcaatt ttatgataaa taaaactaaa 324603 ttgtgctcct agaagttcat agtgctgatc aaatgacact tatatgttgg tctttcttta 324663 aaaatttgtt acagaaaata ataaaaattc taataaaatt aattctactt ctaattaaag 324723 tctagaaata aatccactat gattattttg tcagctttag ctgaggaata acaaaatgaa 324783 ataggataat tagctggagc atggattttc tgaaatagag gacagtaaac tacagttttg 324843 gagagaaata tctaaatctg aagcacaaaa agaagcaaca aagttgttgg aagttctgtt 324903 ctaagcaact atgaatttt ttgtagttgc tctgctgatt tctagggtat ttctctatag 324963 ctaatacttg gaaagatact tcctcattga tatgtgtttc ctaaaggcat cattggaagt 325023 tgcttcctat ttgtctgatg ggttcaggtt ggtatgttga atccagtgat gctggaattc 325083 agggcctaa agttcaaggc agactttagg tccccaagat tagaaatgga ttatctgttt 325143 gtgtagtctg gaatttcata tttcaagttg tatttgaaaa ttcattcctc tgttgcatta 325203 tatgactttt ggctcttgga tcattcaaaa ctctgtcatc gtcttggtcc tttgtgtcaa 325263 tttgttggt tataggtttt cacaaaacat ggagtagcta tgctgcacaa ttgagatttt 325323 tcatttattc tacatctttc ctcagccagc acatgattat gtgattggtt caatagtagg 325383 tcctcaccaa gactcttcac attttatgtt gcctccacta gtgtcatatc agtgtggctt 325443 tagtatcagc caaattcaga tccaggattt tgttgctgaa aacttaaatt tagaatcaca 325503 tggtgtatat ttaaaggaac tcttagattc tccttttaag gaaagatgtc tgaaaatttt 325563 aaacataggt gtctgtcatt gttatggttt ggaatttata ctatggctga aaatatcatt 325623 aaatattgga tgggtatgat agcagtattg tcacatcttt agctcttttt tggttatata 325683 tatatttata taggttatat atatatattt ataggttata tatatgtg tgtgtatttt 325743
```

```
tggggacatc ttgagttctg gacagcctg ctttggtgaa aagagcccca attttggtgt  325803
cagactgagt gtgagtgtag gctacattca gttctatccc tgctattttc caacggtaga  325863
cactttagtt aaacttattt tctctgagct tcagtttctc aactaaaaat gggggtgcta  325923
cattgtcagg ctgctaaaag tttccaatga ggaaatgcta ggaaaaccat catagtattt  325983
agtagagtgg aatcgtaata aataccagct gcctctcttc tctctgcctt attccaaatt  326043
atgtacacca ggatgatttt taatgcaaat gaataccaaa ttttagctat catccaattc  326103
ttccacgatc attcaatccc tgtttagttc atagaatcat aacagcttgg acttgaaagt  326163
gacttaaata gcatctagtg taatctttca cctaaaaggc atggagtctt ccagattatg  326223
gttgaatatt tcccatactg agaactctac ttcacaaagc aacccactat aattttaaa   326283
cttgatcttc aataatagct taaaatcaat tcctgtaatt atcaaaacct tttgcatatc  326343
taaaaccatc tatattacca tgctttaaat attcacatgt gaagacttcc cactatcttc  326403
tgttgtgtct catgtgataa attttcaga tccttcacca ctctactaat tttcactttt   326463
aaagtagtgt gttttaaaat aagttggaca ttttcccctg taaatacga ttgtttcttg    326523
cttcctaat tctaataaag gcattcacct tctcctggcc acacaagaaa gtacagttag    326583
aatgtaccca tgccaatgtt tcttctatac atcttttgaa ataaaagtcc ctaacttgga   326643
tataatatta tactttatat caataaggtg aacagaaaag aacttggaaa gcaccccat   326703
tcatgctttc acaagtggat attatgtact agcattttag aaggcacatt aaaatagtca   326763
agaatttatt tcagcattca gcagttcgtg aatccagcag ctccagacca caaactgctc   326823
agggctctga caaggggtt ggggaagact tttacagggt gaatgtagaa gcaaggcaaa    326883
taaaatattt gatttgttaa agtacagcag tagcctattt ggatcattc cagtgggaat    326943
ccctagtcag aggtatgatt gacttaaaat atgaccattt acactgagtg gggttttgac   327003
ttgcttacat aggaatcaag ggcgctggag ccacctcacc ccgctggcct cccagttaat   327063
tttttaacaa gagaaaacaa aatgaaaaga tattactttt gctaaagaac aaaatgtcta   327123
tttgggaaac caagaaaat aacacagtat tatcttctct aatatagtgc ttctcaaact    327183
acttgtggtg aaggaaagtt taaaagaaa ttttaatatc tgtacagact aatacttttg    327243
ggaaatacaa aaaaaaacga attactagaa aaagttatgt ttaagataca aatctctatt   327303
tgttgtttta atccacaaat tattactttt ttattatttt aagtttagaa tcttgaaaaa   327363
gcttctaaat tcttaattg tatacttact ttgtcccaga taggtaatga atagtttgct    327423
gagaggcacc actctcagtc cacactcagg gtaacactgt attagtgcac ataaaaataa   327483
ggtacaactg aatcaaaaaa aaggatcttg tagatgctag agatacaaca gtgaacagac   327543
caaaggtccc agagtagaga atgacagata ctaaacaaag taaaatacat agctatagaa   327603
tttataacca tgcaatggtt ataaattcca tagaagaaaa aataaagcag gcaaaaagga   327663
taggaataac atatcgaggg ttgcaagaaa aatttaaggc tatttctttt gattcatggt   327723
ataagttttt ttttttttct acaagcgaac gtctaatcac ttatctgtga tggtgattac   327783
atgaggttag ctcttgtaat caactatttt gtaaatgata aaattaggtt ttctgaggag   327843
aaaatagcct tttattcaca agggtaattt ttattttaa tatgttaatt ttaatatttt    327903
aaaatagatt aatatgtttc tgattttggc tactatttgt tttaagatat tttacctatg   327963
gtcataaatg aaattgggct ataaattttt tattgtgttc ttcttattgg ttttactata   328023
aaagctgtat taccccttgta aagaaaattg gatggcattc catctttta aaaaaatctg   328083
```

-continued

```
tgaggcggtt tatgaaaaat agagtttgta tgtattcttt gaagagaatg atgaaatcta   328143
cctataaagt tgggtaaatt gatgagtgtt atcattcagt tcgctatttc tctctttaat   328203
tggtatcaaa tctataatac tttctatcta ctgaggcttc tatttttaatg tctgtattat   328263
tagtttccaa tatgtctaat tttaaaaatc agcctatttt tattcatatc tgctattata   328323
agctctttta aaaatggata ttattaagca tacttatttt tagtctttgt taggttgtta   328383
catcaaataa attcaaagta aattaaagtg acaattttgg ggctgttgct tgtcttttct   328443
atctatacta ggtcacttgt ttaggtactt aggtttacaa gcttattctg agtgaaaagg   328503
caagttagaa gactttcctc ccctccttac tcactgtcgg catttttgca gttgcctagc   328563
ccagaccctc cccacatttg agttgaagcc acttcatccc aattgcagaa gctgttgggt   328623
tgcctggttc aatttctgac taaaatttat ctgtatttaa gccctgtcc ttttataaag    328683
ctaactcccc aaatagcttc agctgtgagt attttgtttt gcttatttct cttgttcaac   328743
ctctcactca acaagggagc tctacctcaa cctctggttt caagcaaaca gcatgaatgt   328803
ctctggtccc ccaaatcatg tggaagatac tttgtttcct ccttttacca caggaggctg   328863
aagttttggc cacctgtgtt cactgtgggc ttagccctgc agctccactt gccgatttgc   328923
atttctctgc tgattttcag tcattgagtt ttcattctgt tcttaagcct ggatttgtct   328983
tttggatttt tttattctta tactttattt acattgccat gtgtttgaag tggaaataat   329043
attttaaatt atgaatgctg taccatcttg actggaattc tccttttgta caaatgaaat   329103
ctataaatgt tttcttaaaa aggactgttt aattgggatc tcctaaagta tagcttcttt   329163
aagtaaaaaa attgtatatt taaccggatg gtaagtggga ctttgcctgg tgaaccagaa   329223
ttttagtaa gcctccaaat ctgaaacaat gttatgggtg cccacacatt ctaaagacat    329283
tactagatcc tcagattgga caccagagaa agaaacctgg ctgtttcatc ttgtttgttt   329343
tagagttaaa aatatataat ttattttcaa agtaattata agaaaaacaa tgatcacttc   329403
tcaactatta caaaaaatta tgacagggtt tcagaaaagg tgtttttttt ttttaattga   329463
gatagtgtgt gacattttag agttagattt taaatggata cgaacagaat gtaggaatca   329523
acaggaaaat gtaagcagct gcaccaaaca taatctctat ttcttttgaa gtcattgccc   329583
acaagaactc acaaaaacta ccccatgaga agtggcacca acacgggtta caactgcact   329643
aattaaataa gattctctct atgccttaag ttctccatct ctctgctgta accatgaccc   329703
agcataatga gtagggagaa ggaactcaag ctgtgaattg tgggaagatg tgactatgca   329763
cacctttccc tctttctctg ttactgcagt tcctaagccc gtcaagccca gcagaagaga   329823
taaaggtatt agactggtct gtaaatttca atgcctaaaa atatccacca agctgtagat   329883
cttcccaaga tatttttcag gaacgaagca tgtaaactta catgagtgaa agacagtggt   329943
aaaaaaaaaa aaaacagtc tattttgggc tttggctcct acctaaatct agcttgttca    330003
ataaacctgt tcattaagtt ttatgttaaa ccatattcgt gcatttttcc ttgccattat   330063
acttaataat gcaactttaa aaatcttaaa ataaatgaat acttgatttg aaatgttcat   330123
gtgtgtacag acttttttgat tgaagcaaaa aatatttaat gaaatcaaac cttccagact   330183
ttaaattgca acccaattca catgaataca aatgagctta aaaataatat tgcatatgta   330243
taaaaaatca ataagggaa atataaatca acagctatgc ttgtatcggt ttaattttaa    330303
ggcatgatac aagaattact ctgctgcggc tcattaacac actactaaaa agcaaatcat   330363
atcttttctc cattttatgt aacatttttat tttgcctgat tatgtgttct cataaaatag  330423
gccttcatga cttatataaa tgtggaaaga agttatttct gagaaatgtt attggcaata   330483
```

-continued

```
aggaattggc ttaggtaaac tattttagaa ttggtaagag cctatatgga gatcaaatgt   330543
attaccatgt aaattcatat accatataca tttcatttca tagctttgct gttattgttg   330603
tttcttatgt atatagccca atacatattt tactcacatt ctccagttgt ctgatatctt   330663
cgtcagattt ttttctcggg tctgtcttta agatttagat aaattgaatg ttattagcgg   330723
tactcgttca attagaatgt ttttatgaaa cccataaaac attacactgc tagagtaaat   330783
gattcagcat atgattcaaa ccaaactaaa tttcccttca acccaaaata atctctaagt   330843
catagtggtc tatacagaat ttagtcatat tttgatattt ataaatatta atcataaata   330903
taatatttag agttagtact gaaatcatat ttagtaatga taagaatcta cttgcttatt   330963
ttgagattaa tcactgtagc tcctattgtc aaatatctac cgacataaat aaaaataaac   331023
atgagtttga acatgttaaa tgcacaaaga tcatctgaaa gtaccaggtt gagtaagaaa   331083
tgattaaaga catgaatgaa tatttatatt ttatagaact ttaatttcat aataagaaga   331143
aagaactagg tatagttgta ttatttggcc tttataatga atagttttc ttaatatcat    331203
ttacatgtaa tatgaagata ttctgggatg ttgaacagtc ttccagatag gtaaaaggaa   331263
gggattcaaa agaaaatttg aatacatatt tcatatttat cttttttgtga gcttcgtaat  331323
aaaccacaca aagctttcat ctggaatact tattactaaa acttgcactg tagctgtaga   331383
ttgacattaa cagggaaaaa taaatataac ccatttccca agacactaaa atatgctaaa   331443
tgaagtaaaa aatgtaaagt aattttgaaa acttaaattg atattgaaat gtgagttagt   331503
tttatcttag tcaacatcat tgttattgaa gaaaggcaga ttttattcac cggaattatt   331563
tattttagtt tagattaaaa gctgctttct gacatatgag ttgactcctg tatctacttt   331623
tctgagatac tattggctga aacatgttga ttaaattttg tagtaactta attacaagat   331683
tcagagatag taaagctttt aatgtaggtt ataatttat aatatgaact gacatttctc    331743
tagtgctctg cagtttcaa aatgctttca taagcattat ctctttccat ttctacaaca    331803
attttgcagt aggaaataat agtatccctc ttttagagat ggaaaagtta aagtttcaga   331863
gagaataaat cacttagcta ctagatggct gaatcagaac tcaagcatgt gaagagaggt   331923
agtatatagc atatcttaag aatcttcgta tcaagattaa cagccttgga gacaaaaggt   331983
cttttgtttaa attcatactt taccctttgg ttgttgcgcg ctcttgggca actgagaaat  332043
ctgattgggt ctcagttttt taatctgttt aatgggatag caaagttcat tattgggtat   332103
tgtgataagt aaatgagttg acacctagaa cgtacttaga ctgtaccttg tatattttta   332163
gtggatgccc agtaaaaatc cattgattgt tgttgattag taccaattca aacgtgaagt   332223
tgcagattgc agttatttga tgttttggtc tgaattgttg tctttagtga gagacatcta   332283
acttaaaata gcttaagaaa aaaaaaggg tgacttatta gaccactgag ttgggaaaag    332343
ttgctatact ttcatacatt caaaggaaaa cctgaatctt ggattaaatg gcactgaaga   332403
ctcagttctt ccccaatcta tatctctgtt catttcttct ttctgctgtc tctgcttctt   332463
catggcctag cctcgttatc ttctaccata gataggcttt gtccagagtg ttcattttc   332523
catcccaggg aagggctctg attggctatg cttaaaattt gcactggctc tttatttcca   332583
aaagtattgt tagagaaaat ggggatatgg atgtcatatg gatatctctg tgtctaaggg   332643
attggtatgt taccagaagc aattgaaaca acatggcttt tggagaaaaa ctgaaaaacc   332703
agaaacaaga tgataatgaa aaagatacaa agtagtatat tctatctgac tttctgcaaa   332763
tcagaaagaa aaactgttaa aaactaagaa aacttggttt tgaactgagt tttgagatca   332823
```

```
gttttaagaa ttaagtctta aaactaagaa cacttagttt ggaaaacctt tgaatataaa    332883
gctgccctat aaggttttca gaggattagt gttccctcat gccaccatca ggctagcacc    332943
aggcagaggt atctagtgtt gcctgacagt gatgtgcagg ggagaatatt gctacaacaa    333003
cagacagaaa ggatggtgat ggtctgattt caaaaacaga tcagtgtaac tatgtagcta    333063
cttagtcaat agcaaatttc ctagacattc ttatgttttg ctaagatggc agtagaagct    333123
tgactctgac agttgctcca aatgaagtaa taaacctaac attctagtta ccttgtcatt    333183
catctgtctt caaggtggaa tacatatatc acctttgagt gagcattcat attgttaaaa    333243
tattgaaatg tcatccaatg ccataatttt caaagcatga aatttaaata aaatcctttg    333303
cccaacctct caaatacctc tgtggtctct ggatgacact gtgcaaacca caaacctata    333363
gaaatttcag gggaggttga attaaagaac tatcgaatta aagggttgat ttgcagtaat    333423
taacatttca ctttctgaaa accccatata tttaacaaca ctattataat aagttaacat    333483
gtgcttcagc ttctttctca ctctacaact ggtttaatgc ttaaacattt cttctctata    333543
cttggtatga tttcctcctt ttcttgcatt ataaagttc tgcacttgtt ttcaatgtcc    333603
aaacttgaac tcatcacctg tccccaaaac ctgtcttcct tttattatgt ctagctcagt    333663
agttgcgcaa atttgaagcc tggataacac ccttgaactt tttctcaacc catgaattca    333723
tctttagtca gtcagttgac tctaattctt aaatagctct taattctatc tatttatgtc    333783
taacatgatg cctccattgc acttttagca ttaagtttaa tttcttgact tgaacttcta    333843
ggtcttttgt aattggttct tgttctgaat ctgaagtcct tcaagatgca attcaaatag    333903
tgttaaaata ttgcataggt tgtttacata atttcacaga aacttctgac aaagaatatc    333963
ctcaacatca tgcaggtaga agcatcataa aataccacta tatgattaat ctataagggt    334023
tcatgaaaca atttagttaa aatatgccta ttttcacata cttagataaa ttcattaatt    334083
aattttatg tcactatctt gcctggtata aagtaggaat ttggtttccc cccaaaagaa    334143
taagataatg aatataatat atagctgtaa aatgaatata caattgggac ctggttagtg    334203
ttacttcttt ttatggtcat ccccacttac tatagctgac aaacactggc acttgcttct    334263
gtttctttc acagttaata ttcattactg ctttgtaata taggactttc caataaaacg    334323
ttttcaaata gaaactatcc tggaatgctc atatgttttt tgttttcttt tcatatatac    334383
aagagccaac aagtgcagtc attgtagata cttttgatca ttgcagatgg tcaaaatgat    334443
ttttcaataa tttagaataa tctattcatt tcctgaatta gggaggctag taatatcagc    334503
tatgtttatt aagcgctgga gtcagttcta ttttcttgta aagtttaggt ataatgatca    334563
ttaagaatca ccatattctc ctgaatttcc cccagtcttt atatagactt ttatttatt    334623
attatatgta tttattttga gacagtgtct tgctctgtca tccagactgg agtgcagtga    334683
tgcaatcaca atccacagca gccttgacct ccatggctca agtgatcccc ctactttagc    334743
ctgctgagta gctgggaata caggtgcaca ccaccatatc cagctaattt ttaattattt    334803
tgtagagata gggtctcact atcttgctca ggctgatctc aaattcctgg gctcaagtga    334863
tcttcctgcc taggcctcct aaagtgctgg gattacaggt gttggccacc atgcctggct    334923
gaatgaattt ttaacgtaaa tgtataaaac atgaatctcc tctgaacttt caactgttga    334983
ttccctggaa aatgaaggtt gttgattaaa tgccggtagta acatatgtat gaataaaaca    335043
tactgtatct gttggtgcta tataggacct tgagagcaca agatttttcc taactattca    335103
ttcttcactt tttagctttt gttgcttaat atctattagt acttatttga tattttaaag    335163
cttaagggga ctgagaaatg tattgttaaa aataatttaa attaaatgta acaaaagata    335223
```

-continued

```
ttttattatt tctgatctta tgcaacagat tttattggag gtggaatgaa gtttgttggt    335283
aaccaataag atctatttca aaatgtatag tatgaaatat tttaaagaaa aagaaggaa     335343
aaccagaaaa gaaaaattaa aaaaaaaaaa caatgtcttg gatatattat tttttatttt   335403
ttgagatgga gtttcactct tgtcactgag gctggagtgc aatggcggga tctcagccca   335463
gtccaacctc cgcctcccag gttcaagcca ttctcctgcc tcagcctccc aagtagctgg   335523
gattacaggc atgcgccacc atgtccagct agttttatt ttcttttgtt ttcagtagag    335583
acaggatttt gccaagttgg tcaggctggt ctctaactcc tgacttcagg tgatccaccc   335643
acctcacctc ccaaagtgct gggattacaa gcatgaccca ccacgcctgg cctatcgtgg   335703
gtattgttat tagtggaact ttcctttctt caaagtatat tgcaataact actaattttc   335763
tccatgtatc tagcaaagat aaccccaata aaggtattaa aattataaag taaaacctag   335823
ctattggaaa gaatttaaaa atagaaaatt aaagctaccc ataattgtat tacctaggaa    335883
taaacaagat tggattccat tcattctagc ccttaaaag taaatatgtg catgttgtct    335943
tagtttgggc tgctataaaa aattaacata cactggatgg attatacaac agagttgtat   336003
ttctcaaagt tcttgagcct gggacatctg atatcaaggt gtcagcgtgg ctaggttctg   336063
gtgagggcca tctccttgct gtatactcat ggcagagaac agagaaagaa aaagcaagct   336123
ctctcttgtc ttttcataaa agcactaatc ccactcgtga aggtttcacg gtcatgatga   336183
aattaccttt aaaggtctca aatcctaata ttacattggg aattagcatt tcaaaatatg    336243
aattttgtg ggacacaagc cttcagtcca tagcattttt tcattgccca cacccccaaat   336303
ttatgttctc acatgccaaa ggcattcctt caatctttac agccctgacg tgccagtgtt   336363
acctctaaaa tttaaagttc agagtattta aaaatcatct aaatcagata tggctgagac   336423
tcaagatact attcatctag aagcaaggag gaaaaattgg ggtatatatt agccttttga   336483
tcttaacata gttacatgaa tgttgatcat tgtccaatat tctattataa tggctatata   336543
attgaatatt tattgctcta tcattcttta ttttataatt ctccaattgc tgaatatatt   336603
aagtttattt aagttttac tattataaat aacactttga tgaacacata tgcatgtaaa    336663
gtctatattt atacttcctt aacatggatt attaatacct ggaaggaaaa ttactatttc   336723
agaggtaaag tttatcaat atcttcactt ctggaaaaca ccagtgtatg tggtgagaag    336783
ggatcaaatt gctaccctgg tataattaat atgatatatt taggttttca ttttcattta   336843
tatttcttat gtcacaaaaa acagaccta attattatgt aggtactata cgagtgaaat    336903
gcatgtgttg ttggtataaa gagatcttgg agctaagata attggctaga agtattgtct   336963
tcttgattgg agcttgcatg attcatttca gatggtaaaa gtgtttataa ctgctttgaa   337023
agtttacata agagattagc ttcatttaat ttgttctaga gtttctcaga gtatcttcac   337083
tactttcttt tcttttcttt tctttttttt ttttttttac aagttctgt tgtatctcta    337143
ttgatatggt ttggatctgt gtccccaacc aaatctcatc ttgaattcta atccccatat   337203
gtccaggcag ggacctgtaa tccccatgtg tcgagggagg gaagtgattg gattatggag   337263
gcagttcccc ccatgctgtt ctcatgacag tgagtgagtt tcatgagatc tgatggattt   337323
aaaggtggca gttttcctg tgcttacact tcacttcttt cgcctgctgc catgtaagac    337383
atgcctgctt cgccttccgc catgattgta agtttcctga ggcttcccca gccatgtgga   337443
actgtgagtc aattaaacct cttttctta taaattacca cgtctgaggc atttctttat    337503
agcagtgcaa aaacggacta atacatctac taaatagaac acttatataa ataagttcaa   337563
```

```
ttaaaaatat agtaatagtg ttataggtag atagataggc ttgaatgggg aaggggaggg    337623
ttctccccc accttcaccc actagaaatg tcaagggatg gttcggcagt tattacattg    337683
cctgtctaaa agtgatacat tgacagccag tgccagggat aggccatttt ctgagggtcc    337743
acacctgtta acattaaagt gtcagttaaa gacaggcctc gggggaaaca acttgctggg    337803
catgcatatt aagagacaga aatgacgaag tatgatcttc caggtaccct ccactggaaa    337863
aaggaagaaa gccttagatg ggcatgctaa caactcccta aacacactgc atgtgctcaa    337923
ttcccaaggg taaggaaggc actgtgcatg cgggaagccc accctaaggg aagaatcatg    337983
ggaaagaggt gagcctataa agtcccagga tcaaggttaa agcttctcct tgttctccc    338043
ttttaccttc aggcacccac ttgcatctct tctgggggtt cttccttc tttcctgttc     338103
taaggctttt taaataaact tccatttctt ctctgaaagt tgcctctgtc tcttttcctg   338163
ctttatgccc ctcagttgaa ttatttcttc tgaggaggca agaattgaag ttgctgcaga   338223
cacatatgga ttcaacgtgg taaccttgga gtaacttgga tctcttccac tgataaaaat   338283
aacatggctg gtagcacatt tgttttaag gtttagaaga gttttgatga tgtcacttaa    338343
taagaggata gaactgatca atttgtaca taacaagtca taatgttgaa taactgtatt    338403
tggaaagaag gcaaaaatcc agaatttcca cttcctgaat tggtactatt tgtctttcca   338463
tttaagggtt gatttgatca cagatcaggg attcttaatt gttggtcaag aatggttaaa   338523
ctcatctgtt ttttctagtg ggtgtcatga ttatttaaca aataaattaa cttgccaatg   338583
atgtacattt aaaaaaaaaa aatacctggg ttctgggatt ggaagagtga tcctggtatg   338643
tttgtgaaga cacaggagag tggttatggg tagagcagag gaagcaaaag gagtactaat   338703
agaagagaaa ataagaaagg taacaggagg aagttttgtc aagcctactg gctttaagga   338763
atggactttt attctgaatg aactagtaca ccattagaag ttttgagcag agaagtggca   338823
tgtaatttcc atctttttt tttttttttt tttttttta atttttaaga cagagtctcg     338883
ctctgtcgcc caggctggag tgtggtggcg cgatctcggc tcactgcaag ctccgcctcc   338943
cgggttcacg ccattctcct gcctcagcct cccgagtagc tgggactaca ggcgcccacc   339003
accgcgcccg gctaattttt tgtatttttt agtagagacg gggtttcacc gtgttagcca   339063
ggatggtctc tgtctcctga cctcgtgatc tgcctgcctc ggccccccgaa agtgctgaga   339123
ttacaggcgt gagccaccgc gcccggccgt aatttccatc ttaaaagcat tagcttagct   339183
gctaagttga gaatatgcgg tcggaaagca gggcagtttt agtaagacat gttgaaatc    339243
tgcttttcaa catgtaagat ggtgatgtat tgacccaggt tgttagcagt gcaggtgttg   339303
aaaagcaaga aataaatttt ggagatagag ccaaagtttt tactagtgga tgaggtgggg   339363
ttaggtatga ctgcaaactt tttagcctga gtaactggga atatagagtt gcagttatct   339423
aagttgagga ttgatatggt ttggctgtgc cccacccaca tctcaacttg aattttatgt   339483
cccagaattg ctatgtgttg tgggagtgac ccagtgtgag gtaattgaat cgtggggcc    339543
ggtctttccc gtgctattct cctggtagtg actaagtctc acgagatctg atgggtttat   339603
cagagtttgc tgcttttgct tcttcctcat ttttctcttg cccctgccat gtaagaagtg   339663
tcctttgcct tctgccatga ttttgaggcc tccccagcca cgtggaactg tgagtctagt   339723
taaacctctt tttcttcccc atctcaggtc tttatcagca gaatgaaaag agattaatac   339783
aagggtgaac gcagtaatgc aggcttaagg gctgtggaga atcacaaacc atatctgggc   339843
atgttagggt atctggcaat ttttagtagg catttacttg gagtgtggaa tttaggagag   339903
gagtccctgc tggagatata tacttggatt ttgtcagctt gtagagtgca ttgaaagcta   339963
```

-continued

```
caaactgaag ctattaatat taccatcatt agattca                              340000

<210> SEQ ID NO 4
<211> LENGTH: 620
<212> TYPE: DNA
<213> ORGANISM: Homo sapiens
<220> FEATURE:
<221> NAME/KEY: CDS
<222> LOCATION: (1)..(195)
<223> OTHER INFORMATION: mRNA of AF486622
<220> FEATURE:
<221> NAME/KEY: misc_feature
<222> LOCATION: (1)..(620)
<223> OTHER INFORMATION: gene

<400> SEQUENCE: 4 tgg aga cac agc tgg gct gaa caa gat ttg ctt caa acg aca aca aga        48
Trp Arg His Ser Trp Ala Glu Gln Asp Leu Leu Gln Thr Thr Thr Arg
 1               5                  10                  15 gag aca gaa agt atc tgg ttc aac cgc tgc ccg agc agg cag gca cca        96
Glu Thr Glu Ser Ile Trp Phe Asn Arg Cys Pro Ser Arg Gln Ala Pro
             20                  25                  30 gaa gag cta gca gcc aat ccg gcc atg ctc gaa gcc agc tct gca gct       144
Glu Glu Leu Ala Ala Asn Pro Ala Met Leu Glu Ala Ser Ser Ala Ala
         35                  40                  45 cag cca atc agt gac atc att gct ttc ttt agc ttg ccc atg gtg atg       192
Gln Pro Ile Ser Asp Ile Ile Ala Phe Phe Ser Leu Pro Met Val Met
     50                  55                  60 tga agatgagaag aaatagcaag gcccaaccag ttcttcatct ggagacagtt           245
caacgttctg caaaccagat cttcaggaat tttactggga taattatcca ataaaattgc    305
aagcattcta tccaaatgga gctctttctg agatgaagag aattctcaat gtcaagattt    365
gaacaagaag agaatggaat acacaatatg gacatccata aaaattcatc agagagcatt    425
ttactactga gctgcaaagg gaaaaactta aaatggatat gaaaagtgaa gaaagtgatc    485
ataggagaaa accatttcag atgacaagag cacctcaaag gcagcagcct caaggagcag    545
ccatggcccc agacttgtcg cacggatgca gaaaacttaa tggaggaggc tgaggtcaga    605
atgggaagag ttttt                                                    620

<210> SEQ ID NO 5
<211> LENGTH: 64
<212> TYPE: PRT
<213> ORGANISM: Homo sapiens

<400> SEQUENCE: 5

Trp Arg His Ser Trp Ala Glu Gln Asp Leu Leu Gln Thr Thr Thr Arg
 1               5                  10                  15

Glu Thr Glu Ser Ile Trp Phe Asn Arg Cys Pro Ser Arg Gln Ala Pro
             20                  25                  30

Glu Glu Leu Ala Ala Asn Pro Ala Met Leu Glu Ala Ser Ser Ala Ala
         35                  40                  45

Gln Pro Ile Ser Asp Ile Ile Ala Phe Phe Ser Leu Pro Met Val Met
     50                  55                  60

<210> SEQ ID NO 6
<211> LENGTH: 1511
<212> TYPE: DNA
<213> ORGANISM: Homo sapiens
<220> FEATURE:
<221> NAME/KEY: CDS
<222> LOCATION: (155)..(1045)
```

-continued

```
<223> OTHER INFORMATION: BTG family, member 3
<220> FEATURE:
<221> NAME/KEY: misc_feature
<222> LOCATION: (155)..(466)
<223> OTHER INFORMATION: tob/btg1 family; The tob/btg1 is a family of
      proteins that inhibit cell proliferation
<220> FEATURE:
<221> NAME/KEY: misc_feature
<222> LOCATION: (155)..(715)
<223> OTHER INFORMATION: pfam01211, Anti-proliferative, BTG1 family, a
      novel family of anti-proliferative proteins
<220> FEATURE:
<221> NAME/KEY: allele
<222> LOCATION: (1320)..(1320)
<223> OTHER INFORMATION: A or C
<220> FEATURE:
<221> NAME/KEY: allele
<222> LOCATION: (1367)..(1367)
<223> OTHER INFORMATION: complement may be G or T.

<400> SEQUENCE: 6
cgacgcggga gccgcacgcg ccggacgagg ctcgctgcgc tccctgttgc ccagcgcggg      60
cccgttgagg cggagccctc agttcccggc caggacacgg tctgggccgc cgaatctccg     120
gccgaagagc ggcggcggca gcggcgggaa aaaa atg aag aat gaa att gct gcc     175
                                      Met Lys Asn Glu Ile Ala Ala
                                        1               5 gtc gtc ttc ttt ttc aca agg cta gtt cga aaa cat gat aag ttg aaa       223
Val Val Phe Phe Phe Thr Arg Leu Val Arg Lys His Asp Lys Leu Lys
         10                  15                  20 aaa gag gca gtt gag agg ttt gct gag aaa ttg acc cta ata ctt caa       271
Lys Glu Ala Val Glu Arg Phe Ala Glu Lys Leu Thr Leu Ile Leu Gln
 25                  30                  35 gaa aaa tat aaa aat cac tgg tat cca gaa aaa cca tcg aaa gga cag       319
Glu Lys Tyr Lys Asn His Trp Tyr Pro Glu Lys Pro Ser Lys Gly Gln
 40                  45                  50                  55 gcc tac aga tgt att cgt gtc aat aaa ttt cag aga gtt gat cct gat       367
Ala Tyr Arg Cys Ile Arg Val Asn Lys Phe Gln Arg Val Asp Pro Asp
                 60                  65                  70 gtc ctg aaa gcc tgt gaa aac agc tgc atc ttg tat agt gac ctg ggc       415
Val Leu Lys Ala Cys Glu Asn Ser Cys Ile Leu Tyr Ser Asp Leu Gly
             75                  80                  85 ttg cca aag gag ctc act ctc tgg gtg gac cca tgt gag gtg tgc tgt       463
Leu Pro Lys Glu Leu Thr Leu Trp Val Asp Pro Cys Glu Val Cys Cys
         90                  95                 100 cgt aga gat ggg gtt tca cca tgt tgg cca gac tgc tct caa act cct       511
Arg Arg Asp Gly Val Ser Pro Cys Trp Pro Asp Cys Ser Gln Thr Pro
 105                 110                 115 gac ctc gtg atc cgc ccg cct tgg cct ccc aaa gcg ctg gat tac agg       559
Asp Leu Val Ile Arg Pro Pro Trp Pro Pro Lys Ala Leu Asp Tyr Arg
 120                 125                 130                 135 cgt gag cca ctg cgc ccg gcc tcc tcc ttt ttg att atg tat gga gag       607
Arg Glu Pro Leu Arg Pro Ala Ser Ser Phe Leu Ile Met Tyr Gly Glu
                 140                 145                 150 aaa aac aat gca ttc att gtt gcc agc ttt gaa aat aaa gat gag aac       655
Lys Asn Asn Ala Phe Ile Val Ala Ser Phe Glu Asn Lys Asp Glu Asn
             155                 160                 165 aag gat gag atc tcc agg aaa gtt acc agg gcc ctt gat aag gtt acc       703
Lys Asp Glu Ile Ser Arg Lys Val Thr Arg Ala Leu Asp Lys Val Thr
         170                 175                 180 tct gat tat cat tca gga tcc tct tct tca gat gaa gaa aca agt aag       751
Ser Asp Tyr His Ser Gly Ser Ser Ser Ser Asp Glu Glu Thr Ser Lys
 185                 190                 195 gaa atg gaa gtg aaa ccc agt tcg gtg act gca gcc gca agt cct gtg       799
Glu Met Glu Val Lys Pro Ser Ser Val Thr Ala Ala Ala Ser Pro Val
```

-continued

```
Glu Met Glu Val Lys Pro Ser Ser Val Thr Ala Ala Ser Pro Val
200                 205                 210                 215 tac cag att tca gaa ctt ata ttt cca cct ctt cca atg tgg cac cct      847
Tyr Gln Ile Ser Glu Leu Ile Phe Pro Pro Leu Pro Met Trp His Pro
                220                 225                 230 ttg ccc aga aaa aag cca gga atg tat cga ggg aat ggc cat cag aat      895
Leu Pro Arg Lys Lys Pro Gly Met Tyr Arg Gly Asn Gly His Gln Asn
            235                 240                 245 cac tat cct cct cct gtt cca ttt ggt tat cca aat cag gga aga aaa      943
His Tyr Pro Pro Pro Val Pro Phe Gly Tyr Pro Asn Gln Gly Arg Lys
        250                 255                 260 aat aaa cca tat cgc cca att cca gtg aca tgg gta cct cct cct gga      991
Asn Lys Pro Tyr Arg Pro Ile Pro Val Thr Trp Val Pro Pro Pro Gly
    265                 270                 275 atg cat tgt gac cgg aat cac tgg att aat cct cac atg tta gca cct     1039
Met His Cys Asp Arg Asn His Trp Ile Asn Pro His Met Leu Ala Pro
280                 285                 290                 295 cac taa cttcgttttt gattgtgttg gtgtcatgtt gagaaaaagg tagaataaac      1095
His cttactacac attaaaagtt aaagttctt actaatagta gtgaagttag atgggccaaa    1155
ccatcaaact tatttttata gaagttattg agaataatct ttcttaaaaa atatatgcac   1215
tttagatatt gatatagttt gagaaatttt attaaagtta gtcaagtgcc taagttttta   1275
atattggact tgagtattta tatattgtgc atcaactctg ttggatacga gaaccctgta   1335
gaagtggacg atttgttta gccccttga gaatttactt tatggagcgt atgtaagtta     1395
tttatataca aggaaatcta ttttatgtcg ttgtttaaga gaattgtgtg aaatcatgta   1455
gttgcaaata aaaatagtt tgaggcaaaa aaaaaaaaa aaaaaaaaaa aaaaaa         1511
```

<210> SEQ ID NO 7
<211> LENGTH: 296
<212> TYPE: PRT
<213> ORGANISM: Homo sapiens

<400> SEQUENCE: 7

```
Met Lys Asn Glu Ile Ala Ala Val Val Phe Phe Thr Arg Leu Val
1               5                   10                  15

Arg Lys His Asp Lys Leu Lys Lys Glu Ala Val Glu Arg Phe Ala Glu
                20                  25                  30

Lys Leu Thr Leu Ile Leu Gln Glu Lys Tyr Lys Asn His Trp Tyr Pro
            35                  40                  45

Glu Lys Pro Ser Lys Gly Gln Ala Tyr Arg Cys Ile Arg Val Asn Lys
        50                  55                  60

Phe Gln Arg Val Asp Pro Asp Val Leu Lys Ala Cys Glu Asn Ser Cys
65                  70                  75                  80

Ile Leu Tyr Ser Asp Leu Gly Leu Pro Lys Glu Leu Thr Leu Trp Val
                85                  90                  95

Asp Pro Cys Glu Val Cys Cys Arg Arg Asp Gly Val Ser Pro Cys Trp
            100                 105                 110

Pro Asp Cys Ser Gln Thr Pro Asp Leu Val Ile Arg Pro Pro Trp Pro
        115                 120                 125

Pro Lys Ala Leu Asp Tyr Arg Arg Glu Pro Leu Arg Pro Ala Ser Ser
    130                 135                 140

Phe Leu Ile Met Tyr Gly Glu Lys Asn Asn Ala Phe Ile Val Ala Ser
145                 150                 155                 160

Phe Glu Asn Lys Asp Glu Asn Lys Asp Glu Ile Ser Arg Lys Val Thr
```

-continued

```
                    165                 170                 175
Arg Ala Leu Asp Lys Val Thr Ser Asp Tyr His Ser Gly Ser Ser Ser
            180                 185                 190

Ser Asp Glu Glu Thr Ser Lys Glu Met Glu Val Lys Pro Ser Ser Val
            195                 200                 205

Thr Ala Ala Ala Ser Pro Val Tyr Gln Ile Ser Glu Leu Ile Phe Pro
            210                 215                 220

Pro Leu Pro Met Trp His Pro Leu Pro Arg Lys Lys Pro Gly Met Tyr
225                 230                 235                 240

Arg Gly Asn Gly His Gln Asn His Tyr Pro Pro Val Pro Phe Gly
            245                 250                 255

Tyr Pro Asn Gln Gly Arg Lys Asn Lys Pro Tyr Arg Pro Ile Pro Val
            260                 265                 270

Thr Trp Val Pro Pro Pro Gly Met His Cys Asp Arg Asn His Trp Ile
            275                 280                 285

Asn Pro His Met Leu Ala Pro His
            290                 295

<210> SEQ ID NO 8
<211> LENGTH: 2537
<212> TYPE: DNA
<213> ORGANISM: Homo sapiens
<220> FEATURE:
<221> NAME/KEY: CDS
<222> LOCATION: (102)..(1199)
<223> OTHER INFORMATION: Homo sapiens coxsackie virus and adenovirus
      receptor (CXADR), mRNA, genbank NM001338.
<220> FEATURE:
<221> NAME/KEY: misc_feature
<222> LOCATION: (186)..(515)
<223> OTHER INFORMATION: IG, Immunoglobulin
<220> FEATURE:
<221> NAME/KEY: misc_feature
<222> LOCATION: (207)..(467)
<223> OTHER INFORMATION: IGv, Immunoglobulin V-Type
<220> FEATURE:
<221> NAME/KEY: misc_feature
<222> LOCATION: (558)..(758)
<223> OTHER INFORMATION: IGc2, Immunoglobulin C-2 Type
<220> FEATURE:
<221> NAME/KEY: misc_feature
<222> LOCATION: (564)..(788)
<223> OTHER INFORMATION: IG, Immunoglobulin
<220> FEATURE:
<221> NAME/KEY: misc_feature
<222> LOCATION: (750)..(750)
<223> OTHER INFORMATION: includes an A or G nucleotide
<220> FEATURE:
<221> NAME/KEY: allele
<222> LOCATION: (969)..(969)
<223> OTHER INFORMATION: may comprise G or A.
<220> FEATURE:
<221> NAME/KEY: allele
<222> LOCATION: (1148)..(1148)
<223> OTHER INFORMATION: may comprise G or A.
<220> FEATURE:
<221> NAME/KEY: Unsure
<222> LOCATION: (1148)..(1148)
<223> OTHER INFORMATION: Comprises A or C.
<220> FEATURE:
<221> NAME/KEY: Unsure
<222> LOCATION: (1210)..(1210)
<223> OTHER INFORMATION: Comprises T or C.
<220> FEATURE:
<221> NAME/KEY: allele
<222> LOCATION: (1269)..(1269)
<223> OTHER INFORMATION: may comprise G or T.
<220> FEATURE:
<221> NAME/KEY: allele
<222> LOCATION: (1278)..(1278)
```

-continued

```
<223> OTHER INFORMATION: may comprise G or T.
<220> FEATURE:
<221> NAME/KEY: allele
<222> LOCATION: (1293)..(1293)
<223> OTHER INFORMATION: may comprise G or A.
<220> FEATURE:
<221> NAME/KEY: allele
<222> LOCATION: (1297)..(1297)
<223> OTHER INFORMATION: may comprise G or A.
<220> FEATURE:
<221> NAME/KEY: allele
<222> LOCATION: (1298)..(1298)
<223> OTHER INFORMATION: may comprise C or T.
<220> FEATURE:
<221> NAME/KEY: allele
<222> LOCATION: (1322)..(1322)
<223> OTHER INFORMATION: may comprise A or G.
<220> FEATURE:
<221> NAME/KEY: allele
<222> LOCATION: (1365)..(1365)
<223> OTHER INFORMATION: may comprise A or G.
<220> FEATURE:
<221> NAME/KEY: allele
<222> LOCATION: (1376)..(1376)
<223> OTHER INFORMATION: may comprise A or G.
<220> FEATURE:
<221> NAME/KEY: allele
<222> LOCATION: (1381)..(1381)
<223> OTHER INFORMATION: may comprise C or T.
<220> FEATURE:
<221> NAME/KEY: allele
<222> LOCATION: (1397)..(1397)
<223> OTHER INFORMATION: may comprise C or A.
<220> FEATURE:
<221> NAME/KEY: allele
<222> LOCATION: (1449)..(1449)
<223> OTHER INFORMATION: may comprise G or T.
<220> FEATURE:
<221> NAME/KEY: allele
<222> LOCATION: (1827)..(1827)
<223> OTHER INFORMATION: may comprise G or A.
<220> FEATURE:
<221> NAME/KEY: allele
<222> LOCATION: (1866)..(1866)
<223> OTHER INFORMATION: may comprise C or T.
<220> FEATURE:
<221> NAME/KEY: Unsure
<222> LOCATION: (1976)..(1976)
<223> OTHER INFORMATION: Comprises A or G.
<220> FEATURE:
<221> NAME/KEY: allele
<222> LOCATION: (2007)..(2007)
<223> OTHER INFORMATION: may comprise C or T.
<220> FEATURE:
<221> NAME/KEY: allele
<222> LOCATION: (2095)..(2095)
<223> OTHER INFORMATION: may comprise A or G.
<220> FEATURE:
<221> NAME/KEY: allele
<222> LOCATION: (2106)..(2106)
<223> OTHER INFORMATION: may comprise A or C.
<220> FEATURE:
<221> NAME/KEY: allele
<222> LOCATION: (2154)..(2154)
<223> OTHER INFORMATION: may comprise T or C.
<220> FEATURE:
<221> NAME/KEY: allele
<222> LOCATION: (2159)..(2159)
<223> OTHER INFORMATION: may comprise T or C.
<220> FEATURE:
<221> NAME/KEY: allele
<222> LOCATION: (2192)..(2192)
<223> OTHER INFORMATION: may comprise T or C.
<220> FEATURE:
<221> NAME/KEY: allele
<222> LOCATION: (2193)..(2193)
<223> OTHER INFORMATION: may comprise A or G.
<220> FEATURE:
<221> NAME/KEY: allele
```

```
<222> LOCATION: (2271)..(2271)
<223> OTHER INFORMATION: may comprise A or C.
<220> FEATURE:
<221> NAME/KEY: Unsure
<222> LOCATION: (2294)..(2294)
<223> OTHER INFORMATION: Comprises T or C.
<220> FEATURE:
<221> NAME/KEY: Unsure
<222> LOCATION: (2328)..(2328)
<223> OTHER INFORMATION: Comprises T or C.
<220> FEATURE:
<221> NAME/KEY: Unsure
<222> LOCATION: (2340)..(2340)
<223> OTHER INFORMATION: Comprises T or A.
<220> FEATURE:
<221> NAME/KEY: Unsure
<222> LOCATION: (2346)..(2346)
<223> OTHER INFORMATION: Comprises G or A.
<220> FEATURE:
<221> NAME/KEY: Unsure
<222> LOCATION: (2354)..(2354)
<223> OTHER INFORMATION: Comprises G or A.
<220> FEATURE:
<221> NAME/KEY: Unsure
<222> LOCATION: (2374)..(2374)
<223> OTHER INFORMATION: Comprises G or A.
<220> FEATURE:
<221> NAME/KEY: Unsure
<222> LOCATION: (2413)..(2413)
<223> OTHER INFORMATION: Comprises C or T.
<220> FEATURE:
<221> NAME/KEY: allele
<222> LOCATION: (2440)..(2440)
<223> OTHER INFORMATION: may comprise A or G.

<400> SEQUENCE: 8
cgccgccgcg agccagtcgg gagcgcgcga ggcgcgggga gcctgggacc aggagcgaga      60
gccgcctacc tgcagccgcc gcccacggca cggcagccac c atg gcg ctc ctg ctg    116
                                              Met Ala Leu Leu Leu
                                                1               5 tgc ttc gtg ctc ctg tgc gga gta gtg gat ttc gcc aga agt ttg agt      164
Cys Phe Val Leu Leu Cys Gly Val Val Asp Phe Ala Arg Ser Leu Ser
             10                  15                  20 atc act act cct gaa gag atg att gaa aaa gcc aaa ggg gaa act gcc      212
Ile Thr Thr Pro Glu Glu Met Ile Glu Lys Ala Lys Gly Glu Thr Ala
         25                  30                  35 tat ctg ccg tgc aaa ttt acg ctt agt ccc gaa gac cag gga ccg ctg      260
Tyr Leu Pro Cys Lys Phe Thr Leu Ser Pro Glu Asp Gln Gly Pro Leu
     40                  45                  50 gac atc gag tgg ctg ata tca cca gct gat aat cag aag gtg gat caa      308
Asp Ile Glu Trp Leu Ile Ser Pro Ala Asp Asn Gln Lys Val Asp Gln
 55                  60                  65 gtg att att tta tat tct gga gac aaa att tat gat gac tac tat cca      356
Val Ile Ile Leu Tyr Ser Gly Asp Lys Ile Tyr Asp Asp Tyr Tyr Pro
 70                  75                  80                  85 gat ctg aaa ggc cga gta cat ttt acg agt aat gat ctc aaa tct ggt      404
Asp Leu Lys Gly Arg Val His Phe Thr Ser Asn Asp Leu Lys Ser Gly
             90                  95                 100 gat gca tca ata aat gta acg aat tta caa ctg tca gat att ggc aca      452
Asp Ala Ser Ile Asn Val Thr Asn Leu Gln Leu Ser Asp Ile Gly Thr
        105                 110                 115 tat cag tgc aaa gtg aaa aaa gct cct ggt gtt gca aat aag aag att      500
Tyr Gln Cys Lys Val Lys Lys Ala Pro Gly Val Ala Asn Lys Lys Ile
    120                 125                 130 cat ctg gta gtt ctt gtt aag cct tca ggt gcg aga tgt tac gtt gat      548
His Leu Val Val Leu Val Lys Pro Ser Gly Ala Arg Cys Tyr Val Asp
135                 140                 145
```

-continued

| | | | | | | | | | | | | | | | | |
|---|---|---|---|---|---|---|---|---|---|---|---|---|---|---|---|---|
| gga | tct | gaa | gaa | att | gga | agt | gac | ttt | aag | ata | aaa | tgt | gaa | cca | aaa | 596 |
| Gly | Ser | Glu | Glu | Ile | Gly | Ser | Asp | Phe | Lys | Ile | Lys | Cys | Glu | Pro | Lys | |
| 150 | | | | | 155 | | | | | 160 | | | | | 165 | |
| gaa | ggt | tca | ctt | cca | tta | cag | tat | gag | tgg | caa | aaa | ttg | tct | gac | tca | 644 |
| Glu | Gly | Ser | Leu | Pro | Leu | Gln | Tyr | Glu | Trp | Gln | Lys | Leu | Ser | Asp | Ser | |
| | | | 170 | | | | | 175 | | | | | 180 | | | |
| cag | aaa | atg | ccc | act | tca | tgg | tta | gca | gaa | atg | act | tca | tct | gtt | ata | 692 |
| Gln | Lys | Met | Pro | Thr | Ser | Trp | Leu | Ala | Glu | Met | Thr | Ser | Ser | Val | Ile | |
| | | 185 | | | | | 190 | | | | | 195 | | | | |
| tct | gta | aaa | aat | gcc | tct | tct | gag | tac | tct | ggg | aca | tac | agc | tgt | aca | 740 |
| Ser | Val | Lys | Asn | Ala | Ser | Ser | Glu | Tyr | Ser | Gly | Thr | Tyr | Ser | Cys | Thr | |
| | 200 | | | | | 205 | | | | | 210 | | | | | |
| gtc | aga | aac | aga | gtg | ggc | tct | gat | cag | tgc | ctg | ttg | cgt | cta | aac | gtt | 788 |
| Val | Arg | Asn | Arg | Val | Gly | Ser | Asp | Gln | Cys | Leu | Leu | Arg | Leu | Asn | Val | |
| 215 | | | | | 220 | | | | | 225 | | | | | | |
| gtc | cct | cct | tca | aat | aaa | gct | gga | cta | att | gca | gga | gcc | att | ata | gga | 836 |
| Val | Pro | Pro | Ser | Asn | Lys | Ala | Gly | Leu | Ile | Ala | Gly | Ala | Ile | Ile | Gly | |
| 230 | | | | | 235 | | | | | 240 | | | | | 245 | |
| act | ttg | ctt | gct | cta | gcg | ctc | att | ggt | ctt | atc | atc | ttt | tgc | tgt | cgt | 884 |
| Thr | Leu | Leu | Ala | Leu | Ala | Leu | Ile | Gly | Leu | Ile | Ile | Phe | Cys | Cys | Arg | |
| | | | | 250 | | | | | 255 | | | | | 260 | | |
| aaa | aag | cgc | aga | gaa | gaa | aaa | tat | gaa | aag | gaa | gtt | cat | cac | gat | atc | 932 |
| Lys | Lys | Arg | Arg | Glu | Glu | Lys | Tyr | Glu | Lys | Glu | Val | His | His | Asp | Ile | |
| | | | 265 | | | | | 270 | | | | | 275 | | | |
| agg | gaa | gat | gtg | cca | cct | cca | aag | agc | cgt | acg | tcc | act | gcc | aga | agc | 980 |
| Arg | Glu | Asp | Val | Pro | Pro | Pro | Lys | Ser | Arg | Thr | Ser | Thr | Ala | Arg | Ser | |
| | | 280 | | | | | 285 | | | | | 290 | | | | |
| tac | atc | ggc | agt | aat | cat | tca | tcc | ctg | ggg | tcc | atg | tct | cct | tcc | aac | 1028 |
| Tyr | Ile | Gly | Ser | Asn | His | Ser | Ser | Leu | Gly | Ser | Met | Ser | Pro | Ser | Asn | |
| | 295 | | | | | 300 | | | | | 305 | | | | | |
| atg | gaa | gga | tat | tcc | aag | act | cag | tat | aac | caa | gta | cca | agt | gaa | gac | 1076 |
| Met | Glu | Gly | Tyr | Ser | Lys | Thr | Gln | Tyr | Asn | Gln | Val | Pro | Ser | Glu | Asp | |
| 310 | | | | | 315 | | | | | 320 | | | | | 325 | |
| ttt | gaa | cgc | act | cct | cag | agt | ccg | act | ctc | cca | cct | gct | aag | gta | gct | 1124 |
| Phe | Glu | Arg | Thr | Pro | Gln | Ser | Pro | Thr | Leu | Pro | Pro | Ala | Lys | Val | Ala | |
| | | | | 330 | | | | | 335 | | | | | 340 | | |
| gcc | cct | aat | cta | agt | cga | atg | ggt | gcg | att | cct | gtg | atg | att | cca | gca | 1172 |
| Ala | Pro | Asn | Leu | Ser | Arg | Met | Gly | Ala | Ile | Pro | Val | Met | Ile | Pro | Ala | |
| | | | 345 | | | | | 350 | | | | | 355 | | | |
| cag | agc | aag | gat | ggg | tct | ata | gta | tag | agcctccata | tgtctcatct | | | | | | 1219 |
| Gln | Ser | Lys | Asp | Gly | Ser | Ile | Val | | | | | | | | | |
| | | 360 | | | | | 365 | | | | | | | | | |

| | |
|---|---|
| gtgctctccg tgttcctttc cttttttga tatatgaaaa cctattctgg tctaaattgt | 1279 |
| gttactagcc tcaaataca tcaaaaaata agttaatcag gaactgtacg gaatatattt | 1339 |
| ttaaaatttt ttgtttggtt atatcgaaat agttacaggc actaaagtta gtaaagaaaa | 1399 |
| gtttaccatc tgaaaagct ggatttttctt taagaggttg attataaagt tttctaaatt | 1459 |
| tatcagtacc taagtaagat gtagcgctttt gaatatgaaa tcataggtga agacatgggt | 1519 |
| gaacttactt gcataccaag ttgatacttg aataaccatc tgaaagtggt acttgatcat | 1579 |
| ttttaccatt attttttagga tgtgtatttc atttatttat ggcccaccag tctcccccaa | 1639 |
| attagtacag aaatatccat gacaaaatta cttacgtatg tttgtacttg gttttacagc | 1699 |
| tcctttgaaa actctgtgtt tggaatatct ctaaaaacat agaaaacact acagtggttt | 1759 |
| agaaattact aatttttactt ctaagtcatt cataaacctt gtctatgaaa tgacttctta | 1819 |
| aatatttagt tgatagactg ctacaggtaa tagggactta gcaagctctt ttatatgcta | 1879 |
| aaggagcatc tatcagatta agttagaaca tttgctgtca gccacatatt gagatgacac | 1939 |

-continued

```
taggtgcaat agcagggata gattttgttg gtgagtagtc tcatgccttg agatctgtgg    1999
tggtcttcaa aatggtggcc agccagatca aggatgtagt atctcatagt tcccaggtga    2059
tatttttctt attagaaaaa tattataact catttgttgt ttgacactta tagattgaaa    2119
tttcctaatt tattctaaat tttaagtggt tctttggttc cagtgcttta tgttgttgtt    2179 gttttggat ggtgttacat attatatgtt ctagaaacat gtaatcctaa atttaccctc    2239
ttgaatataa tccctggatg atattttta tcataaatgc agaataatca aatacatttt    2299
aagcaagtta agtgtcctcc atcaattctg tattccagac ttgggaggat gtacagttgc    2359
tgttgtgtga tcaaacatgt ctctgtgtag ttccagcaaa tcaagctgag ctttgaaaaa    2419
gtttgtctta gttttgtgaa ggtgatttat tcttaaaaaa aaaaaaaaaa aaaaaaaaaa    2479
aaaaaaaaaa aaaaaaaaaa aaaaaaaaaa aaaaaaaaaa aaaaaaaaaa aaaaaaa       2537
```

<210> SEQ ID NO 9
<211> LENGTH: 365
<212> TYPE: PRT
<213> ORGANISM: Homo sapiens

<400> SEQUENCE: 9

```
Met Ala Leu Leu Leu Cys Phe Val Leu Leu Cys Gly Val Val Asp Phe
1               5                   10                  15

Ala Arg Ser Leu Ser Ile Thr Thr Pro Glu Glu Met Ile Glu Lys Ala
            20                  25                  30

Lys Gly Glu Thr Ala Tyr Leu Pro Cys Lys Phe Thr Leu Ser Pro Glu
        35                  40                  45

Asp Gln Gly Pro Leu Asp Ile Glu Trp Leu Ile Ser Pro Ala Asp Asn
    50                  55                  60

Gln Lys Val Asp Gln Val Ile Ile Leu Tyr Ser Gly Asp Lys Ile Tyr
65                  70                  75                  80

Asp Asp Tyr Tyr Pro Asp Leu Lys Gly Arg Val His Phe Thr Ser Asn
                85                  90                  95

Asp Leu Lys Ser Gly Asp Ala Ser Ile Asn Val Thr Asn Leu Gln Leu
            100                 105                 110

Ser Asp Ile Gly Thr Tyr Gln Cys Lys Val Lys Lys Ala Pro Gly Val
        115                 120                 125

Ala Asn Lys Lys Ile His Leu Val Val Leu Val Lys Pro Ser Gly Ala
    130                 135                 140

Arg Cys Tyr Val Asp Gly Ser Glu Glu Ile Gly Ser Asp Phe Lys Ile
145                 150                 155                 160

Lys Cys Glu Pro Lys Glu Gly Ser Leu Pro Leu Gln Tyr Glu Trp Gln
                165                 170                 175

Lys Leu Ser Asp Ser Gln Lys Met Pro Thr Ser Trp Leu Ala Glu Met
            180                 185                 190

Thr Ser Ser Val Ile Ser Val Lys Asn Ala Ser Ser Glu Tyr Ser Gly
        195                 200                 205

Thr Tyr Ser Cys Thr Val Arg Asn Arg Val Gly Ser Asp Gln Cys Leu
    210                 215                 220

Leu Arg Leu Asn Val Val Pro Pro Ser Asn Lys Ala Gly Leu Ile Ala
225                 230                 235                 240

Gly Ala Ile Ile Gly Thr Leu Leu Ala Leu Ala Leu Ile Gly Leu Ile
                245                 250                 255

Ile Phe Cys Cys Arg Lys Lys Arg Arg Glu Glu Lys Tyr Glu Lys Glu
            260                 265                 270
```

```
Val His His Asp Ile Arg Glu Asp Val Pro Pro Lys Ser Arg Thr
        275                 280                 285

Ser Thr Ala Arg Ser Tyr Ile Gly Ser Asn His Ser Ser Leu Gly Ser
        290                 295                 300

Met Ser Pro Ser Asn Met Glu Gly Tyr Ser Lys Thr Gln Tyr Asn Gln
305                 310                 315                 320

Val Pro Ser Glu Asp Phe Glu Arg Thr Pro Gln Ser Pro Thr Leu Pro
                325                 330                 335

Pro Ala Lys Val Ala Ala Pro Asn Leu Ser Arg Met Gly Ala Ile Pro
            340                 345                 350

Val Met Ile Pro Ala Gln Ser Lys Asp Gly Ser Ile Val
        355                 360                 365

<210> SEQ ID NO 10
<211> LENGTH: 1042
<212> TYPE: DNA
<213> ORGANISM: Homo sapiens
<220> FEATURE:
<221> NAME/KEY: CDS
<222> LOCATION: (45)..(710)
<223> OTHER INFORMATION: C21orf91
<220> FEATURE:
<221> NAME/KEY: allele
<222> LOCATION: (389)..(389)
<223> OTHER INFORMATION: Comprises C or G.
<220> FEATURE:
<221> NAME/KEY: allele
<222> LOCATION: (394)..(394)
<223> OTHER INFORMATION: Comprises A or G.
<220> FEATURE:
<221> NAME/KEY: allele
<222> LOCATION: (452)..(452)
<223> OTHER INFORMATION: Comprises C or G.

<400> SEQUENCE: 10
cgcacggaac ggcggtggtg gcccgcggag cggacagggg cact atg aac gaa gag      56
                                                Met Asn Glu Glu
                                                  1 gag cag ttt gta aac att gat ttg aat gat gac aac att tgc agt gtt     104
Glu Gln Phe Val Asn Ile Asp Leu Asn Asp Asp Asn Ile Cys Ser Val
  5                  10                  15                  20 tgt aaa ctg gga aca gac aaa gaa aca ctc tcc ttc tgc cac att tgt     152
Cys Lys Leu Gly Thr Asp Lys Glu Thr Leu Ser Phe Cys His Ile Cys
                 25                  30                  35 ttt gag cta aat att gag ggg gta cca aag tct gat ctc ttg cac acc     200
Phe Glu Leu Asn Ile Glu Gly Val Pro Lys Ser Asp Leu Leu His Thr
             40                  45                  50 aaa tca tta agg ggc cat aaa gac tgc ttt gaa aaa tac cat tta att     248
Lys Ser Leu Arg Gly His Lys Asp Cys Phe Glu Lys Tyr His Leu Ile
         55                  60                  65 gca aac cag ggt tgt cct cga tct aag ctt tca aaa agt act tat gaa     296
Ala Asn Gln Gly Cys Pro Arg Ser Lys Leu Ser Lys Ser Thr Tyr Glu
     70                  75                  80 gaa gtt aaa acc att ttg agt aag aag ata aac tgg att gtg cag tat     344
Glu Val Lys Thr Ile Leu Ser Lys Lys Ile Asn Trp Ile Val Gln Tyr
 85                  90                  95                 100 gcc aaa aat aag gat ctg gat tca gat tct gaa tgt tct aaa aac ccc     392
Ala Lys Asn Lys Asp Leu Asp Ser Asp Ser Glu Cys Ser Lys Asn Pro
                105                 110                 115 cag cat cat ctg ttt aat ttc agg cat aag cca gaa gaa aaa tta ctc     440
Gln His His Leu Phe Asn Phe Arg His Lys Pro Glu Glu Lys Leu Leu
            120                 125                 130
```

```
cca cag ttt gac tcc caa gta cca aaa tat tct gca aaa tgg ata gat      488
Pro Gln Phe Asp Ser Gln Val Pro Lys Tyr Ser Ala Lys Trp Ile Asp
        135                 140                 145 gga agt gca ggt ggc atc tct aac tgt aca caa aga att ttg gag cag      536
Gly Ser Ala Gly Gly Ile Ser Asn Cys Thr Gln Arg Ile Leu Glu Gln
150                 155                 160 agg gaa aat aca gac ttt gga ctt tct atg tta caa gat tca ggt gcc      584
Arg Glu Asn Thr Asp Phe Gly Leu Ser Met Leu Gln Asp Ser Gly Ala
165                 170                 175                 180 act tta tgt cgt aac agt gta ttg tgg cct cat agt cac aac cag gca      632
Thr Leu Cys Arg Asn Ser Val Leu Trp Pro His Ser His Asn Gln Ala
                185                 190                 195 cag aaa aaa gaa gag aca atc tct agt cca gag gct aat gtc cag acc      680
Gln Lys Lys Glu Glu Thr Ile Ser Ser Pro Glu Ala Asn Val Gln Thr
            200                 205                 210 cag cat cca cat tac agc aga gag gaa taa gtttttgaag agttaactca        730
Gln His Pro His Tyr Ser Arg Glu Glu
        215                 220 ccaagtgcaa gaaaaagatt ctttggcctc acagctccat gtccgccacg ttgccatcga    790
acagcttctg aagaactgtt ctaagttacc atgtctgcaa gtagggcgaa caggaatgaa    850
gtcgcaccta cccataaaca actgacctaa acagacttac ttcgtatgcc ctgcccttta    910
ttggtctccc agacatgcaa actttgaaga agtttgaaga agttgtggt ccgtttttt     970 atggtcatta aatttgccaa acataaggca gtatttaaca tctttgtcaa ataaagcaga   1030
tcattatact ct                                                       1042

<210> SEQ ID NO 11
<211> LENGTH: 221
<212> TYPE: PRT
<213> ORGANISM: Homo sapiens

<400> SEQUENCE: 11

Met Asn Glu Glu Glu Gln Phe Val Asn Ile Asp Leu Asn Asp Asp Asn
1               5                   10                  15

Ile Cys Ser Val Cys Lys Leu Gly Thr Asp Lys Glu Thr Leu Ser Phe
                20                  25                  30

Cys His Ile Cys Phe Glu Leu Asn Ile Glu Gly Val Pro Lys Ser Asp
            35                  40                  45

Leu Leu His Thr Lys Ser Leu Arg Gly His Lys Asp Cys Phe Glu Lys
        50                  55                  60

Tyr His Leu Ile Ala Asn Gln Gly Cys Pro Arg Ser Lys Leu Ser Lys
65                  70                  75                  80

Ser Thr Tyr Glu Glu Val Lys Thr Ile Leu Ser Lys Lys Ile Asn Trp
                85                  90                  95

Ile Val Gln Tyr Ala Lys Asn Lys Asp Leu Asp Ser Asp Ser Glu Cys
            100                 105                 110

Ser Lys Asn Pro Gln His His Leu Phe Asn Phe Arg His Lys Pro Glu
        115                 120                 125

Glu Lys Leu Leu Pro Gln Phe Asp Ser Gln Val Pro Lys Tyr Ser Ala
    130                 135                 140

Lys Trp Ile Asp Gly Ser Ala Gly Gly Ile Ser Asn Cys Thr Gln Arg
145                 150                 155                 160

Ile Leu Glu Gln Arg Glu Asn Thr Asp Phe Gly Leu Ser Met Leu Gln
                165                 170                 175

Asp Ser Gly Ala Thr Leu Cys Arg Asn Ser Val Leu Trp Pro His Ser
            180                 185                 190
```

-continued

```
His Asn Gln Ala Gln Lys Lys Glu Glu Thr Ile Ser Ser Pro Glu Ala
        195                 200                 205
Asn Val Gln Thr Gln His Pro His Tyr Ser Arg Glu Glu
    210                 215                 220

<210> SEQ ID NO 12
<211> LENGTH: 2625
<212> TYPE: DNA
<213> ORGANISM: Homo sapiens
<220> FEATURE:
<221> NAME/KEY: gene
<222> LOCATION: (1)..(2625)
<223> OTHER INFORMATION: CHODL
<220> FEATURE:
<221> NAME/KEY: CDS
<222> LOCATION: (392)..(1213)
<223> OTHER INFORMATION: The gene is CHODL, encoding chondrolectin,
      NM024944.
<220> FEATURE:
<221> NAME/KEY: misc_feature
<222> LOCATION: (506)..(928)
<223> OTHER INFORMATION: C-type lectin (CTL) or carbohydrate-recognition
      domain (CRD)
<220> FEATURE:
<221> NAME/KEY: misc_feature
<222> LOCATION: (539)..(931)
<223> OTHER INFORMATION: C-type lectin domain (CRD), including both the
      long and short form C-type.
<220> FEATURE:
<221> NAME/KEY: allele
<222> LOCATION: (1975)..(1975)
<223> OTHER INFORMATION: Comprises A or G.
<220> FEATURE:
<221> NAME/KEY: allele
<222> LOCATION: (2032)..(2032)
<223> OTHER INFORMATION: Comprises A or G.
<220> FEATURE:
<221> NAME/KEY: allele
<222> LOCATION: (2121)..(2121)
<223> OTHER INFORMATION: Comprises A or T.
<220> FEATURE:
<221> NAME/KEY: allele
<222> LOCATION: (2349)..(2349)
<223> OTHER INFORMATION: Comprises G or T.
<220> FEATURE:
<221> NAME/KEY: allele
<222> LOCATION: (2403)..(2404)
<223> OTHER INFORMATION: TCTA
<220> FEATURE:
<221> NAME/KEY: allele
<222> LOCATION: (2543)..(2543)
<223> OTHER INFORMATION: Comprises A or G.

<400> SEQUENCE: 12
gctgctgctg tgatccagga ccagggcgca ccggctcagc ctctcacttg tcagaggccg      60
gggaagagaa gcaaagcgca acggtgtggt ccaagccggg gcttctgctt cgcctctagg     120
acatacacgg gacccctaa cttcagtccc ccaaacgcgc accctcgaag tcttgaactc      180
cagccccgca catccacgcg cggcacaggc gcggcaggcg caggtcccg gccgaaggcg      240 atgcgcgcag ggggtcgggc agctgggctc gggcggcggg agtagggccc ggcagggagg     300
cagggaggct gcagagtcag agtcgcgggc tgcgccctgg gcagaggccg ccctcgctcc     360
acgcaacacc tgctgctgcc accgcgccgc g atg agc cgc gtg gtc tcg ctg        412
                                  Met Ser Arg Val Val Ser Leu
                                   1               5 ctg ctg ggc gcc gcg ctg ctc tgc ggc cac gga gcc ttc tgc cgc cgc       460
Leu Leu Gly Ala Ala Leu Leu Cys Gly His Gly Ala Phe Cys Arg Arg
        10                  15                  20 gtg gtc agc ggc caa aag gtg tgt ttt gct gac ttc aag cat ccc tgc       508
```

-continued

| | |
|---|---|
| Val Val Ser Gly Gln Lys Val Cys Phe Ala Asp Phe Lys His Pro Cys<br>    25                      30                      35 | |
| tac aaa atg gcc tac ttc cat gaa ctg tcc agc cga gtg agc ttt cag<br>Tyr Lys Met Ala Tyr Phe His Glu Leu Ser Ser Arg Val Ser Phe Gln<br> 40                      45                      50                      55 | 556 |
| gag gca cgc ctg gct tgt gag agt gag gga gga gtc ctc ctc agc ctt<br>Glu Ala Arg Leu Ala Cys Glu Ser Glu Gly Gly Val Leu Leu Ser Leu<br>                60                      65                      70 | 604 |
| gag aat gaa gca gaa cag aag tta ata gag agc atg ttg caa aac ctg<br>Glu Asn Glu Ala Glu Gln Lys Leu Ile Glu Ser Met Leu Gln Asn Leu<br>        75                      80                      85 | 652 |
| aca aaa ccc ggg aca ggg att tct gat ggt gat ttc tgg ata ggg ctt<br>Thr Lys Pro Gly Thr Gly Ile Ser Asp Gly Asp Phe Trp Ile Gly Leu<br>            90                      95                      100 | 700 |
| tgg agg aat gga gat ggg caa aca tct ggt gcc tgc cca gat ctc tac<br>Trp Arg Asn Gly Asp Gly Gln Thr Ser Gly Ala Cys Pro Asp Leu Tyr<br>        105                      110                      115 | 748 |
| cag tgg tct gat gga agc aat tcc cag tac cga aac tgg tac aca gat<br>Gln Trp Ser Asp Gly Ser Asn Ser Gln Tyr Arg Asn Trp Tyr Thr Asp<br>120                      125                      130                      135 | 796 |
| gaa cct tcc tgc gga agt gaa aag tgt gtt gtg atg tat cac caa cca<br>Glu Pro Ser Cys Gly Ser Glu Lys Cys Val Val Met Tyr His Gln Pro<br>                140                      145                      150 | 844 |
| act gcc aat cct ggc ctt ggg ggt ccc tac ctt tac cag tgg aat gat<br>Thr Ala Asn Pro Gly Leu Gly Gly Pro Tyr Leu Tyr Gln Trp Asn Asp<br>                155                      160                      165 | 892 |
| gac agg tgt aac atg aag cac aat tat att tgc aag tat gaa cca gag<br>Asp Arg Cys Asn Met Lys His Asn Tyr Ile Cys Lys Tyr Glu Pro Glu<br>        170                      175                      180 | 940 |
| att aat cca aca gcc cct gta gaa aag cct tat ctt aca aat caa cca<br>Ile Asn Pro Thr Ala Pro Val Glu Lys Pro Tyr Leu Thr Asn Gln Pro<br>185                      190                      195 | 988 |
| gga gac acc cat cag aat gtg gtt gtt act gaa gca ggt ata att ccc<br>Gly Asp Thr His Gln Asn Val Val Val Thr Glu Ala Gly Ile Ile Pro<br>200                      205                      210                      215 | 1036 |
| aat cta att tat gtt gtt ata cca aca ata ccc ctg ctc tta ctg ata<br>Asn Leu Ile Tyr Val Val Ile Pro Thr Ile Pro Leu Leu Leu Leu Ile<br>                220                      225                      230 | 1084 |
| ctg gtt gct ttt gga acc tgt tgt ttc cag atg ctg cat aaa agt aaa<br>Leu Val Ala Phe Gly Thr Cys Cys Phe Gln Met Leu His Lys Ser Lys<br>                235                      240                      245 | 1132 |
| gga aga aca aaa act agt cca aac cag tct aca ctg tgg att tca aag<br>Gly Arg Thr Lys Thr Ser Pro Asn Gln Ser Thr Leu Trp Ile Ser Lys<br>        250                      255                      260 | 1180 |
| agt acc aga aaa gaa agt ggc atg gaa gta taa taactcattg acttggttcc<br>Ser Thr Arg Lys Glu Ser Gly Met Glu Val<br>        265                      270 | 1233 |
| agaattttgt aattctggat ctgtataagg aatggcatca gaacaatagc ttggaatggc | 1293 |
| ttgaaatcac aaaggatctg caagatgaac tgtaagctcc cccttgaggc aaatattaaa | 1353 |
| gtaattttta tatgtctatt atttcattta aagaatatgc tgtgctaata atggagtgag | 1413 |
| acatgcttat tttgctaaag gatgcaccca aacttcaaac ttcaagcaaa tgaaatggac | 1473 |
| aatgcagata aagttgttat caacacgtcg ggagtatgtg tgttagaagc aattcctttt | 1533 |
| atttctttca cctttcataa gttgttatct agtcaatgta atgtatattg tattgaaatt | 1593 |
| tacagtgtgc aaaagtattt tacctttgca taagtgtttg ataaaaatga actgttctaa | 1653 |
| tatttatttt tatggcatct cattttttcaa tacatgctct tttgattaaa gaaacttatt | 1713 |

-continued

```
actgttgtca actgaattca cacacacaca aatatagtac catagaaaaa gtttgttttc    1773
tcgaaataat tcatctttca gcttctctgc ttttggtcaa tgtctaggaa atctcttcag    1833
aaataagaag ctatttcatt aagtgtgata taaacctcct caaacatttt acttagaggc    1893
aaggattgtc taatttcaat tgtgcaagac atgtgcctta taattatttt tagcttaaaa    1953
ttaaacagat tttgtaataa tgtaactttg ttaataggtg cataaacact aatgcagtca    2013
atttgaacaa aagaagtgac atacacaata taaatcatat gtcttcacac gttgcctata    2073
taatgagaag cagctctctg agggttctga atcaatgtg gtccctctct tgcccactaa     2133
acaaagatgg ttgttcgggg tttgggattg acactggagg cagatagttg caaagttagt    2193
ctaaggtttc cctagctgta tttagcctct gactatatta gtatacaaag aggtcatgtg    2253
gttgagacca ggtgaatagt cactatcagt gtggagacaa gcacagcaca cagacatttt    2313
aggaaggaaa ggaactacga aatcgtgtga aaatgggttg gaacccatca gtgatcgcat    2373
attcattgat gagggtttgc ttgagataga aaatggtggc tcctttctgt cttatctcct    2433
agtttcttca atgcttacgc cttgttcttc tcaagagaaa gttgtaactc tctggtcttc    2493
atatgtccct gtgctccttt taaccaaata aagagttctt gtttctgaag aaaaaaaaaa    2553
aaaaaaaaaa aaaaaaaaaa aaaaaaaaaa aaaaaaaaaa aaaaaaaaaa aaaaaaaaaa    2613
aaaaaaaaaa aa                                                       2625
```

<210> SEQ ID NO 13
<211> LENGTH: 273
<212> TYPE: PRT
<213> ORGANISM: Homo sapiens

<400> SEQUENCE: 13

```
Met Ser Arg Val Val Ser Leu Leu Leu Gly Ala Ala Leu Leu Cys Gly
1               5                   10                  15

His Gly Ala Phe Cys Arg Arg Val Val Ser Gly Gln Lys Val Cys Phe
            20                  25                  30

Ala Asp Phe Lys His Pro Cys Tyr Lys Met Ala Tyr Phe His Glu Leu
        35                  40                  45

Ser Ser Arg Val Ser Phe Gln Glu Ala Arg Leu Ala Cys Glu Ser Glu
    50                  55                  60

Gly Gly Val Leu Leu Ser Leu Glu Asn Glu Ala Glu Gln Lys Leu Ile
65                  70                  75                  80

Glu Ser Met Leu Gln Asn Leu Thr Lys Pro Gly Thr Gly Ile Ser Asp
                85                  90                  95

Gly Asp Phe Trp Ile Gly Leu Trp Arg Asn Gly Asp Gly Gln Thr Ser
            100                 105                 110

Gly Ala Cys Pro Asp Leu Tyr Gln Trp Ser Asp Gly Ser Asn Ser Gln
        115                 120                 125

Tyr Arg Asn Trp Tyr Thr Asp Glu Pro Ser Cys Gly Ser Glu Lys Cys
    130                 135                 140

Val Val Met Tyr His Gln Pro Thr Ala Asn Pro Gly Leu Gly Gly Pro
145                 150                 155                 160

Tyr Leu Tyr Gln Trp Asn Asp Asp Arg Cys Asn Met Lys His Asn Tyr
                165                 170                 175

Ile Cys Lys Tyr Glu Pro Glu Ile Asn Pro Thr Ala Pro Val Glu Lys
            180                 185                 190

Pro Tyr Leu Thr Asn Gln Pro Gly Asp Thr His Gln Asn Val Val Val
        195                 200                 205
```

-continued

```
Thr Glu Ala Gly Ile Ile Pro Asn Leu Ile Tyr Val Val Ile Pro Thr
    210             215                 220

Ile Pro Leu Leu Leu Leu Ile Leu Val Ala Phe Gly Thr Cys Cys Phe
225             230                 235                 240

Gln Met Leu His Lys Ser Lys Gly Arg Thr Lys Thr Ser Pro Asn Gln
                245             250                 255

Ser Thr Leu Trp Ile Ser Lys Ser Thr Arg Lys Glu Ser Gly Met Glu
            260             265                 270

Val
```